(12) United States Patent
Margulies et al.

(10) Patent No.: US 12,332,246 B2
(45) Date of Patent: *Jun. 17, 2025

(54) QUINOLINE BASED CYANINE DYE TURN-ON FLUORESCENT PROBES AND METHODS OF USE THEREOF

(71) Applicant: YEDA RESEARCH AND DEVELOPMENT CO. LTD., Rehovot (IL)

(72) Inventors: David Margulies, Rehovot (IL); Leila Motiei, Rehovot (IL); Pragati Prasad, Rehovot (IL); Tom Granot, Rehovot (IL); Ohad Suss, Rehovot (IL)

(73) Assignee: YEDA RESEARCH AND DEVELOPMENT CO. LTD., Rehovot (IL)

(*) Notice: Subject to any disclaimer, the term of this patent is extended or adjusted under 35 U.S.C. 154(b) by 1149 days.

This patent is subject to a terminal disclaimer.

(21) Appl. No.: 17/140,075

(22) Filed: Jan. 3, 2021

(65) Prior Publication Data

US 2021/0156867 A1 May 27, 2021

Related U.S. Application Data

(63) Continuation-in-part of application No. 16/783,524, filed on Feb. 6, 2020, now Pat. No. 11,639,929, and
(Continued)

(51) Int. Cl.
*G01N 33/58* (2006.01)
*C07C 227/18* (2006.01)
(Continued)

(52) U.S. Cl.
CPC ....... *G01N 33/582* (2013.01); *G01N 21/6428* (2013.01); *G01N 21/6458* (2013.01);
(Continued)

(58) Field of Classification Search
CPC ............ G01N 33/582; G01N 21/6428; G01N 21/6458; G01N 33/5008; G01N 33/6803;
(Continued)

(56) References Cited

U.S. PATENT DOCUMENTS 9,696,310 B2 * 7/2017 Margulies .............. G01N 33/53
10,281,459 B2   5/2019 Margulies et al.
(Continued)

FOREIGN PATENT DOCUMENTS

WO   WO 2000/047548        8/2000
WO   WO-0047548 A1 *   8/2000   ........... C07C 217/28
(Continued)

OTHER PUBLICATIONS

Unger-angel. Protein recognition by bivalent, 'turn-on' fluorescent molecular probes. Chem. Sci., 2015, 6, 5419-5425. (Year: 2015).*
(Continued)

*Primary Examiner* — Shafiqul Haq
(74) *Attorney, Agent, or Firm* — Mark S. Cohen; PEARL COHEN ZEDEK LATZER BARATZ LLP

(57) ABSTRACT

This invention is directed to a turn-on fluorescent probe, wherein said probe comprises a quinoline based cyanine dye derivative (QBC) and a specific protein binder covalently attached thereto directly or via a linker. This invention is further directed to His-tag binding compounds and uses thereof in the preparation of genetically targeted detectable molecules and sensors which can specifically bind tag-labeled proteins. This invention further describes methods for using these turn-on probes and compounds for detecting and labelling a wide range of proteins in their native environment.

8 Claims, 68 Drawing Sheets

Specification includes a Sequence Listing.

Related U.S. Application Data a continuation-in-part of application No. PCT/IL2019/050639, filed on Jun. 5, 2019, said application No. 16/783,524 is a continuation-in-part of application No. 15/307,011, filed as application No. PCT/IL2015/050441 on Apr. 28, 2015.

(60) Provisional application No. 61/985,555, filed on Apr. 29, 2014.

(51) Int. Cl.
   *G01N 21/64* (2006.01)
   *G01N 33/50* (2006.01)
   *G01N 33/68* (2006.01)

(52) U.S. Cl.
   CPC ..... *G01N 33/5008* (2013.01); *G01N 33/6803* (2013.01); *G01N 2021/6439* (2013.01)

(58) Field of Classification Search
   CPC .......... G01N 2021/6439; C07D 417/06; C07D 249/04
   See application file for complete search history.

(56) References Cited

U.S. PATENT DOCUMENTS

| | | | |
|---|---|---|---|
| 10,557,852 B2 | 2/2020 | Margulies et al. | |
| 10,557,853 B2 * | 2/2020 | Margulies | ............ G01N 33/573 |
| 11,639,929 B2 * | 5/2023 | Margulies | .......... G01N 33/6803 435/7.1 |
| 2008/0038750 A1 | 2/2008 | Piehler et al. | |
| 2011/0091893 A1 | 4/2011 | Heyduk et al. | |
| 2014/0038856 A1 | 2/2014 | Gee et al. | |
| 2015/0112047 A1 | 4/2015 | Schmidt | |

FOREIGN PATENT DOCUMENTS

| | | | |
|---|---|---|---|
| WO | WO 2012/159051 A2 | 11/2012 | |
| WO | WO 2015/166491 A2 | 11/2015 | |

OTHER PUBLICATIONS

Tschammer et al. One-step, purification-free and site-specific labeling of polyhistidine-tagged proteins for MST. NanoTemper Technologies GmbH. 2016. (Year: 2016).*

You, C., & Piehler, J. (2014). Multivalent chelators for spatially and temporally controlled protein functionalization. Analytical and bioanalytical chemistry, 406, 3345-3357.

Abendroth, Frank, et al. DNA-controlled bivalent presentation of ligands for the estrogen receptor. Angewandte Chemie International Edition, 2011, 50.37: 8592-8596.

André, Thomas, et al. Selectivity of competitive multivalent interactions at interfaces. ChemBioChem, 2009, 10.11: 1878-1887.

Arai, Satoshi, et al. Fluorescent "Turn-on" system utilizing a quencher-conjugated peptide for specific protein labeling of living cells. Biochemical and biophysical research communications, 2011, 404.1: 211-216.

Battle, Cooper; CHU, Xiaozhu; Jayawickramarajah, Janarthanan. Oligonucleotide-based systems for input-controlled and non-covalently regulated protein binding. Supramolecular chemistry, 2013, 25.12: 848-862.

Bausch-Fluck, Damaris, et al. The in silico human surfaceome. Proceedings of the National Academy of Sciences, 2018, 115.46: E10988-E10997.

Benincasa, Monica, et al. Rapid and reliable detection of antimicrobial peptide penetration into gram-negative bacteria based on fluorescence quenching. Antimicrobial agents and chemotherapy, 2009, 53.8: 3501-3504.

Berne, Cécile, et al. Adhesins involved in attachment to abiotic surfaces by Gram-negative bacteria. Microbial Biofilms, 2015, 163-199.

Beutner, Ernst H. Immunofluorescent staining: the fluorescent antibody method. Bacteriological reviews, 1961, 25.1: 49.

Bi et al. "Chemical and enzymatic strategies for bacterial and mammalian cell surface engineering" Chemistry—A European Journal. Jun. 7, 2018;24(32):8042-50.

Bi, Xiaobao, et al. Frontispiece: Chemical and Enzymatic Strategies for Bacterial and Mammalian Cell Surface Engineering. Chemistry—A European Journal, 2018, 24.32.

Block, Helena, et al. Immobilized-metal affinity chromatography (IMAC): a review. In: Methods in enzymology. Academic Press, 2009. p. 439-473.

Borisenko, Grigory G., et al. DNA modification of live cell surface. Nucleic acids research, 2009, 37.4: e28-e28.

Bornhorst, Joshua A.; Falke, Joseph J. [16] Purification of proteins using polyhistidine affinity tags. In: Methods in enzymology. Academic Press, 2000. p. 245 -254.

Brandman, Onn; Meyer, Tobias. Feedback loops shape cellular signals in space and time. Science, 2008, 322.5900: 390-395.

Braun, Pascal; Labaer, Josh. High throughput protein production for functional proteomics. Trends in biotechnology, 2003, 21.9: 383-388.

Brellier, M. et al. (2009)—Insight into the Complexation Mode of Bis (nitrilotriacetic acid)(NTA) Ligands with Ni2+ Involved in the Labeling of Histidine-Tagged Proteins—Chemistry—A European Journal, 15(46), 12689-12701.

Cardona, Claudia M.; Gawley, Robert E. An improved synthesis of a trifurcated Newkome-type monomer and orthogonally protected two-generation dendrons. The Journal of Organic Chemistry, 2002, 67.4: 1411-1413.

Chakraborty, Kasturi, et al. Nucleic acid-based nanodevices in biological imaging. Annual Review of Biochemistry, 2016, 85: 349-373.

Chen, Irwin, et al. Site-specific labeling of cell surface proteins with biophysical probes using biotin ligase. Nature methods, 2005, 2.2: 99-104.

Chen, Yong-Xiang, et al. Synthesis of the Rheb and K-Ras4B GTPases. Angewandte Chemie, 2010, 122.35: 6226-6231.

Cheng, Bo, et al. Metabolic remodeling of cell-surface sialic acids: principles, applications, and recent advances. ChemBioChem, 2016, 17.1: 11-27.

Cohen, Bruce E., et al. Probing protein electrostatics with a synthetic fluorescent amino acid. Science, 2002, 296.5573: 1700-1703.

Coltharp, Carla; Xiao, Jie. Superresolution microscopy for microbiology. Cellular microbiology, 2012, 14.12: 1808-1818.

Crivici, Anna; Ikura, Mitsuhiko. Molecular and structural basis of target recognition by calmodulin. Annual review of biophysics and biomolecular structure, 1995, 24.1: 85-116.

Dan, Krishna, et al. DNA nanodevices map enzymatic activity in organelles. Nature nanotechnology, 2019, 14.3: 252-259.

Danylchuk, Dmytro I., et al. Switchable Solvatochromic Probes for Live-Cell Super-resolution Imaging of Plasma Membrane Organization. Angewandte Chemie International Edition, 2019, 58.42: 14920-14924.

Dube, Danielle H.; Bertozzi, Carolyn R. Metabolic oligosaccharide engineering as a tool for glycobiology. Current opinion in chemical biology, 2003, 7.5: 616-625.

Dubel, Natali, et al. Exploring the limits of bivalency by DNA-based spatial screening. Angewandte Chemie International Edition, 2019, 58.3: 907-911.

Dumas, Anaëlle, et al. Designing logical codon reassignment—Expanding the chemistry in biology. Chemical science, 2015, 6.1: 50-69.

Elahipanah, Sina, et al. Rewiring gram-negative bacteria cell surfaces with bio-orthogonal chemistry via liposome fusion. Bioconjugate Chemistry, 2016, 27.4: 1082-1089.

Fluorophores.org—Database of Fluorescent Dyes, Properties and Applications. Download Jul. 9, 2018 from: http://www.fluorophores.org.

Foot, Natalie; Henshall, Tanya; Kumar, Sharad. Ubiquitination and the regulation of membrane proteins. Physiological reviews, 2017, 97.1: 253-281.

(56) References Cited

OTHER PUBLICATIONS

Fujishima, Sho-hei, et al. Design of a multinuclear Zn (ii) complex as a new molecular probe for fluorescence imaging of His-tag fused proteins. Chemical Communications, 2012, 48.4: 594-596.

Fukuda, Tomohiro, et al. Aggregation of Alzheimer amyloid β peptide (1-42) on the multivalent sulfonated sugar interface. Bioconjugate chemistry, 2010, 21.6: 1079-1086.

Furst, Ariel L.; Smith, Matthew J.; Francis, Matthew B. New techniques for the generation and analysis of tailored microbial systems on surfaces. Biochemistry, 2018, 57.21: 3017-3026.

Gabrielse, Kari, et al. Reversible Re-programing of Cell-Cell Interactions. Angewandte Chemie, 2014, 126.20: 5212-5216.

Gartner, Zev J.; Bertozzi, Carolyn R. Programmed assembly of 3-dimensional microtissues with defined cellular connectivity. Proceedings of the National Academy of Sciences, 2009, 106.12: 4606-4610.

Gatterdam, Karl, et al. The Scaffold Design of Trivalent Chelator Heads Dictates Affinity and Stability for Labeling His-tagged Proteins in vitro and in Cells. Angewandte Chemie, 2018, 130.38: 12575-12579.

Gautam, Samir, et al. Exterior design: strategies for redecorating the bacterial surface with small molecules. Trends in biotechnology, 2013, 31.4: 258-267.

Ghosh, Rajeshwary; Gilda, Jennifer E.; Gomes, Aldrin V. The necessity of and strategies for improving confidence in the accuracy of western blots. Expert review of proteomics, 2014, 11.5: 549-560.

Gilbert, Charlie; Ellis, Tom. Biological engineered living materials: growing functional materials with genetically programmable properties. ACS synthetic biology, 2018, 8.1: 1-15.

Gilbert, Michele; Albala, Joanna S. Accelerating code to function: sizing up the protein production line. Current opinion in chemical biology, 2002, 6.1: 102-105.

Goodman, Russell P., et al. A facile method for reversibly linking a recombinant protein to DNA. ChemBioChem, 2009, 10.9: 1551-1557.

Govers, Roland; James, David E.; Coster, Adelle CF. High-throughput analysis of the dynamics of recycling cell surface proteins. In: Exocytosis and Endocytosis. Humana Press, 2008. p. 129-146.

Grabchev, I.; Chovelon, J.-M.; Qjan, X1. A copolymer of 4-N,N-dimethylaminoethylene-N-allyl-1, 8-naphthalimide with methylmethacrylate as a selective fluorescent chemosensor in homogeneous systems for metal cations. Journal of Photochemistry and Photobiology A: chemistry, 2003, 158.1: 37-43.

Griffin, B. Albert; Adams, Stephen R.; Tsien, Roger Y. Specific covalent labeling of recombinant protein molecules inside live cells. Science, 1998, 281.5374: 269-272.

Grunwald, Christian, et al. Quantum-yield-optimized fluorophores for site-specific labeling land super-resolution imaging. Journal of the American Chemical Society, 2011, 133.21: 8090-8093.

Guignet, Emmanuel G.; Hovius, Ruud; Vogel, Horst. Reversible site-selective labeling of membrane proteins in live cells. Nature biotechnology, 2004, 22.4: 440-444.

Halo, Tiffany L., et al. Selective recognition of protein tetraserine motifs with a cell-permeable, pro-fluorescent bis-boronic acid. Journal of the American Chemical Society, 2009, 131.2: 438-439.

Harris, D. Calvin; Saks, Benjamin R.; Jayawickramarajah, Janarthanan. Protein-binding molecular switches via host-guest stabilized DNA hairpins. Journal of the American Chemical Society, 2011, 133.20: 7676-7679.

Hauser, Christina T.; Tsien, Roger Y. A hexahistidine-Zn2+-dye label reveals STIM1 surface exposure. Proceedings of the National Academy of Sciences, 2007, 104.10: 3693-3697.

Hayashi, Takahiro, et al. Analysis of cell-surface receptor dynamics through covalent labeling by catalyst-tethered antibody. Journal of the American Chemical Society, 2015, 137.16: 5372-5380.

Hochuli, E.; Döbeli, H.; Schacher, A. New metal chelate adsorbent selective for proteins and peptides containing neighbouring histidine residues. Journal of Chromatography A, 1987, 411: 177-184.

Honda, Kei, et al. Pyrene Excimer-Based Dual-Emission Detection of a Oligoaspartate Tag-Fused Protein by Using a Znil-DpaTyr Probe. ChemBioChem, 2007, 8.12: 1370-1372.

Huang, Zhaohua, et al. Facile synthesis of multivalent nitrilotriacetic acid (NTA) and NTA conjugates for analytical and drug delivery applications. Bioconjugate chemistry, 2006, 17.6: 1592-1600.

Huang, Zhaohua, et al. Tris-nitrilotriacetic acids of subnanomolar affinity toward hexahistidine tagged molecules. Bioconjugate chemistry, 2009, 20.8: 1667-1672.

Hurley, Amanda; Bassler, Bonnie L. Asymmetric regulation of quorum-sensing receptors drives autoinducer-specific gene expression programs in Vibrio cholerae. PLoS genetics, 2017, 13.5: e1006826.

Jerabek-Willemsen, Moran, et al. Molecular interaction studies using microscale thermophoresis. Assay and drug development technologies, 2011, 9.4: 342-353.

Kamoto, Mie, et al. Novel probes showing specific fluorescence enhancement on binding to a hexahistidine tag. Chemistry—A European Journal, 2008, 14.26: 8004-8012.

Kamoto, Mie, et al. Turn-on fluorescent probe with visible light excitation for labeling of hexahistidine tagged protein. Bioorganic & medicinal chemistry letters, 2009, 19.8: 2285-2288.

Kapanidis, Achillefs N.; Ebright, Yon W.; Ebright, Richard H. Site-specific incorporation of fluorescent probes into protein: hexahistidine-tag-mediated fluorescent labeling with (Ni2+: nitrilotriacetic acid) n-fluorochrome conjugates. Journal of the American Chemical Society, 2001, 123.48: 12123-12125.

Khan, Farid; He, Mingyue; Taussig, Michael J. Double-hexahistidine tag with high-affinity binding for protein immobilization, purification, and detection on Ni-nitrilotriacetic acid surfaces. Analytical chemistry, 2006, 78.9: 3072-3079.

Kim, Kyung Lock, et al. Supramolecular latching system based on ultrastable synthetic binding pairs as versatile tools for protein imaging. Nature communications, 2018, 9.1: 1-10.

Knezevic, Jelena, et al. Quantitation of affinity, avidity, and binding kinetics of protein analytes with a dynamically switchable biosurface. Journal of the American Chemical Society, 2012, 134.37: 15225-15228.

Kollmannsperger, Alina, et al. Live-cell protein labelling with nanometre precision by cell squeezing. Nature communications, 2016, 7.1: 1-7.

Kubota, Ryou; Hamachi, Itaru. Protein recognition using synthetic small-molecular binders toward optical protein sensing in vitro and in live cells. Chemical Society Reviews, 2015, 44.13: 4454-4471.

Lahav-Mankovski, Naama, et al. Decorating bacteria with self-assembled synthetic receptors. Nature communications, 2020, 11.1: 1-12.

Lai, Yau-Tsz, et al. Rapid labeling of intracellular His-tagged proteins in living cells. Proceedings of the National Academy of Sciences, 2015, 112.10: 2948-2953.

Lang, Kathrin; Chin, Jason W. Cellular incorporation of unnatural amino acids and bioorthogonal labeling of proteins. Chemical reviews, 2014, 114.9: 4764-4806.

Lata, Suman, et al. High-affinity adaptors for switchable recognition of histidine-tagged proteins. Journal of the American Chemical Society, 2005, 127.29: 10205-10215.

Lata, Suman, et al. Specific and stable fluorescence labeling of histidine-tagged proteins for dissecting multi-protein complex formation. Journal of the American Chemical Society, 2006, 128.7: 2365-2372.

Lee, Jae-Jung, et al. Bodipy-diacrylate imaging probes for targeted proteins inside live cells. Chemical Communications, 2011, 47.15: 4508-4510.

Lee, Marissa K., et al. Small-molecule labeling of live cell surfaces for three-dimensional super-resolution microscopy. Journal of the American Chemical Society, 2014, 136.40: 14003-14006.

Lemmon, Mark A.; Schlessinger Joseph. Cell signaling by receptor tyrosine kinases. Cell, 2010, 141.7: 1117-1134.

Link, A. James; Vink, Mandy KS; Tirrell, David A. Presentation and detection of azide functionality in bacterial cell surface proteins. Journal of the American Chemical Society, 2004, 126.34: 10598-10602.

(56) References Cited

OTHER PUBLICATIONS

Loving, Galen; Imperiali, Barbara. A versatile amino acid analogue of the solvatochromic fluorophore 4-N, N-dimethylamino-1, 8-naphthalimide: a powerful tool for the study of dynamic protein interactions. Journal of the American Chemical Society, 2008, 130.41: 13630-13638.

Loving, Galen S.; Sainlos, Matthieu; Imperiali, Barbara. Monitoring protein interactions and dynamics with solvatochromic fluorophores. Trends in biotechnology, 2010, 28.2: 73-83.

Lugtenberg, Ben, et al. Influence of cultural conditions and mutations on the composition of the outer membrane proteins of Escherichia coli. Molecular and General Genetics MGG, 1976, 147.3: 251-262.

Mali, Prashant, et al. Barcoding cells using cell-surface programmable DNA-binding domains. Nature methods, 2013, 10.5: 403-406.

Martin, E.; Weigand, R.; Pardo, A. Solvent dependence of the inhibition of intramolecular charge-transfer in N-substituted 1, 8-naphthalimide derivatives as dye lasers. Journal of luminescence, 1996, 68.2-4: 157-164.

Melkko, Samu, et al. Isolation of high-affinity trypsin inhibitors from a DNA-encoded chemical library. Angewandte Chemie, 2007, 119.25: 4755-4758.

Mishra, Manish; Tiwari, Shuchita; Gomes, Aldrin V. Protein purification and analysis: next generation Western blotting techniques. Expert review of proteomics, 2017, 14.11: 1037-1053.

Moorthy, Sudha; Keklak, Julia; Klein, Eric A. Perspective: adhesion mediated signal transduction in bacterial pathogens. Pathogens, 2016, 5.1: 23.

Motiei, Leila, et al. Targeted protein surface sensors as a tool for analyzing small populations of proteins in biological mixtures. Angewandte Chemie, 2014, 126.35: 9443-9447.

Mukherjee, Purba, et al. Design of a DNA-programmed plasminogen activator. Journal of the American Chemical Society, 2018, 140.45: 15516-15524.

Murata, Atsushi, et al. Construction of a 'turn-on' fluorescent probe system for His-tagged proteins. Bioorganic & medicinal chemistry letters, 2010, 20.23: 6905-6908.

Neet, Kenneth E.; Lee, J. Ching, Biophysical characterization of proteins in the post-genomic era of proteomics. Molecular & Cellular Proteomics, 2002, 1.6: 415-420.

Nelson, James W., et al. A biosynthetic strategy for re-engineering the *Staphylococcus aureus* cell wall with non-native small molecules. ACS chemical biology, 2010, 5.12: 1147-1155.

Nissinkorn, Yael, et al. Sensing protein surfaces with targeted fluorescent receptors. Chemistry—A European Journal, 2015, 21.45: 15981-15987.

Nonaka, Hiroshi, et al. Selective covalent labeling of tag-fused GPCR proteins on live cell surface with a synthetic probe for their functional analysis. Journal of the American Chemical Society, 2010, 132.27: 9301-9309.

Ojida, Akio, et al. Oligo-Asp tag/Zn (II) complex probe as a new pair for labeling and fluorescence imaging of proteins. Journal of the American Chemical Society, 2006, 128.32: 10452-10459.

Overton, Tim W. Recombinant protein production in bacterial hosts. Drug discovery today, 2014, 19.5: 590-601.

Papaneophytou, Christos P.; Kontopidis, George. Statistical approaches to maximize recombinant protein expression in *Escherichia coli*: a general review. Protein expression and purification, 2014, 94: 22-32.

Park, Jooyeon, et al. Engineering the surface of therapeutic "living" cells. Chemical reviews, 2018, 118.4: 1664-1690.

Peng, Ruizi, et al. Engineering a 3D DNA-logic gate nanomachine for bispecific recognitionand computing on target cell surfaces. Journal of the American Chemical Society, 2018, 140.31: 9793-9796.

Pereira, Catarina S.; Thompson, Jessica A.; Xavier, Karina B. AI-2-mediated signalling in bacteria. FEMS microbiology reviews, 2013, 37.2: 156-181.

Peri-Naor, Ronny, et al. Protein-protein communication and enzyme activation mediatedby a synthetic chemical transducer. Journal of the American Chemical Society, 2015, 137.30: 9507-9510.

Peri-Naor, Ronny, et al. Glycoform Differentiation by a Targeted, Self-Assembled, Pattern-Generating Protein Surface Sensor. Journal of the American Chemical Society, 2020, 142.37: 15790-15798.

Pode, Zohar, et al. Protein recognition by a pattern-generating fluorescent molecular probe. Nature Nanotechnology, 2017, 12.12: 1161-1168.

Porchetta, Alessandro, et al. Programmable nucleic acid nanoswitches for the rapid, single-step detection of antibodies in bodily fluids. Journal of the American Chemical Society, 2018, 140.3: 947-953.

Qian, Xiangping, et al. Arrays of self-assembled monolayers for studying inhibition of bacterial adhesion. Analytical Chemistry, 2002, 74.8: 1805-1810.

Rabuka, David, et al. Noncovalent cell surface engineering: incorporation of bioactive synthetic glycopolymers into cellular membranes. Journal of the American Chemical Society, 2008, 130.18: 5947-5953.

Ranallo, Simona, et al. Antibody-powered nucleic acid release using a DNA-based nanomachine. Nature communications, 2017, 8.1: 1-9.

Raulf, Anika, et al. Click chemistry facilitates direct labelling and super-resolution imaging of nucleic acids and proteins. RSC advances, 2014, 4.57: 30462.

Reinhardt, Ulrike, et al. Peptide-templated acyl transfer: a chemical method for the labeling of membrane proteins on live cells. Angewandte Chemie International Edition, 2014, 53.38: 10237-10241.

Riglar, David T.; Silver, Pamela A. Engineering bacteria for diagnostic and therapeutic applications. Nature Reviews Microbiology, 2018, 16.4: 214.

Rosen, Christian B., et al. Template-directed covalent conjugation of DNA to native antibodies, transferrin and other metal-binding proteins. Nature chemistry, 2014, 6.9: 804-809.

Rosenzweig, Brooke A., et al. Multivalent protein binding and precipitation by self-assembling molecules on a DNA pentaplex scaffold. Journal of the American Chemical Society, 2009, 131.14: 5020-5021.

Rouhanifard, Sara H., et al. Chemical probing of glycans in cells and organisms. Chemical Society Reviews, 2013, 42.10: 4284-4296.

Saccà, Barbara; Niemeyer, Christof M. Functionalization of DNA nanostructures with proteins. Chemical Society Reviews, 2011, 40.12: 5910-5921.

Saghatelian, Alan, et al. DNA detection and signal amplification via an engineered allosteric enzyme. Journal of the American Chemical Society, 2003, 125.2: 344-345.

Saroja, G., et al. 4-Aminophthalimide derivatives as environment-sensitive probes. Journal of Fluorescence, 1998, 8.4: 405-410.

Saxon, Eliana; Bertozzi, Carolyn R. Cell surface engineering by a modified Staudinger reaction. Science, 2000, 287.5460: 2007-2010.

Schneider, Ann-Kathrin; Niemeyer, Christof M. DNA surface technology: From gene sensors to integrated systems for life and materials sciences. Angewandte Chemie International Edition, 2018, 57.52: 16959-16967.

Selvakumar, Karuthapandi; Motiei, Leila; Margulies, David. Enzyme—artificial enzyme interactions as a means for discriminating among structurally similar isozymes. Journal of the American Chemical Society, 2015, 137.15: 4892-4895.

Soh, Nobuaki, et al. Methodology of reversible protein labeling for ratiometric fluorescent measurement. Molecular BioSystems, 2006, 2.2: 128-131.

Soh, Nobuaki. Selective chemical labeling of proteins with small fluorescent molecules based on metal-chelation methodology. Sensors, 2008, 8.2: 1004-1024.

Spicer, Christopher D.; Triemer, Therese; Davis, Benjamin G. Palladium-mediated cell-surface labeling. Journal of the American Chemical Society, 2012, 134.2: 800-803.

Spicer, Christopher D.; Davis, Benjamin G. Selective chemical protein modification. Nature communications, 2014, 5.1: 1-14.

Sprengel, Andreas, et al. Tailored protein encapsulation into a DNA host using geometrically organized supramolecular interactions. Nature communications, 2017, 8.1: 1-12.

(56) References Cited

OTHER PUBLICATIONS

Szent-Gyorgyi, Christopher, et al. Fluorogen-activating single-chain antibodies for imaging cell surface proteins. Nature biotechnology, 2008, 26.2: 235-240.

Takaoka, Yousuke; Ojida, Akio; Hamachi, Itaru. Protein Organic Chemistry and Applications for Labeling and Engineering in Live-Cell Systems. Angewandte Chemie International Edition, 2013, 52.15: 4088-4106.

Tanaka, Tsutomu, et al. Site-specific protein modification on living cells catalyzed by sortase. ChemBioChem, 2008, 9.5: 802-807.

Thorley, Jennifer A.; Pike, Jeremy; Rappoport, Joshua Z. Super-resolution microscopy: a comparison of commercially available options. In: Fluorescence Microscopy. Academic Press, 2014. p. 199-212.

Tsukiji, Shinya, et al. Ligand-directed tosyl chemistry for protein labeling in vivo. Nature chemical biology, 2009, 5.5: 341-343.

Uchinomiya, Sho-hei, et al. Site-specific covalent labeling of His-tag fused proteins with a reactive Ni (II)-NTA probe. Chemical communications, 2009, 39: 5880-5882.

Unger-Angel, Linor, et al. Protein recognition by bivalent, 'turn-on' fluorescent molecular probes. Chemical Science, 2015, 6.10: 5419-5425.

Utsumi, Ryutaro, et al. Isolation and characterization of the heat-responsive genes in *Escherichia coli*. Bioscience, biotechnology, and biochemistry, 1996, 60.2: 309-315.

Vassiliou, Gerard; Jakobsen, Karen; Parish, Christopher R. Detection of low-affinity adhesion ligands by linking recombinant cell adhesion molecules in uniform orientation to a fluorescently labelled dextran molecule by means of hexahistidine tagging: the case of multimeric CD40. Journal of immunological methods, 1998, 215. 1-2: 9-15.

Verbeke, Frederick, et al. Peptides as quorum sensing molecules: measurement techniques and obtained levels in vitro and in vivo. Frontiers in neuroscience, 2017, 11: 183.

Vinkenborg, Jan L.; Mayer, Günter; Famulok, Michael. Aptamer-Based Affinity Labeling of Proteins. Angewandte Chemie International Edition, 2012, 51.36: 9176-9180.

Wakayama, Sho, et al. Chemical labelling for visualizing native AMPA receptors in live neurons. Nature communications, 2017, 8.1: 1-14.

Wang, Hangxiang, et al. Chemical cell-surface receptor engineering using affinity-guided, multivalent organocatalysts. Journal of the American Chemical Society, 2011, 133.31: 12220-12228.

Weber, Gregorio; Farris, Fay J. Synthesis and spectral properties of a hydrophobic fluorescent probe: 6-propionyl-2-(dimethylamino) naphthalene. Biochemistry, 1979, 18.14: 3075-3078.

Wegner, Seraphine V.; Spatz, Joachim P. Cobalt (III) as a Stable and Inert Mediator Ion between NTA and His6-Tagged Proteins. Angewandte Chemie International Edition, 2013, 52.29: 7593-7596.

Wieneke, Ralph, et al. SLAP: Small Labeling Pair for Single-Molecule Super-Resolution Imaging. Angewandte Chemie International Edition, 2015, 54.35: 10216-10219.

Wu, Peng, et al. Site-specific chemical modification of recombinant proteins produced in mammalian cells by using the genetically encoded aldehyde tag. Proceedings of the National Academy of Sciences, 2009, 106.9: 3000-3005.

Xiong, Xiangling, et al. DNA Aptamer-Mediated Cell Targeting. Angewandte Chemie, 2013, 125.5: 1512-1516.

Xu, Zhaohui; Lee, Sang Yup. Display of Polyhistidine Peptides on the *Escherichia coli* Cell Surface by Using Outer Membrane Protein C as an Anchoring Motif. Applied and Environmental Microbiology, 1999, 65.11: 5142-5147.

Yang, Ya, et al. Green fluorescent probe for imaging His6-tagged proteins inside living cells. ACS sensors, 2019, 4.5: 1190-1196.

Zenmyo, Naoki, et al. Optimized reaction pair of the cyshis tag and Ni (II)-NTA probe for highly selective chemical labeling of membrane proteins. Bulletin of the Chemical Society of Japan, 2019, 92.5: 995-1000.

Zhou, Xiao, et al. Host-guest tethered DNA transducer: ATP fueled release of a protein inhibitor from Cucurbit [7] uril. Journal of the American Chemical Society, 2017, 139.39: 13916-13921.

Zhou, Chao; Yang, Zhongqiang; Liu, Dongsheng. Reversible regulation of protein binding affinity by a DNA machine. Journal of the American Chemical Society, 2012, 134.3: 1416-1418.

Zhu, Hao, et al. Fluorescent probes for sensing and imaging within specific cellular organelles. Accounts of Chemical Research, 2016, 49.10: 2115-2126.

\* cited by examiner

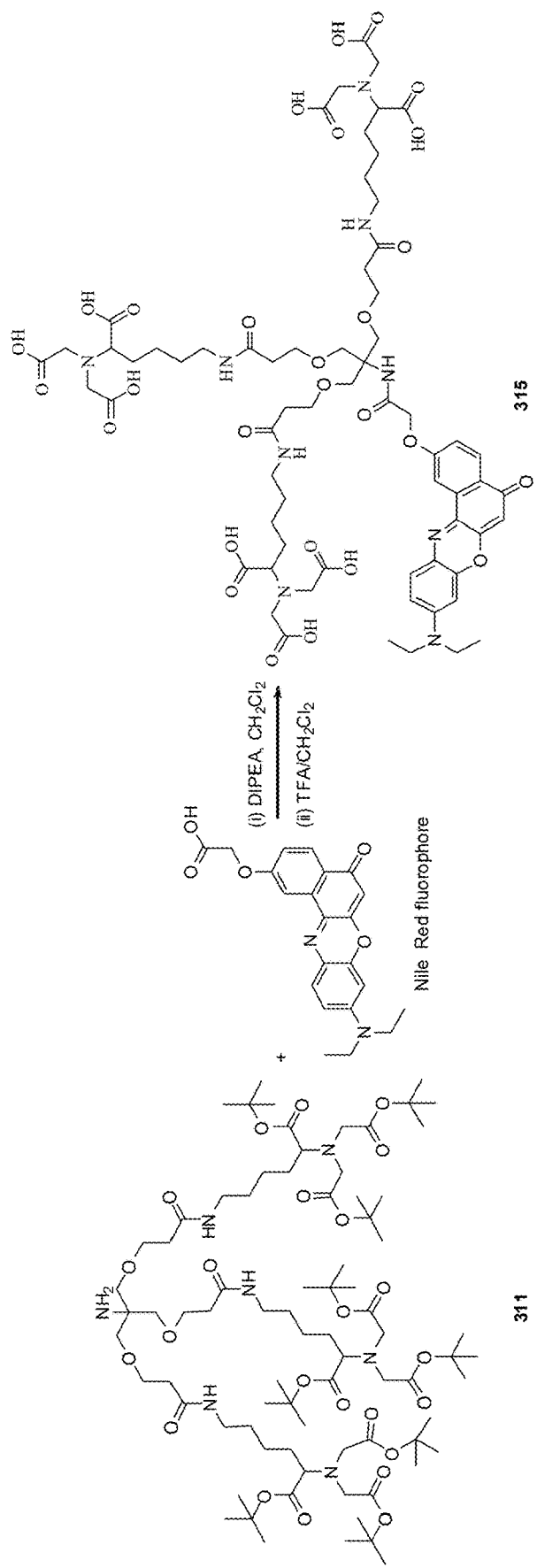
FIGURE 40 - CONTINUE

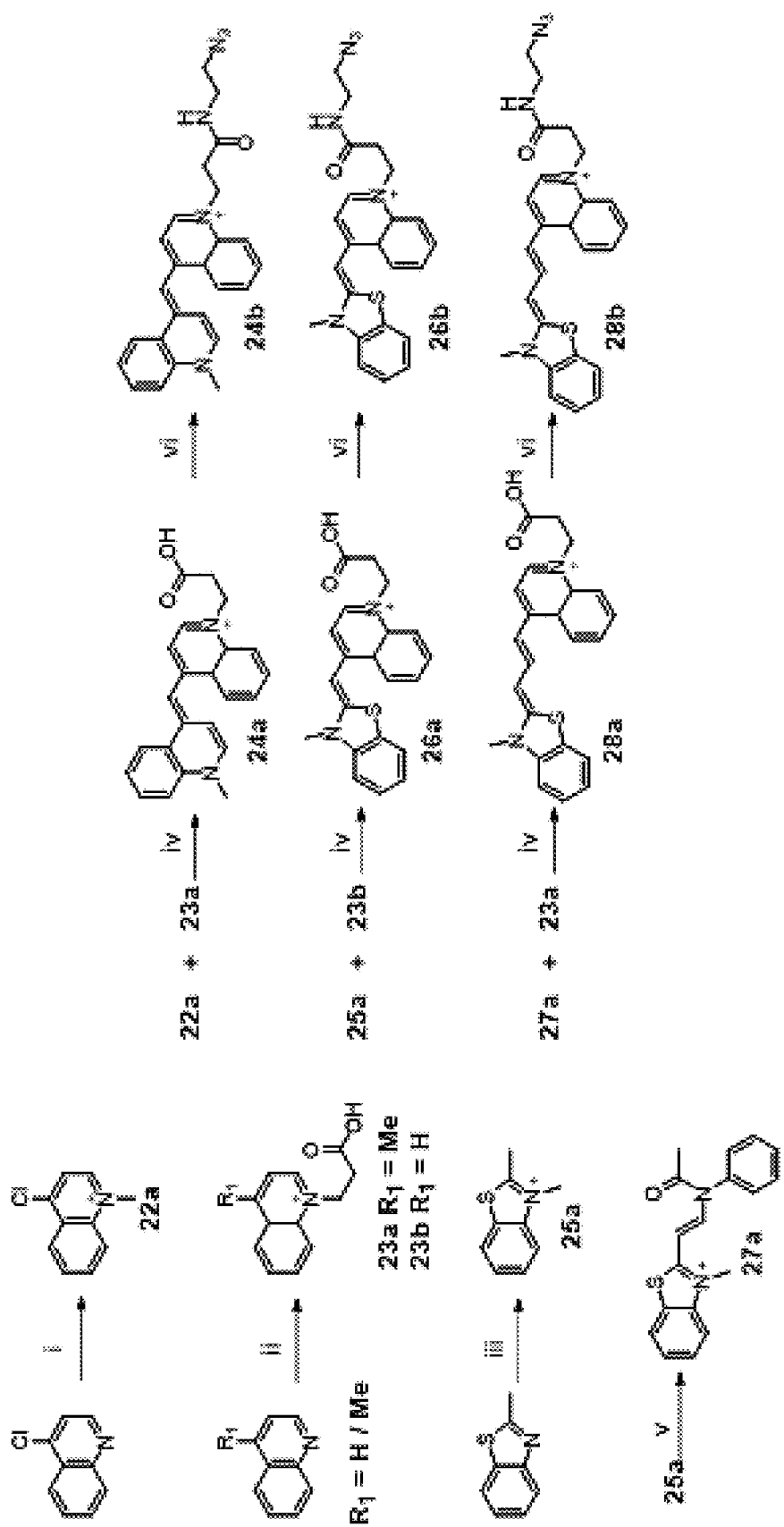
FIGURE 48 (CONT. 1)

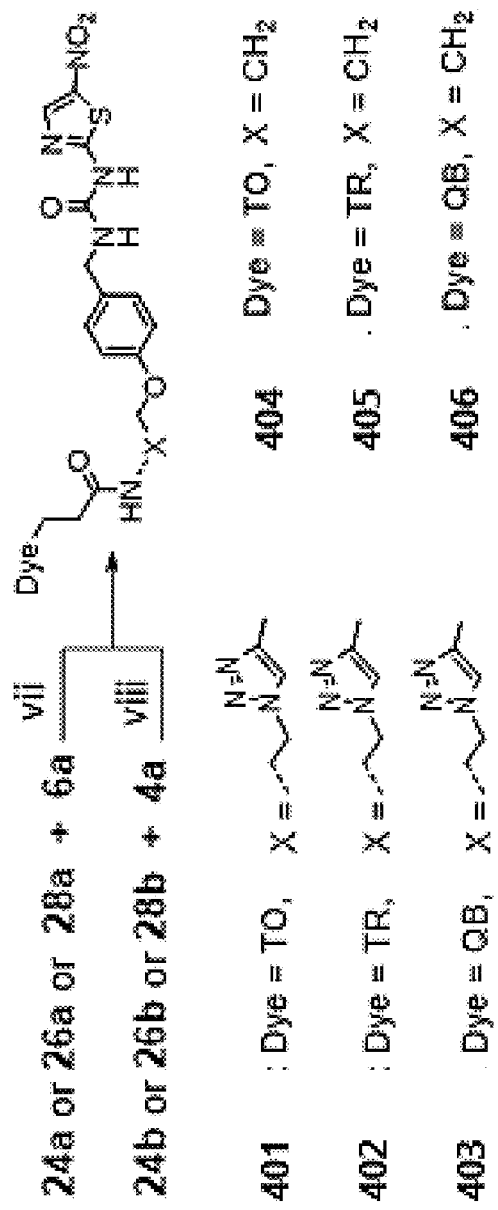
FIGURE 48 (CONT. 2)

QUINOLINE BASED CYANINE DYE TURN-ON FLUORESCENT PROBES AND METHODS OF USE THEREOF

CROSS-REFERENCE TO RELATED APPLICATIONS

This application is a Continuation-in-Part of United-States application Ser. No. 16/783,524, filed Feb. 6, 2020, which is a Continuation-in-Part of United-States application Ser. No. 15/307,011, filed Oct. 27, 2016, which is a national stage application, filled under 35 U.S.C § 371, of International Patent Application No. PCT/IL2015/050441, filed Apr. 28, 2015, which claims priority of U.S. Provisional Application Ser. No. 61/985,555, filed Apr. 29, 2014; and this Application is a Continuation-In-Part of International Application Serial No. PCT/IL2019/050639, filed Jun. 5, 2019; each of the above listed documents is hereby incorporated by reference in its entirety.

SEQUENCE LISTING STATEMENT

The instant application contains a Sequence Listing which has been submitted electronically in ASCII format and is hereby incorporated by reference in its entirety. Said ASCII copy, created on Apr. 23, 2020, is named P-78104-US2-SQL-23APR20_ST25.txt and is 5,553 bytes in size.

FIELD OF THE INVENTION

This invention is directed to a turn-on fluorescent probe, wherein said probe comprises a quinoline based cyanine dye derivative (QBC) and a specific protein binder covalently attached thereto directly or via a linker. This invention is further directed to His-tag binding compounds and uses thereof in the preparation of genetically targeted detectable molecules and sensors which can specifically bind tag-labeled proteins. This invention further describes methods for using these turn-on probes and compounds for detecting and labelling a wide range of proteins in their native environment.

BACKGROUND OF THE INVENTION

Fluorescent molecular probes that can label, detect, or image specific proteins serve as a powerful tool for developing in-vitro proteomic assays, for identifying disease biomarkers, as well as for tracking proteins in complex environments.

Such fluorescent molecular probes have become valuable tools in the analytical biosciences owing to their sensitive detection mode, down to the level of a single molecule, the feasibility of naked eye visualization, their versatility, and their small size, which enable them to penetrate the cell membrane and track the rise and fall of various bio-analytes within living cells. Although fluorescent probes that utilize photo-induced electron transfer (PET), electronic energy transfer (EET) (or fluorescence resonance energy transfer (FRET), and internal charge transfer (ICT) processes have been developed and used to detect various proteins, most of them suffer from a high background signal that complicates their use in complex biochemical mixtures and within cells.

The proposed QBC-based turn-on fluorescent probes constitute a unique class of fluorescent molecular sensors whose activation does not involve FRET, ICT, or PET processes. Instead, their fluorescence emission is turned on upon restriction of their torsional motion.

Asymmetrical cyanine dyes constitute a unique class of fluorescent molecular sensors whose activation does not involve FRET, ICT, or PET processes. Instead, their fluorescence emission is turned on upon restriction of their torsional motion. For example, the emission of Thiazole Orange (TO) is quenched due to excited state twisting of benzothiazole and quinoline rings around the methine bridge, which leads to a non-radiative decay. Binding to DNA or peptide aptamers, or interchelation into DNA duplexes restricts this torsional motion and leads to an enhanced fluorescence signal.

There is a growing interest in developing "genetically targeted fluorescent molecules", namely, small molecule-based fluorescent probes that can bind to short, peptide motifs on the protein of interest and, in doing so, enable the protein's labeling or detection in complex biological environments such as within live cells. Such sensors provide an alternative to using recombinant technology to create a fusion protein comprising the protein of interest with fluorescent proteins (FPs) (e.g., green fluorescent proteins or GFPs) whose large size can interrupt the normal function of many proteins. These genetically targeted probes have already become commercial, for example, the FlAsH-and-ReAsH probes for the selective labeling of tetra-cysteine motifs that are now sold online by Life Technologies.

Genetically encoded fluorescent proteins (FPs) have revolutionized the study of biology by allowing one to track protein expression and localization in living cells at spatial and temporal resolution. This method, however, involves the use of very large protein that can interfere with the normal function of the labeled protein. Over the last few years, it has been demonstrated that this problem can be circumvented by expressing the proteins with a very short peptide sequence to which a small fluorescent molecular sensor, termed "genetically-targeted sensors" can attach. For example, sensors that can bind to an oligohistidine sequence (i.e. His-tag) with high affinity and can be applied for labeling and detecting a wide range of His-tagged proteins in living cells, have been developed.

Surprisingly, despite the remarkable analytical power of fluorescent molecular sensors and their success in detecting various biomolecules and ions in aqueous solutions, the development of 'turn-on' fluorescent molecular switches for proteins, which do not rely on enzymatic reactions, has been relatively scarce.

Ideally, a sensor (or a probe) that detected a protein should act as 'turn-on' fluorescent molecular sensors, which do not generate any background signal in the absence of the bio-analyte, but emit very strongly in the presence of the protein target. In practice, however, developing fluorescent molecular switches that can recognize their target proteins with high affinity, selectivity, and sensitivity is challenging. Obtaining highly selective sensors is complicated by the fact that many protein groups, which can be targeted by small-molecule-based sensors, possess well-defined recognition sites that are conserved among structurally similar isoforms of the same family.

High sensitivity is also difficult to achieve because common fluorescence signaling mechanisms, such as photo-induced electron transfer (PET), charge transfer (CT), or fluorescence resonance energy transfer (FRET) often lead to a background emission signal by the unbound sensors. Consequently, an excess of protein is generally required to obtain a sufficient fluorescence response. Finally, a limitation of many molecular sensors, when compared with the corresponding antibodies or aptamers, is that they bind their target with lower affinities, which prevents them from detecting proteins at low concentrations.

This invention shows that the conversion of quinoline based cyanine dyes (QBCs)(e.g., Thiazole Orange, Thiazole Red and Quinoline Blue) into protein binders, by covalently linking them to specific protein binders directly or through linkers, could lead to the realization of a novel class of fluorescent molecular sensors that detect proteins, with high affinity, selectivity, and excellent signal-to-noise (S/N) ratio. The feasibility of the approach is demonstrated with monomolecular sensors that light-up in the presence of various proteins (e.g. GSK-3, LDHA and various His-tagged proteins) at low concentrations and with minimal background signal.

The protein sensors presented herein are expected to contribute to the development of 'turn-on' fluorescent molecular switches for proteins, which do not rely on enzymatic reactions, by affording a novel methodology for selective and sensitive detection of a wide range of different proteins.

The histidine tag is currently the most widely used tag in protein purification. It is typically composed of six or ten histidine residues fused at the amino or carboxyl terminus of a protein. Recombinant proteins containing a histidine tag are commonly purified on a matrix with nickel(II)-nitrilotriacetate (Ni-NTA) complexes that are prepared from nickel (II)-activation of nitrilotriacetic acid (NTA). In addition to protein purification, this technology has been used in label-free surface plasmon resonance (SPR) biosensors for biomolecular interaction analysis that involves histidine-tagged proteins.

Genetic engineering has been used for many years to functionalize the bacterial membrane with heterologous proteins, which can be used for many applications such as biosensing, biofuel production, and cancer therapeutics. However, this method is limited, since it can be utilized only for genetically encoded molecules. In order to overcome this limitation and incorporate non-genetically encoded small molecules such as fluorescent probes, drugs, and affinity tags, methods for chemical surface display were developed. This research focuses on using "genetically targeted" protein binders for developing a novel method to functionalize the bacterial membrane and utilizing this method for super-resolution imaging and for programing bacterial behavior and response.

SUMMARY OF THE INVENTION

In some embodiments, this invention is directed to a turn-on fluorescent probe, wherein said probe comprises a quinoline based cyanine dye (QBC) selected from Thiazole red (TR) or Quinoline Blue (QB) or derivative thereof, and a specific protein binder covalently attached thereto directly or via a linker. In some embodiments, the linker is a substituted or unsubstituted linear or branched alkyl chain of 1-12 carbon atoms, substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms, substituted or unsubstituted linear or branched alkyl carbamate chain of 1-50 carbon atoms, substituted or unsubstituted linear or branched alkyl triazole chain of 1-50 carbon atoms or any combination thereof. In some embodiments, the linker is a combination of unsubstituted linear or branched alkyl ether chain and alkyl amide chain; or a combination of substituted or unsubstituted linear or branched alkyl chain of 1-8 carbon atoms, substituted or unsubstituted linear or branched alkyl ether chain of 1-10 carbon atoms, triazole, and amide; or comprises at least one selected from: substituted or unsubstituted linear or branched alkyl chain of 1-8 carbon atoms, substituted or unsubstituted linear or branched alkyl ether chain of 1-10 carbon atoms, amide, and triazole. In some embodiments, the specific protein binder comprises an LDHA inhibitor, a GSK-3 inhibitor, marimastat, ethacrynic acid, bisethacrynic acid, a metal complex of nitrilotriacetic acid (NTA) (His-tag binder), a metal complex of bis NTA (His-tag binder), a metal complex of tris-NTA (His-tag binder), Ni-nitrilotriacetic acid (Ni-NTA), bis-Ni-NTA, tris-Ni-NTA, PDGF-BB, heparin, FGF aptamer, biotin, tacrine, estrogen, DNA aptamer, RNA aptamer, peptide aldehyde, estrogen, suberoylanilidehydroxamic acid (SAHA), autoinducer, siderophore, folate, anisamide, antibody, antigen or a peptide binder. In some embodiments, the protein is a lactate dehydrogenase A (LDHA), glycogen synthase kinase-3 (GSK-3), matrix metalloproteases (MMPs) protein and its isoforms, glutathione S-Transferase (GSTs) protein and its isoforms, platelet derived growth factor, a Histidine-tagged protein, estrogen receptor, fibroblast growth factor (FGF), caspases, PSA, fibronecin, lysozyme, 0-amyloid, avidin, streptavidin, Acetylcholinesterase, histone deacetylases (HDACs), quorum sensing receptor, siderophore receptors, growth factor, membrane receptors, nuclear receptors, growth factor receptors, antibody, kinase, phosphatase or any protein to which a selective binder exists In some embodiments, this invention is directed to a turn-on fluorescent probe, wherein said probe comprises a Thiazole Orange (TO) or derivative thereof, and a specific protein binder covalently attached thereto directly or via a linker, wherein the specific protein binder is glycogen synthase kinase-3 (GSK-3) inhibitor or lactate dehydrogenase A (LDHA) inhibitor.

In some embodiments, this invention is directed to a turn-on fluorescent probe, wherein said probe comprises a Thiazole Orange (TO) or derivative thereof, and a specific protein binder covalently attached thereto directly or via a linker, wherein the probe is represented by the structure of any one of compounds 401, 404, or 408 as described hereinbelow.

In some embodiments, this invention is directed to a compound, represented by the structure of Formula XXX:

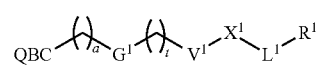

XXX wherein
a and t are each independently an integer between 0 and 15;
QBC is a quinoline-based cyanine dye, or a quinoline-based cyanine dye derivative selected from thiazole red (TR) and quinoline blue (QB);
$G^1$ is a bond, a carbamate, an amide [—C(O)NH or —NHC(O)], an amine, $C_1$-$C_{12}$ alkyl amine, ester, ketone, O, N, S, carbonate, —O-alkyl-NH—, carbamoyl phosphate or phosphate;
$V^1$ is a bond, a triazole, an amide [—C(O)NH or —NHC(O)], —C(O)O—, —OC(O)—, O, NH, N-alkyl, S, —PO$_4$H—, C$_1$-C$_{12}$ alkyl ether, —NH-alkyl-NH—, —O-alkyl-NH—, —NH-alkyl-O— wherein said alkyl is optionally substituted or wherein said alkyl is optionally interrupted by an heteroatom consisting of O, N, P, S or combination thereof;

X$^1$ is a bond or C$_1$-C$_{12}$alkyl, —C(O)NH—, —NHC(O), —C(O)O—, —OC(O)—, O, NH, N-alkyl, S, —PO$_4$H—, C$_1$-C$_{12}$ alkyl ether, C$_1$-C$_{12}$-alkyl-NH-alkyl-NHC(O)-alkyl, -alkyl-C(O)NH-alkyl, —NH—alkyl-NH—, —O-alkyl-NH—, —NH-alkyl-O— wherein said alkyl is optionally substituted or wherein said alkyl is optionally interrupted by an heteroatom consisting of O, N, P, S or combination thereof;

L$^1$ is a bond or C$_1$-C$_{12}$ alkyl, C(O), an amide [—C(O)NH or —NHC(O)], —C(O)O—, —OC(O)—O, NH, C$_1$-C$_{12}$N-alkyl, S, —PO$_4$H, —PO$_4$H—{[(CH$_2$)O]$_x$}$_z$—PO$_3$H—, wherein y is between 1-5, x is between 1-10 and z is between 1-10, —PO$_4$H—PEG, C$_1$-C$_{12}$ alkyl ether, C$_1$-C$_{12}$ alkylamine, C$_1$-C$_{12}$ alkyl-NH, —C(O)NH-alkyl, —NHC(O)-alkyl, NH-alkyl-NH—, —O-alkyl-NH—, —NH-alkyl-O—, wherein said alkyl is optionally substituted or wherein said alkyl is optionally interrupted by an heteroatom consisting of O, N, P, S or combination thereof, and R$^1$ is a specific protein binder;
or a suitable salt thereof.

In some embodiments, the salt is a tosylate, iodide, chloride, bromide, fluoride, TFA or a PF$_6$ salt.

In some embodiments, the compound is represented by the structure of Formula XXXI:

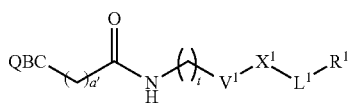

XXXI wherein a' and t' are each independently an integer between 0-6.

In some embodiments, the compound is represented by the structure of Formula XXXII:

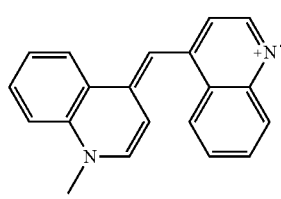

XXXII

In some embodiments, the compound is represented by the structure of Formula XXXIII:

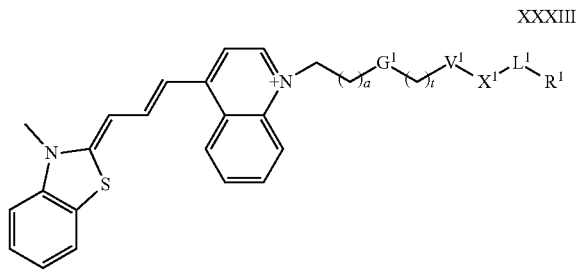

XXXIII

In some embodiments, the compound is represented by the structure of Formula XXXV:

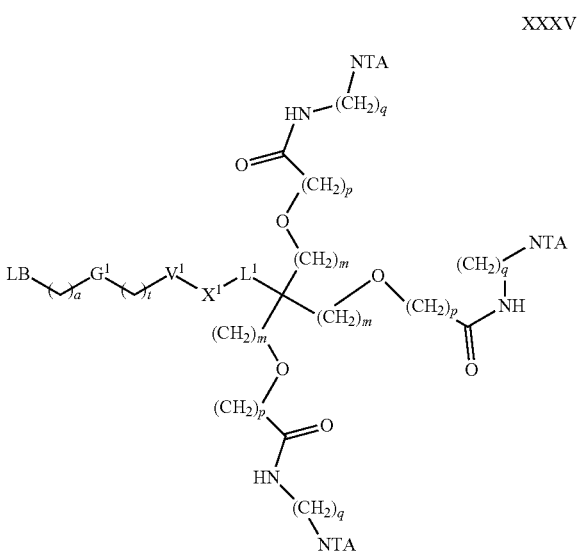

XXXV wherein
m, p and q are each independently an integer between 1 and 8; (e.g m:1, p:2, q:4)
LB is a quinoline-based cyanine dye, or a quinoline-based cyanine dye derivative (QBC); and
NTA is nitrilotriacetic acid, nitrilotriacetic acid complexed with at least one metal ion, or a protected derivative thereof.

In some embodiments, the compound is represented by the structure of Formula XXXVI:

XXXVI

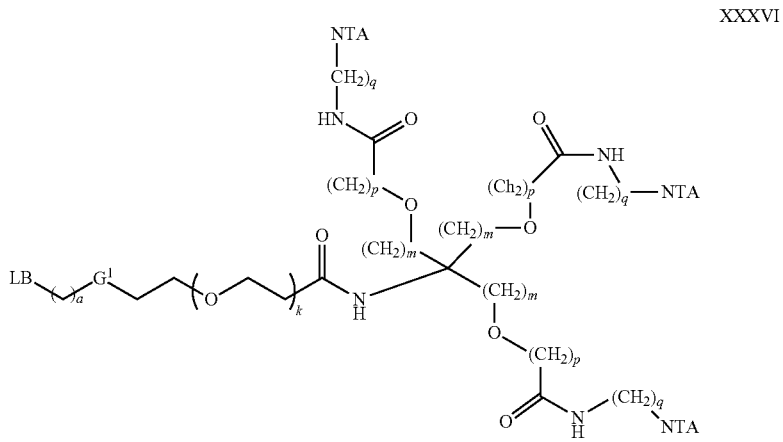

wherein
k is an integer between 0 and 8.

In some embodiments, the compound is represented by the structure of Formula XXXVII:

XXXVII

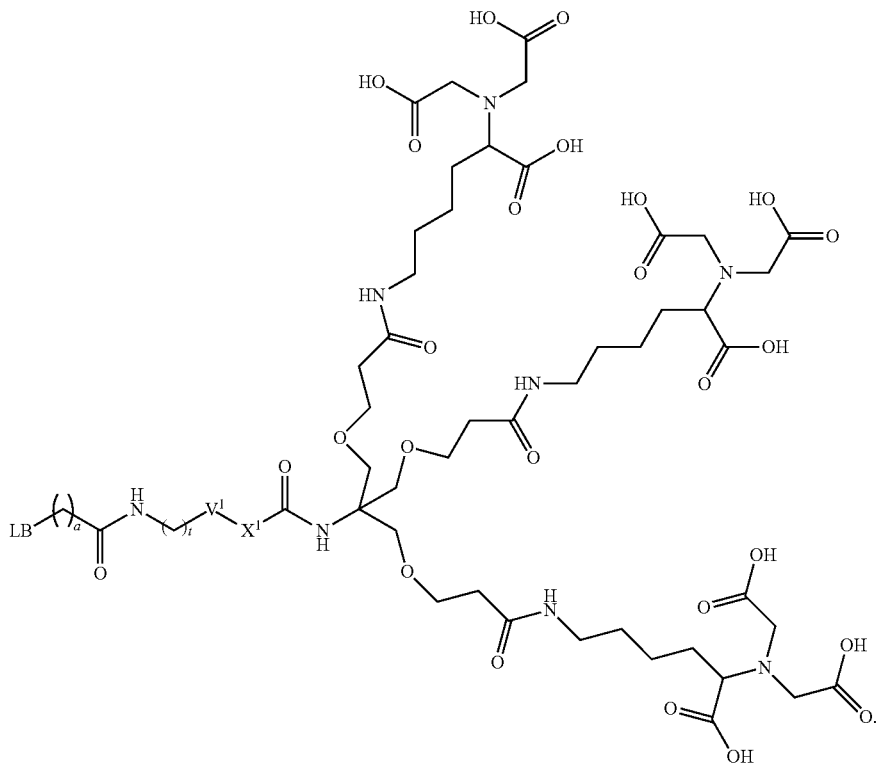

In some embodiments, the compound is represented by the structure of any one of compounds 402, 403, 405, 406, 407, 409, and 410 as described hereinbelow.

In some embodiments, this invention is directed to a method of detecting a protein of interest (POI) in a solution, said method comprises:

a. measuring an optical signal of the probe according to this invention;

b. placing said probe in said solution;

c. re-measuring the optical signal of said probe in said solution, wherein an enhancement in the optical signal of said probe indicates on the presence of said POI in said solution.

In some embodiments, the optical signal is fluorescence emission. In some embodiments, the POI is a native protein or a recombinant protein (engineered protein). In some embodiments, the recombinant protein is a Histidine-tagged protein, and said native protein is a lactate dehydrogenase A (LDHA), glycogen synthase kinase-3 (GSK-3), matrix metalloproteases (MMPs) protein and its isoforms, glutathione S-Transferase (GSTs) protein and its isoforms, platelet derived growth factor, estrogen receptor, fibroblast growth factor (FGF), caspases, PSA, fibronecin, lysozyme, β-amyloid, avidin, streptavidin, Acetylcholinesterase, histone deacetylases (HDACs), quorum sensing receptor, siderophore receptors, growth factor, membrane receptors, nuclear receptors, growth factor receptors, antibody, kinase, phosphatase or any protein to which a selective binder exists. In some embodiments, the solution is a biological medium. In some embodiments, the solution is a buffer solution. In some embodiments, the fluorescence emission indicates on the presence of said POI in a biological medium. In some embodiments, the biological medium is blood, tissue, serum, or urine. In some embodiments, the GSK-3 is a biomarker for diabetes, cancer and/or neurodegenerative disorders. In some embodiments, the biological medium comprises living cells. In some embodiments, the method is conducted without any subsequent washing steps. In some embodiments, the method is for use in cell based high throughput screening (HTS) assays. In some embodiments, the cell is a living cell. In some embodiments, the method is for use in screening for potential modulators (i.e. agonists or antagonists) for said POI in vitro or in living cells. In some embodiments, the modulators are potential drugs.

In some embodiments, this invention is directed to a method for identifying a disease biomarker in a subject, said method comprises:
(a) collecting a biological sample from a subject;
(b) incubating said biological sample with a compound according to this invention;
(c) measuring the fluorescence resulting from binding of said sensor to a protein of interest (POI), which is a biomarker for a disease, in said sample;
wherein an enhancement in the emission intensity from said sample is an indicator of the presence of said POI in said sample.

In some embodiments, the disease is diabetes, cancer and/or neurodegenerative disorder.

In some embodiments, this invention is directed to a method of identifying a compound that binds a protein of interest (POI), said method comprises:
a. incubating a compound according to this invention with said POI in solution;
b. measuring the fluorescence intensity of said solution;
c. adding a test compound to said solution;
d. re-measuring the fluorescence intensity of said solution; and
e. determining binding of said test compound to said POI based on a change in fluorescence intensity, wherein decreased fluorescent intensity indicates binding of said test compound to said POI;
thereby identifying a compound that binds said POI.

In some embodiments, the POI is a matrix metalloproteases (MMPs) protein and its isoforms, glutathione S-Transferase (GSTs) protein and its isoforms, platelet derived growth factor, Histidine-tagged proteins, estrogen receptor, fibroblast growth factor (FGF), caspases, PSA, fibronecin, lysozyme, β-amyloid, avidin, streptavidin, Acetylcholinesterase, histone deacetylases (HDACs), glycogen synthase kinase-3 (GSK-3), lactate dehydrogenase A (LDHA), quorum sensing receptor, siderophore receptors, growth factor, membrane receptors, nuclear receptors, growth factor receptors, antibody, kinase, phosphatase or any protein to which a selective binder exists.

In some embodiments, this invention relates to a method for imaging a protein of interest (POI) within a cell, said method comprises:
a. incubating cells comprising said POI with a probe according to this invention;
b. visualizing the fluorescence emission of said cells;
wherein an enhancement in the fluorescence emission is indicative of binding of said sensor to a protein of interest (POI) in said cells.

In some embodiments, this invention relates to a compound represented by the structure of Formula XXXV:

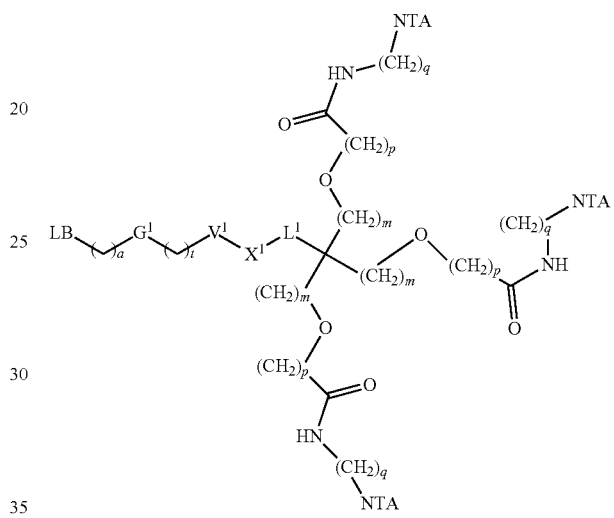

XXXV wherein
a and t are each independently an integer between 0 and 15 (e.g., a:1, 2; t:2);

$G^1$ is a bond, carbamate, an amide [—C(O)NH or —NHC(O)], amine, $C_1$-$C_{12}$ alkyl amine, ester, ketone, O, N, S, carbonate, —O-alkyl-NH—, carbamoyl phosphate or phosphate;

$V^1$, is a bond, a triazole, an amide [—C(O)NH or —NHC(O)], —C(O)O—, —OC(O)—, O, NH, N-alkyl, S, —PO$_4$H—, alkyl ether (e.g., —[O—(CH$_2$)$_2$]$_k$, k=3), —NH-alkyl-NH—, —O-alkyl-NH—, —NH— alkyl-O— wherein said alkyl is optionally substituted and wherein said alkyl is optionally interrupted by an heteroatom consisting of O, N, P, S or combination thereof;

$X^1$, is a bond or $C_1$-$C_{12}$ alkyl, an amide [—C(O)NH or —NHC(O)], —C(O)O—, —OC(O)—, O, NH, N-alkyl, S, —PO$_4$H—, $C_1$-$C_{12}$ alkyl ether, $C_1$-$C_{12}$-alkyl-NH, -alkyl-NHC(O)-alkyl, -alkyl-C(O)NH-alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;

$L^1$, is a bond or $C_1$-$C_{12}$ alkyl, C(O), an amide [—C(O)NH or —NHC(O)], —C(O)O—, —OC(O)—, O, NH, $C_1$-$C_{12}$—N-alkyl, S, —PO$_4$H, —PO$_4$H—PO$_4$H— {[(CH$_2$)$_y$O]$_x$}$_z$—PO$_3$H—, wherein y is between 1-5, x is between 1-10 and z is between 1-10, —PO$_4$H—PEG, $C_1$-$C_{12}$ alkyl ether, $C_1$-$C_{12}$ alkylamine, $C_1$-$C_{12}$ alkyl-NH, —C(O)NH-alkyl, —NHC(O)-alkyl, NH-alkyl-NH—, —O-alkyl-NH—, —NH-alkyl-O—, wherein said alkyl is optionally substituted and wherein said alkyl is optionally interrupted by an heteroatom consisting of O, N, P, S or combination thereof;

m, p and q are each independently an integer between 1 and 8 (e.g., m:1; p:2; q:4);

NTA is nitrilotriacetic acid, nitrilotriacetic acid complexed with at least one metal ion, or a protected derivative thereof; and LB is a labeling moiety;

or a suitable salt thereof.

In some embodiments, the compound represented by the structure of Formula XXXVI:

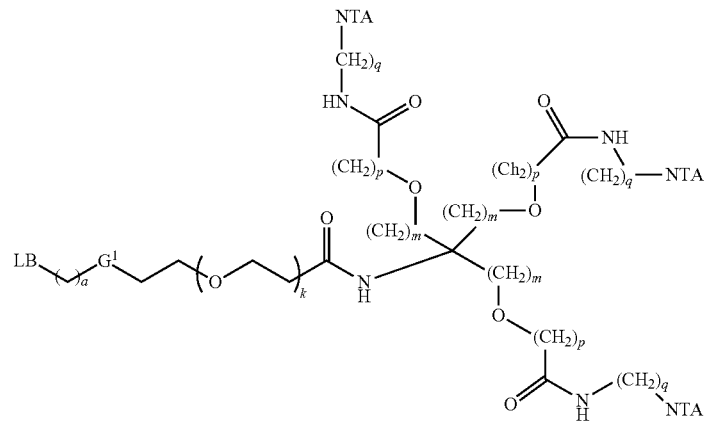

wherein
k is an integer between 0 and 8.

In some embodiments, the compound is represented by the structure of Formula XXXVII:

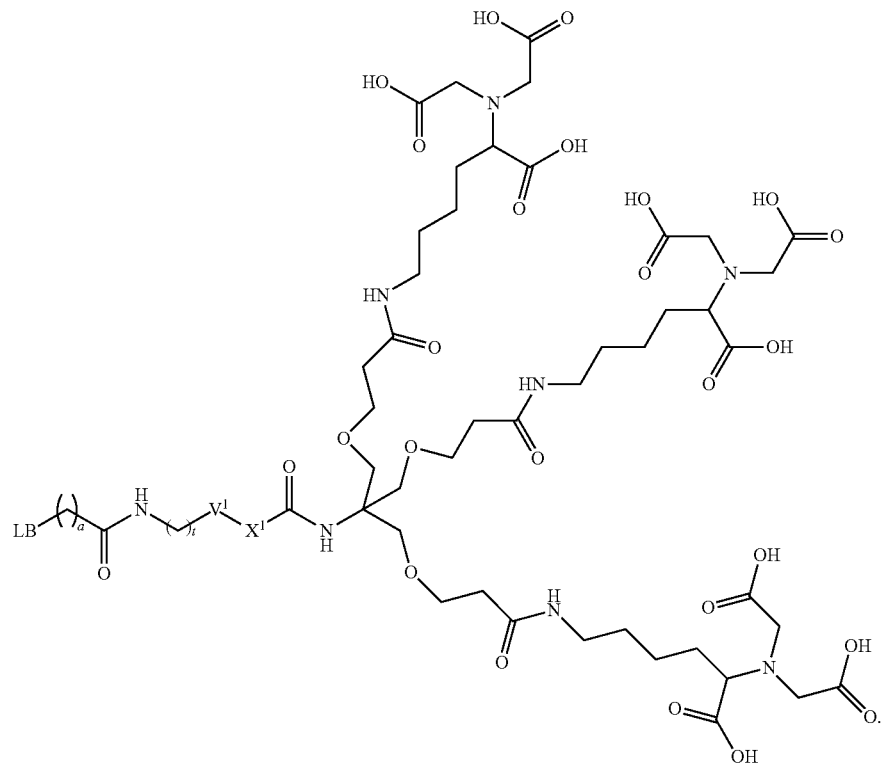

In some embodiments, the compound is represented by the structure of compounds 408-410 as described hereinbelow.

In some embodiments, this invention relates to a fluorescent probe that can selectively label a His-tagged polypeptide, comprising a compound according to this invention complexed to at least one metal ion.

In some embodiments, the compound is complexed to three Ni(II) ions, wherein the labeling moiety is a fluorescent dye, or combination thereof. In some embodiments, the fluorescent dye is selected from a group comprising dansyl, fluorescein (6-FAM), FAM, cyanine dyes (e.g. Cy3, Cy5, SCy3, SCy5), sulfoindocyanine, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or derivative thereof. In some embodiments, the probe specifically binds to an oligohistidine sequence (His-tag) of a His-tagged polypeptide to generate a fluorescent signal. In some embodiments, the His-tag sequence consists of at least 6 histidines. In some embodiments, the fluorescent probe does not perturb living cells function. In some embodiments, the fluorescent probe is capable of traversing a biological membrane.

In some embodiments, this invention relates to a method for imaging a His-tagged polypeptide of interest within a cell, said method comprises:
a. expressing said His-tagged polypeptide in a recombinant cell;
b. incubating said recombinant cell with a His-tag binding fluorescent probe according to this invention; and
c. visualizing the fluorescence emission of said fluorescent probe.

In some embodiments, this invention relates to a method for measuring the expression level of a His-tagged polypeptide of interest in a cell, said method comprises the steps of:
a. expressing a His-tagged polypeptide in a cell;
b. incubating said cell with a His-tag binding fluorescent probe according to this invention; and
c. measuring the fluorescence of said cell;
wherein detection of a fluorescent signal is dependent on the formation of a His-tagged polypeptide:fluorescent probe complex.

In some embodiments, the cell is a living cell. In some embodiments, the fluorescent probe does not perturb living cells function.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 32A shows an embodiment to decorate E. coli with artificial receptors appended with a specific functionality (X). A first molecule X-ODN-1 binds a hexa-histidine tag (His-tag) fused to recombinant OmpC. Recombinant OmpC is inserted into the cell membrane. Reversibility of this process is achieved by subjecting the bacteria to EDTA. A further way to introduce an unnatural recognition motif (Y) to the bacterial surface is adding to the bacteria-bound ODN-1 a complementary strand modified with the desired functionality (Y-ODN-2). Y-ODN-2 can be selectively removed by adding a complementary strand, ODN-3. FIG. 32B shows the structure of X-ODN-1.

FIG. 33A shows fluorescence images of: (i) E. coli expressing His-OmpC incubated with 500 nM of Compound 100 and Ni (II), (ii) Native bacteria (that lack His-tag) incubated with 500 nM of Compound 100 and Ni (II), (iii) E. coli expressing His-OmpC incubated with 500 nM of Compound 100 in the absence of Ni (II), and (iv) E. coli expressing His-OmpC incubated with 500 nM of Cy5-ODN (that lacks the NTA group) and Ni (II). FIG. 33B shows flow cytometry analysis of His-tagged bacteria (right peak) and native bacteria (left peak) incubated with Compound 101. FIG. 33C shows fluorescence images of E. coli expressing His-OmpC decorated with Compound 100 in the presence of increasing concentrations of EDTA (0, 5, and 10 mM) (left), and following subsequent addition of Compound 100 in the absence of Ni (II) (right). FIG. 33D shows the growth curve of E. coli expressing His-OmpC (black) and of the same bacteria decorated with Compound 101 (gray). FIG. 33E shows bright field (top) and fluorescence images (bottom) of bacteria decorated Compound 101 monitored at 0, 12, and 24 hours.

FIG. 34A shows a schematic illustration of the methods used in the experiment. His-tagged bacteria were sequentially modified by attaching them with ectopic molecules. First, cells were attached with-an oligonulcotide comprising TAMRA (TAMRA-ODN-2). Then, this strand was removed by incubating the cells with ODN-3. Then, cells were attached with a compound comprising Cy5 (Cy5-ODN-2). Then Cy5-ODN-2 was detached by incubating the cells with ODN-3. Then, cells were attached with a compound comprising FAM. Then FAM-ODN-2 was detached by incubating the cells with ODN-3. FIG. 34B shows microscopic images of these states by simultaneously observing the emissions of TAMRA, Cy5, and FAM using 590 nm, 700/775 nm, and 510/550 nm emission filters, respectively.

FIG. 35A shows a schematic illustration of the experiment. (i) Different sub-populations of His-tagged cells were incubated with three types of ODN-1: Compound 102, Compound 103, and Compound 104. (ii) cells were incubated with three types of ODN-2: Compound 202, Compound 203, and Compound 204, complementary to Compound 102, Compound 103, and Compound 104, respectively. Compound 202, Compound 203, and Compound 204 were appended with FAM, TAMRA, and Cy5, respectively. FIG. 35B shows a fluorescence overlay image of the labeled mixed population. Bacteria were imaged using 488 nm, 561 nm, and 647 nm excitation lasers and 488/50, 610/60, and 685/50 emission filters. FIG. 35C shows percentages of each sub-population counted and averaged from six different frames. FIG. 35D shows a flow cytometry analysis of the mixed population.

FIG. 36A shows a schematic illustration of an experiment in which modified His-tagged bacteria were treated with Alexa 647-modified streptavidin (Alexa-SA). Left: Bacteria were modified with a duplex generated from ODN-1 and Compound 205. Right: Bacteria were modified with a duplex lacking biotin. FIG. 36B shows Alexa-SA fluorescence in the cells incubated with Alexa 647-modified streptavidin. FIG. 36C shows images recorded following the incubation of the bacteria bound to Alexa-SA with ODN-3. FIG. 36D shows a schematic illustration of an experiment in which decorated bacteria were incubated with KB-cells. Left: Bacteria decorated with a duplex consisting of ODN-1 and TAMRA-labeled Compound 206. Right: Bacteria decorated with a duplex that lacks the folate group. FIG. 36E shows TAMRA-labeling of KB cells incubated with bacteria decorated with folate. FIG. 36F shows fluorescent images obtained after treating the bacteria that are bound to KB cells with ODN-3. FIG. 36G shows that incubating a KB-cell with a duplex consisting of ODN-1 and TAMRA-folate-ODN-2 (Compound 206), in the absence of bacteria, did not lead to fluorescent KB-cell labeling.

FIG. 37A shows microscopic images of: (i) bear gold substrate after incubation with unmodified bacteria, (ii) passivated gold substrate after incubation with unmodified bacteria, and (iii) passivated gold substrate following incubation with bacteria modified with a thiol-modified duplex (ODN-1:Compound 207). FIG. 37B shows the average bacteria count on passivated gold surfaces, which corresponds to an image area of ~0.0165 mm².

FIG. 38A shows whole bacteria. FIG. 38B shows a transverse cut viewed from the plane of the cell axis.

FIG. 53A depicts the fluorescence images of MDA-MB-231 cells incubated with probes 401, 402 and 403. FIG. 53B depicts the fluorescence emission measured from cells loaded with probe 402 before (black bar) and after the addition of increasing concentrations of a GSK-3 inhibitor (AR-A014418).

Figure 1:
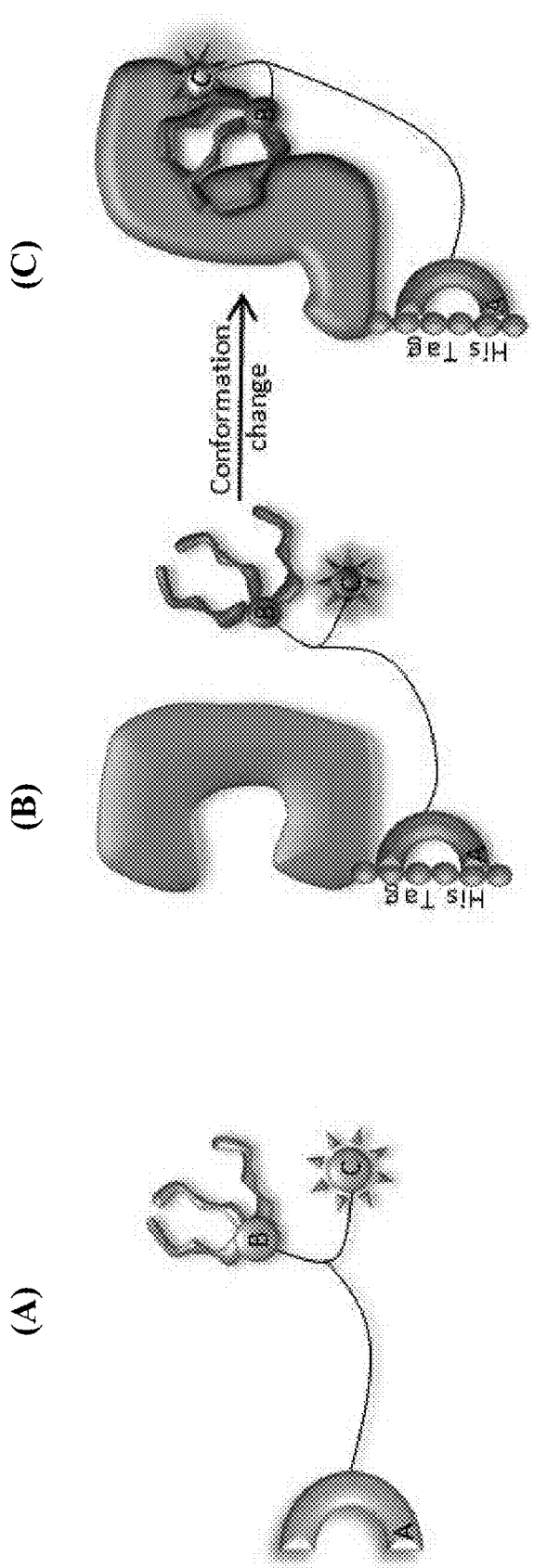
FIG. 1 depicts the design principles of sensors for detecting 3D changes on a protein surface according to this invention. (a): The sensor contains three components: A: A genetically targeted molecule. B: A non-selective protein surface binder. C: A solvatochromic fluorophore. (b) and (c): Preferential binding of the surface receptor (B) to the protein in one of its conformational states (c) induces a change in the fluorescence signal.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Turn-on Fluorescent Molecular Probes Comprising Quinoline Based Cyanine Dyes

This invention is directed to a turn-on fluorescent probe that can identify a specific protein with high affinity, selectivity, and a high signal-to-noise (S/N) ratio, wherein said turn-on fluorescent probe comprises a quinoline-based cyanine dye or derivative thereof and one selective protein binder attached thereto directly or via a linker. In some embodiments, the turn-on fluorescent probes provided herein, are lighting up upon binding to their protein targets.

This invention further relates to the conversion of quinoline-based cyanine dyes such as: Thiazole orange (TO), Quinoline blue (QB), and Thiazole red (TR), into turn-on fluorescent probes (or sensors) for protein detection. Specifically, attaching these dyes to a specific protein binder affords a new class of fluorescent molecular sensors/probes that fluoresces upon binding to their protein targets. This enables their detection with high affinity, selectivity, and a high signal-to-noise (S/N) ratio.

Accordingly, in some embodiments, this invention is directed to a turn on fluorescent probe, wherein said probe comprises a quinoline based cyanine dye (QBC) or derivative thereof, and a specific protein binder covalently attached thereto directly or via a linker. In some embodiments, the QBC is covalently attached to the specific protein binder directly. In some embodiments, the QBC is covalently attached to the specific protein binder via a linker. In some embodiments, the QBC is covalently attached to the specific protein binder via an amide bond, a carbamate, an ester bond, a phosphate bond, an ether bond, a thioether bond and the like; each represents a separate embodiment according to this invention. In some embodiments, the QBC is covalently attached to the linker (which binds the QBC and the specific protein binder) via an amide bond, a carbamate, an ester bond, a phosphate bond, an ether bond, a thioether bond and the like; each represents a separate embodiment according to this invention. In some embodiments, the QBC is thiazole orange, thiazole red or quinoline blue; each represents a separate embodiment according to this invention. In some embodiments, the linker covalently attaches the specific protein binder and the quinoline-based cyanine dye. In some embodiments, the probe is represented by the structure of any one of compounds 401-410 described hereinbelow. In some embodiments, the probe is represented by the structure of any one of formulas XXXI-XXXVII described hereinbelow.

A "specific protein binder" is defined herein as any compound or derivative thereof that can binds particular protein or protein groups with high affinity and specificity/selectivity, wherein the term "derivative" includes but not limited to alkyl derivatives, amide derivatives, carboxy derivatives, ether derivatives, ester derivatives, carbamate derivatives, phosphate derivative and the like. In some embodiments, the specific protein binder is an antagonist (protein inhibitor). In some embodiments, the specific protein binder is an agonist (protein activator). In some embodiments, the specific protein binder is a protein modulator (partial agonist/antagonist). In some embodiments, the specific binder is a synthetic inhibitor, a natural ligand or an aptamer that is selective toward a specific protein, protein group, or protein isoform. In some embodiments, the specific protein binder is an inhibitor that binds to an enzyme active site. In some embodiments, the specific binder is a synthetic inhibitor, a natural ligand or an aptamer that is selective toward a specific protein group, but also broad spectrum which binds particular protein groups with high affinity and selectivity. In some embodiments, the specific protein binder of this invention is any selective/specific protein binder known in the art. In some embodiments, the specific binder is a targeted protein receptor comprising a protein tag binder, wherein "protein tags" include, but not limited to: a His-tag, FLAG tag, HA tag, C-myc tag, AviTag, Calmodulin-tag, polyglutamate tag, E-tag, Myc-tag, S-tag, SBP-tag, Softag, Strep-tag, TC tag, V5 tag, VSV-tag, Xpress tag, etc. In some embodiments, the specific protein binder of this invention comprises any selective/specific protein binder known in the art. In some embodiments, the specific protein binder comprises an LDHA inhibitor, a GSK-3 inhibitor (e.g., AR-A014418), marimastat, ethacrynic acid, bisethacrynic acid, a metal complex of nitrilotriacetic acid (NTA) (His-tag binder), a metal complex of bis NTA (His-tag binder), a metal complex of tris-NTA (His-tag binder), Ni-nitrilotriacetic acid (Ni-NTA), bis-Ni-NTA, tris-Ni-NTA, PDGF-BB, heparin, FGF aptamer, biotin, tacrine, estrogen, DNA aptamer, RNA aptamer, peptide aldehyde, estrogen, suberoylanilidehydroxamic acid (SAHA), autoinducer, siderophore, folate, anisamide, antibody, antigen or a peptide binder. In some embodiments, the metal complex of NTA, metal complex of bis-NTA, and/or metal complex of tris NTA is a nickel or cobalt complex. In some embodiments, a specific binder is any molecule that can target different type of fusion proteins that contain certain protein tags such as: a polyhistidine tag, (e.g., 6×His-tag, 10×His-tag), tetra cysteine peptide (CCPGCC, TC tag), etc. In some embodiments, the specific protein binder comprises FlAsH or ReAsH (TC tag binder). A "protein tag" refers herein to a peptide sequence genetically grafted onto a recombinant protein. Protein tags include but not limited to: a His-tag, FLAG tag, HA tag, C-myc tag, AviTag, Calmodulin-tag, polyglutamate tag, E-tag, Myc-tag, S-tag, SBP-tag, Softag, Strep-tag, TC tag, V5 tag, VSV-tag, Xpress tag, etc. A "tagged-protein" refers to a recombinant protein onto which the specified peptide motif (i.e., protein tag) is grafted. In some embodiments, the specific binder comprises a "Tag-binding region". In some embodiments, the specific binder is a targeted protein receptor comprising a protein tag binder.

In some embodiments, the specific protein binder comprises a His-tag binder. A "polyhistidine tag" (His-tag) commonly known as "His-tag" is an amino acid motif in proteins that typically consists of at least six histidine residues, often at the N- or C-terminus of the protein. It is also known as hexa histidine-tag, 6×His-tag, His6 tag, by the US trademarked name HIS TAG, and most commonly as His-Tag. In some embodiments, a His-tag according to this invention comprises at least 2, at least 3, at least 4, at least 5, at least 6, at least 7, at least 8, at least 9, at least 10 histidine residues. In some embodiments, the His-tag comprises hexa-histidine peptide (6×His-tag). In some embodiments, the His-tag comprises deca-histidine peptide (10×His-tag).

In some embodiments, the specific protein binder comprises a His-tag binder. In some embodiments, the specific binder comprises a His-tag binder according to this invention. In some embodiments, the specific protein binder of this invention comprises Ni-nitrilotriacetic acid (Ni-NTA), bis-Ni-NTA, or tris-Ni-NTA. In some embodiments, the specific protein binder of this invention comprises a derivative of Ni-nitrilotriacetic acid (Ni-NTA), bis-Ni-NTA, or tris-Ni-NTA, wherein the term "derivative" includes but not limited to alkyl derivatives, amide derivatives, amine derivatives, carboxy derivatives, and the like. In some embodiments, the His-Tag binder comprises a derivative of tris-Ni-nitrilotriacetic acid (tris-Ni-NTA). In some embodiments, a derivative of bis-Ni-nitrilotriacetic acid (bis-Ni-NTA). In some embodiments, a derivative of mono-Ni-nitrilotriacetic acid (Ni-NTA). In some embodiments, the His-tag binder is any monomolecular compound which comprises three Ni-NTA moieties (i.e., tris-Ni-NTA) comprises Ni-nitrilotriacetic acid (Ni-NTA), bis-Ni-NTA, or tris-Ni-NTA.

In some embodiments, the His-tag binder comprised in the fluorescent probe of the invention is represented by the structure of formula D:

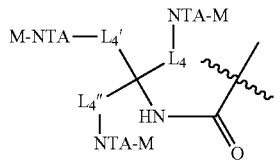

D wherein each of $L_4$, $L_4'$, and $L_4''$ is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof, each combination represents a separate embodiment according to this invention;

NTA is nitrilotriacetic acid or a protected derivative thereof; and

M is a metal ion.

In some embodiments, M is cobalt (Co). In some embodiments, M is nickel (Ni). In some embodiments, M is Ni(II). In some embodiments, M is Co(II). In some embodiments, M is Co(III). In some embodiments, each of $L_4$, $L_4'$, and $L_4''$ is independently a combination of alkyl ether and alkyl amide (i.e., alkylether-alkylamide). In some embodiments, each of $L_4$, $L_4'$, and $L_4''$ is independently —$(CH_2)_n$—NHCO—$(CH_2)_m$—O—$(CH_2)_l$—, wherein n, m and l are each independently an integer between 1 and 6. In some embodiments, n is 4, m is 2 and l is 1. In some embodiments, each of $L_4$, $L_4'$, and $L_4''$ is -$(CH_2)_4$—NHCO—$(CH_2)_2$O—$CH_2$—. In some embodiments, each of $L_4$, $L_4'$, and $L_4''$ is represented by the following structure:

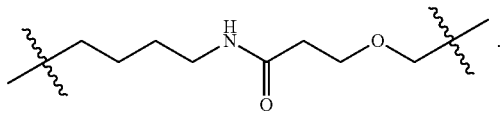 [SMILES: *CCCCNC(=O)CCOC*]

In some embodiments, the His-tag binder comprised in the sensor of the invention is represented by the structure of formula D(a):

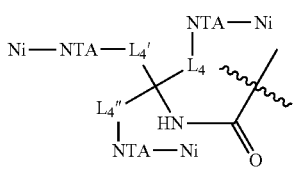

D(a)

wherein
each of $L_4$, $L_4'$, and $L_4''$ is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof; and NTA is nitrilotriacetic acid or a protected derivative thereof.

In some embodiments, each of $L_4$, $L_4'$, and $L_4''$ is independently is a combination of alkyl ether and alkyl amide (i.e., alkylether-alkylamide). In some embodiments, each of $L_4$, $L_4'$, and $L_4''$ is independently —$(CH_2)_n$—NHCO—$(CH_2)_m$—O—$(CH_2)_l$—, wherein n, m and l are each independently an integer between 1 and 6. In some embodiments, n is 4, m is 2 and l is 1. In some embodiments, each of $L_4$, $L_4'$, and $L_4''$ is-$(CH_2)_4$—NHCO—$(CH_2)_2$O—$CH_2$—. In some embodiments, each of $L_4$, $L_4'$, and $L_4''$ is represented by the following structure:

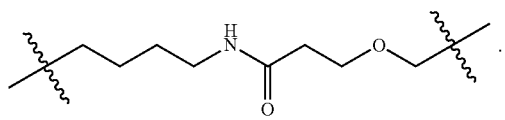 [SMILES: *CCCCNC(=O)CCOC*]

In some embodiments, the His-tag binder comprised in the sensor of the invention is represented by the structure of formula E:

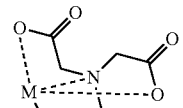

E

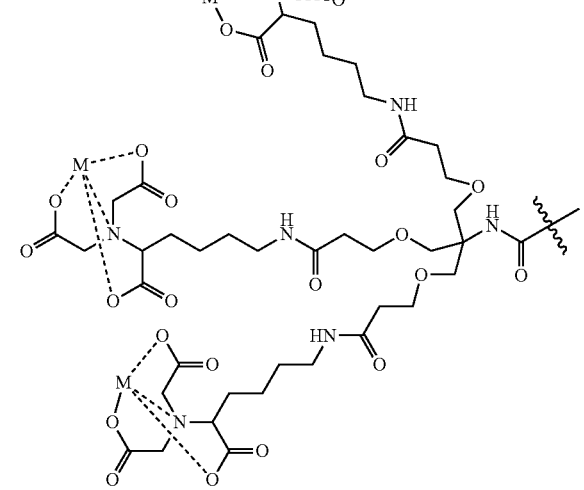

wherein M is a metal ion.

In some embodiments, M is cobalt (Co). In some embodiments, M is nickel (Ni). In some embodiments, M is Ni(II). In some embodiments, M is Co(II). In some embodiments, M is Co(III).

In some embodiments, the His-tag binder comprised in the sensor of the invention is represented by the structure of formula F:

F

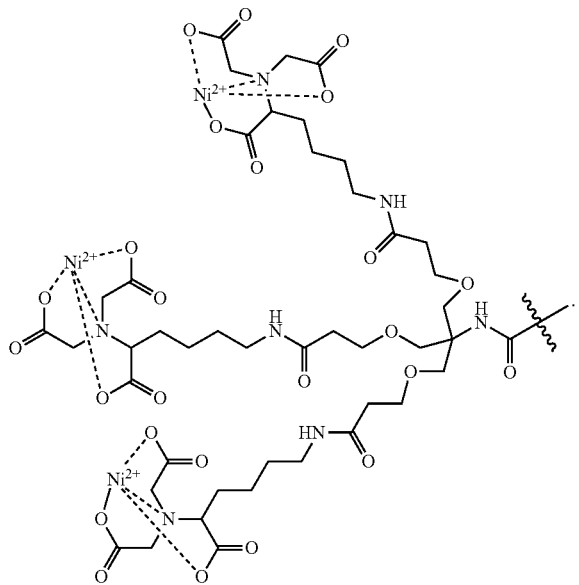

In some embodiments, the specific binder comprises a GSK inhibitor. In another embodiment, the specific binder comprises a glycogen-synthase kinase-3 (GSK-3) Inhibitor. In some embodiments, the GSK-3 inhibitor is AR-A014418. In some embodiments, the GSK-3 inhibitor is N-(4-Methoxybenzyl)-N'-(5-nitro-1,3-thiazol-2-yl)urea.

In some embodiments, the specific binder comprises an LDHA inhibitor. In some embodiments, the LDHA inhibitor comprises {4-[4-({3-[(2-Methyl-1,3-benzothiazol-6-yl)amino]-3-oxopropyl}amino)-4-oxobutyl]benzyl}propanedioic acid (i.e., AZ-33, or LDHA inhibitor 33).

In some embodiments, the specific protein binder comprises an LDHA inhibitor, a GSK-3 inhibitor, marimastat, ethacrynic acid, bisethacrynic acid, a metal complex of nitrilotriacetic acid (NTA) (His-tag binder), a metal complex of bis NTA (His-tag binder), a metal complex of tris-NTA (His-tag binder), Ni-nitrilotriacetic acid (Ni-NTA), bis-Ni-NTA, tris-Ni-NTA, PDGF-BB, heparin, FGF aptamer, biotin, tacrine, estrogen, DNA aptamer, RNA aptamer, peptide aldehyde, estrogen, suberoylanilidehydroxamic acid (SAHA), autoinducer, siderophore, folate, anisamide, antibody, antigen or a peptide binder.

In some embodiments, the protein target, or the protein of interest (POI) of the turn-on fluorescent probe according to this invention is a lactate dehydrogenase A (LDHA), glycogen synthase kinase-3 (GSK-3), matrix metalloproteases (MMPs) protein and its isoforms, glutathione S-Transferase (GSTs) protein and its isoforms, platelet derived growth factor, a Histidine-tagged protein, estrogen receptor, fibroblast growth factor (FGF), caspases, PSA, fibronecin, lysozyme, 0-amyloid, avidin, streptavidin, Acetylcholinesterase, histone deacetylases (HDACs), quorum sensing receptor, siderophore receptors, growth factor, membrane receptors, nuclear receptors, growth factor receptors, antibody, kinase, phosphatase or any protein to which a selective binder exists. In some embodiments, the protein target, or the protein of interest (POI) comprises a polyhistidine tag of this invention, at its N-terminus. In some embodiments, the protein target, or the protein of interest (POI) comprises a polyhistidine tag of this invention, at its C-terminus. In some embodiments, the protein target, or the protein of interest (POI) comprises a polyhistidine tag of this invention, at an internal location of the contiguous amino acid sequence.

A "linker" is defined herein as any compound derivative or moiety that covalently links between the QBC and the specific binder according to this invention. In some embodiments, the linker is hydrophilic linker. In some embodiments, the linker is flexible linker. In some embodiments, the linker is flexible hydrophilic linker. In some embodiments, the linker is a triazole derivative. In some embodiments, the linker is a carbamate derivative. In some embodiments, the linker is a $C_1$-$C_{12}$ alkyl derivative. In some embodiments, the linker is a $C_1$-$C_{12}$ alkyl ether derivative. In some embodiments, the linker is a phosphate derivative. In some embodiments, the linker is a polyethylene glycol (PEG) derivative. In some embodiments, the linker comprises one or more moieties selected from: substituted or unsubstituted linear or branched alkyl chain of 1-8 carbon atoms, substituted or unsubstituted linear or branched alkyl ether chain of 1-10 carbon atoms, polyethylene glycol (PEG) moiety, carbamate, triazole, amide, and phosphate; each combination is a separate embodiment according to this invention. In some embodiments, the linker is a substituted or unsubstituted linear or branched alkyl chain of 1-12 carbon atoms, substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms, substituted or unsubstituted linear or branched alkyl carbamate chain of 1-50 carbon atoms, substituted or unsubstituted linear or branched alkyl triazole chain of 1-50 carbon atoms or any combination thereof. In some embodiments, the linker is a combination of unsubstituted linear or branched alkyl ether chain and alkyl amide chain. In some embodiments, the linker is a combination of unsubstituted linear or branched alkyl ether chain and alkyl diamide chain.

In some embodiments, the linker comprises a substituted or unsubstituted linear or branched alkyl chain of 1-12 carbon atoms, substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms, substituted or unsubstituted linear or branched alkyl carbamate chain of 1-50 carbon atoms, substituted or unsubstituted linear or branched alkyl triazole chain of 1-50 carbon atoms, or any combination thereof, each combination is a separate embodiment according to this invention. In some embodiments the linear or branched alkyl chain is of 1-12, 1-10, 1-8, 1-7, 2-8, 1-6, 2-7, 1-5, 2-6, 1-4, 2-5, 1-3, 1, 2, 3, 4, 5, 6, 7, 8, 9, 10, 11, 12, 13, 14 or 15 carbon atoms; each represents a separate embodiment according to this invention. In some embodiments the linear or branched alkyl ether chain is of 1-12, 1-10, 1-8, 1-7, 2-8, 1-6, 2-7, 1-5, 2-6, 1-4, 2-5, 1-3, 1, 2, 3, 4, 5, 6, 7, 8, 9, 10, 11, 12, 13, 14 or 15 carbon atoms; each represents a separate embodiment according to this invention. In some embodiments the linear or branched alkyl ether chain is polyethylene glycol (PEG) of 2-20, 2-16, 2-8, 2-12, 2-14, 2-6, 4-8, 4-10, 4-6, 4-20, 4-16, 2, 4, 6, 8, 10, 12, 14 or 16 carbon atoms; each represents a separate embodiment according to this invention. In some embodiments the linear or branched alkyl phosphate chain is of 1-12, 1-10, 1-8, 1-7, 2-8, 1-6, 2-7, 1-5, 2-6, 1-4, 2-5, 1-3, 1, 2, 3, 4, 5, 6, 7, 8, 9, 10, 11, 12, 13, 14 or 15 carbon atoms; each represents a separate embodiment according to this invention. In some embodiments the linear or branched alkyl amide chain is of 1-12, 1-10, 1-8, 1-7, 2-8, 1-6, 2-7, 1-5, 2-6, 1-4, 2-5, 1-3, 1, 2, 3, 4, 5, 6, 7, 8, 9, 10, 11, 12, 13, 14 or 15 carbon atoms; each represents a separate embodiment according to this invention. In some embodiments the linear or branched alkyl diamide chain is of 1-12, 1-10, 1-8, 1-7, 2-8, 1-6, 2-7, 1-5, 2-6, 1-4, 2-5, 1-3, 1, 2, 3, 4, 5, 6, 7, 8, 9, 10, 11, 12, 13, 14 or 15 carbon atoms; each represents a separate embodiment according to this invention. In some embodiments the linear or branched alkyl amine chain is of 1-12, 1-10, 1-8, 1-7, 2-8, 1-6, 2-7, 1-5, 2-6, 1-4, 2-5, 1-3, 1, 2, 3, 4, 5, 6, 7, 8, 9, 10, 11, 12, 13, 14 or 15 carbon atoms; each represents a separate embodiment according to this invention. In some embodiments the linear or branched alkyl carbamate chain is of 1-12, 1-10, 1-8, 1-7, 2-8, 1-6, 2-7, 1-5, 2-6, 1-4, 2-5, 1-3, 1, 2, 3, 4, 5, 6, 7, 8, 9, 10, 11, 12, 13, 14 or 15 carbon atoms; each represents a separate embodiment according to this invention. In some embodiments the linear or branched alkyl triazole chain is of 1-12, 1-10, 1-8, 1-7, 2-8, 1-6, 2-7, 1-5, 2-6, 1-4, 2-5, 1-3, 1, 2, 3, 4, 5, 6, 7, 8, 9, 10, 11, 12, 13, 14 or 15 carbon atoms; each represents a separate embodiment according to this invention. In some embodiments, the linker is a combination of unsubstituted linear or branched alkyl ether chain and alkyl amide chain. In some embodiments, the linker is a combination of substituted or unsubstituted linear or branched alkyl chain of 1-8 carbon atoms, substituted or unsubstituted linear or branched alkyl ether chain of 1-10 carbon atoms, triazole, and amide. In some embodiments, the linker comprises at least one selected from: substituted or unsubstituted linear or branched alkyl chain of 1-8 carbon atoms, substituted or unsubstituted linear or branched alkyl ether chain of 1-10 carbon atoms, amide, and triazole.

In some embodiments, the linker is represented by the following structure:

wherein a, t, $G^1$, $V^1$, $X^1$ and $L^1$ are as defined in formula XXX hereinbelow.

In some embodiments, the linker is represented by the following structure:

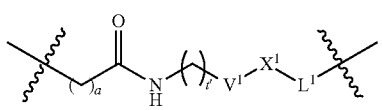

wherein a', t', $V^1$, $X^1$ and $l^1$ are as defined in formula XXXI hereinbelow.

In some embodiments, the linker is represented by the following structure:

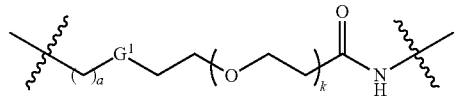

wherein a, $G^1$, and k are as defined in formula XXXVI hereinbelow.

In some embodiments, the linker is represented by the following structure:

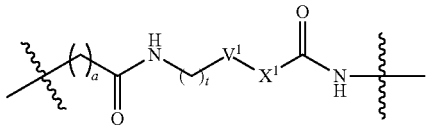

wherein a, t, $V^1$, and $X^1$ are as defined in formula XXXI hereinbelow.

In some embodiments, this invention is directed to a turn on fluorescent probe, wherein said probe comprises a Thiazole Orange (TO) or derivative thereof, and a specific protein binder covalently attached thereto directly or via a linker, wherein the specific protein binder is glycogen synthase kinase-3 (GSK-3) inhibitor or lactate dehydrogenase A (LDHA) inhibitor. In some embodiments, the TO is covalently attached to the specific protein binder via a linker. In some embodiments, the TO is covalently attached to the specific protein binder directly. In some embodiments, the linker covalently attaches the specific protein binder and the TO.

In some embodiments, this invention is directed to a turn on fluorescent probe, wherein said probe comprises a Thiazole Orange (TO) or a derivative thereof, and a specific protein binder covalently attached thereto directly or via a linker, wherein the probe is represented by the structure of compounds 401, 404, or 408 described hereinbelow.

In some embodiments, the probe is useful in the detection and/or imaging of proteins. In some embodiments, the detected and/or imaged protein is a disease biomarker. In some embodiments, the proteins are native proteins, engineered proteins, or recombinant proteins; each represents a separate embodiment according to this invention.

In some embodiments, the probe is useful for identifying diseases biomarkers. In some embodiments, the disease biomarker is a specific protein. In some embodiments, the disease biomarker is a specific protein isoform.

In some embodiments, the probe is useful for tracking proteins in their native environments. In some embodiments, the native environment is blood, serum, plasma, urine, saliva, tissue, peritoneal, stool, mucus, tear, sweat, biopsy, sperm or a cerebrospinal fluid sample. In some embodiments, the native environment is within a cell. In some embodiments, the cell is a living cell, a fixed cell, a human cell, a recombinant primary culture cell, or a tissue culture cell. In some embodiments, the cell is comprised in a biological sample.

In some embodiments, the probe is useful for identifying a specific protein at low concentrations and with a minimal background signal in biological medium. In some embodiments, the biological medium is blood, serum, plasma, urine, saliva, tissue, peritoneal, stool, mucus, tear, sweat, biopsy, sperm or a cerebrospinal fluid sample. In some embodiments, the biological medium is urine. In some embodiments, the turn-on probes are sensing the protein-of-interest (POI) in vitro and/or in living cells.

In some embodiments, the probe is useful for developing high-throughput screening (HTS) assays for detecting new PPI inhibitors.

In some embodiments, the probe is inherently non-fluorescent in the unbound state, however, it becomes highly emissive once its torsional motion of the QBC is restricted upon binding to the protein of interest (POI). In some embodiments, the POI is GSK-3, an LDHA, a His-tagged protein; each represents a separate embodiment according to this invention. In some embodiments, the protein target to be detected by the turn on probe are GSK protein, LDHA protein or a His-tagged protein.

In some embodiments, the turn-on probe does not generate any background signal in the absence of the desired bioanalyte. In some embodiments, said turn-on probe emit strongly in the presence of a desired protein target. In some embodiments, said turn-on probe is able to detect specific proteins at low concentration. In some embodiments, said turn-on probe is able to detect individual protein isoforms.

The ways by which these probes or sensors can be applied in inhibitor screening, cellular imaging, and biomarker detection are further described herein below.

In some embodiments, this invention is directed to a molecular sensor or probe comprising a fluorophore and one specific protein binder wherein the fluorophore's emission is enhanced once the internal torsional motion of the fluorophore is restricted. The internal torsional motion of the fluorophore can be restricted upon binding of the fluorophore derivative to the protein's binding site and to the amino acids on the protein surface (e.g., by pi-pi interactions with the fluorophore's core). Non limiting examples of such fluorophores are thiazole orange, thiazole red, and quinoline blue. In some embodiments, upon restriction of the fluorophore's torsional motion (i.e upon binding to an analyte), a fluorescent emission is generated. In some embodiments, upon restriction of the fluorophore's torsional motion (i.e upon binding to an analyte), the fluorescent emission is enhanced.

In some embodiments, the fluorescence enhancement is about 10 to 100 fold of the fluorescence of the sensor in the unbound state. In some embodiments, the fluorescence enhancement is about 20 to 70 fold of the fluorescence of the sensor in the unbound state. In some embodiments, the fluorescence enhancement is about 50 to 60 fold of the fluorescence of the sensor in the unbound state. In some embodiments, the fluorescence enhancement is about 55 fold of the fluorescence of the sensor in the unbound state. In some embodiments, the fluorescence enhancement is about 33 fold of the fluorescence of the sensor in the unbound state. In some embodiments, the fluorescence enhancement is about 22 fold of the fluorescence of the sensor in the unbound state. In some embodiments, the fluorescence enhancement is about 7 fold of the fluorescence of the sensor in the unbound state. In some embodiments, the fluorescence enhancement is about 16 fold of the fluorescence of the sensor in the unbound state.

In some embodiments, attaching quinoline-based cyanine dyes to specific protein binders affords turn-on fluorescent probes which emission turns on and/or enhances in the presence of the target proteins.

A unique property of the probes and/or sensors according to this invention is their ability to light up upon binding to their protein targets and this enables their detection with high affinity, selectivity, and a high signal-to-noise (S/N) ratio.

The terms "fluorescent molecular sensors", "turn-on probe" or "turn-on fluorescent probe" are used interchangeably, and refer in some embodiments, to quinoline-based cyanine dyes (or derivatives thereof) covalently attached to specific protein binders, directly or via a linker, as defined herein above and below.

In some embodiments, the fluorescent probes light up upon binding to their protein targets. In some embodiments, the fluorescent probes fluoreces upon binding to their protein targets. In some embodiments, the fluorescence emission of the probes is enhanced upon binding to their protein targets.

In some embodiments, the turn-on fluorescent probes selectively bind to a specific site on an engineered protein of interest (POI). In some embodiments, the turn-on fluorescent probes selectively bind to a specific site on a native POI. In some embodiments, the engineered protein is a tagged protein. In some embodiments, the engineered protein is a His-tagged protein.

In some embodiments, the interaction of the specific binder with the POI promotes the binding of the quinoline-based cyanine dye (QBC) to the POI's surface, which disrupt the torsional motion of the dye leading to an enhanced fluorescence emission by the dye.

Molecular Structures of Quinoline Based Cyanine Dyes Derivative (QBC) Turn-on Fluorescent Probes of the Invention In some embodiments, this invention is directed to a compound, represented by the structure of Formula XXX:

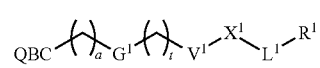

XXX wherein
a and t are each independently an integer between 0 and 15 (e.g., a: 1, t: 2); QBC is quinoline-based cyanine dye, or quinoline-based cyanine dye derivative (e.g., TO, TR, QB);

$G^1$ is a bond, a carbamate, an amide [—C(O)NH or —NHC(O)], an amine, $C_1$-$C_{12}$ alkyl amine, ester, ketone, O, N, S, carbonate, —O-alkyl-NH—, carbamoyl phosphate or phosphate;

$V^1$ is a bond, a triazole, an amide [—C(O)NH or —NHC(O)], —C(O)O—, —OC(O)—, O, NH, N-alkyl, S, —PO$_4$H—, $C_1$-$C_{12}$ alkyl ether, —NH-alkyl-NH—, —O-alkyl-NH—, —NH-alkyl-O— wherein said alkyl is optionally substituted or wherein said alkyl is optionally interrupted by an heteroatom consisting of O, N, P, S or combination thereof;

$X^1$ is a bond or $C_1$-$C_{12}$alkyl, —C(O)NH—, —NHC(O), —C(O)O—, —OC(O)—, O, NH, N-alkyl, S, —PO$_4$H—, $C_1$-$C_{12}$ alkyl ether, $C_1$-$C_{12}$-alkyl-NH, -alkyl-NHC(O)-alkyl, -alkyl-C(O)NH-alkyl, —NH—alkyl-NH—, —O-alkyl-NH—, —NH-alkyl-O— wherein said alkyl is optionally substituted or wherein said alkyl is optionally interrupted by an heteroatom consisting of O, N, P, S or combination thereof, $L^1$ is a bond or $C_1$-$C_{12}$ alkyl, C(O), an amide [—C(O)NH or —NHC(O)], —C(O)O—, —OC(O)—, O, NH, $C_1$-$C_{12}$ N-alkyl, S, —PO$_4$H, —PO$_4$H—{[(CH$_2$)$_y$O]$_x$}$_z$—PO$_3$H—, wherein y is between 1-5, x is between 1-10 and z is between 1-10, —PO$_4$H—PEG, $C_1$-$C_{12}$ alkyl ether, $C_1$-$C_{12}$ alkylamine, $C_1$-$C_{12}$ alkyl-NH, —C(O)NH-alkyl, —NHC(O)-alkyl, NH-alkyl-NH—, —O-alkyl-NH—, —NH-alkyl-O—, wherein said alkyl is optionally substituted or wherein said alkyl is optionally interrupted by an heteroatom consisting of O, N, P, S or combination thereof, and $R^1$ is a specific protein binder;

or a suitable salt thereof.

In some embodiments, the suitable salt thereof is a tosylate, iodide, chloride, bromide, fluoride, TFA or a $PF_6$ salt.

In some embodiments, the compound is a sensor. In some embodiments, the compound is a probe. In some embodiments, the compound is a turn-on fluorescent probe. In some embodiments, a is 1 or 2; $G^1$ is an amide; t is 2; $V^1$ is a bond, a triazol, or an alkyl ether; $X^1$ is a bond, an alkyl, or an alkyl ether; $L^1$ is a bond, an amide or C(O); or any combination thereof, each represents a separate embodiment according to this invention. In some embodiments, the alkyl ether is-[(O—$CH_2$—$CH_2)_k$]—, wherein k is an integer between 1 and 6. In some embodiments, k is 3. In some embodiments, the alkyl of $X^1$ is an ethyl. In some embodiments, the amide $L^1$ is [—C(O)NH—].

In some embodiments, the specific protein binder is GSK-3 inhibitor. In some embodiments, the specific protein binder is an LDHA inhibitor. In some embodiments, the specific protein binder is a His-tag binder. In some embodiments, the specific protein binder is a His-tag binder as defined herein below.

In some embodiments, this invention is directed to a compound, represented by the structure of Formula XXXI.

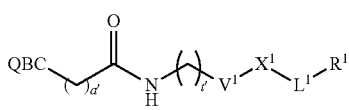

XXXI wherein
QBC is a quinoline-based cyanine dye, or a quinoline-based cyanine dye derivative;
a' and t' are each independently is an integer between 0 and 6;
$V^1$ is a bond, a triazole, an amide [—C(O)NH or —NHC(O)], —C(O)O—, —OC(O)—, O, NH, N-alkyl, S, —$PO_4$H—, $C_1$-$C_{12}$ alkyl ether, —NH-alkyl-NH—, —O-alkyl-NH—, —NH-alkyl-O— wherein said alkyl is optionally substituted or wherein said alkyl is optionally interrupted by an heteroatom consisting of O, N, P, S or combination thereof;
$X^1$ is a bond or $C_1$-$C_{12}$alkyl, —C(O)NH—, —NHC(O), —C(O)O—, —OC(O)—, O, NH, N-alkyl, S, —$PO_4$H—, $C_1$-$C_{12}$ alkyl ether, $C_1$-$C_{12}$-alkyl-NH, -alkyl-NHC(O)-alkyl, -alkyl-C(O)NH-alkyl, —NH—alkyl-NH—, —O-alkyl-NH—, —NH-alkyl-O— wherein said alkyl is optionally substituted or wherein said alkyl is optionally interrupted by an heteroatom consisting of O, N, P, S or combination thereof,
$L^1$ is a bond or $C_1$-$C_{12}$ alkyl, C(O), an amide [—C(O)NH or —NHC(O)], —C(O)O—, —OC(O)—, O, NH, $C_1$-$C_{12}$ N-alkyl, S, —$PO_4$H, —$PO_4$H—{[($CH_2)_y$O]$_x$}$_z$$PO_3$H—, wherein y is between 1-5, x is between 1-10 and z is between 1-10, —$PO_4$H—PEG, $C_1$-$C_{12}$ alkyl ether, $C_1$-$C_{12}$ alkylamine, $C_1$-$C_{12}$ alkyl-NH, —C(O)NH-alkyl, —NHC(O)-alkyl, NH-alkyl-NH—, —O-alkyl-NH—, —NH-alkyl-O—, wherein said alkyl is optionally substituted or wherein said alkyl is optionally interrupted by an heteroatom consisting of O, N, P, S or combination thereof, and $R^1$ is a specific protein binder;

or a suitable salt thereof.

In some embodiments, the suitable salt thereof is a tosylate, iodide, chloride, bromide, fluoride, TFA or a $PF_6$ salt.

In some embodiments, the compound is a sensor. In some embodiments, the compound is a probe. In some embodiments, the compound is a turn-on probe.

In some embodiments, the specific protein binder is GSK-3 inhibitor. In some embodiments, the specific protein binder is a His-tag binder. In some embodiments, the specific protein binder is a His-tag binder as defined herein below. In some embodiments, the specific protein binder is an LDHA inhibitor.

In some embodiments, a' is 1 or 2; t' is 2; $V^1$ is a bond, a triazol, or an alkyl ether; $X^1$ is a bond, an alkyl, or an alkyl ether; $L^1$ is a bond, an amide or C(O); or any combination thereof, each represents a separate embodiment according to this invention. In some embodiments, the alkyl ether is PEG. In some embodiments, the alkyl ether is-[(O—$CH_2$—$CH_2)_k$]—, wherein k is an integer between 1 and 6. In some embodiments, k is 3. In some embodiments, the alkyl of $X^1$ is methyl or ethyl. In some embodiments, the amide of $L^1$ is-C(O)NH—.

In some embodiments, this invention is directed to a compound, represented by the structure of Formula XXXII.

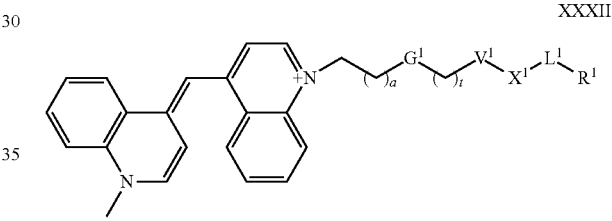

XXXII wherein
a and t are each independently an integer between 0 and 15 (e.g., a:1, t:2);
$G^1$ is a bond, a carbamate, an amide [—C(O)NH or —NHC(O)], amine, $C_1$-$C_{12}$ alkyl amine, an ester, a ketone, O, N, S, carbonate, —O-alkyl-NH—, carbamoyl phosphate, or phosphate;
$V^1$ is a bond, a triazole, an amide [—C(O)NH or —NHC(O)], —C(O)O—, —OC(O)—, O, NH, N-alkyl, S, —$PO_4$H—, $C_1$-$C_{12}$ alkyl ether, —NH-alkyl-NH—, —O-alkyl-NH—, —NH-alkyl-O— wherein said alkyl is optionally substituted or wherein said alkyl is optionally interrupted by an heteroatom consisting of O, N, P, S or any combination thereof;
$X^1$ is a bond or $C_1$-$C_{12}$alkyl (e.g., methyl, ethyl), an amide [—C(O)NH or —NHC(O)], —C(O)O—, —OC(O)—, O, NH, N-alkyl, S, —$PO_4$H—, $C_1$-$C_{12}$ alkyl ether, $C_1$-$C_{12}$-alkyl-NH, -alkyl-NHC(O)-alkyl, -alkyl-C(O)NH-alkyl, —NH-alkyl-NH—, —O-alkyl-NH—, —NH-alkyl-O— wherein said alkyl is optionally substituted or wherein said alkyl is optionally interrupted by an heteroatom consisting of O, N, P, S or combination thereof,
$L^1$ is a bond or $C_1$-$C_{12}$ alkyl, C(O), an amide [—C(O)NH or —NHC(O)], —C(O)O—, —OC(O)—O, NH, $C_1$-$C_{12}$ N-alkyl, S, —$PO_4$H, —$PO_4$H—{[($CH_2)_y$O]$_x$}—$PO_3$H—, wherein y is between 1-5, x is between 1-10 and z is between 1-10, —$PO_4$H—PEG, $C_1$-$C_{12}$ alkyl ether, $C_1$-$C_{12}$ alkylamine, $C_1$-$C_{12}$ alkyl-NH, —C(O)NH-alkyl, —NHC(O)-alkyl, NH-alkyl-NH—, —O-alkyl-NH—, —NH-alkyl-O—, wherein said alkyl is optionally substituted or wherein said alkyl is optionally interrupted by an heteroatom consisting of O, N, P, S or combination thereof, and $R^1$ is a specific protein binder;

or a suitable salt thereof.

In some embodiments, the suitable salt thereof is a tosylate, iodide, chloride, bromide, fluoride, TFA or a $PF_6$ salt.

In some embodiments, the compound is a sensor. In some embodiments, the compound is a probe.

In some embodiments, the compound is a turn-on probe.

In some embodiments, the specific protein binder is GSK-3 inhibitor. In some embodiments, the specific protein binder is a His-tag binder. In some embodiments, the specific protein binder is a His-tag binder as defined herein below. In some embodiments, the specific protein binder is an LDHA inhibitor.

In some embodiments, this invention is directed to a compound, represented by the structure of Formula XXXIII:

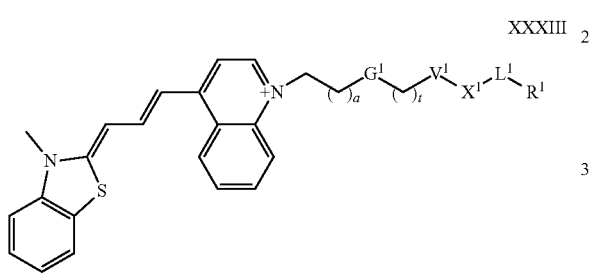

XXXIII wherein
- a and t are each independently an integer between 0 and 15 (e.g., a:1, t:2);
- $G^1$ is a bond, carbamate, an amide [—C(O)NH or —NHC(O)], amine, $C_1$-$C_{12}$ alkyl amine, ester, ketone, O, N, S, carbonate, —O-alkyl-NH—, carbamoyl phosphate or phosphate;
- $V^1$ is a bond, a triazole, an amide [—C(O)NH or —NHC(O)], —C(O)O—, —OC(O)—, O, NH, N-alkyl, S, —$PO_4H$—, $C_1$-$C_{12}$ alkyl ether, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;
- $X^1$ is a bond or $C_1$-$C_{12}$alkyl (e.g., methyl, ethyl), an amide [—C(O)NH or —NHC(O)], —C(O)O—, —OC(O)—, O, NH, N-alkyl, S, —$PO_4H$—, $C_1$-$C_{12}$ alkyl ether, $C_1$-$C_{12}$-alkyl-NH, -alkyl-NHC(O)-alkyl, -alkyl-C(O)NH-alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;
- $L^1$ is a bond or $C_1$-$C_{12}$ alkyl, C(O), an amide [—C(O)NH or —NHC(O)], —C(O)O—, —OC(O)—O, NH, $C_1$-$C_{12}$N-alkyl, S, —$PO_4H$, —$PO_4H$—{[($CH_2$)$_y$O]$_x$}$_z$—$PO_3H$—, wherein y is between 1-5, x is between 1-10 and z is between 1-10, —$PO_4H$—PEG, $C_1$-$C_{12}$ alkyl ether, $C_1$-$C_{12}$ alkylamine, $C_1$-$C_{12}$ alkyl-NH, —C(O)NH-alkyl, —NHC(O)-alkyl, NH-alkyl-NH—, —O-alkyl-NH—, —NH-alkyl-O—, wherein said alkyl is optionally substituted and wherein said alkyl is optionally interrupted by an heteroatom consisting of O, N, P, S or combination thereof; and $R^1$ is a specific protein binder;

or a suitable salt thereof.

In some embodiments, the suitable salt thereof is a tosylate, iodide, chloride, bromide, fluoride, TFA or a $PF_6$ salt.

In some embodiments, the compound is a sensor. In some embodiments, the compound is a probe. In some embodiments, the compound is a turn-on probe.

In some embodiments, the specific protein binder is GSK-3 inhibitor. In some embodiments, the specific protein binder is a His-tag binder. In some embodiments, the specific protein binder is a His-tag binder as defined herein below. In some embodiments, the specific protein binder is an LDHA inhibitor.

In some embodiments, this invention is directed to a compound, represented by the structure of Formula XXXIV:

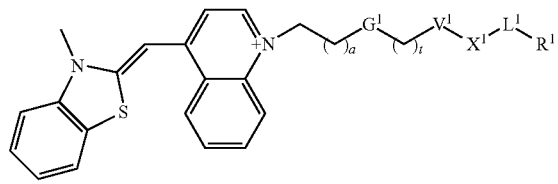

XXXIV wherein
- a and t are each independently an integer between 0 and 15 (e.g., a:1, t:2);
- $G^1$ is a bond, carbamate, an amide [—C(O)NH or —NHC(O)], amine, $C_1$-$C_{12}$ alkyl amine, ester, ketone, O, N, S, carbonate, —O-alkyl-NH—, carbamoyl phosphate or phosphate;
- $V^1$ is a bond, a triazole, an amide [—C(O)NH or —NHC(O)], —C(O)O—, —OC(O)—, O, NH, N-alkyl, S, —$PO_4H$—, $C_1$-$C_{12}$ alkyl ether, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;
- $X^1$ is a bond, $C_1$-$C_{12}$alkyl (e.g., methyl, ethyl), an amide [—C(O)NH or —NHC(O)], —C(O)O—, —OC(O)—, O, NH, N-alkyl, S, —$PO_4H$—, $C_1$-$C_{12}$ alkyl ether, $C_1$-$C_{12}$-alkyl-NH, -alkyl-NHC(O)-alkyl, -alkyl-C(O)NH-alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof,
- $L^1$ is a bond, $C_1$-$C_{12}$ alkyl, C(O), an amide [—C(O)NH or —NHC(O)], —C(O)O—, —OC(O)—, O, NH, $C_1$-$C_{12}$N-alkyl, S, —$PO_4H$, —$PO_4H$—{[($CH_2$)$_y$O]$_x$}$_z$—$PO_3H$—, wherein y is between 1-5, x is between 1-10 and z is between 1-10, —$PO_4H$—PEG, $C_1$-$C_{12}$ alkyl ether, $C_1$-$C_{12}$ alkylamine, $C_1$-$C_{12}$ alkyl-NH, —C(O)NH-alkyl, —NHC(O)-alkyl, NH-alkyl-NH—, —O-alkyl-NH—, —NH-alkyl-O—, wherein said alkyl is optionally substituted and wherein said alkyl is optionally interrupted by an heteroatom consisting of O, N, P, S or combination thereof, and $R^1$ is a specific protein binder;

or a suitable salt thereof.

In some embodiments, the suitable salt thereof is a tosylate, iodide, chloride, bromide, fluoride, TFA or a $PF_6$ salt.

In some embodiments, the compound is a sensor. In some embodiments, the compound is a probe. In some embodiments, the compound is a turn-on probe.

In some embodiments, the specific protein binder is GSK-3 inhibitor. In some embodiments, the specific protein binder is a His-tag binder. In some embodiments, the specific protein binder is a His-tag binder as defined herein below. In some embodiments, the specific protein binder is an LDHA inhibitor.

In some embodiments, this invention is directed to a compound, represented by the structure of Formula XXXV:

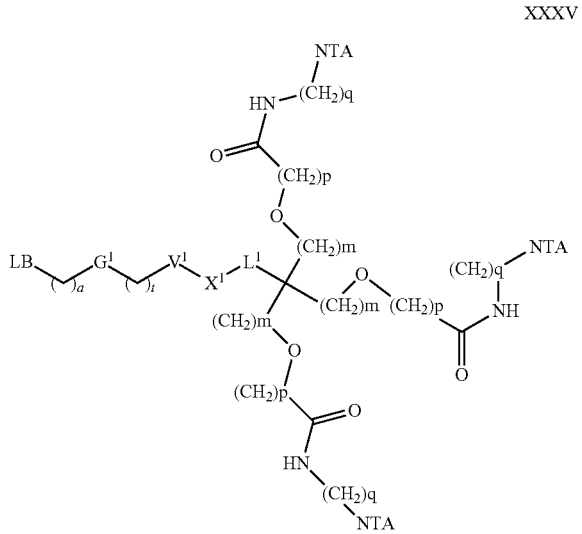

XXXV a and t are each independently an integer between 0 and 15 (e.g., a:1, 2; t:2);

$G^1$ is a bond, carbamate, an amide [—C(O)NH or —NHC(O)], amine, $C_1$-$C_{12}$ alkyl amine, ester, ketone, O, N, S, carbonate, —O-alkyl-NH—, carbamoyl phosphate or phosphate;

$V^1$, is a bond, a triazole, an amide [—C(O)NH or —NHC(O)], —C(O)O—, —OC(O)—, O, NH, N-alkyl, S, —$PO_4H$—, alkyl ether (e.g., —[O—$(CH_2)_2$]$_k$, k=3), —NH-alkyl-NH—, —O-alkyl-NH—, —NH— alkyl-O— wherein said alkyl is optionally substituted and wherein said alkyl is optionally interrupted by an heteroatom consisting of O, N, P, S or combination thereof;

$X^1$, is a bond or $C_1$-$C_{12}$ alkyl, an amide [—C(O)NH or —NHC(O)], —C(O)O—, —OC(O)—, O, NH, N-alkyl, S, —$PO_4H$—, $C_1$-$C_{12}$ alkyl ether, $C_1$-$C_{12}$-alkyl-NH, -alkyl-NHC(O)-alkyl, -alkyl-C(O)NH-alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;

$L^1$, is a bond or $C_1$-$C_{12}$ alkyl, C(O), an amide [—C(O)NH or —NHC(O)], —C(O)O—, —OC(O)—, O, NH, $C_1$-$C_{12}$-N-alkyl, S, —$PO_4H$, —$PO_4H$—$PO_4H$—{[$(CH_2)_yO$]$_x$}$_z$—$PO_3H$—, wherein y is between 1-5, x is between 1-10 and z is between 1-10, —$PO_4H$—PEG, $C_1$-$C_{12}$ alkyl ether, $C_1$-$C_{12}$ alkylamine, $C_1$-$C_{12}$ alkyl-NH, —C(O)NH-alkyl, —NHC(O)-alkyl, NH-alkyl-NH—, —O-alkyl-NH—, —NH-alkyl-O—, wherein said alkyl is optionally substituted and wherein said alkyl is optionally interrupted by an heteroatom consisting of O, N, P, S or combination thereof;

m, p and q are each independently an integer between 1 and 8 (e.g., m:1; p:2; q:4);

NTA is nitrilotriacetic acid, nitrilotriacetic acid complexed with at least one metal ion, or a protected derivative thereof; and LB is a labeling moiety;

or a suitable salt thereof.

In some embodiments, the suitable salt thereof is a tosylate, iodide, chloride, bromide, fluoride, TFA or a $PF_6$ salt.

In some embodiments, the compound is a sensor. In some embodiments, the compound is a probe.

In some embodiments, the compound is a turn-on probe.

In some embodiments, LB is a fluorescent dye. In some embodiments, LB is a quinoline-based cyanine dye as defined herein above (QBC). In some embodiments, LB is a TO, TR or QB; each represents a separate embodiment according to this invention. In some embodiments, LB is a TR or QB.

In some embodiments, the compound comprises a His-tag binder. In some embodiments, the compound is a His-tag binder.

In some embodiments, m of compound of formula XXXV is 1; p is 2; q is 4; a is 1 or 2; t is 2; $G^1$ is an amide (e.g., —C(O)NH); $V^1$ is alkyl ether or a bond; $X^1$ is alkyl ether, a bond or an amide; $L^1$ is a bond or an amide; or any combination thereof. In some embodiments, m is 1; p is 2; q is 4; a is 1; $G^1$ is an amide; t is 2; $V^1$ is a bond, a triazol, or an alkyl ether; $X^1$ is a bond, an alkyl, or an alkyl ether; $L^1$ is a bond, an amide or C(O); or any combination thereof. In some embodiments, the amide is-[C(O)NH]—. In some embodiments, the alkyl ether is-[$(CH_2$—$CH_2$—O$)_k$]—, wherein an integer between 1 and 6. In some embodiments, k is 3.

In some embodiments, the compound is represented by the structure of formula XXXVI:

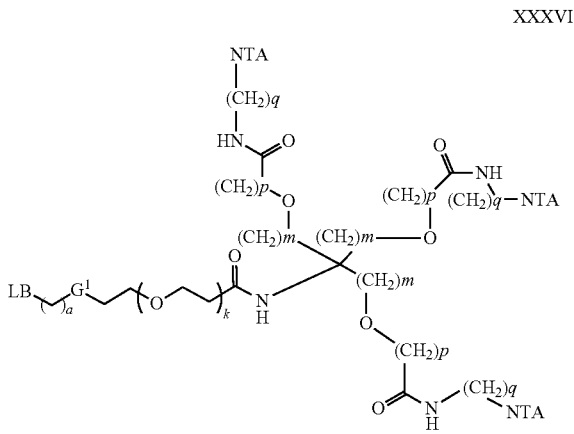

XXXVI wherein m, p, q and k are each independently an integer between 1 and 8 (e.g., m:1; p:2; q:4, k:3);

a is an integer between 0 and 15 (e.g., 1, 2);

$G^1$ is a bond, carbamate, an amide [—C(O)NH or —NHC(O)], amine, $C_1$-$C_{12}$ alkyl amine, ester, ketone, O, N, S, carbonate, —O-alkyl-NH—, carbamoyl phosphate or phosphate;

NTA is nitrilotriacetic acid, nitrilotriacetic acid complexed with at least one metal ion, or a protected derivative thereof; and LB is a labeling moiety;

or a suitable salt thereof.

In some embodiments, the suitable salt thereof is a tosylate, iodide, chloride, bromide, fluoride, TFA or a $PF_6$ salt.

In some embodiments, the compound is a sensor. In some embodiments, the compound is a probe.

In some embodiments, the compound is a turn-on probe.

In some embodiments, LB is a fluorescent dye. In some embodiments, LB is a quinoline-based cyanine dye as defined herein above (QBC). In some embodiments, LB is a TO, TR or QB; each represents a separate embodiment according to this invention. In some embodiments, LB is a TR or QB.

In some embodiments, the compound comprises a His-tag binder. In some embodiments, the compound is a His-tag binder.

In some embodiments, k is 3, m is 1, p is 2, q is 4, a is 1, NTA is nitrilotriacetic acid, and LB is quinoline-based cyanine dye. In some embodiments, k is 3, and LB is Thiazole orange (TO), Quinoline blue (QB) or Thiazole red (TR); each represents a separate embodiment according to this invention.

In some embodiments, the compound is represented by the structure of formula XXXVII:

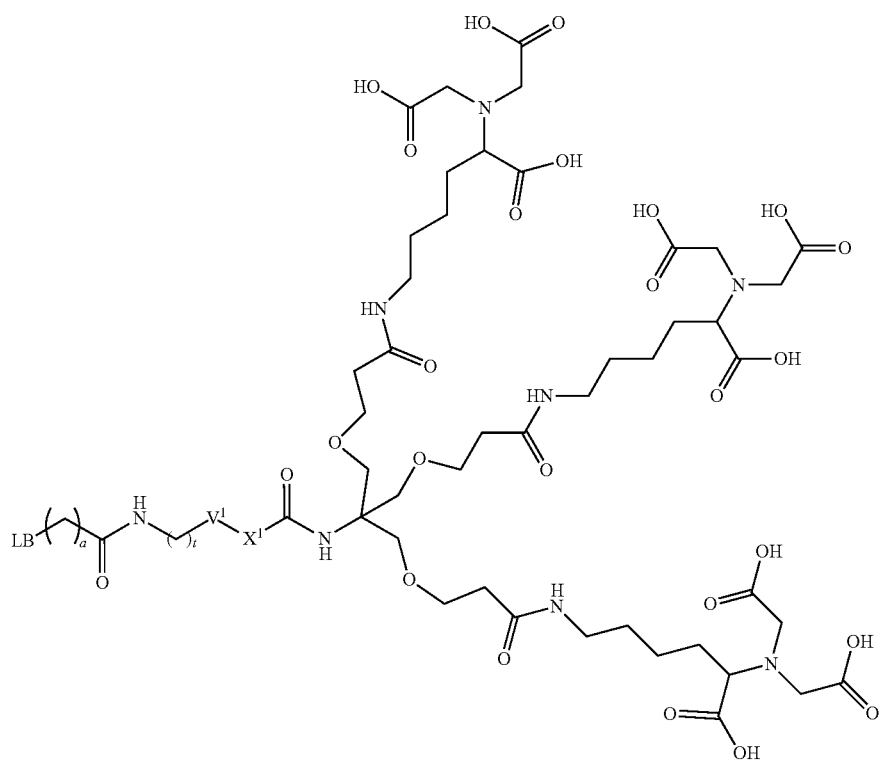

XXXVII wherein a and t are each independently an integer between 0 and 15 (e.g., a:1, 2; t:2);

$V^1$ is a bond, a triazole, an amide [—C(O)NH or —NHC(O)], —C(O)O—, —OC(O)—, O, NH, N-alkyl, S, —PO$_4$H—, alkyl ether (e.g., —[O—(CH$_2$)$_2$]$_k$, k=3), —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof, $X^1$, is a bond or $C_1$-$C_{12}$ alkyl, an amide [—C(O)NH or —NHC(O)], —C(O)O—, —OC(O)—, O, NH, N-alkyl, S, —PO$_4$H—, $C_1$-$C_{12}$ alkyl ether, $C_1$-$C_{12}$-alkyl-NH, -alkyl-NHC(O)-alkyl, -alkyl-C(O)NH-alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof, and LB is a labeling moiety;

or a suitable salt thereof.

In some embodiments, the suitable salt thereof is a tosylate, iodide, chloride, bromide, fluoride, TFA or a $PF_6$ salt.

In some embodiments, the compound is a sensor. In some embodiments, the compound is a probe. In some embodiments, the compound is a turn-on probe.

In some embodiments, LB is a fluorescent dye. In some embodiments, LB is a quinoline-based cyanine dye as defined herein above (QBC). In some embodiments, LB is a TO, TR or QB; each represents a separate embodiment according to this invention. In some embodiments, LB is a TR or QB.

In some embodiments, the compound comprises a His-tag binder. In some embodiments, the compound is a His-tag binder.

In some embodiments, a is 1; t is 2; and LB is QBC. In some embodiments, QBC is Thiazole orange (TO), Quinoline blue (QB) or Thiazole red (TR); each represents a separate embodiment according to this invention. In some embodiments, the alkyl ether is-[O—$(CH_2)_2]_k$ wherein k is between 1 and 6. In some embodiments, k is 3.

Specific Embodiments for Compounds of the Invention

In some embodiments, a and/or t, of any one of formula XXX, XXXII-XXXIV, XXXV or XXXVII are each independently an integer between 0-15, 0-5, 1-5, 2-6, 0-6, 1-10, or 0-10; each represents a separate embodiment according to this invention. In some embodiments, a and/or t, are each independently 1, 2, 3, 4, 5, 6, 7, 8, 9, 10, 11, 12, 13, 14 or 15; each represents a separate embodiment according to this invention. In some embodiments, a is 1, 2 or 3. In some embodiments, a is 1 or 2. In some embodiments, t is 1, 2 or 6.

In some embodiments, t is 1 or 2.

In some embodiments, a' and/or t' of Formula XXXI are each independently an integer between 0-15, 0-5, 1-5, 2-6, 0-6, 1-10, or 0-10; each represents a separate embodiment according to this invention. In some embodiments, a' and/or t' are each independently 1, 2, 3, 4, 5, 6, 7, 8, 9, 10, 11, 12, 13, 14 or 15; each represents a separate embodiment according to this invention. In another embodiment, a' and/or t' of Formula XXXI are each independently 1 or 2.

In some embodiments, $G^1$ of any one of formula XXX, and XXXII-XXXV is a bond, carbamate [—OC(O)NH or —NHC(O)O], an amide [—C(O)NH or —NHC(O)], amine, alkyl amine, ester, ketone, O, N, S, carbonate, —O-alkyl-NH—, carbamoyl phosphate or phosphate; each represents a separate embodiment according to this invention. In some embodiments, $G^1$ is a bond. In some embodiments, $G^1$ is a carbamate. In some embodiments, $G^1$ is an amide. In some embodiments, $G^1$ is [—C(O)NH. In some embodiments, $G^1$ is an amine (—NH—). In some embodiments, $G^1$ is an amine alkyl (—NH-alkyl-). In some embodiments, $G^1$ is an ester (—COO—). In some embodiments, $G^1$ is a ketone. In some embodiments, $G^1$ is a carbonate. In some embodiments, $G^1$ is an —O-alkyl-NH—. In some embodiments, $G^1$ is a carbamoyl phosphate. In some embodiments, $G^1$ is a phosphate. In some embodiments, $G^1$ is a $C_1$-$C_{12}$alkyl amine.

In some embodiments, $V^1$ of any one of formula XXX-XXXV and XXXVII is a bond, a triazole, an amide [—C(O)NH or —NHC(O)], —C(O)O—, —OC(O)—, O, NH, N-alkyl, S, —$PO_4H$—, $C_1$-$C_{12}$alkyl ether, —NH— alkyl-NH—, —O-alkyl-NH—, —NH-alkyl-O— wherein said alkyl is optionally substituted and wherein said alkyl is optionally interrupted by an heteroatom consisting of O, N, P, S or combination thereof, ach represents a separate embodiment according to this invention. In some embodiments, $V^1$ is a bond. In some embodiments, $V^1$ is a triazole. In some embodiments, $V^1$ is an amide. In some embodiments, $V^1$ is-C(O)NH. In some embodiments, $V^1$ is-NHC(O). In some embodiments, $V^1$ is-C(O)O—. In some embodiments, $V^1$ is-OC(O)—. In some embodiments, $V^1$ is 0. In some embodiments, $V^1$ is NH. In some embodiments, $V^1$ is N-alkyl. In some embodiments, $V^1$ is S. In some embodiments, $V^1$ is-$PO_4H$—. In some embodiments, $V^1$ is $C_1$-$C_{12}$ alkyl ether. In some embodiments, the alkyl ether is-[O—$(CH_2)_2]_k$, wherein k is an integer between 2 and 8. In some embodiments, k is 2, 3, 4, 5, 6, or 7; each represents a separate embodiment according to this invention. In some embodiments, k is 3. In some embodiments, $V^1$ is-NH-alkyl-NH—. In some embodiments, $V^1$ is-O— alkyl-NH—. In some embodiments, $V^1$ is-NH-alkyl-O—. In some embodiments, the alkyl is substituted. In some embodiments the alkyl is interrupted by an heteroatom consisting of O, N, P, S or combination thereof, each represents a separate embodiment according to this invention.

In some embodiments, $X^1$ of any one of formula XXX-XXXV and XXXVII is a bond, $C_1$-$C_{12}$alkyl, —C(O)NH—, —NHC(O), —C(O)O—, —OC(O)—, O, NH, N-alkyl, S, —$PO_4H$—, $C_1$-$C_{12}$alkyl ether, $C_1$-$C_{12}$-alkyl-NH, -alkyl-NHC(O)-alkyl, -alkyl-C(O)NH-alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof, each represents a separate embodiment according to this invention. In some embodiments, $X^1$ is a bond. In some embodiments, $X^1$ is $C_1$-$C_{12}$alkyl. In some embodiments, the alkyl is methyl, ethyl, propyl, butyl; each represents a separate embodiment according to this invention. In some embodiments, $X^1$ is-C(O)NH—. In some embodiments, $X^1$ is-NHC(O). In some embodiments, $X^1$ is-C(O)O—. In some embodiments, $X^1$ is-OC(O)—. In some embodiments, $X^1$ is 0. In some embodiments, $X^1$ is NH. In some embodiments, $X^1$ is N-alkyl. In some embodiments, $X^1$ is S. In some embodiments, $X^1$ is-$PO_4H$—. In some embodiments, $X^1$ is $C_1$-$C_{12}$ alkyl ether. In some embodiments, $X^1$ is $C_1$-$C_{12}$-alkyl-NH. In some embodiments, $X^1$ is -alkyl-NHC(O)-alkyl. In some embodiments, $X^1$ is -alkyl-C(O)NH-alkyl. In some embodiments, $X^1$ is-NH-alkyl-NH—. In some embodiments, $X^1$ is-O-alkyl-NH—. In some embodiments, $X^1$ is-NH-alkyl-O—. In some embodiments, the alkyl is optionally substituted. In some embodiments the alkyl is interrupted by an heteroatom consisting of O, N, P, S or combination thereof.

In some embodiments, L of any of formula XXX-XXXV is a bond, $C_1$-$C_{12}$alkyl, C(O), —C(O)NH—, —NHC(O)—, —C(O)O—, —OC(O)—, O, NH, $C_1$-$C_{12}$N-alkyl, S, —$PO_4H$, —$PO_4H$—$\{[(CH_2)_yO]_x\}_z$—$PO_3H$—, wherein y is between 1-5, x is between 1-10 and z is between 1-10, —$PO_4H$—PEG, $C_1$-$C_{12}$ alkyl ether, $C_1$-$C_{12}$ alkylamine, $C_1$-$C_{12}$ alkyl-NH, —C(O)NH-alkyl, —NHC(O)-alkyl, NH-alkyl-NH—, —O-alkyl-NH—, —NH-alkyl-O—, wherein said alkyl is optionally substituted or wherein said alkyl is optionally interrupted by an heteroatom consisting of O, N, P, S or combination thereof; each represents a separate embodiment according to this invention. In some embodiments, $L^1$ is a bond. In some embodiments, $L^1$ is C(O). In some embodiments, $L^1$ is-C(O)NH—. In some embodiments, $L^1$ is-NHC(O)—. In some embodiments, $L^1$ is-$C_1$-$C_{12}$ alkyl. In some embodiments, $L^1$ is-C(O)O—. In some embodiments, $L^1$ is-OC(O)—. In some embodiments, $L^1$ is O. In some embodiments, $L^1$ is NH. In some embodiments, $L^1$ is $C_1$-$C_{12}$N-alkyl. In some embodiments, $L^1$ is S. In some embodiments, $L^1$ is-$PO_4H$. In some embodiments, $L^1$ is-$PO_4H$—. In some embodiments, $L^1$ is $\{[(CH_2)_yO]_x\}_z$—$PO_3H$—, wherein y is between 1-5, x is between 1-10 and z is between 1-10. In some embodiments, $L^1$ is-$PO_4H$—PEG. In some embodiments, $L^1$ is $C_1$-$C_{12}$ alkyl ether. In some embodiments, $L^1$ is $C_1$-$C_{12}$ alkylamine. In some embodiments, $L^1$ is $C_1$-$C_{12}$ alkyl-NH. In some embodiments, $L^1$ is-C(O)NH— alkyl. In some embodiments, $L^1$ is-NHC(O)-alkyl. In some embodiments, $L^1$ is NH-alkyl-NH—. In some embodiments, $L^1$ is-O-alkyl-NH—. In some embodiments, $L^1$ is-NH-alkyl-O—. In some embodiments, the alkyl is substituted. In some embodiments, the alkyl is interrupted by an heteroatom consisting of O, N, P, S or combination thereof.

In some embodiments, NTA of formula XXXV or XXXVI, is nitrilotriacetic acid. In some embodiments, NTA is nitrilotriacetic acid complexed with at least one metal ion. In some embodiments, the metal ion is Ni(II), Co(II), Co(III) or any combination thereof. In some embodiments, the compound is complexed with three Ni(II) ions. In some embodiments NTA is Ni-nitrilotriacetic acid (Ni-NTA). In some embodiments, NTA is a protected derivative of nitrilotriacetic acid.

In some embodiments, the protected derivative of nitrilotriacetic acid is represented by the structure of fragment (B):

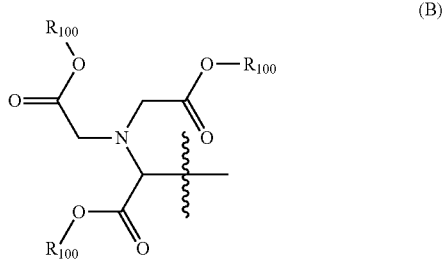

(B)

wherein
$R_{100}$ is a substituted or unsubstituted linear, branched or cyclic $C_1$-$C_{10}$ alkyl, including: tert-butyl, ethyl, methyl, neo-pentyl, cyclopropyl, and cyclohexyl; benzyl or a substituted or unsubstituted aryl.

In some embodiments, QBC of any one of Formula XXX-XXXIV is quinoline-based cyanine dye. Non limiting examples of quinoline based cyanine dyes include: Thiazole orange (TO), Quinoline blue (QB), Thiazole red (TR), and Disperse Yellow 54. In some embodiments, QBC is TR or QB. In some embodiments, QBC is TO, TR or QB. In some embodiments, QBC is TO. In some embodiments, QBC is TR. In some embodiments, QBC is QB. In some embodiments, QBC is a derivative of TO, TR or QB, wherein derivatives including but not limited to: alkyl derivatives, amide derivatives, amine derivatives, carboxy derivatives, and the like.

In some embodiments, LB of any one of Formula XXXV-XXXVII is quinoline-based cyanine dye. In some embodiments, LB is a quinoline based cyanine dye derivative, wherein derivatives including but not limited to: alkyl derivatives, amide derivatives, amine derivatives, carboxy derivatives, and the like. In some embodiments, LB is Thiazole orange. In some embodiments, LB is Quinoline blue. In some embodiments, LB is Thiazole red.

In some embodiments, the term "quinoline-based cyanine dye" of this invention comprises Thiazole orange (TO), Quinoline blue (QB), and Thiazole red (TR). In some embodiments, the term includes also derivatives quinoline based cyanine dyes (e.g. TO, TR or QB). In some embodiments, such derivatives include but not limited to: alkyl derivatives, amide derivatives, amine derivatives, carboxy derivatives, and the like.

In some embodiments, QBC of Formula XXX-XXXIV is quinoline-based cyanine dye. In some embodiments, QBC is a quinoline based cyanine dye derivative. In some embodiments, QBC is Thiazole orange. In some embodiments, QBC is Quinoline blue. In some embodiments, QBC is Thiazole red.

In some embodiments, k of Formula XXXVI is an integer between 1 and 8. In some embodiments, k is an integer between 2-6, 3-6, 1-5, 3-8, or 2-4; each represents a separate embodiment according to this invention. In some embodiments, k is 1, 2, 3, 4, 5, 6, 7, or 8; each represents a separate embodiment according to this invention. In some embodiments, k is 3.

In some embodiments, m, p and/or q of formula XXXV and/or XXXVI are each independently an integer between 1-8, 1-4, 1-6, or 1-5; each represents a separate embodiment according to this invention. In some embodiments, m, p and/or q are each independently 1, 2, 3, 4, 5, 6, 7, or 8; each represents a separate embodiment according to this invention. In some embodiments, m is 1, p is 2, and q is 4.

In some embodiments, $R^1$ of any one of Formula XXX-XXXIV is a specific protein binder. In some embodiments, the specific binder, of this invention, is any compound or derivative that can bind particular protein or protein groups with high affinity and selectivity. In some embodiments, the specific binder is a synthetic inhibitor, a natural ligand or an aptamer that is selective toward a specific protein group, but also broad spectrum which binds particular protein groups with high affinity and selectivity. In some embodiments, the specific protein binder of this invention is any specific protein binder known in the art. In some embodiments, a specific binder is any molecule that can target different type of fusion proteins that contain certain protein tags such as: a polyhistidine tag, (e.g., 6×His-tag, 10×His-tag), tetra cysteine peptide (CCPGCC, TC tag), etc. In some embodiments, the specific binder comprises a "Tag-binding region". In some embodiments, the specific binder is a targeted protein receptor comprising a protein tag binder. In some embodiments, the specific binder comprises a His-tag binder. In some embodiments, the specific binder of this invention comprises Ni-nitrilotriacetic acid (Ni-NTA), bis-Ni-NTA, or tris-Ni-NTA. In some embodiments, the specific binder of this invention comprises a derivative of Ni-nitrilotriacetic acid (Ni-NTA), bis-Ni-NTA, or tris-Ni-NTA, wherein the term "derivative" includes but not limited to alkyl derivatives, amide derivatives, carboxy derivatives, and the like. In some embodiments, the specific binder comprises a GSK specific inhibitor. In some embodiments, the specific binder comprises GSK-3 beta Inhibitor VIII. In some embodiments, the specific binder comprises GSK-3 inhibitor (i.e AR-synthase kinase-3 (GSK-3)). In some embodiments, the GSK-3 inhibitor is AR-A014418. In some embodiments, the specific binder is LDHA inhibitor. In some embodiments, the specific binder is {4-[4-({3-[(2-Methyl-1,3-benzothiazol-6-yl)amino]-3-oxopropyl}amino)-4-oxobutyl]benzyl}propanedioic acid. In some embodiments, the specific protein binder comprises: an LDHA inhibitor, a GSK-3 inhibitor (e.g., AR-A014418), marimastat, ethacrynic acid, bisethacrynic acid, a metal complex of nitrilotriacetic acid (NTA) (His-tag binder), a metal complex of bis NTA (His-tag binder), a metal complex of tris-NTA (His-tag binder), Ni-nitrilotriacetic acid (Ni-NTA), bis-Ni-NTA, tris-Ni-NTA, PDGF-BB, heparin, FGF aptamer, biotin, tacrine, estrogen, DNA aptamer, RNA aptamer, peptide aldehyde, estrogen, suberoylanilidehydroxamic acid (SAHA), autoinducer, siderophore, folate, anisamide, antibody, antigen or a peptide binder; each represents a separate embodiment according to this invention. In some embodiments, the specific protein binder is: an LDHA inhibitor, a GSK-3 inhibitor (e.g., AR-A014418), marimastat, ethacrynic acid, bisethacrynic acid, a metal complex of nitrilotriacetic acid (NTA) (His-tag binder), a metal complex of bis NTA (His-tag binder), a metal complex of tris-NTA (His-tag binder), Ni-nitrilotriacetic acid (Ni-NTA), bis-Ni-NTA, tris-Ni-NTA, PDGF-BB, heparin, FGF aptamer, biotin, tacrine, estrogen, DNA aptamer, RNA aptamer, peptide aldehyde, estrogen, suberoylanilidehydroxamic acid (SAHA), autoinducer, siderophore, folate, anisamide, antibody, antigen or a peptide binder; each represents a separate embodiment according to this invention.

In some embodiments, R₁ of Formula XXX-XXXIII is a His-tag binder according to this invention as defined herein below.
In some embodiments, the compound of formula XXX or XXXI is represented by the structure of Compounds 401-410:
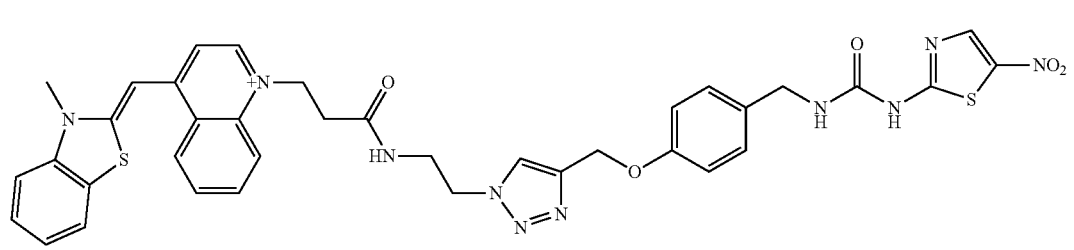
401
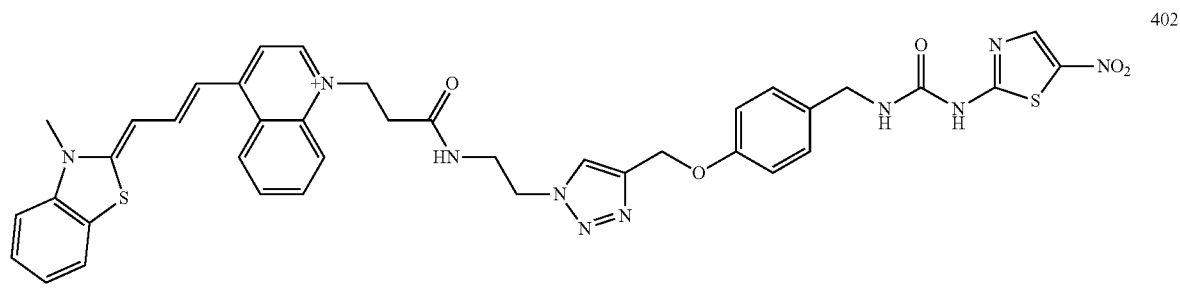
402
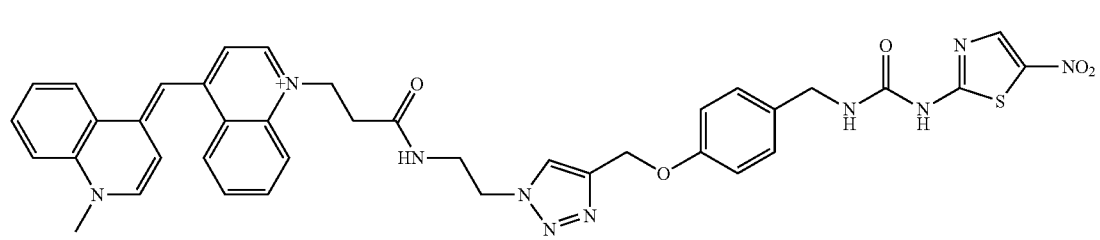
403
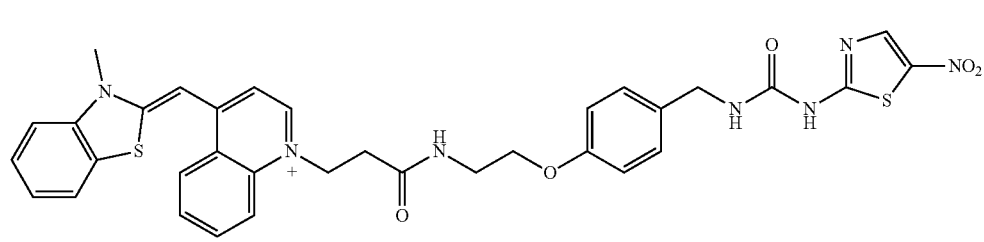
404
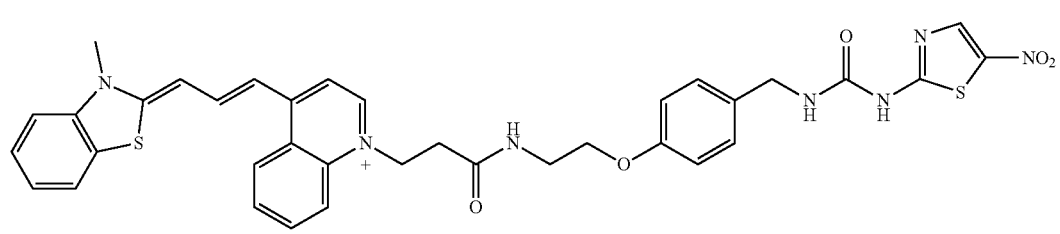
405
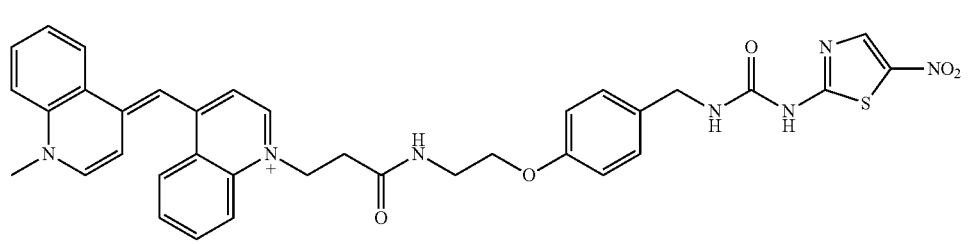
406

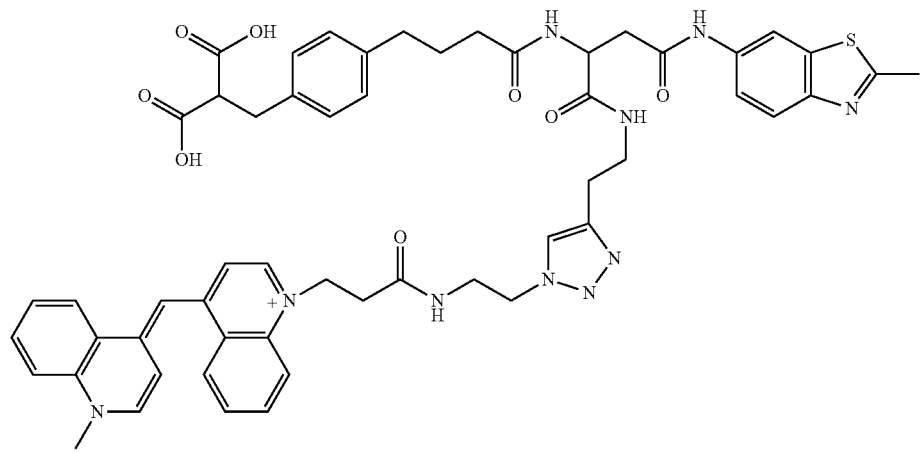
407
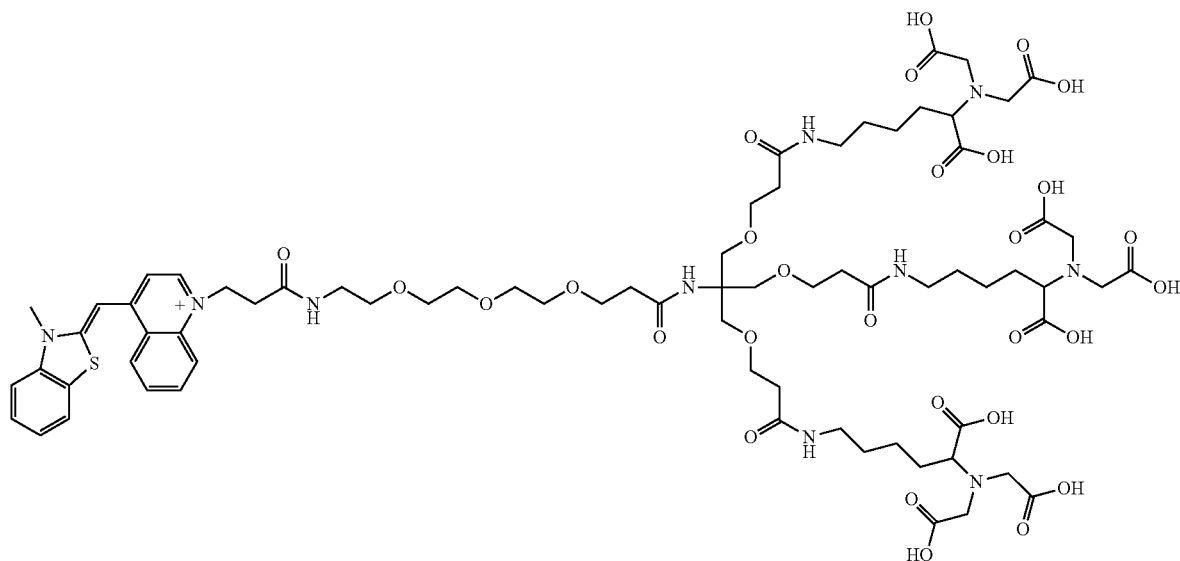
408
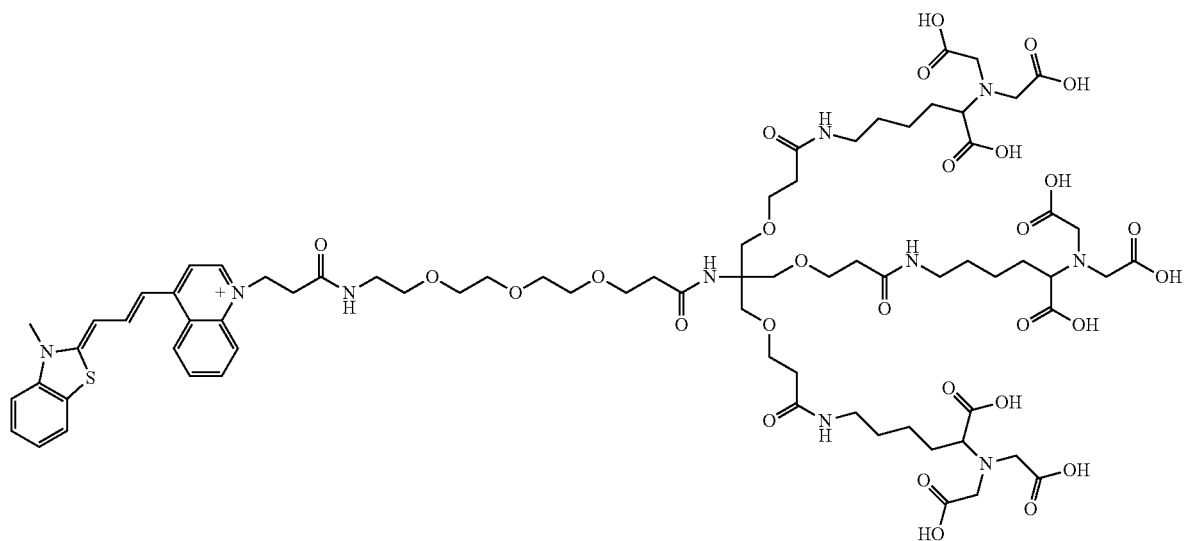
409

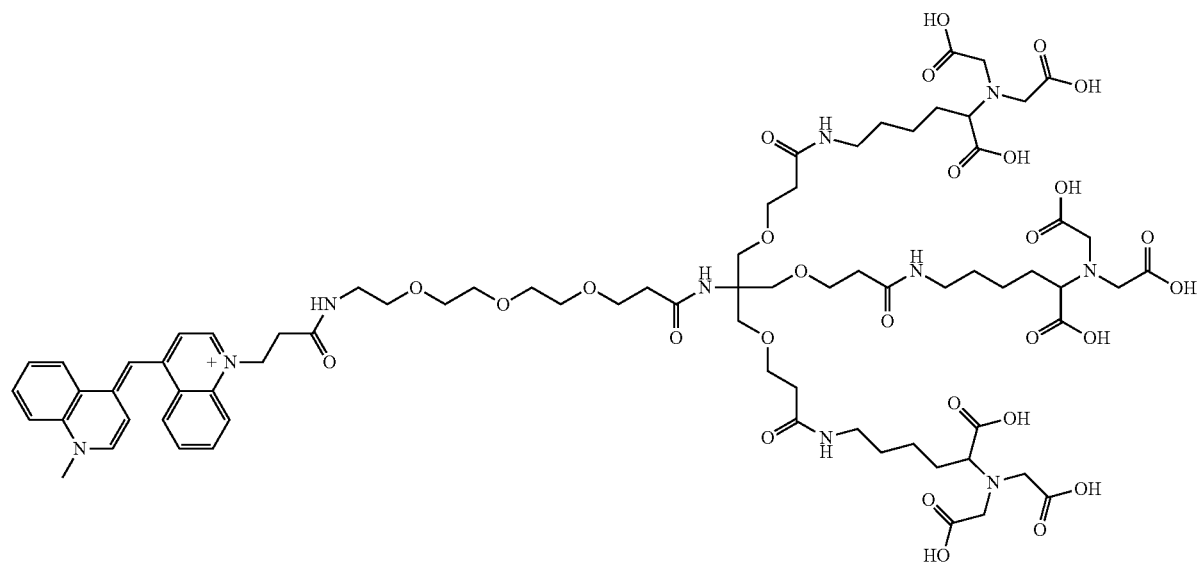
In some embodiments, a compound of any one of Formula XXX, XXXI and XXXV-XXXVII is represented by the structure of Compounds 408, 409 and 410:
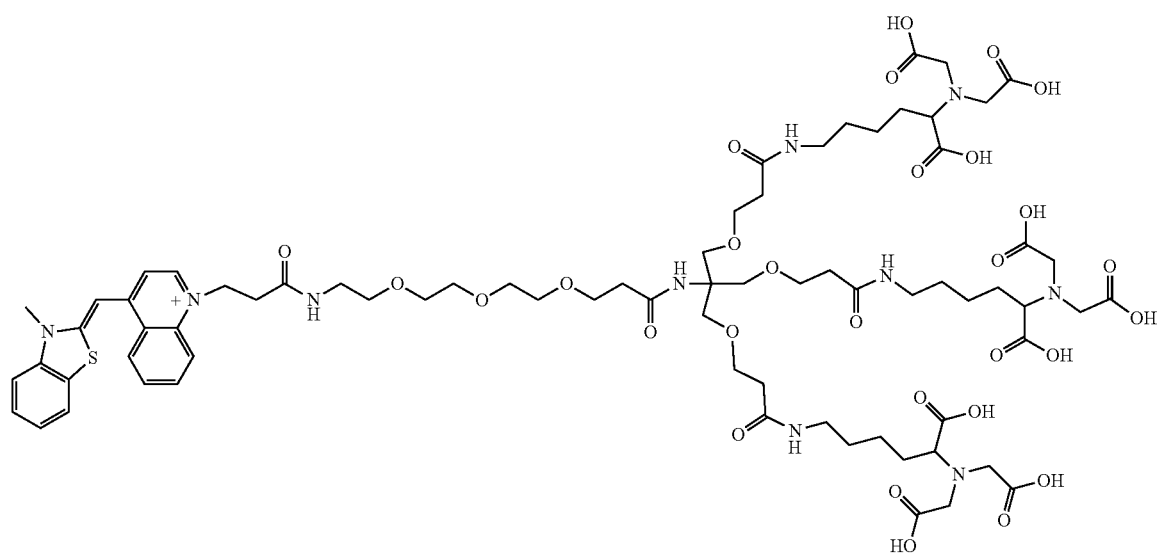

-continued
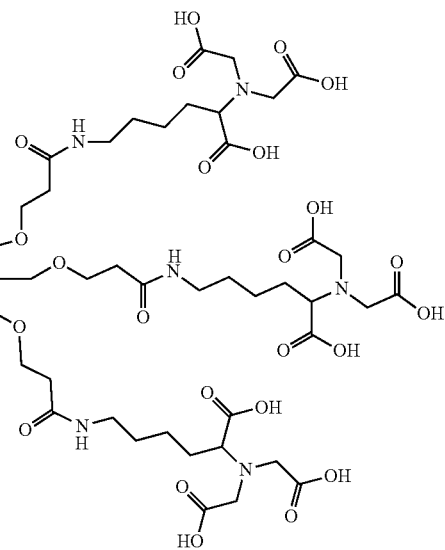
409
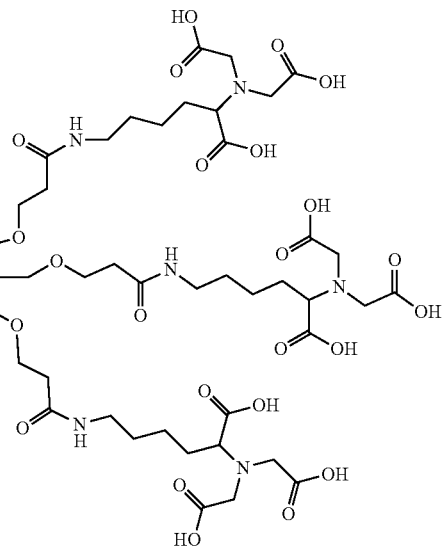
410
In some embodiments, a compound of any one of Formula XXX, XXXI and XXXII, wherein QBC is quinoline blue, is represented by the structure of Compounds 403, 406, 407 and 410:
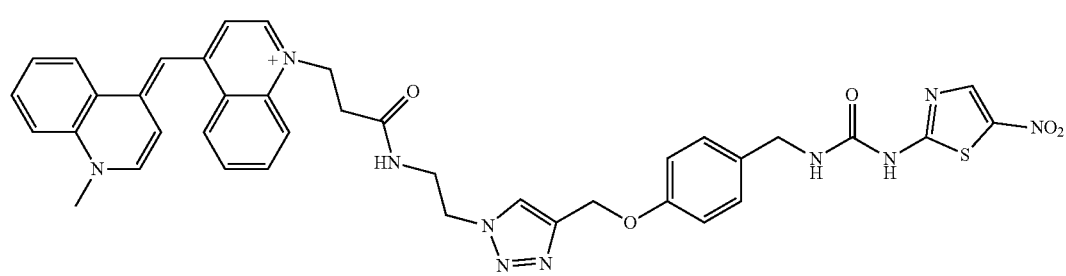
403

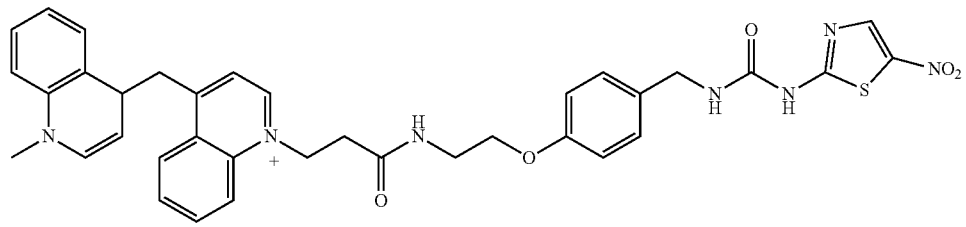
406
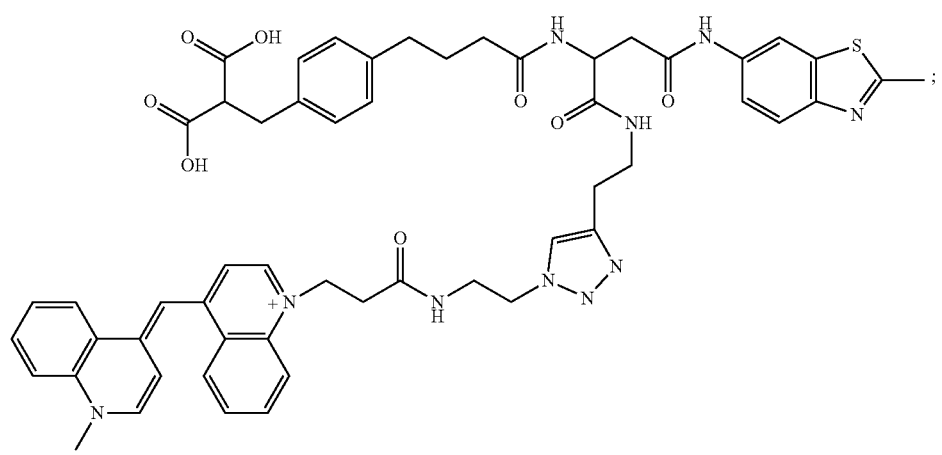
407
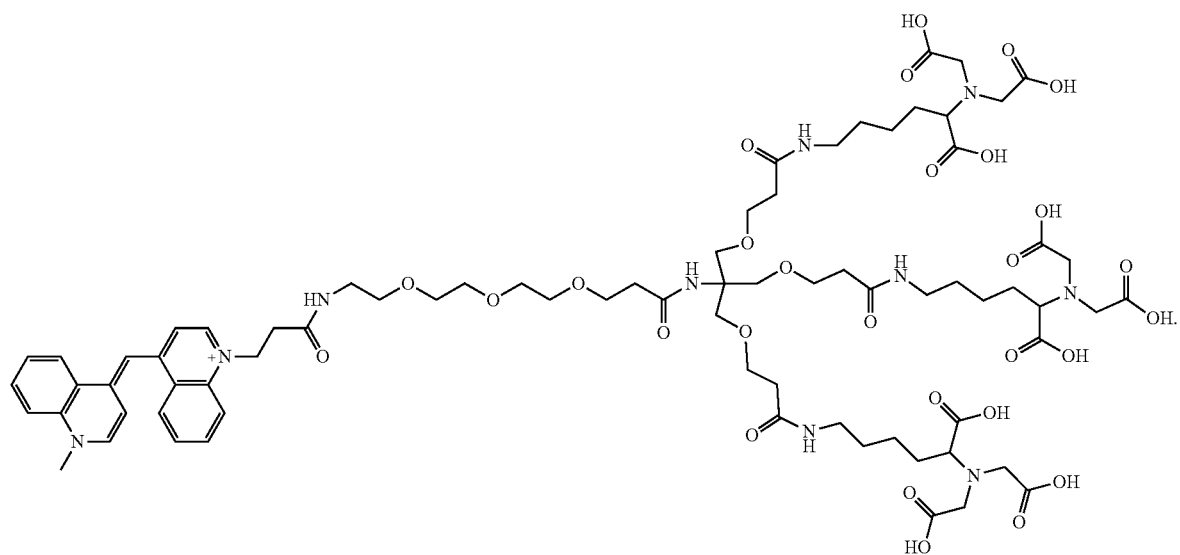
410

In some embodiments, a compound of any one of Formula XXX, XXXI and XXXIII, wherein QBC is thiazole red, is represented by the structure of Compounds 402, 405, and 409:
402
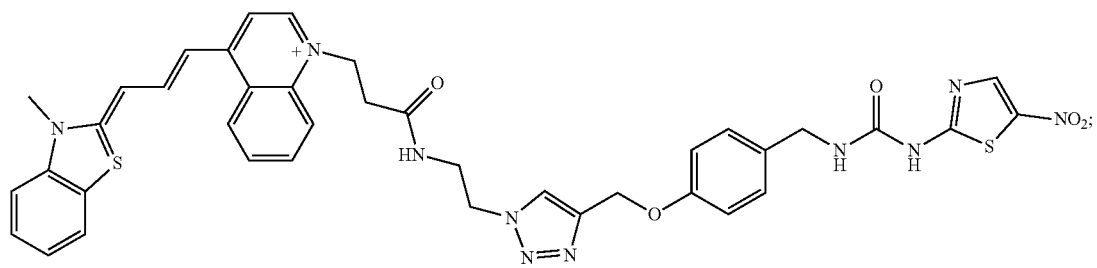
405
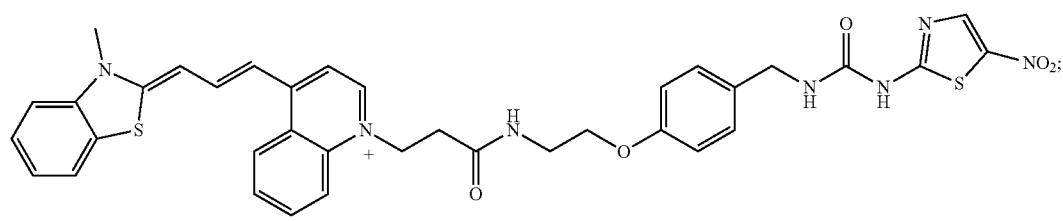
409
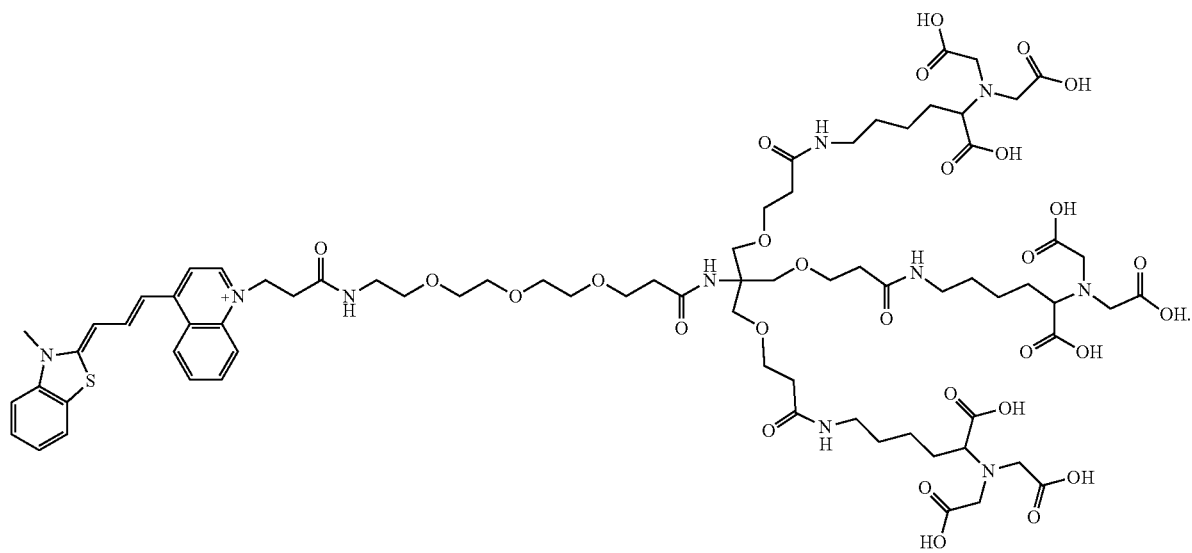
In some embodiments, a compound of any one of Formula XXX, XXXI and XXXIV, wherein QBC is thiazole orange, is represented by the structure of Compounds 401, 404, and 408:
401
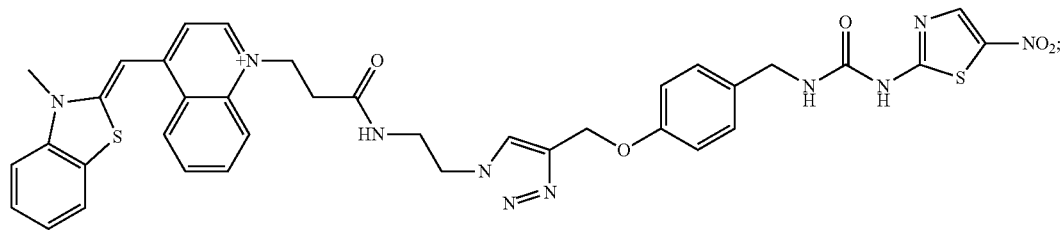

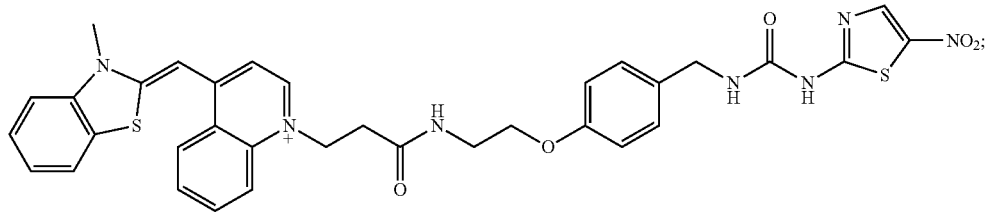

404

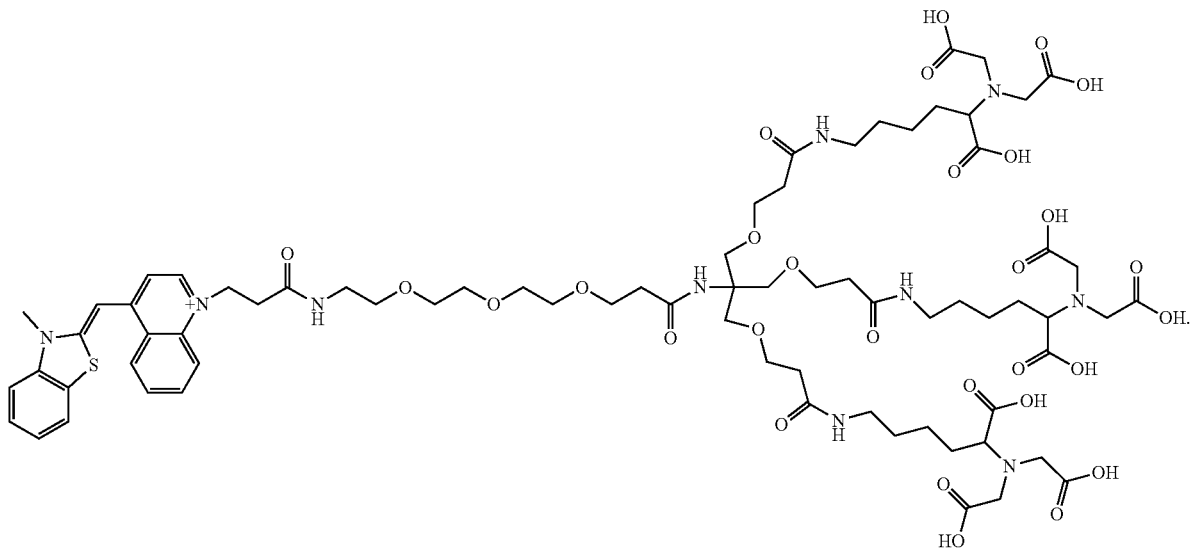

408

Applications of the Turn-on Fluorescent Molecular Probes of the Invention

This invention relates to the conversion of quinoline-based cyanine dyes: Thiazole orange (TO), Quinoline blue (QB), and Thiazole red (TR) into turn-on fluorescent probes (or sensors) for protein detection and imaging. Specifically, it is shown that attaching these dyes to specific protein binders affords a new class of fluorescent molecular sensors that light up upon binding to their protein targets; this enables their detection with high affinity, selectivity, and a high signal-to-noise (S/N) ratio.

In some embodiments, this invention provides a method of diagnosing a disease by detecting/identifying a protein in a biological medium comprising contacting a turn on probe of this invention and a protein, wherein contacting said protein and said probe results in restricted rotation of said probe and thereby to an enhancement in fluorescence signal, and thereby identifying/detecting said protein; wherein by detecting or identifying a protein biomarker in a biological medium said protein biomarker being characteristic of a disease; or measuring a change in a concentration of a protein biomarker in said sample compared to normative values, wherein said change is characteristic of a disease; thereby, diagnosing a disease in a subject.

In some embodiments, the turn-on probes are used for sensing the protein-of-interest (POI) in vitro and/or in living cells.

In some embodiments, the turn-on probes are used for imaging the POI in living cells with a minimal background signal.

In some embodiments, the turn-on probes are used for detecting in vitro and in living cells the binding of the POI to potential inhibitors.

In some embodiments, this invention relates to a method of detecting a protein of interest (POI) in a solution, said method comprises:
  a. measuring an optical signal of a compound according to this invention;
  b. placing said compound in said solution;
  c. re-measuring the optical signal of said compound in said solution,
wherein an enhancement in the optical signal of said compound indicates on the presence of said POI in said solution.

In some embodiments, the compound is compound of formula XXX, XXXI, XXXII, XXXIII, XXXIV, XXXV, XXXVI, or XXXVII; each represents a separate embodiment according to this invention. in some embodiments, the compound is any one of compounds 401-410; each represents a separate embodiment according to this invention.

In some embodiments, the optical signal is fluorescence emission. In some embodiments, the method is conducted without any subsequent washing steps. In some embodiments, the solution is a biological medium. In some embodiments, the solution is a buffer solution. In some embodiments, the biological medium is in is blood, serum, plasma, urine, saliva, tissue, peritoneal, stool, mucus, tear, sweat, biopsy, sperm or a cerebrospinal fluid sample; each represents a separate embodiment according to this invention. In some embodiments, the biological medium is within a cell. In some embodiments, the cell is a living cell, a fixed cell, a human cell, a recombinant primary culture cell, or a tissue culture cell; each represents a separate embodiment according to this invention. In some embodiments, the cell is comprised in a biological sample. In some embodiments, the protein of interest (POI) is a native protein, a recombinant protein, or an engineered protein; each represents a separate embodiment according to this invention. In some embodiments, the recombinant protein is a tagged protein. In some embodiments, the recombinant protein is a Histidine-tagged protein. In some embodiments, the native protein is lactate dehydrogenase A (LDHA), glycogen synthase kinase-3 (GSK-3), matrix metalloproteases (MMPs) protein and its isoforms, glutathione S-Transferase (GSTs) protein and its isoforms, platelet derived growth factor, Histidine-tagged proteins, estrogen receptor, fibroblast growth factor (FGF), caspases, PSA, fibronecin, lysozyme, β-amyloid, avidin, streptavidin, Acetylcholinesterase, histone deacetylases (HDACs), quorum sensing receptor, siderophore receptors, growth factor, membrane receptors, nuclear receptors, growth factor receptors, antibody, kinase, phosphatase or any protein to which a selective binder exists; each represents a separate embodiment according to this invention.

In some embodiments, this invention is directed to a method of detecting a protein of interest (POI) in a biological medium, said method comprises:
 a. measuring an optical signal of a fluorescent probe according to this invention;
 b. placing said fluorescent probe in said biological medium;
 c. re-measuring the optical signal of said probe in said biological medium,
wherein an enhancement in the optical signal of said probe indicates on the presence of said POI in said biological medium.

In some embodiments, the method is conducted without any subsequent washing steps. In some embodiments, the optical signal is fluorescence emission. In some embodiments, the fluorescence emission indicates on the presence of said POI in said biological medium. In some embodiments, the biological medium is blood, tissue, serum, or urine; each represents a separate embodiment according to this invention.

In some embodiments, the biological medium comprises living cells. In some embodiments, the POI is a native protein. In some embodiments, the native protein is a lactate dehydrogenase A (LDHA), glycogen synthase kinase-3 (GSK-3), matrix metalloproteases (MMPs) protein and its isoforms, glutathione S-Transferase (GSTs) protein and its isoforms, platelet derived growth factor, estrogen receptor, fibroblast growth factor (FGF), caspases, PSA, fibronecin, lysozyme, β-amyloid, avidin, streptavidin, Acetylcholinesterase, histone deacetylases (HDACs), quorum sensing receptor, siderophore receptors, growth factor, membrane receptors, nuclear receptors, growth factor receptors, antibody, kinase, phosphatase or any protein to which a selective binder exists; each represents a separate embodiment according to this invention. In some embodiments, the POI is an engineered protein. In some embodiments, the POI is a recombinant protein. In some embodiments, the recombinant protein is a Histidine-tagged protein.

In some embodiments, the GSK-3 is a biomarker for diabetes, cancer and/or neurodegenerative disorders.

In some embodiments, the compound is compound of formula XXX, XXXI, XXXII, XXXIII, XXXIV, XXXV, XXXVI, or XXXVII; each represents a separate embodiment according to this invention.

In some embodiments, the compound is any one of compounds 401-410; each represents a separate embodiment according to this invention.

In some embodiments, the method is useful in cell based high throughput screening (HTS) assays. In some embodiments, the cell is a living cell. In some embodiments, the method is useful in screening for potential modulators (i.e. agonists or antagonists) for said POI in vitro or in living cells. In some embodiments, the modulators are potential drugs.

Accordingly, this invention is further directed to a turn-on fluorescent probe for use in inhibitor screening assays, wherein said probe comprises a quinoline based cyanine dye (QBC) or derivative thereof, and a specific protein binder covalently attached thereto directly or via a linker. In some embodiments, a labelled substrate is not required for the screening assay. In some embodiments, the screening assay is a high-throughput assay.

In some embodiments, this invention is directed to a method for identifying a disease biomarker in a subject, said method comprises:
 (a) collecting a biological sample from a subject;
 (b) incubating said biological sample with a turn on fluorescent probe according to this invention;
 (c) measuring the fluorescence resulting from binding of said probe to a protein of interest (POI), which is a biomarker for a disease, in said sample;
wherein an enhancement in the emission intensity from said sample is an indicator of the presence of said POI in said sample.

In some embodiments, the method is conducted without any subsequent washing steps. In some embodiments, the disease is diabetes, cancer and/or neurodegeneragive disorder. In some embodiments, the POI is a lactate dehydrogenase A (LDHA), glycogen synthase kinase-3 (GSK-3), matrix metalloproteases (MMPs) protein and its isoforms, glutathione S-Transferase (GSTs) protein and its isoforms, platelet derived growth factor, a Histidine-tagged protein, estrogen receptor, fibroblast growth factor (FGF), caspases, PSA, fibronecin, lysozyme, β-amyloid, avidin, streptavidin, Acetylcholinesterase, histone deacetylases (HDACs), quorum sensing receptor, siderophore receptors, growth factor, membrane receptors, nuclear receptors, growth factor receptors, antibody, kinase, phosphatase or any protein to which a selective binder exists; each represents a separate embodiment according to this invention. In some embodiments, the POI is GSK-3. In some embodiments, the POI is LDHA.

In some embodiments, the compound is compound of formula XXX, XXXI, XXXII, XXXIII, XXXIV, XXXV, XXXVI, or XXXVII; each represents a separate embodiment according to this invention. in some embodiments, the compound is any one of compounds 401-410; each represents a separate embodiment according to this invention.

In some embodiments, this invention is directed to a method of identifying a compound that binds a protein of interest (POI), said method comprises:
 a. incubating a turn of fluorescent probe according to this invention, with a POI in solution;
 b. measuring the fluorescence intensity of said solution;
 c. adding a test compound to said solution;
 d. re-measuring the fluorescence intensity of said solution; and
 e. determining binding of said test compound to said POI based on a change in fluorescence intensity, wherein decreased fluorescent intensity indicates binding of said test compound to said POI;
thereby identifying a compound that binds said POI.

In some embodiments, the compound is compound of formula XXX, XXXI, XXXII, XXXIII, XXXIV, XXXV, XXXVI, or XXXVII; each represents a separate embodiment according to this invention. in some embodiments, the compound is any one of compounds 401-410; each represents a separate embodiment according to this invention.

In some embodiments, the method is conducted without any subsequent washing steps. In some embodiments, the test compound is a potential drug. In some embodiments, the test compound is a potential modulator of said POI. In some embodiments, the POI is a matrix metalloproteases (MMPs) protein and its isoforms, glutathione S-Transferase (GSTs) protein and its isoforms, platelet derived growth factor, Histidine-tagged proteins, estrogen receptor, fibroblast growth factor (FGF), caspases, PSA, fibronecin, lysozyme, β-amyloid, avidin, streptavidin, Acetylcholinesterase, histone deacetylases (HDACs), glycogen synthase kinase-3 (GSK-3), lactate dehydrogenase A (LDHA), quorum sensing receptor, siderophore receptors, growth factor, membrane receptors, nuclear receptors, growth factor receptors, antibody, kinase, phosphatase or any protein to which a selective binder exists; each represents a separate embodiment according to this invention.

In some embodiments, this invention is directed to a method for imaging a protein of interest (POI) within a cell, said method comprises:
  a. incubating cells comprising said POI with a turn-on fluorescent probe according to this invention;
  b. visualizing the fluorescence emission of said cells;
wherein an enhancement in the fluorescence emission is indicative of binding of said probe to a protein of interest (POI) in said cells.

In some embodiments, the cells are living cells. In some embodiments, the method is useful in cellular imaging. In some embodiments, a labelled substrate is not required for the cellular imaging. In some embodiments, the method is conducted without any subsequent washing steps.

In some embodiments, the turn-on probe is represented by the structure of formula XXXI-XXXVII described herein below. In some embodiments, the probe is represented by the structure of compounds 401-410; each represents a separate embodiment according to this invention.

In some embodiments, the methods of this invention further comprise detecting, identifying specific protein isoforms or differentiating between proteins and protein isoforms.

In some embodiments, the compounds, probes and methods of use thereof comprise a specific protein binder. In some embodiments, the specific protein binder is as described hereinabove. In some embodiments, the specific protein binder is GSK-3 inhibitor (e.g., AR-A014418), LDHA inhibitor (e.g., AZ-33), marimastat, ethacrynic acid, bisethacrynic acid, complexed nitrilotriacetic acid (NTA), complexed bis NTA, complexed tris-NTA, Ni-nitrilotriacetic acid (Ni-NTA), bis Ni-NTA, tris-Ni-NTA, PDGF-BB, heparin, FGF aptamer, estrogen, DNA aptamer, RNA aptamer, peptide aldehyde, estrogen, suberoylanilidehydroxamic acid (SAHA), biotin, tacrine, autoinducer, siderophore, folate, anisamide, antibody, antigen or a peptide binder. In other embodiments, said specific protein binder is marimastat, ethacrynic acid, bisethacrynic acid, complexed nitrilotriacetic acid (NTA), complexed bis NTA, complexed tris-NTA, Ni-nitrilotriacetic acid (Ni-NTA), bis (Ni-NTA), tris (Ni-NTA), PDGF-BB, biotin, tacrine, heparin or estrogen; each represents a separate embodiment according to this invention. In some embodiments, the complexed NTA, complexed bis-NTA, complexed tris NTA is a nickel or cobalt complex.

In some embodiments, the GSK-3 inhibitor is selective to GSK-3 protein. In some embodiments, the LDHA inhibitor is selective to LDHA protein. In some embodiments, the ethacrynic acid or bisethacrynic acid is selective to glutathione S-Transferase (GSTs) protein. In some embodiments, Ni-nitrilotriacetic acid (Ni-NTA), bis-Ni-NTA or tris-Ni-NTA is selective to a His-tag protein. In some embodiments, Co-nitrilotriacetic acid (Co-NTA), bis-Co-NTA or tris-Co-NTA is selective to a His-tag protein In some embodiments, the PDGF-BB, heparin and estrogen are selective to platelet derived growth factor, fibroblast growth factor and to estrogen receptor, respectively. In some embodiments, the tacrine is selective to Acetylcholinesterase (AChE) protein. In some embodiments, the biotin is selective to avidin and/or streptavidin.

In certain embodiments, the DNA aptamer is selective to lysozyme. In some embodiments, said peptide binder is selective to firbronectin or β-amyloid. In some embodiments, the DNA or RNA aptamer is selective to PSA. In some embodiments, the peptide aldehyde is selective to caspases and the SAHA is selective to histone deacetylases (HDACs).

In some embodiments, the methods of this invention comprise diagnosing, detecting, identifying and/or differentiating between proteins and protein isoforms. In some embodiments, the detecting/identifying is performed by obtaining a fluorescence emission signal due to the interaction of the protein of interest (POI) and the sensor of this invention.

In some embodiments, said fluorescence signal indicates the presence of said protein of interest (POI) in said biological medium. In some embodiments, said fluorescence signal enhancement indicates the presence of said protein in said biological medium.

In some embodiments, the compounds, sensors, and/or turn-on probes according to this invention, are used in live cell-based, high-throughput screening (HTS) assays for detecting new inhibitors (e.g., potential new drugs).

In some embodiments, this invention is directed to a method of identifying a binding partner of protein of interest (POI), said method comprises:
  a. incubating a compound according to this invention with a tagged POI in solution, wherein said compound comprises a tag binding region;
  b. measuring the fluorescence intensity of said solution;
  c. adding a test compound to said solution;
  d. remeasuring the fluorescence intensity of said solution; and
  e. determining binding of said test compound to said tagged POI based on a change in fluorescence intensity, wherein decreased fluorescent intensity indicates binding of said test compound;
thereby identifying said binding partner for said POI.

In some embodiments, the method is conducted without any subsequent washing steps.

In some embodiments, the compound is compound of formula XXX, XXXI, XXXII, XXXIII, XXXIV, XXXV, XXXVI, or XXXVII; each represents a separate embodiment according to this invention. in some embodiments, the compound is any one of compounds 401-410; each represents a separate embodiment according to this invention.

In some embodiments, this invention is directed to a method of identifying binding partners of protein of interest (POI) in a complex environment, said method comprises:
  a. incubating a compound according to this invention with a tagged POI in solution, wherein said compound comprises a tag binding region;
  b. measuring the fluorescence intensity of said solution;
  c. adding a complex environment comprising a test compound to said solution;
  d. remeasuring the fluorescence intensity of said solution; and e. determining binding of said test compound in complex environment to said tagged POI based on a change in fluorescence intensity, wherein decreased fluorescent intensity indicates binding of said test compound;

thereby identifying a binding partner for said POI in a complex environment.

In some embodiments, said tagged-POI comprises an affinity tag. In some embodiments, said tagged-POI comprises any tag known in the art. Non limiting examples for tag are: His-tag, FLAG tag, HA tag, C-myc tag, AviTag, Calmodulin-tag, polyglutamate tag, E-tag, Myc-tag, S-tag, SBP-tag, Softag, Strep-tag, TC tag, V5 tag, VSV-tag, Xpress tag, etc. In some embodiments, said tagged-POI comprises a polyhistidine tag (His-tag). In some embodiments, said polyhistidine tag (His-tag) comprises a 6×His-tag. In some embodiments, said polyhistidine tag (His-tag) comprises a 10×His-tag. In some embodiments, said polyhistidine tag (His-tag) comprises at least six histidine residues. In some embodiments, said tagged-POI comprises a FLAG-tag. In some embodiments, a FLAG-tag label is a multi-FLAG tag. In some embodiments, a FLAG tag is a dimmer (2×). In some embodiments, a FLAG tag is a 3× tag. In some embodiments, said tagged-POI comprises a c-myc tag. In some embodiments, said tag does not interfere with a protein's tertiary structure. In some embodiments, said tag does not interfere with a proteins quaternary structure.

In some embodiments, the binding partner is a protein. In some embodiments, the binding partner is a peptide. In some embodiments, the binding partner is a synthetic molecule. In some embodiments, the binding partner is a small molecule. In some embodiments, the binding partner is a drug. Each possibility comprises an embodiment of this invention.

In some embodiments, the compound is compound of formula XXX, XXXI, XXXII, XXXIII, XXXIV, XXXV, XXXVI, or XXXVII; each represents a separate embodiment according to this invention. in some embodiments, the compound is any one of compounds 401-410; each represents a separate embodiment according to this invention.

In some embodiments, this invention is directed to a method of measuring the expression level of a His-tagged polypeptide in a cell, said method comprising the steps of:
a. expressing a His-tagged polypeptide in a cell;
b. incubating the cell with a His-tag binding compound according to this invention; and
c. measuring the fluorescence of said cell;
wherein detection of a fluorescent signal is dependent on the formation of a His-tagged polypeptide:compound complex.

In some embodiments, said tag binding region is a His-tag binder according to this invention. In some embodiments, said His-tagged polypeptide comprises a polyhistidine-tag.

In some embodiments, said compound comprises a fluorophore according to this invention. In some embodiments, said fluorescence is measured over time. In some embodiments, said measuring is of a live cell. In some embodiments, said measuring of is a fixed cell. In some embodiments, said cell is a human cell. In some embodiments, said cell is a recombinant primary culture cell. In some embodiments, said cell is a tissue culture cell. In some embodiments, said cell is a living cell.

In some embodiments, the compound is compound of formula XXX, XXXI, XXXII, XXXIII, XXXIV, XXXV, XXXVI, or XXXVII; each represents a separate embodiment according to this invention. in some embodiments, the compound is any one of compounds 401-410; each represents a separate embodiment according to this invention.

In some embodiments, this invention is directed to a method of localizing and/or imaging a His-tagged polypeptide of interest within a cell, said method comprises the steps of:
a. expressing said His-tagged polypeptide in a recombinant cell;
b. incubating said recombinant cell with a His-tag binding compound according to this invention; and
c. visualizing the fluorescence emission of said sensor.

In some embodiments, said recombinant cell is fixed using any method known in the art, prior to the incubating step. In some embodiments, the compound passively crosses the plasma membrane of a live cell. In some embodiments, the compound is micro-injected into a live cell. In some embodiments, the compound is derivatized in a way that allows its crossing of the plasma membrane of a live cell. In some embodiments, said visualizing is observing under a microscope. In some embodiments, a fluorescent microscope is used to detect and localize the fluorescent signal. In some embodiments, a fluorescent microscope with a plate reader or the ability to record images at multiple locations over time is used to detect and localize the fluorescent signal.

In some embodiments, the compound is compound of formula XXX, XXXI, XXXII, XXXIII, XXXIV, XXXV, XXXVI, or XXXVII; each represents a separate embodiment according to this invention. in some embodiments, the compound is any one of compounds 401-410; each represents a separate embodiment according to this invention.

Universal His-Tag Binding Compounds.

In some embodiments, this invention is directed to a universal building block for preparing various His-tag-binding compounds and genetically targeted sensors.

The His-tag binding compound (or building block) according to this invention, comprises three nitrilotriacetic acid (NTA) units that upon complexation with nickel (II) or other metal ions, can bind an oligohistidine sequence of a polypeptide (His-tag) with low nanomolar affinities. The compound of the invention, also comprises an auxiliary unit ($R_1$, as described herein below), a functional group, that enables one to modify it using a wide range of functionalities. This building block is general for various protein binders, DNA binders and sensors, and can be easily modified through the auxiliary unit to bind to various synthetic agents, labeling moieties, solid support, oligonucleotides and detectable groups.

This invention is therefore directed to a universal His-tag binding compounds as well as to their building blocks and precursors, that upon complexation with metal ions (e.g., Ni(II), Co(II), or Co(III)) can selectively bind histidine-tags of various labeled proteins with nanomolar affinities. Therefore, the His tag binding compounds, and their building blocks and precursors according to this invention, are useful in the preparation of various fluorescent probes and genetically targeted sensors for various applications as described herein below.

In some embodiments, the compound, is represented by the structure of formula XI:

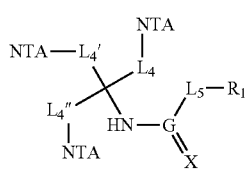

wherein
R₁ is selected from: H, azide, amine, $C_2$-$C_6$ alkynyl, $C_2$-$C_6$ alkenyl, thioester, disulfide, maleimide, biotin, carboxyl, thiol, triazole, alkylamide, ketone, aldehyde and carbamate;
or R₁ is selected from:

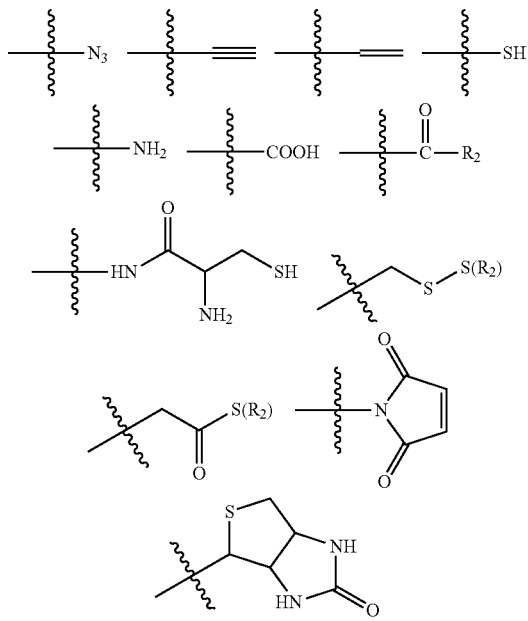

wherein
R₂ is hydrogen, substituted or unsubstituted linear or branched $C_1$-$C_{12}$ alkyl, substituted or unsubstituted linear or branched $C_1$-$C_{12}$ arylalkyl or benzyl;
G=X is absent, or is $CH_2$, C=O, C(O)NH, C=S, C(S)NH, C(O)O, S=O or $SO_2$;
L₄, L₄', and L₄" are each independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof,
L₅ is absent, or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof; and
NTA is nitrilotriacetic acid or a protected derivative thereof.

In some embodiments, the compound is represented by the structure of formula XII:

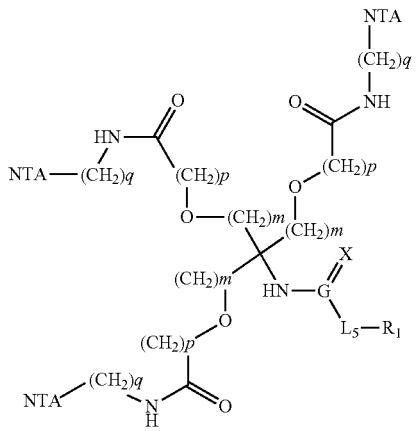

XII wherein
R₁ is selected from: H, azide, amine, $C_2$-$C_6$ alkynyl, $C_2$-$C_6$ alkenyl, thioester, disulfide, maleimide, biotin, carboxyl, thiol, triazole, alkylamide, ketone, aldehyde and carbamate;
or R₁ is selected from:

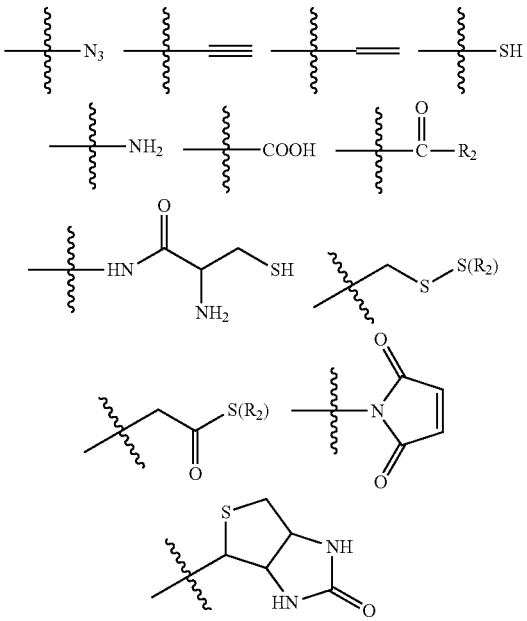

wherein
R₂ is hydrogen, substituted or unsubstituted linear or branched $C_1$-$C_{12}$ alkyl, substituted or unsubstituted linear or branched $C_1$-$C_{12}$ arylalkyl or benzyl;
m, p and q are each independently an integer number between 1 and 8; and
G=X is absent, or is $CH_2$, C=O, C(O)NH, C=S, C(S)NH, C(O)O, S=O or $SO_2$;
L₅ is absent or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof, and NTA is nitrilotriacetic acid or a protected derivative thereof.

In some embodiments, the compound is represented by the structure of formula XIII:

XIII

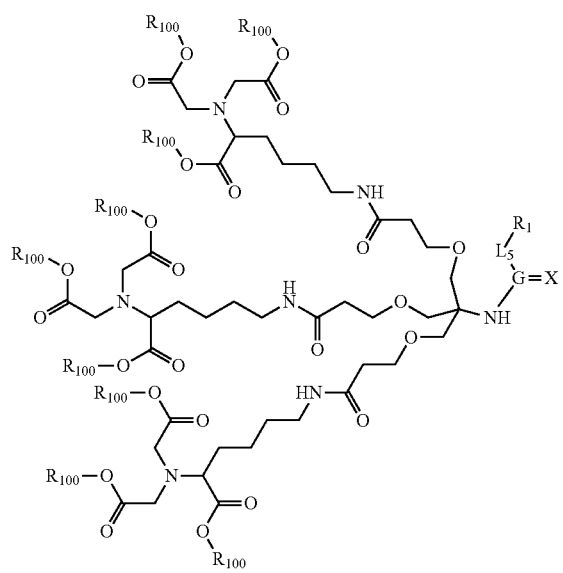

wherein $R_{100}$ is a protecting group;

$R_1$ is selected from: H, azide, amine, $C_2$-$C_6$ alkynyl, $C_2$-$C_6$ alkenyl, thioester, disulfide, maleimide, biotin, carboxyl, thiol, triazole, alkylamide, ketone, aldehyde and carbamate;

or $R_1$ is selected from:

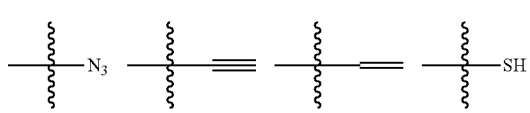

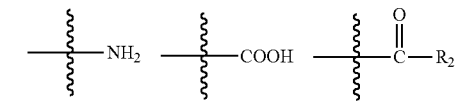

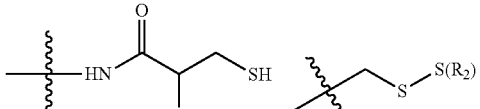

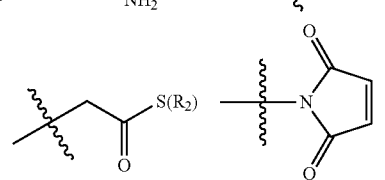

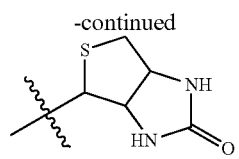

wherein $R_2$ is hydrogen, substituted or unsubstituted linear or branched $C_1$-$C_{12}$ alkyl, substituted or unsubstituted linear or branched $C_1$-$C_{12}$ arylalkyl or benzyl;

G=X is absent, or is $CH_2$, C=O, C(O)NH, C=S, C(S)NH, C(O)O, S=O or $SO_2$;

$L_5$ is absent or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof.

In some embodiments, the compound is represented by the structure of formula XIV:

XIV

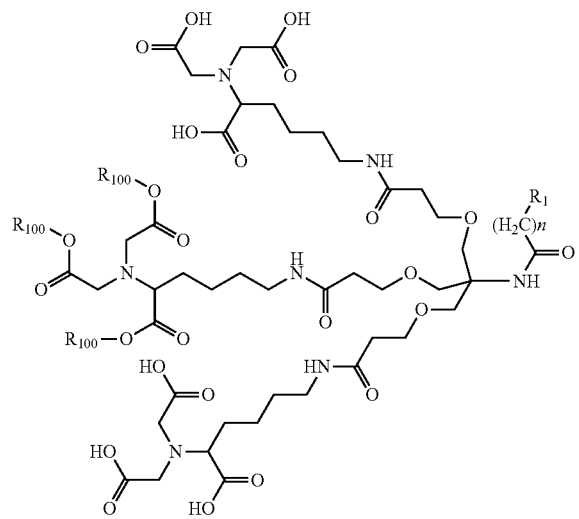

wherein $R_1$ is selected from: H, azide, amine, $C_2$-$C_6$ alkynyl, $C_2$-$C_6$ alkenyl, thioester, disulfide, maleimide, biotin, carboxyl, thiol, triazole, alkylamide, ketone, aldehyde and carbamate;

or $R_1$ is selected from:

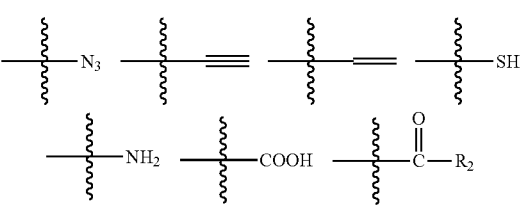

-continued

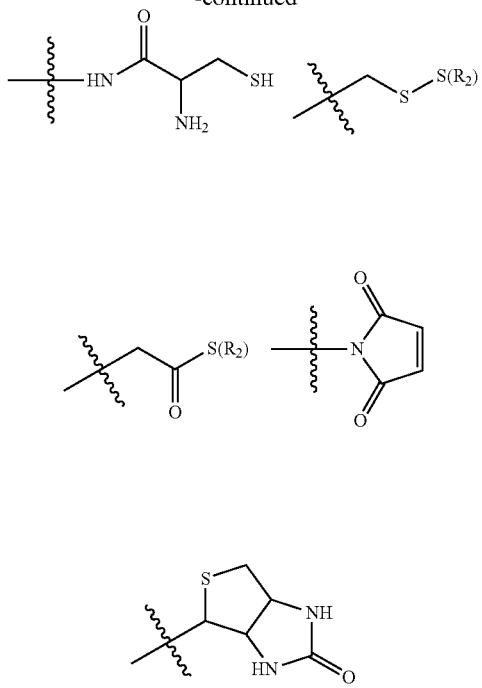

wherein
- $R_2$ is hydrogen, substituted or unsubstituted linear or branched $C_1$-$C_{12}$ alkyl, substituted or unsubstituted linear or branched $C_1$-$C_{12}$ arylalkyl or benzyl; and
- n is an integer between 0 and 20 (e.g., 2).

In some embodiments, the compound is represented by the structure of formula XV:

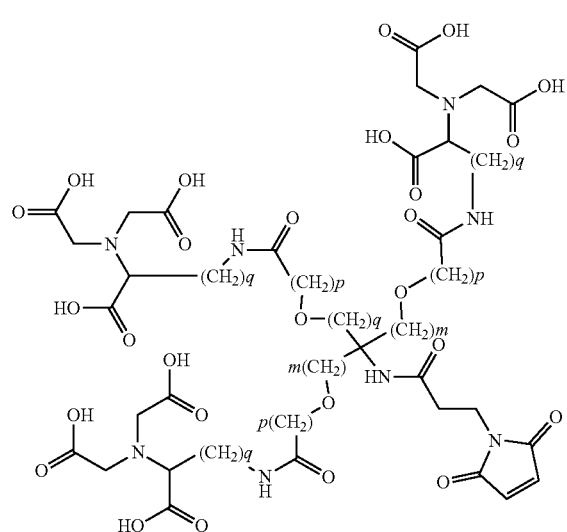

XV wherein
- m, p and q are each independently an integer number between 1 and 8.

In some embodiments, the compound is represented by the structure of formula XVI:

XVI wherein
- $R_{100}$ is H or a protecting group.

In some embodiments, upon complexation to a metal ion, compound of formula XI-XVI can selectively bind an oligohistidine sequence of various His-tagged polypeptides and proteins. In some embodiments, the metal ion is cobalt (Co). In some embodiments, the metal ion is nickel (Ni). In some embodiments, the metal ion is Ni(II). In some embodiments, the metal ion is Co(II). In some embodiments, the metal ion is Co(III).

Specific Embodiments for His-Tag Binding Compounds of the Invention

In some embodiments, the compound according to this invention is a His-tag binding compound. In some embodiments, the compound according to this invention is a His-tag binding compound precursor.

In some embodiments, $R_1$ of formula XI-XIV is a functional group. In some embodiments, $R_1$ of compound of formula XI-XIV is H. In some embodiments, $R_1$ is azide. In some embodiments, $R_1$ is amine.

In some embodiments, $R_1$ is $C_2$-$C_6$ alkynyl. In some embodiments, $R_1$ is $C_2$-$C_6$ alkenyl. In some embodiments, $R_1$ is ketone. In some embodiments, $R_1$ is aldehyde. In some embodiments, $R_1$ is thioester. In some embodiments, $R_1$ is disulfide. In some embodiments, $R_1$ is maleimide. In some embodiments, $R_1$ is biotin. In some embodiments, $R_1$ is carboxyl. In some embodiments, $R_1$ is thiol. In some embodiments, $R_1$ is triazole. In some embodiments, $R_1$ is alkylamide. In some embodiments, $R_1$ is carbamate. In some embodiments, $R_1$ is In some embodiments, $R_1$ is

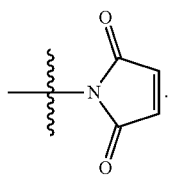 [SMILES: *N1C(=O)C=CC1=O]

In some embodiments, $R_1$ is

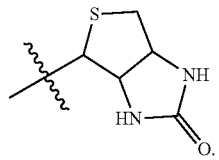 [SMILES: *C1SCC2NC(=O)NC21]

In some embodiments, $R_1$ is

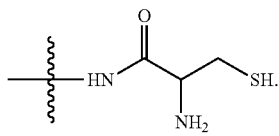

In some embodiments, $R_1$ is

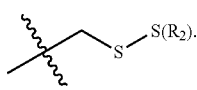

In some embodiments, $R_1$ is

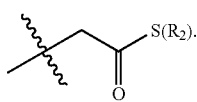

In some embodiments, $R_2$ of formula XI-XIV is a hydrogen. In some embodiments, substituted or unsubstituted linear or branched arylalkyl. In some embodiments, unsubstituted linear arylalkyl. In some embodiments, benzyl (i.e., —CH$_2$-Ph). In some embodiments, substituted or unsubstituted linear or branched $C_1$-$C_{12}$ alkyl. In some embodiments, unsubstituted linear $C_1$-$C_6$ alkyl. In some embodiments, methyl. In some embodiments, propyl. In some embodiments, ethyl. In some embodiments, t-Butyl. In some embodiments, hexyl. In some embodiments, $C_1$-$C_{12}$ haloalkyl. In some embodiments, $CF_3$.

In some embodiments, NTA of compound of formula XI and XII, is nitrilotriacetic acid. In some embodiments, NTA is a protected derivative of nitrilotriacetic acid. Non limiting examples for protecting groups of carboxylic acids include but are not limited to: methyl esters, benzyl esters, tert-butyl esters, esters of 2,6-disubstituted phenols (e.g. 2,6-dimethylphenol, 2,6-diisopropylphenol, 2,6-di-tert-butylphenol), silyl esters, orthoesters, and oxazoline; each represents a separate embodiment according to this invention.

In some embodiments, NTA is represented by the structure of fragment (A):

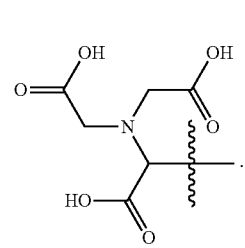

In some embodiments, NTA or a protected derivative of NTA is represented by the structure of fragment (B):

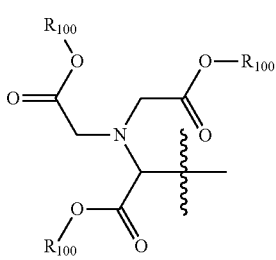

wherein $R_{100}$ is H or a protecting group.

In some embodiments, a protected derivative of NTA is represented by the structure of fragment (B):

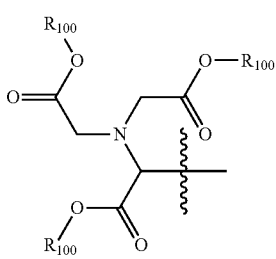

wherein $R_{100}$ is a protecting group.

In some embodiments, $R_{100}$ of fragment (B), is H. In some embodiments, $R_{100}$ of fragment (B), is a protecting group. In some embodiments, $R_{100}$ of fragment (B), is a substituted or unsubstituted linear, branched or cyclic $C_1$-$C_{10}$ alkyl. In some embodiments, $R_{100}$ is an unsubstituted linear, branched or cyclic $C_1$-$C_{10}$ alkyl. In some embodiments, $R_{100}$ is H. In some embodiments, $R_{100}$ is tert-butyl. In some embodiments, $R_{100}$ is iso-propyl. In some embodiments, $R_{100}$ is ethyl. In some embodiments, $R_{100}$ is methyl.

In some embodiments, $R_{100}$ is neo-pentyl. In some embodiments, $R_{100}$ is cyclopropyl. In some embodiments, $R_{100}$ is cyclohexyl. In some embodiments, $R_{100}$ is a substituted linear, branched or cyclic $C_1$-$C_{10}$ alkyl. In some embodiments, $R_{100}$ is benzyl. In some embodiments, $R_{100}$ is a substituted or unsubstituted aryl.

In some embodiments, a protected derivative of NTA is represented by the structure of fragment (C):

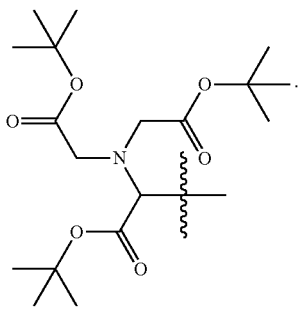

(C)

In some embodiments, the compound according to this invention is a His-tag binding compound precursor. In some embodiments, $R_{100}$ of fragment (B) is tert-Bu, G=X is absent, $L_5$ is absent, $R_1$ is H, or any combination thereof, each represents a separate embodiment according to this invention.

In some embodiments, G=X of compound of formula XI-XIII is absent. In some embodiments, G=X is C=O. In some embodiments, G=X is $CH_2$. In some embodiments, G=X is C(O)NH. In some embodiments, G=X is C(S)NH. In some embodiments, G=X is C(O)O. In some embodiments, G=X is C=S. In some embodiments, G=X is S=O. In some embodiments, G=X is $SO_2$.

In some embodiments, each of $L_4$, $L_4'$, and $L_4''$ of the structure of formula XI, is independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof, each represents a separate embodiment according to this invention. In some embodiments, each of $L_4$, $L_4'$, and $L_4''$ is a combination of alkyl ether and alkyl amide (i.e., alkylether-alkylamide). In some embodiments, each of $L_4$, $L_4'$, and $L_4''$ is independently —$(CH_2)_q$—NHCO—$(CH_2)_p$—O—$(CH_2)_m$—, wherein q, p and m are each independently an integer between 1 and 8. In some embodiments, q is 4, p is 2 and m is 1. In some embodiments, each of $L_4$, $L_4'$, and $L_4''$ is-$(CH_2)_4$—NHCO—$(CH_2)_2$O—$CH_2$—. In some embodiments, each of $L_4$, $L_4'$, and $L_4''$ is represented by the following structure:

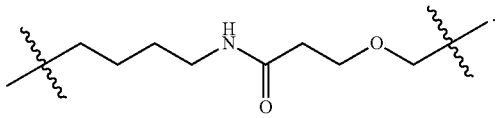 [SMILES: *CCCCNC(=O)CCOC*]

In some embodiments, $L_4$, $L_4'$ and $L_4''$ are different. In some embodiments, $L_4$, $L_4'$ and $L_4''$ are the same. In some embodiments, $L_4$ and $L_4'$ are the same and $L_4''$ is different. In some embodiments, $L_4$ and $L_4''$ are the same and $L_4'$ is different. In some embodiments, $L_4'$ and $L_4''$ are the same and $L_4$ is different.

In some embodiments, $L_5$ of the structures of formulas XI-XIII is absent. In other embodiments, $L_5$ is a substituted or unsubstituted linear or branched alkyl chain of 1-50 carbon atoms. In other embodiments, $L_5$ is a linear alkyl of 2-6 carbon atoms. In other embodiments, $L_5$ is ethylene. In other embodiments, $L_5$ is propylene. In other embodiments, $L_5$ is butylene. In other embodiments, $L_5$ is methylene. In other embodiments, $L_5$ is $(CH_2)_n$, wherein n is an integer between 1 and 8; in some embodiments n is 1, 2, 3, 4, 5, 6, 7, or 8; each is a separate embodiment according to this invention. In other embodiments, $L_5$ is-$CH_2$—$CH_2$—. In other embodiments, $L_5$ is a substituted or unsubstituted linear or branched alkyl ether chain of 1-50 carbon atoms. In other embodiments, $L_5$ is substituted or unsubstituted linear or branched alkyl phosphate chain of 1-50 carbon atoms. In other embodiments, $L_5$ is substituted or unsubstituted linear or branched alkyl amide chain of 1-50 carbon atoms. In other embodiments, $L_5$ is substituted or unsubstituted linear or branched alkyl diamide chain of 1-50 carbon atoms. In other embodiments, $L_5$ is substituted or unsubstituted linear or branched alkyl amine chain of 1-50 carbon atoms. In other embodiments, $L_5$ is any combination of the embodiments above.

In some embodiments, m of the structure of formula XII or XV is 1. In some embodiments, m is 2. In some embodiments, m is 3. In some embodiments, m is 4.

In some embodiments, p of the structure of formula XII or XV is 1. In some embodiments, p is 2. In some embodiments, p is 3. In some embodiments, p is 4.

In some embodiments, q of the structure of formula XII or XV is 1. In some embodiments, q is 2. In some embodiments, q is 3. In some embodiments, q is 4. In some embodiments, q is 5. In some embodiments, q is 6.

In some embodiments, m is 1, p is 2 and q is 4.

In some embodiments, n of the structure of formula XIV is 1. In some embodiments, n is 2. In some embodiments, n is 3. In some embodiments, n is 4.

In some embodiments, this invention is directed to a His-tag binding compound of formula XI-XIV, coupled through the $R_1$ moiety to an oligonucleotide, a peptide, a protein, a labeling moiety, a drug, a solid support, a small molecule, or any combination thereof. In some embodiments, this invention is directed to a His-tag binding compound of formula XV, coupled through the maleimide moiety to an oligonucleotide, a peptide, a protein, a labeling moiety, a drug, a solid support, a small molecule, or any combination thereof. In some embodiments, this invention is directed to a His-tag binding compound of formula XVI, coupled through the $NH_2$ moiety to an oligonucleotide, a peptide, a protein, a labeling moiety, a drug, a solid support, a small molecule, or any combination thereof. In some embodiments, the oligonucleotide is DNA. In some embodiments, the oligonucleotide is RNA. In some embodiments, the labeling moiety is as described hereinbelow. In some embodiments, the labeling moiety is a quinoline based cyanine dye (QBC). In some embodiments, the QBC is TO, TR or QB; each represents a separate embodiment according to this invention. In some embodiments, the labeling moiety is a fluorescent dye. Examples of fluorescent dyes include but are not limited to: dansyl, fluorescein (6-FAM), FAM, cyanine dyes (e.g. Cy3, Cy5), sulfoindocyanine, SCy5, Nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or derivative thereof. In some embodiments, the dye is FITC. In some embodiments, the dye is Nile Red. In some embodiments, the dye is SCy5. In some embodiments, the dye is Thiazole orange, Quinoline blue, Thiazole red, or derivative thereof. In some embodiments, the labeling moiety is a solvatochromic dye.

In some embodiments, the His-tag binding compound of formula XVI, coupled through the $NH_2$ moiety to a labeling moiety, is represented by the structure of formula XXXV-XXXVII as described hereinabove.

In some embodiments, the small molecule is a therapeutically active molecule.

Fluorescent Probes for Sensing and Imaging Comprising His-Tag Binding Compounds of the Invention.

In some embodiments, this invention if directed to a compound according to this invention, or a derivative thereof, coupled to a labeling moiety as described hereinbelow.

As used herein, "labeling moieties" or "labels" are chemical or biochemical moieties useful for labeling a compound. Such labeling moieties include fluorescent agents, quinoline-based cyanine dyes, chemiluminescent agents, chromogenic agents, quenching agents, radionucleotides, enzymes, substrates, cofactors, inhibitors, nanoparticles, magnetic particles, and other moieties known in the art. Labels are capable of generating a measurable signal and may be covalently or noncovalently joined to a his-tag compound according to this invention. In some embodiments, the labeling moieties are covalently bound to the compounds of the invention. In some embodiments, the labeling moieties are covalently bound to the compounds of the invention through a linker or a spacer.

In illustrative embodiments, the compounds according to this invention, may be labeled with a "fluorescent dye", a "fluorophore" or "quinoline-based cyanine dyes". As used herein, a "fluorescent dye", "fluorophore" or "quinoline-based cyanine dyes" is a chemical group that can be excited by light to emit fluorescence. Some fluorophores may be excited by light to emit phosphorescence. Dyes may include acceptor dyes that are capable of quenching a fluorescent signal from a fluorescent donor dye. In some embodiments, a "quinoline-based cyanine dyes" used in this invention, comprises quinoline derivative of fluorescent dye. In some embodiments, a "quinoline-based cyanine dyes" used in this invention are also "turn-on fluorescent". In some embodiments, the "quinoline-based cyanine dyes" comprises Thiazole orange (TO), Quinoline blue (QB), and Thiazole red (TR). In some embodiments, the dye is selected from: dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or a derivative thereof. Non limiting examples of Dyes that may be used in the disclosed compounds, system and methods include, but are not limited to, the following dyes and/or dyes sold under the following trade names: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-Hydroxy Tryptamine (HAT); 5-ROX (carboxy-X-rhodamine); 6-Carboxyrhodamine 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™_3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue™; Calcium Crimson™; Calcium Green; Calcium Orange; Calcofluor White; Cascade Blue™; Cascade Yellow; Catecholamine; CCF2 (GeneBlazer); CFDA; CFP-Cyan Fluorescent Protein; CFP/YFP FRET; Chlorophyll; Chromomycin A; CL-NERF (Ratio Dye, pH); CMFDA; Coelenterazine f, Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3. 1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF;

Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant Iavin EBG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO—PRO-1; YO—PRO-3; YOYO-1; YOYO-3; and salts thereof; each is a separate embodiment according to this invention.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

In some embodiments, the labeling moiety on the compounds according to the invention, is a quencher. Quenching may include dynamic quenching (e.g., by FRET), static quenching, or both. Illustrative quenchers may include Dabcyl. Illustrative quenchers may also include dark quenchers, which may include black hole quenchers sold under the tradename "BHQ" (e.g., BHQ-0, BHQ-1, BHQ-2, and BHQ-3, Biosearch Technologies, Novato, Calif.). Dark quenchers also may include quenchers sold under the tradename "QXL™" (Anaspec, San Jose, Calif). Dark quenchers also may include DNP-type non-fluorophores that include a 2,4-dinitrophenyl group.

The labels can be conjugated to the compounds according to this invention directly, or indirectly through linkers or spacers, by a variety of techniques. In some embodiments, the labeling moiety is a fluorescent agent, fluorescent dye, fluorophore, solvatochromic dye, chemiluminescent agent, chromogenic agent, quenching agent, radionucleotide, or a magnetic particle; each is a separate embodiment according to this invention.

In some embodiments, the labeling moiety is a fluorescent dye. In some embodiments, the labeling moiety is a quinoline based cyanine dye (QBC). In some embodiments, the QBC is TO, TR or QB; each represents a separate embodiment according to this invention. In some embodiments, the QBC is a derivative of TO, TR or QB; each represents a separate embodiment according to this invention, wherein the term derivative is as described hereinabove. In some embodiments, the labeling moiety is covalently bound to the compound. In some embodiments, the labeling moiety is covalently bound to the compound via a first linker. In some embodiments, the compound is further complexed with at least one metal ion. In some embodiments, upon complexation to at least one metal ion, the compound can selectively bind histidine-tags of various labeled proteins, thereby becoming a His-tag binding compound. In some embodiments, the His-tag binding compound is a molecular probe for fluorescence sensing and imaging. In some embodiments, the His-tag binding compound is a turn on fluorescent probe as defined hereinabove. In some embodiments, the His-tag binding compound is a fluorescent probe. In some embodiments, the His-tag binding compound does not perturb living cells function. In some embodiments, the His-tag binding compound is capable of traversing a biological membrane. In some embodiments, the His-tag binding compound is a genetically targeted sensor.

In some embodiments, this invention if directed to a small molecule probe for fluorescence sensing and imaging, comprising a His-tag binding compound according to this invention, or a derivative thereof, complexed to at least one metal ion.

In some embodiments, this invention if directed to a genetically targeted sensor, comprising a His-tag binding compound according to this invention, or a derivative thereof. In some embodiments, the sensor comprises a His-tag binding compound according to this invention, or derivative thereof, and a labeling moiety bound thereto. In some embodiments, the labeling moiety is a fluorescent dye. In some embodiments, the labeling moiety is a quinoline based cyanine dye (QBC). In some embodiments, the QBC is TO, TR or QB; each represents a separate embodiment according to this invention. In some embodiments, the QBC is a derivative of TO, TR or QB; each represents a separate embodiment according to this invention, wherein the term derivative is as described hereinabove. In some embodiments, the compound is complexed to at least one metal ion. In some embodiments, the metal ion is selected from: Ni(II), Co(II) and Co(III).

In some embodiments, this invention is directed to a fluorescent probe, comprising a compound according to this invention as described hereinabove and a fluorescent dye bound thereto, directly or via a first linker, wherein the compound is complexed to at least one metal ion.

In some embodiments, this invention is directed to a turn on fluorescent probe, comprising a compound according to this invention as described hereinabove and a quinoline based cyanine dye bound thereto, directly or via a linker, wherein the compound is complexed to at least one metal ion.

In some embodiments, the His-tag binding compound which is coupled through $R_1$ to a labeling moiety is represented by the structure of formula XXI-XXIII as described herein below.

In some embodiments, the His-tag binding compound which is coupled through $R_1$ to a labeling moiety is represented by the structure of formula XXXV-XXXVII as described herein above.

In some embodiments, the His-tag binding compound which is coupled through $R_1$ to a labeling moiety is represented by the structure of compounds 401-410 described herein above.

Molecular Structures of His-Tag Binding Fluorescent Probes of the Invention

In some embodiments, this invention is directed to a compound, represented by the structure of formula XXI:

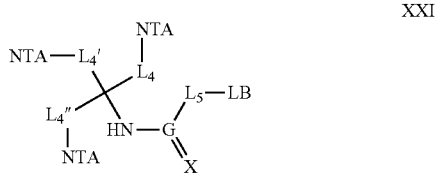

XXI wherein
- $L_4$, $L_4'$, and $L_4''$ are each independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof,
- $L_5$ is absent or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof,
- G=X is absent, or is $CH_2$, C=O, C(O)NH, C=S, C(S)NH, C(O)O, S=O or $SO_2$;
- LB is a labeling moiety; and
- NTA is nitrilotriacetic acid or a protected derivative thereof.

In some embodiments, G=X is C=O. In some embodiments, $L_5$ is a combination of alkyl ether chain and alkyl amide chain. In some embodiments, the alkyl ether is unsubstituted. In some embodiments, the alkyl ether is linear. In some embodiments, the alkyl ether is of 2-8, 1-10, 1-4, 2-20, 2-6, 2, 3, 4, 5, 6, 7, 8, 9, 10, or 12 carbon atoms; each represents a separate embodiment according to this invention. In some embodiments, the alkyls ether is PEG of 4-12 carbon atoms. In some embodiments, the alkyl ether is PEG of 4, 6, 8, 10, or 12 carbon atoms; each represents a separate embodiment according to this invention. In some embodiments, the alkyl ether is represented by the following formula: $[(CH_2)_2—O]_k$, wherein k is between 1 and 10, 1 and 4, 1 and 8, 1 and 6; each represents a separate embodiment according to this invention. In some embodiments, k is 1, 2, 3, 4, 5, 6, 7, 8, 9 or 10; each represents a separate embodiment according to this invention. In some embodiments, k is 3. In some embodiments, the alkyl amide is linear. In some embodiments, the alkyl amide is unsubstituted. In some embodiments, the alkyl amide is of 2-8, 1-10, 1-4, 2-20, 2-6, 2, 3, 4, 5, 6, 7, 8, 9, 10, or 12 carbon atoms; each represents a separate embodiment according to this invention. In some embodiments, the alkyl amide is of 1 or 2 carbon atoms. In some embodiments, LB is a fluorescent dye. In some embodiments, LB is a quinoline based cyanine dye (QBC). In some embodiments, LB is a derivative of QBC. In some embodiments, LB is TO, TR or QB; each represents a separate embodiment according to this invention.

In some embodiments, the compound is represented by the structure of formula XXXV, XXXVI or XXXVII as described hereinabove. In some embodiments, the compound is represented by the structure of compounds 408-410 as described hereinabove.

In some embodiments, the compound is represented by the structure of formula XXII:

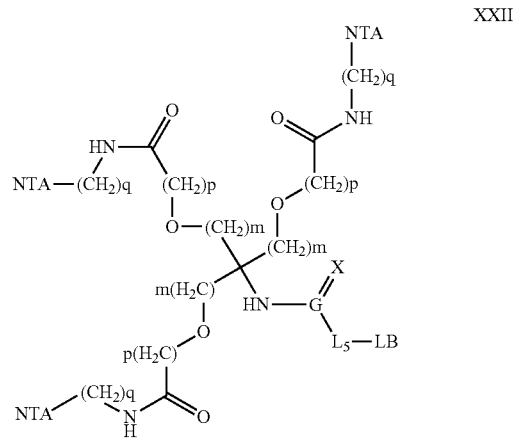

XXII wherein
- m, p and q are each independently an integer between 1 and 8;
- $L_5$ is absent or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof,
- G=X is absent, or is $CH_2$, C=O, C(O)NH, C=S, C(S)NH, C(O)O, S=O or $SO_2$;

LB is a labeling moiety; and

NTA is nitrilotriacetic acid or a protected derivative thereof.

In some embodiments, G=X is C=O. In some embodiments, $L_5$ is a combination of alkyl ether chain and alkyl amide chain. In some embodiments, the alkyl ether is unsubstituted. In some embodiments, the alkyl ether is linear. In some embodiments, the alkyl ether is of 2-8, 1-10, 1-4, 2-20, 2-6, 2, 3, 4, 5, 6, 7, 8, 9, 10, or 12 carbon atoms; each represents a separate embodiment according to this invention. In some embodiments, the alkyls ether is PEG of 4-12 carbon atoms. In some embodiments, the alkyl ether is PEG of 4, 6, 8, 10, or 12 carbon atoms; each represents a separate embodiment according to this invention. In some embodiments, the alkyl ether is represented by the following formula: $[(CH_2)_2-O]_k$, wherein k is between 1 and 10, 1 and 4, 1 and 8, 1 and 6; each represents a separate embodiment according to this invention. In some embodiments, k is 1, 2, 3, 4, 5, 6, 7, 8, 9 or 10; each represents a separate embodiment according to this invention. In some embodiments, k is 3. In some embodiments, the alkyl amide is linear. In some embodiments, the alkyl amide is unsubstituted. In some embodiments, the alkyl amide is of 2-8, 1-10, 1-4, 2-20, 2-6, 2, 3, 4, 5, 6, 7, 8, 9, 10, or 12 carbon atoms; each represents a separate embodiment according to this invention. In some embodiments, the alkyl amide is of 1 or 2 carbon atoms. In some embodiments, LB is a fluorescent dye. In some embodiments, LB is a quinoline based cyanine dye (QBC).

In some embodiments, LB is a derivative of QBC. In some embodiments, LB is TO, TR or QB; each represents a separate embodiment according to this invention.

In some embodiments, the compound is represented by the structure of formula XXXV, XXXVI or XXXVII as described hereinabove. In some embodiments, the compound is represented by the structure of compounds 408-410 as described hereinabove.

In some embodiments, the compound is represented by the structure of formula XXIII:

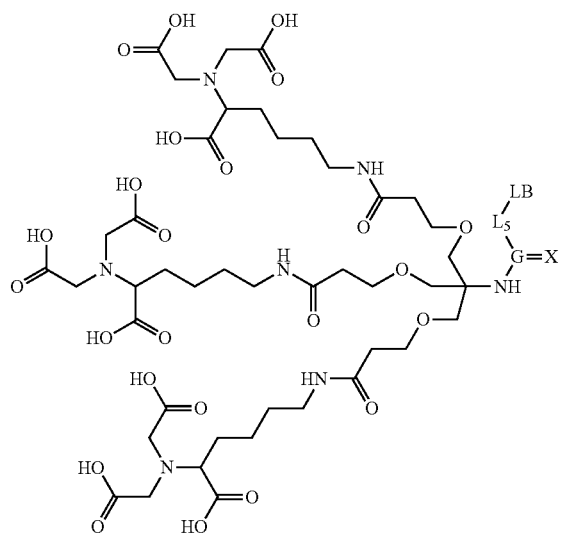

XXIII wherein $L_5$ is absent or is a substituted or unsubstituted linear or branched alkyl chain of 1-50 carbon atoms (e.g. ethylene: —$CH_2$—$CH_2$—), substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof, G=X is absent, or is $CH_2$, C=O, C(O)NH, C=S, C(S)NH, C(O)O, S=O or $SO_2$;

LB is a labeling moiety.

In some embodiments, G=X is C=O. In some embodiments, $L_5$ is a combination of alkyl ether chain and alkyl amide chain. In some embodiments, the alkyl ether is unsubstituted. In some embodiments, the alkyl ether is linear. In some embodiments, the alkyl ether is of 2-8, 1-10, 1-4, 2-20, 2-6, 2, 3, 4, 5, 6, 7, 8, 9, 10, or 12 carbon atoms; each represents a separate embodiment according to this invention. In some embodiments, the alkyls ether is PEG of 4-12 carbon atoms. In some embodiments, the alkyl ether is PEG of 4, 6, 8, 10, or 12 carbon atoms; each represents a separate embodiment according to this invention. In some embodiments, the alkyl ether is represented by the following formula: $[(CH_2)_2-O]_k$, wherein k is between 1 and 10, 1 and 4, 1 and 8, 1 and 6; each represents a separate embodiment according to this invention. In some embodiments, k is 1, 2, 3, 4, 5, 6, 7, 8, 9 or 10; each represents a separate embodiment according to this invention. In some embodiments, k is 3. In some embodiments, the alkyl amide is linear.

In some embodiments, the alkyl amide is unsubstituted. In some embodiments, the alkyl amide is of 2-8, 1-10, 1-4, 2-20, 2-6, 2, 3, 4, 5, 6, 7, 8, 9, 10, or 12 carbon atoms; each represents a separate embodiment according to this invention. In some embodiments, the alkyl amide is of 1 or 2 carbon atoms. In some embodiments, LB is a fluorescent dye. In some embodiments, LB is a quinoline based cyanine dye (QBC). In some embodiments, LB is a derivative of QBC. In some embodiments, LB is TO, TR or QB; each represents a separate embodiment according to this invention.

In some embodiments, the compound is represented by the structure of formula XXXV, XXXVI or XXXVII as described hereinabove. In some embodiments, the compound is represented by the structure of compounds 408-410 as described hereinabove.

In some embodiments, "Labeling moiety" or "LB" of formula XXXV-XXXVII and/or XXI-XXIII is a solvatochromic dye. In some embodiments, a fluorophore. In some embodiments, a quinoline based cyanine dye. In some embodiments, TO, TR or QB. In some embodiments, dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, Tamra, BODIPY, FITC, Thiazole orange, Quinoline blue, Thiazole red, or derivative thereof, each represents a separate embodiment according to this invention.

In some embodiments, dansyl. In some embodiments, fluorescein (6-FAM). In some embodiments, FAM. In some embodiments, cyanine dyes (e.g. Cy3, Cy5). In some embodiments, sulfoindocyanine. In some embodiments, nile red. In some embodiments, rhodamine. In some embodiments, perylene. In some embodiments, fluorenyl. In some embodiments, coumarin. In some embodiments, 7-methoxycoumarin (Mca). In some embodiments, dabcyl. In some embodiments, NBD. In some embodiments, Nile blue. In some embodiments, Tamra. In some embodiments, BODIPY. In some embodiments, a derivative of any one of dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, Tamra, BODIPY, FITC, Thiazole orange, Quinoline blue, or Thiazole red.

In some embodiments, LB is a fluorescent agent, cyanine dye, quinoline based cyanine dye, fluorescent dye, fluorophore, solvatochromic dye, chemiluminescent agent, chromogenic agent, quenching agent, radionucleotide, or a magnetic particle; each represents a separate embodiment according to this invention. In some embodiments, LB is a quinoline based cyanine dye. In some embodiments, the fluorescent dye is selected from: dansyl, fluorescein (6-FAM), FAM, cyanine dyes (e.g. Cy3, Cy5, SCy3, SCy5), sulfoindocyanine, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or a derivative thereof, each represents a separate embodiment according to this invention.

In some embodiments, G=X is C=O. In some embodiments, $V^1$ is alkyl ether. In some embodiments, the alkyl ether is -[(CH$_2$)$_2$—O]$_k$—, wherein k is between 2 and 8. In some embodiments, k is 3. In some embodiments, $X^1$ is a bond. In some embodiments, $X^1$ is a $C_1$-$C_{12}$ alkyl. In some embodiments, the alkyl is ethyl. In some embodiments, $X^1$ is -alkyl-NHC(O)-alkyl. In some embodiments, $X^1$ the alkyl-NHC(O)-alkyl is (CH$_2$)$_2$—NHC(O)—CH$_2$ or (CH$_2$)$_2$—NHC(O)—CH$_2$)$_2$); each represents a separate embodiment according to this invention. In some embodiments, $L^1$ is a bond. In some embodiments, $L^1$ is $C_1$-$C_{12}$ alkyl. In some embodiments, $L^1$ is ethylene or methylene; (e.g., (CH$_2$)$_2$, CH$_2$); each represents a separate embodiment according to this invention. In some embodiments, m is 1, p is 2 and q is 4.

In some embodiments, this invention is directed to a fluorescent probe that can selectively label a His-tagged protein binder, comprising a compound according to this invention, complexed to at least one metal ion.

In some embodiments, the labeling moiety is a fluorescent dye. In some embodiments, the labeling moiety is quinoline-based cyanine dyes. In some embodiments, the quinoline based cyanine dye is TO, TR or QB; each represents a separate embodiment according to this invention.

In some embodiments, the compound is represented by the structure of formula XXIV:

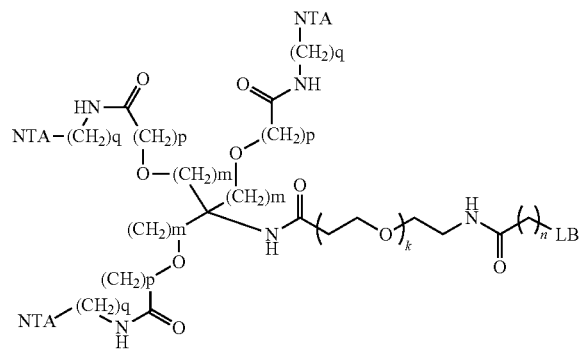

XXIV wherein
  m, p, q and k are each independently an integer between 1 and 8 (e.g., m:1, p:2, q:4);
  n is an integer between 0 and 8 (e.g., 2);
  LB is a labeling moiety; and
  NTA is nitrilotriacetic acid, nitrilotriacetic acid complexed to at least one metal ion, or a protected derivative thereof;
or a suitable salt thereof.

In some embodiments, the suitable salt thereof is a tosylate, iodide, chloride, bromide, fluoride, TFA or a $PF_6$ salt.

In some embodiments, k is 3, m is 1, p is 2, q is 4, n is 1, NTA is nitrilotriacetic acid, and LB is quinoline-based cyanine dye. In some embodiments, k is 3, and LB is Thiazole orange (TO). In some embodiments, k is 3, and LB is Quinoline blue (QB). In some embodiments, k is 3, and LB is Thiazole red (QB).

In some embodiments, the labeling moiety is a fluorescent dye. In some embodiments, the labeling moiety is quinoline-based cyanine dyes. In some embodiments, the quinoline based cyanine dye is TO, TR or QB; each represents a separate embodiment according to this invention.

In some embodiments, the compound is represented by the structure of formula XXV:

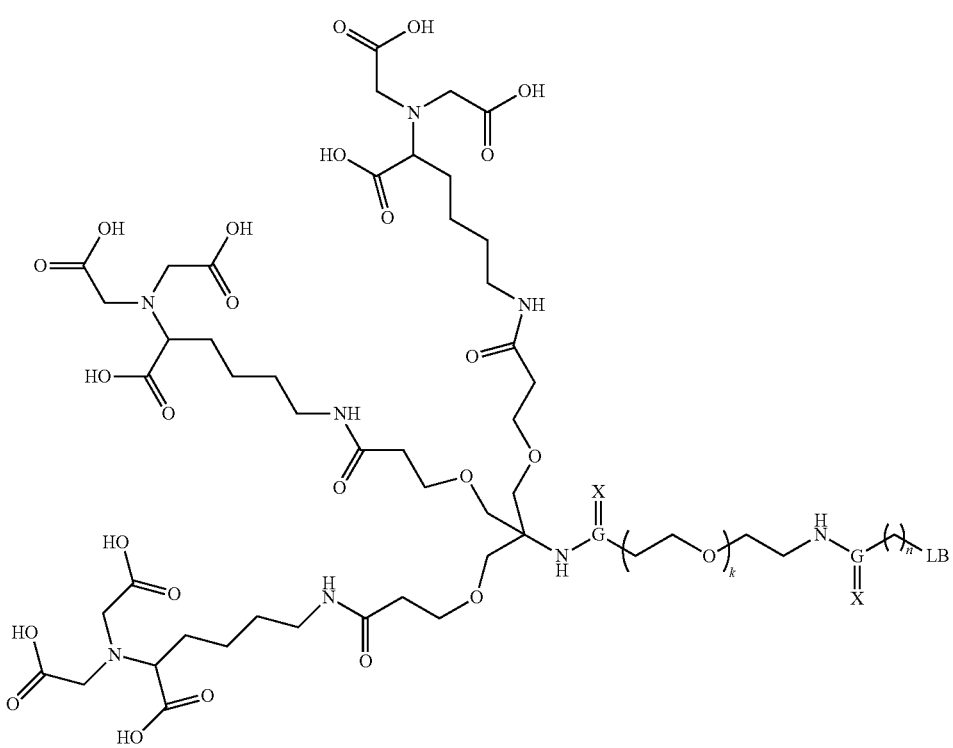

XXV wherein
G=X is absent, or is $CH_2$, C=O, C(O)NH, C=S, C(S)NH, C(O)O, S=O or $SO_2$; and
k is an integer between 1 and 8 (e.g., 3);
n is an integer between 0 and 8 (e.g., 2);

In some embodiments, the suitable salt thereof is a tosylate, iodide, chloride, bromide, fluoride, TFA or a $PF_6$ salt.

In some embodiments, the compound is a probe. In some embodiments, the compound is a turn-on probe.

In some embodiments, the labeling moiety is a fluorescent dye. In some embodiments, the labeling moiety is quinoline-based cyanine dye. In some embodiments, the quinoline based cyanine dye is TO, TR or QB; each represents a separate embodiment according to this invention.

In some embodiments, G=X is C=O, k is 3, and LB is quinoline-based cyanine dye. In some embodiments, G=X is C=O, k is 3, and LB is Thiazole orange (TO). In some embodiments, G=X is C=O, k is 3, and LB is Quinoline blue (QB). In some embodiments, G=X is C=O, k is 3, and LB is Thiazole red (QB).

In some embodiments, LB of any one of formula XXI-XXV is a fluorophore. The fluorophore is an environmentally sensitive probe, introduced in the vicinity of the protein specific binder, which should enable the system to fluoresce when the specific protein binder binds to the target protein (POI). In some embodiments, the fluorophore is a solvatochromic dye. Solvatochromic fluorophores display sensitivity to the polarity of the local environment. These molecules exhibit a low quantum yield in aqueous solution, but become highly fluorescent in nonpolar solvents or when bound to hydrophobic sites in proteins or membranes. In certain embodiments, solvatochromic fluorophores include 2-propionyl-6-dimethylaminonaphthalene (PRODAN) (Weber et al. *Biochemistry* 1979, 18, 3075-3078; Cohen et al. *Science* 2002, 296, 1700-1703), 4-dimethylamino phthalimide (4-DMAP) (Saroja et al. *J. Fluoresc.* 1998, 8, 405-410), and 4-amino-1,8-naphthalimide derivatives (Grabchev et al. *J Photochem. Photobiol., A* 2003, 158, 37-43; Martin et al. J. *Lumin.* 1996, 68, 157-146). In some embodiments, the solvatochromic dye is dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, Tamra, BODIPY, FITC, Thiazole orange, Quinoline blue, Thiazole red, or derivative thereof, each represents a separate embodiment according to this invention.

In some embodiments, the fluorophore of this invention is a fluorescent dye. In some embodiments, the fluorescent dye is substituted or unsubstituted anthracene; substituted or unsubstituted nile red; substituted or unsubstituted dansyl; substituted or unsubstituted fluorenyl; substituted or unsubstituted naphthalene; substituted or unsubstituted tetracene; substituted or unsubstituted perylene; substituted or unsubstituted pyrene substituted or unsubstituted fluorescein; substituted or unsubstituted rhodamine; substituted or unsubstituted cyanine, substituted or unsubstituted coumarin; substituted or unsubstituted NBD; substituted or unsubstituted Nile blue; substituted or unsubstituted Tamra; substituted or unsubstituted BODIPY; or any other fluorescent dye known in the art and/or disclosed in http://www.fluorophores.org which is incorporated herein by reference. In some embodiments, the fluorescent dye of this invention is anthracene, naphthalene, fluorenyl, dansyl, nile red, fluorescein, rhodamine, perylene, cyanine, Cy3, Cy5, coumarin, NBD, Nile blue, Tamra, BODIPY, FITC, Thiazole orange, Quinoline blue, Thiazole red, derivative thereof, or combination thereof, each represents a separate embodiment according to this invention. In some embodiments, the fluorescent dye of this invention is substituted by one to three substituents. In another embodiment the fluorescent dye is substituted by alkyl, alkenyl, haloalkyl, aryl, O-aryl, —$(CH_2)_n$-aryl, cycloalkyl, O-cycloalkyl, $CF_3$, F, I, Br, $C_1$, $NO_2$, CN, $N(Z)_2$, COOH, CO—Z, NHCOZ, CONHZ, $(CH_2)_n$ $NH_2$, $(CH_2)_n$NH—Z, S—Z, SH, O—Z, $(CH_2)_n$OH, $(CH_2)_n$COOH, or OH; wherein Z is H, alkyl, haloalkyl, dihaloalkyl, trihaloalkyl, aryl, phenyl or halogen and n is between 0 and 8. In another embodiment n is between 1 and 6.

In some embodiments, the fluorophore of this invention is a quinoline-based cyanine dye. In some embodiments, the quinoline-based cyanine dye of this invention comprises Thiazole orange (TO), Quinoline blue (QB), and Thiazole red (TR).

In some embodiments, G=X of any one of formula XXI-XXV is absent, or is $CH_2$, C=O, C(O)NH, C=S, C(S)NH, C(O)O, S=O or $SO_2$; each represents a separate embodiment according to this invention. In some embodiments, G=X is C=O.

In some embodiments, k of Formula XXIV and/or XXV, is an integer between 1-8, 2-8, 2-6, 3-6, 1-5, 1-7 or 3-8; each represents a separate embodiment according to this invention. In some embodiments, k is 1, 2, 3, 4, 5, 6, 7, or 8; each represents a separate embodiment according to this invention. In some embodiments, k is 3.

In some embodiments, n of Formula XXIV and/or XXV, is an integer between 0 and 8, 1-8, 2-8, 1-5, 2-5, 1-4 or 2-4; each represents a separate embodiment according to this invention. In some embodiments, n is 0, 1, 2, 3, 4, 5, 6, 7 or 8; each represents a separate embodiment according to this invention.

In some embodiments, $L_5$ of compound of formula XXI-XXIII is a combination of alkyl ether chain and alkyl amide chain. In some embodiments, the alkyl ether is unsubstituted. In some embodiments, the alkyl ether is linear. In some embodiments, the alkyl ether is of 2-8, 1-10, 1-4, 2-20, 2-6, 2, 3, 4, 5, 6, 7, 8, 9, 10, or 12 carbon atoms; each represents a separate embodiment according to this invention. In some embodiments, the alkyls ether is PEG of 4-12 carbon atoms. In some embodiments, the alkyl ether is PEG of 4, 6, 8, 10, or 12 carbon atoms; each represents a separate embodiment according to this invention. In some embodiments, the alkyl ether is represented by the following formula: $[(CH_2)_2—O]_k$, wherein k is between 1 and 10, 1 and 4, 1 and 8, 1 and 6; each represents a separate embodiment according to this invention. In some embodiments, k is 1, 2, 3, 4, 5, 6, 7, 8, 9 or 10; each represents a separate embodiment according to this invention. In some embodiments, k is 3. In some embodiments, the alkyl amide is linear. In some embodiments, the alkyl amide is unsubstituted. In some embodiments, the alkyl amide is of 2-8, 1-10, 1-4, 2-20, 2-6, 2, 3, 4, 5, 6, 7, 8, 9, 10, or 12 carbon atoms; each represents a separate embodiment according to this invention. In some embodiments, the alkyl amide is of 1 or 2 carbon atoms.

In some embodiments, $L_4$, $L_4'$, and $L_4''$ of the structure of formula XXI, is each independently a substituted or unsubstituted linear or branched alkyl chain of 1-20 carbon atoms, substituted or unsubstituted linear or branched alkyl ether chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl diamide chain of 1-20 carbon atoms, substituted or unsubstituted linear or branched alkyl amine chain of 1-20 carbon atoms or any combination thereof, each represents a separate embodiment according to this invention. In some embodiments, each of $L_4$, $L_4'$, and $L_4''$ is a combination of alkyl ether and alkyl amide (i.e., alkylether-alkylamide). In some embodiments, each of $L_4$, $L_4'$, and $L_4''$ is independently —$(CH_2)_q$—NHCO—$(CH_2)_p$—O—$(CH_2)_m$—, wherein q, p and m are each independently an integer between 1 and 8. In some embodiments, q is 4, p is 2 and m is 1. In some embodiments, each of $L_4$, $L_4'$, and $L_4''$ is -$(CH_2)_4$—NHCO—$(CH_2)_2$O—$CH_2$—. In some embodiments, each of $L_4$, $L_4'$, and $L_4''$ is represented by the following structure:

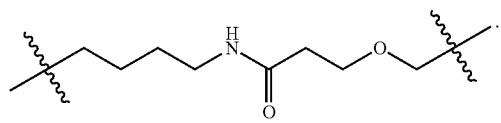 [SMILES: *CCCCNC(=O)CCOC*]

In some embodiments, $L_4$, $L_4'$ and $L_4''$ are different. In some embodiments, $L_4$, $L_4'$ and $L_4''$ are the same. In some embodiments, $L_4$ and $L_4'$ are the same and $L_4''$ is different. In some embodiments, $L_4$ and $L_4''$ are the same and $L_4'$ is different. In some embodiments, $L_4'$ and $L_4''$ are the same and $L_4$ is different.

In some embodiments, a compound according to any one of formula XXI-XXV wherein LB is a quinoline based cyanine dye, is represented by the structure of compounds 408, 409 and 410:

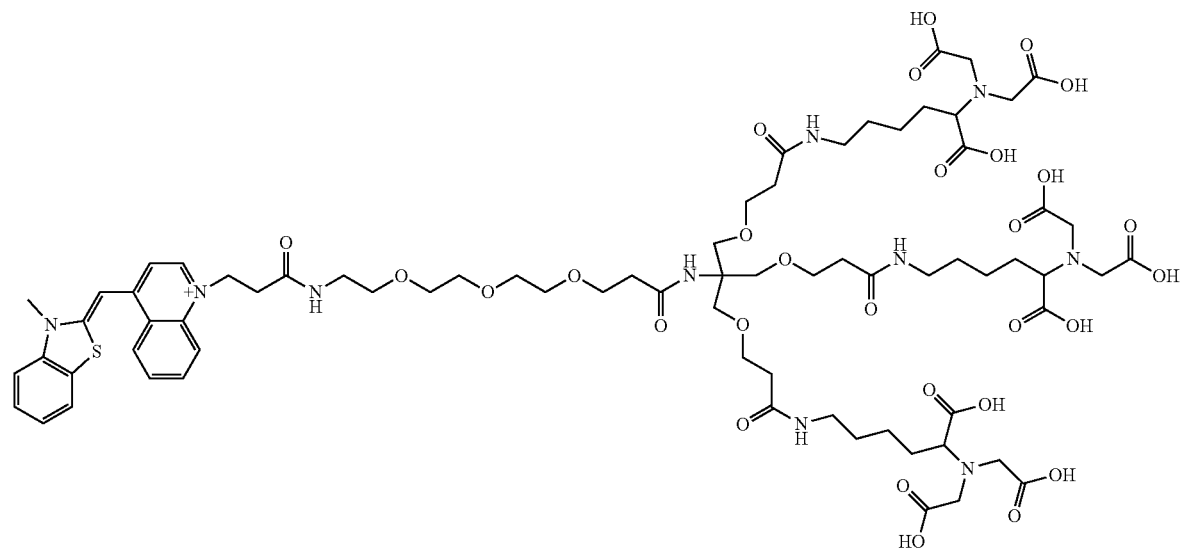
408
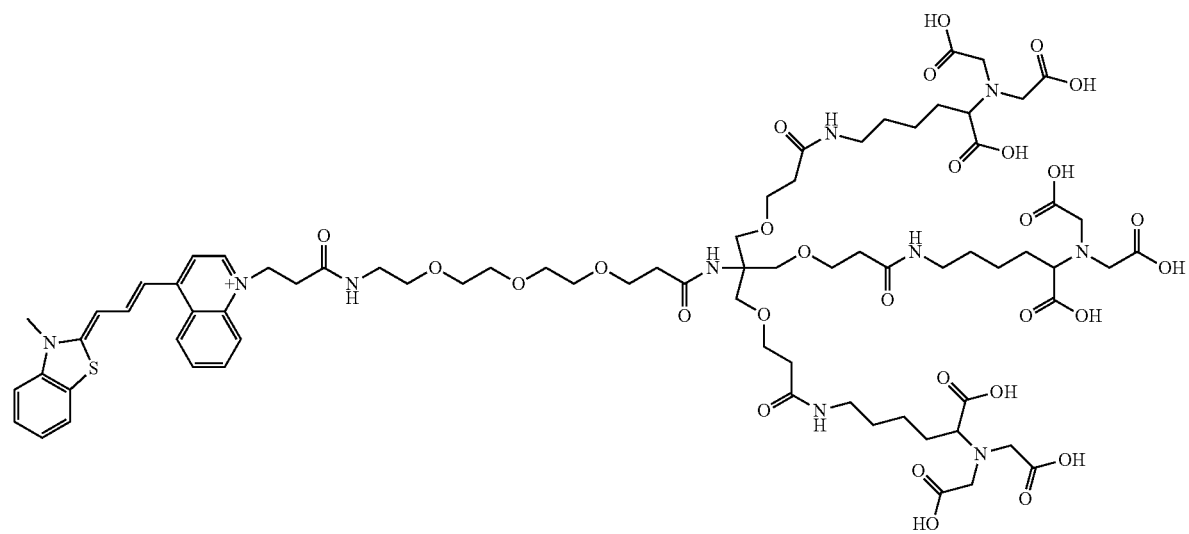
409

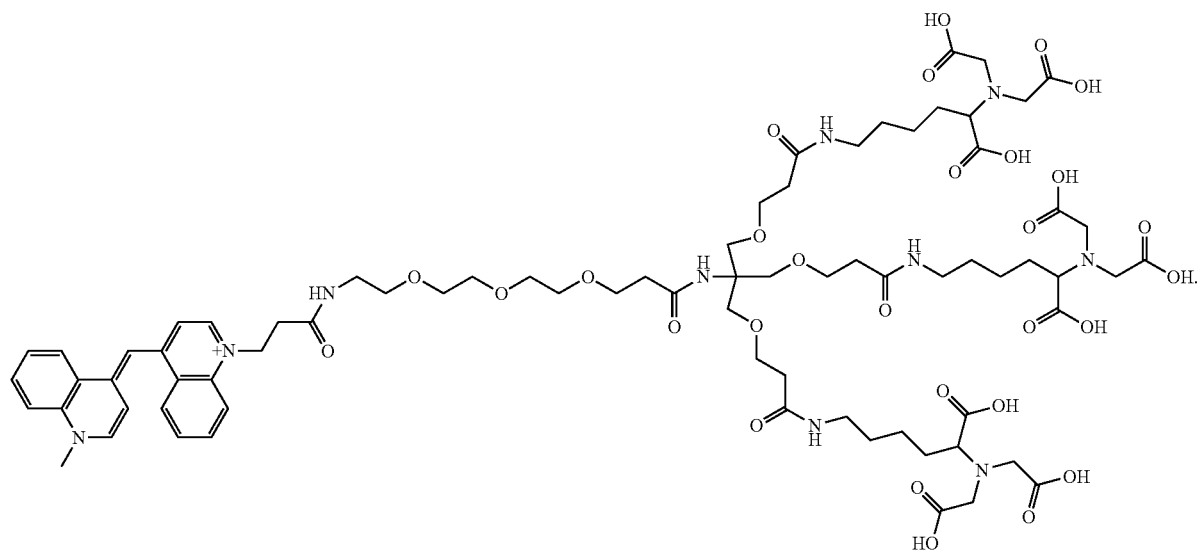
410
In some embodiments, a compound according to any one of formula XXI-XXV, wherein LB is a fluorescent dye, is represented by the structure of compounds 313, 314, and 315:
wherein ❋ is:
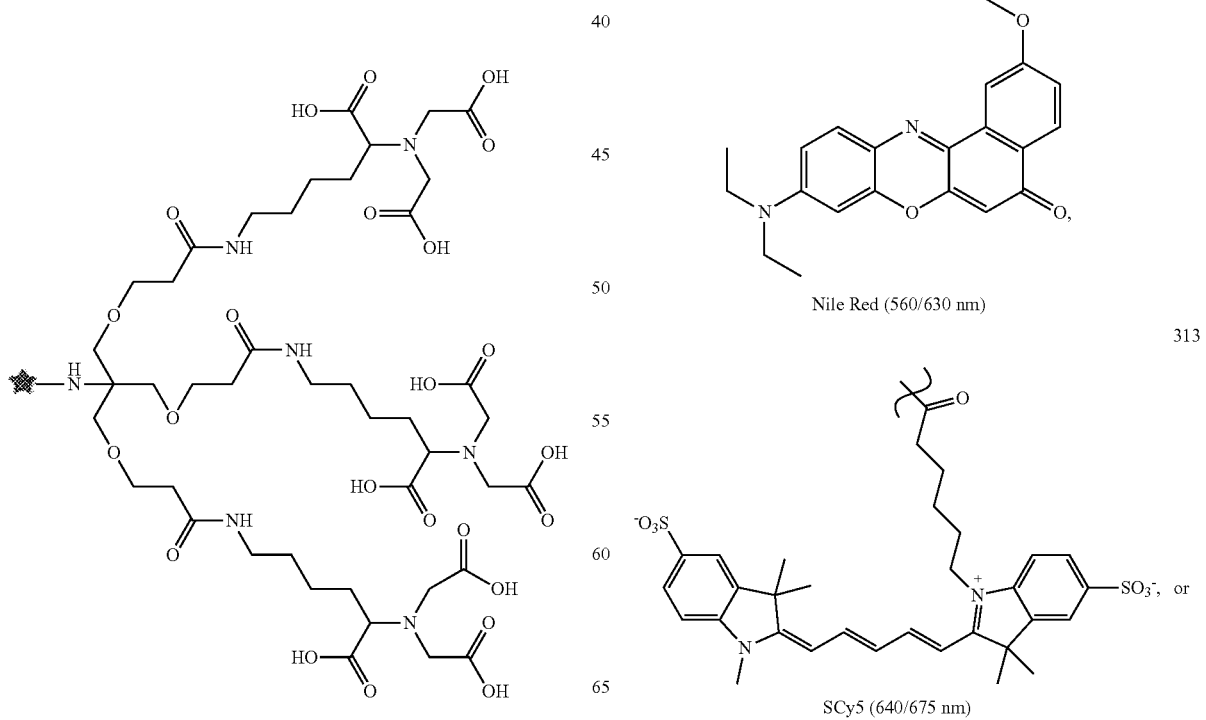

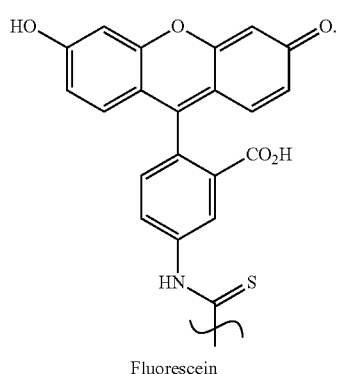

Fluorescein

In some embodiments, upon complexation to at least one metal ion, compound of formula XXI-XXV, and compounds 313, 314 and 315, can selectively bind His-tags of various labeled proteins, thereby becoming a fluorescent probe, a turn-on probe or a molecular probe for fluorescence sensing and imaging. In some embodiments, the compound is a genetically targeted sensor. In some embodiments, the metal ion is cobalt (Co). In some embodiments, the metal ion is nickel (Ni). In some embodiments, the metal ion is Ni(II). In some embodiments, the metal ion is Co(II). In some embodiments, the metal ion is Co(III). In some embodiments, the compound is complexed to three; two; one metal ions; each is a separate embodiment according to this invention. In some embodiments, the compound is complexed to three Ni(II) ions.

In some embodiments, LB comprises labeling moiety as described hereinbelow for labeling moiety. In some embodiments, LB is a fluorescent dye. In some embodiment LB comprises a fluorescent dye. In some embodiments, LB comprises a quinoline based cyanine dye (QBC) or derivative thereof. In some embodiments, the QBC is TO, TR or QB; each represents a separate embodiment according to this invention. Examples of fluorescent dyes include but are not limited to: dansyl, fluorescein (6-FAM), FAM, cyanine dyes (e.g. Cy3, Cy5), sulfoindocyanine, SCy5, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or derivative thereof. In some embodiments, LB comprises FITC, Nile Red or SCy5. In some embodiments, FITC is a derivative of fluorescein. In some embodiments, LB comprises TO, TR or QB. In some embodiments, LB comprises the following structures:

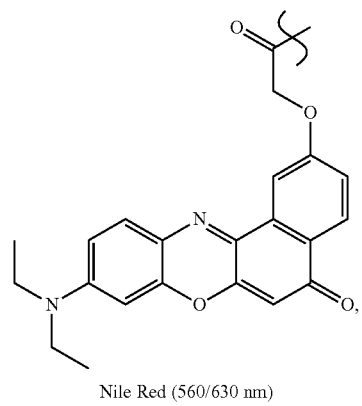

Nile Red (560/630 nm)

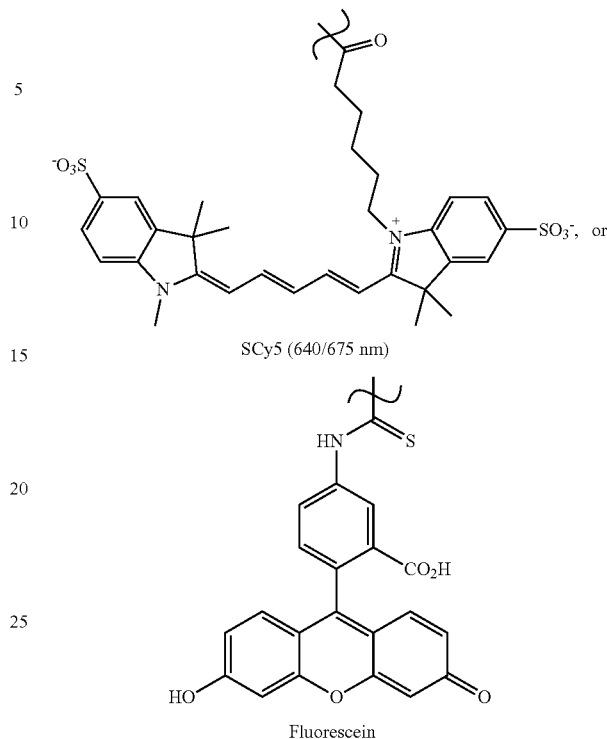

SCy5 (640/675 nm)

Fluorescein

In some embodiments, the His-tag binding compound of formula XI-XVI, described hereinabove, is coupled through the $R_1$ moiety to a labeling moiety. In some embodiments, the His-tag binding compound which is coupled through $R_1$ to a labeling moiety is represented by the structure of compounds 313, 314 or 315:

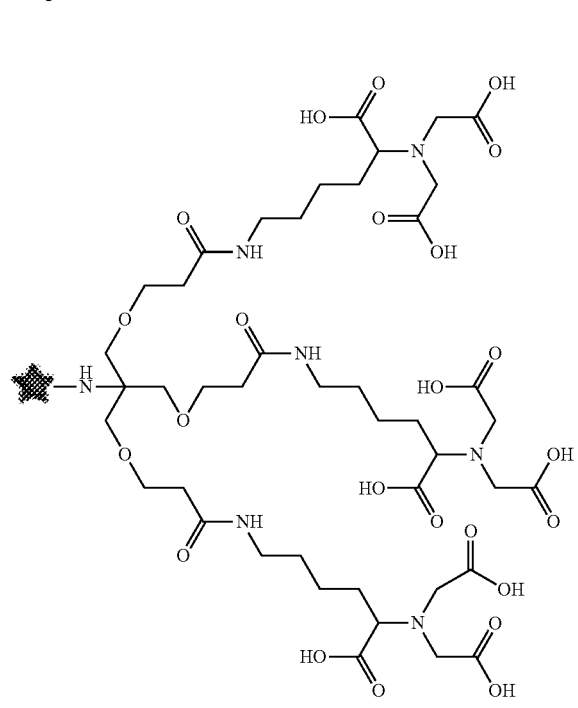

wherein ✱ is:

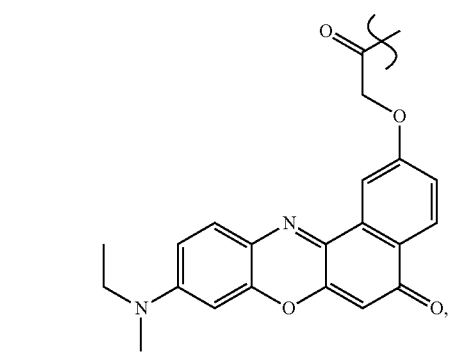

Nile Red (560/630 nm)

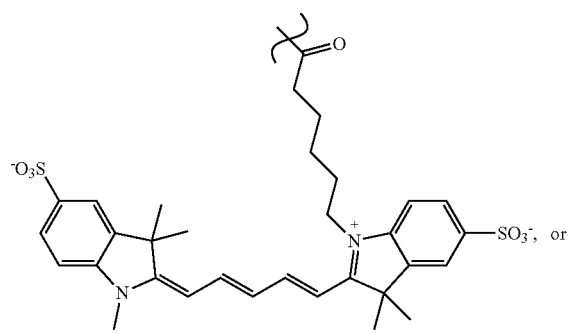

SCy5 (640/675 nm)

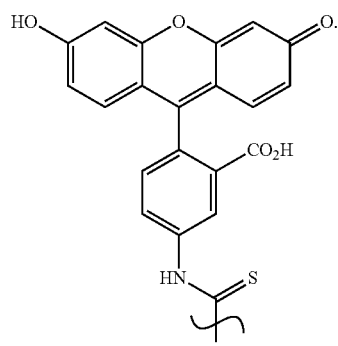

Fluorescein

In some embodiments, the His-tag binding compound which is coupled through the $R_1$ moiety to a labeling moiety is a fluorescent probe. In some embodiments, the His-tag binding compound which is coupled through the $R_1$ moiety to a labeling moiety is a genetically targeted sensor. In some embodiments, the His-tag binding compound which is coupled through the $R_1$ moiety to a labeling moiety is a turn on fluorescent probe.

In some embodiments, this invention is directed to a fluorescent probe, comprising the compound of formula XI-XVI wherein said compound is covalently bound to a labeling moiety. In some embodiments, the compound is covalently bound to the labeling moiety through the $R_1$ moiety, directly or via a first linker.

In some embodiments, the compound is complexed to at least one metal ion. In some embodiments, the metal ion is Ni(II). In some embodiments, the fluorescent probe is a genetically targeted sensor. In some embodiments, the fluorescent probe is a turn on probe. In some embodiments, the fluorescent probe is compound 313, 314 or 315; each represents a separate embodiment according to this invention.

In some embodiments, this invention is directed to a fluorescent probe, comprising the compound of formula XI-XVI, wherein said compound is covalently bound to a labeling moiety through a first linker, which links between the $R_1$ moiety of said compound and said labeling moiety. In some embodiments, the compound is complexed to at least one metal ion. In some embodiments, the metal ion is Ni(II). In some embodiments, the fluorescent probe is a genetically targeted sensor. In some embodiments, the fluorescent probe is a turn on probe. In some embodiments, the fluorescent probe is compound 408, 409 or 410; each represents a separate embodiment according to this invention.

In some embodiments, this invention is directed to a fluorescent probe, comprising a compound of formula XI-XV, covalently bound to an oligonucleotide through a first linker, which links between the $R_1$ moiety of said compound and said oligonucleotide. In some embodiments, the compound is further bound to a labeling moiety. In some embodiments, the labeling moiety is bound to the oligonucleotide. In some embodiments, the labeling moiety is bound to the oligonucleotide via a third linker. In some embodiments, the compound is complexed to at least one metal ion. In some embodiments, the metal ion is Ni(II).

In some embodiments, the labeling moiety is a fluorescent dye.

In some embodiments, the compound is coupled through the $R_1$ moiety to an oligonucleotide, a peptide, a protein, a labeling moiety, a drug, a solid support, or a small molecule via a first linker.

In some embodiments, this invention is directed to a fluorescent probe, comprising the compound of formula XXI-XXV or XXXV-XXXVII, wherein said compound is covalently bound to a labeling moiety through a first linker, which links between the LB moiety of said compound and the His-tag binding moiety.

In some embodiments, the compound is complexed to at least one metal ion. In some embodiments, the metal ion is Ni(II). In some embodiments, the fluorescent probe is a genetically targeted sensor. In some embodiments, the fluorescent probe is a turn on probe. In some embodiments, the fluorescent probe is compound 408, 409 or 410; each represents a separate embodiment according to this invention.

A First Linker

In some embodiments, the His-tag binding compound or precursor of the invention, is coupled through the $R_1$ moiety to an oligonucleotide, a peptide, a protein, a labeling moiety, a drug, a solid support, or a small molecule via a first linker. In some embodiments, the first linker comprises at least one phosphate moiety, a PEG moiety, an alkyl moiety, an amide moiety, a thioalkyl moiety or any combination thereof; each represents a separate embodiment according to the invention. In some embodiments, the first linker is covalently bound to the oligonucleotide, a peptide, a protein, a labeling moiety, a drug, a solid support, a small molecule through an amide bond, an ester bond, a phosphate bond, an ether bond, a thioether bond; each represents a separate embodiment according to this invention.

In some embodiments, the first linker is a substituted or unsubstituted linear or branched alkyl chain of 1-20 carbon atoms, substituted or unsubstituted linear or branched alkyl ether chain of 1-20 carbon atoms, oligoethylene glycol, polyethylene glycol (PEG), oligopropylene glycol, polypropylene glycol (PPG), substituted or unsubstituted linear or branched thioalkyl chain of 1-20 carbon atoms, substituted or unsubstituted linear or branched alkyl phosphate chain of 1-20 carbon atoms, substituted or unsubstituted linear or branched alkyl amide chain of 1-20 carbon atoms, substituted or unsubstituted linear or branched alkyl ester of 1-20 carbon atoms, substituted or unsubstituted linear or branched alkyl diamide chain of 2-10 carbon atoms, substituted or unsubstituted linear or branched alkyl triazole of 1-20 carbon atoms, substituted or unsubstituted linear or branched alkyl amine chain of 1-20 carbon atoms or any combination thereof; each represents a separate embodiment according to this invention.

In some embodiments, the first linker comprises at least one polyethyleneglycol (PEG) moiety. In some embodiments, at least one alkyl ether moiety. In some embodiments, at least one alkyl diamide moiety. In some embodiments, at least one alkyl amide moiety. In some embodiments, at least one alkyl moiety. In some embodiments, at least one thioalkyl moiety. In some embodiments, at least one polyethyleneglycol (PEG) moiety, at least one alkyl amide moiety, at least one phosphate moiety, at least one thioalkyl moiety, at least one alkyl moiety, or any combination thereof. In some embodiments, the first linker comprises a combination of at least one polyethyleneglycol (PEG) moiety and at least one alkyl amide moiety.

Applications of His-Tag Binding Compounds of the Invention.

Upon complexation with at least one metal ion, the compound described herein above, which comprise tri-NTA group, can selectively bind a His-tagged labeled polypeptides inside living (in vivo) and/or fixed cells (in-vitro). Because the His-tag binding compounds and their precursors according to this invention can bear various functional groups, these tri-NTA derivatives can be easily attached to various detectable probes. In some embodiments, functional groups are at position $R_1$ of compounds of formulas XI-XVI as described above. In some embodiments, derivatives may be attached by using, for example, the 'click' chemistry, amide coupling, thiol-maleimide conjugation, etc. Such probes, (e.g. fluorescent probes) therefore, could be easily generated and complexed with metal ions to detect or label His-tagged proteins (e.g. within cells). Owing to the simple conjugation methods (e.g., 'click' chemistry, amide coupling, thiol-maleimide conjugation, etc.), this approach should enable one to attach various synthetic agents (e.g., fluorescent dyes, small molecules, peptides, oligonudleotides (e.g., DNA, RNA), solid support and the like), to the compounds of this invention, which will enable bringing these synthetic agents into close proximity of His-tagged polypeptides and proteins targeted by the His-tag-binding compounds comprising the specific agents.

Accordingly, the compounds according to this invention may be engineered to comprise a variety of synthetic agents, labeling moieties and/or detectable groups. These synthetic agents, labeling moieties and/or detectable groups can be covalently bound to the compound, either directly or through linkers as described hereinabove.

According to this invention, the term "synthetic agent" refers to any chemical moiety, which provides a chemical or biological function to the system, or to the cell, to which it is attached. In some embodiments, synthetic agent refers to any chemical moiety, which is capable of binding to various extracellular signals such as ions, small molecules, proteins, and cells, and can control the response of cells to their surroundings. In some embodiments, a synthetic agent refers to any chemical moiety, which has a chemical, physical or biological effect on the cell to which it is attached. In some embodiments, a synthetic agent refers to any chemical moiety, which has a biological effect on a living organism, a tissue or a cell (also referred herein as "a bioactive moiety"). In some embodiments, a biological effect comprises affecting the growth, the survival, the replication, the differentiation, the transcriptome, the proteome, or the function of a cell. In some embodiments, synthetic agent refers to any chemical moiety, which can bind, either covalently or non-covalently, to a solid support, and/or to an abiotic surface (also referred herein as "a surface binder"). In some embodiments, a synthetic agent refers an artificial receptor appended with a specific functionality. In some embodiments, a synthetic agent refers to any chemical moiety, which provides the cell, system or compound to which it is attached, with a specific functionality (e.g., fluorescence, therapeutic effect, solid surface binding capability, specific cell targeting, etc.).

In some embodiments, the synthetic agent is a detectable group as described herein below. In some embodiments, the detectable group is a labeling moiety. In some embodiments, the labeling moiety is a dye. In some embodiments, the dye is a fluorescent dye. In some embodiments, the fluorescent dye is selected from a group consisting of: dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, TAMRA, BODIPY, FITC, Thiazole orange, Quinoline blue, Thiazole red, or a derivative thereof.

In some embodiments, the synthetic agent is a therapeutically active agent. In some embodiments, the therapeutically active agent is a drug. In some embodiments, the therapeutically active agent is selected from: anticancer agents, DNA-interacting molecules, cholesterol-lowering compounds, antibiotics, anti-AIDS molecules, each represents a separate embodiment according to the invention.

In some embodiments, the synthetic agent is a is an oligonucleotide, a nucleic acid construct, an antisense, a plasmid, a polynucleotide, an amino acid, a peptide, a polypeptide, a hormone, a steroid, an antibody, an antigen, a radioisotope, a chemotherapeutic agent, a toxin, an anti-inflammatory agent, a growth factor or any combination thereof, each represents a separate embodiment according to the invention.

In some embodiments, the synthetic agent is a molecular marker. In some embodiments, the synthetic agent is an adhesion molecule. In some embodiments, synthetic agent is a cancer cell binder. In some embodiments, "cancer cell binder" refers to any chemical moiety capable of interacting with proteins expressed by cancer cells. In some embodiments, "cancer cell binder" refers to a protein binder capable of interacting with proteins expressed by cancer cells. In some embodiments, the synthetic agent is a protein ligand. In some embodiments, the synthetic agent is a protein binder. In some embodiments, the synthetic agent is a protein receptor. In some embodiments, the synthetic agent is a drug. In some embodiments, the synthetic agent is an anticancer agent. In some embodiments, the synthetic agent is a growth factor. In some embodiments, the synthetic agent is a surface binder. In some embodiments, the synthetic agent is an abiotic surface binder. In some embodiments, the surface binder is a functional group capable of binding a solid surface or a solid support.

In some embodiments, the synthetic agent is a protein binder. In some embodiments, a "protein binder" refers to any biological research reagent which binds to a specific target protein. Non limiting examples of protein binders known in the art include: drugs, folate, biotin, marimastat, ethacrynic acid, bisethacrynic acid, Ni-nitrilotriacetic acid (Ni-NTA), bis Ni-NTA, tris-Ni-NTA, PDGF-BB, heparin, FGF aptamer, estrogen, DNA aptamer, RNA aptamer, peptide aldehyde, estrogen, suberoylanilidehydroxamic acid (SAHA), autoinducer, siderophore, folate, anisamide, antibody, antigen or a peptide binder; each represents a separate embodiment according to this invention.

In some embodiments, the synthetic agent is a molecular marker. In some embodiments, the synthetic agent is an angiogenic factor. In some embodiments, the synthetic agent is a cytokine. In some embodiments, the synthetic agent is a hormone. In some embodiments, the synthetic agent is a DNA molecule. In some embodiments, the synthetic agent is a siRNA molecule. In some embodiments, the synthetic agent is an oligosaccharide.

In some embodiments, the synthetic agent is a protein receptor. In some embodiments, the synthetic agent is a protein binder. In some embodiments, the synthetic agent is an immune activator. In some embodiments, the synthetic agent is an immune suppressor. In some embodiments, the synthetic agent is a small molecule. In some embodiments, the small molecule is a drug.

In some embodiments, the synthetic agent is a surface binder. In some embodiments, the synthetic agent is an abiotic surface binder. In some embodiments, the synthetic agent is a binder for abiotic surfaces. In some embodiments, the synthetic agent is an agent capable of binding to solid support. In some embodiments, the surface binder is capable of binding a surface. According to this invention, a "surface binder" is any chemical moiety, or functional group, that is capable of binding solid surfaces. In some embodiments, the binding is covalent, electrostatic, van der Waals or any combination thereof, each is a separate embodiment. In some embodiments, attachment of the surface binder to the surface comprises covalent bond, coordination bond, polar bond, van der Waals bond or any combination thereof. In some embodiments, the surface binder comprises a functional moiety capable of binding a surface. According to this aspect and in some embodiments, the surface binder comprises a thiol end group (SH) or an end group comprising a sulfur-sulfur bond (—S—S—). Such bonds are capable of binding to a noble metal. For example, thiol or —S—S— moieties binds strongly to gold surfaces and to other noble metal surface including but not limited to silver, platinum and palladium. Thiols and —S—S— bonds also bind to semiconductor surfaces such as GaAs etc. In some embodiments, the surface binder comprises a thiol group (HS). In some embodiments, the surface binder is a $C_1$-$C_{20}$ thioalkyl. In some embodiments, the surface binder is a $C_2$-$C_8$ thioalkyl. In some embodiments, the surface binder is a thiohexyl. In some embodiments, attachment of the surface binder to a surface comprise silicon chemistry. According to this aspect and in some embodiments, the surface is or comprises silicon. In some embodiments, the surface comprises silicon oxide. In some embodiments, the silicon oxide surface comprises glass or quartz. In some embodiments, the surface comprises silicon coated by a silicon oxide layer. According to this aspect and in some embodiments, the surface binder comprises a functional group capable of binding to silicon oxide. In some embodiments, the functional group comprises silicon atom. In some embodiments, the functional group comprises silicon bonded to a halogen atom. In some embodiments, the halogen atom is Cl, Br, F or I. In one embodiment the silicon-halogen functional group comprise Si-trichloride, Si-tribromide, Si-dichloride, Si dibromide. In some embodiments, the functional group comprises Si bonded to oxygen atom. In some embodiments, the functional group comprises Si bonded to two or three oxygen atoms. In some embodiments, the functional group of the surface binder comprises Si-halogen bond and upon reaction with the surface, the halogen atom is replaced by an oxygen atom, and bonding to the surface occurs. In some embodiments, the surface binder comprises a pyridine moiety.

In some embodiments, the synthetic agent is a detectable group as described herein below.

"Detectable group" as used herein refers to any atom or molecule that can be engineered into the His-tag binding compound to aid in the detection of the His-tag binding compounds without significantly destroying the His-tag binding compound's ability to react with a target sequence. The His-tag binding compound may be substituted at one or more positions to add a signal generating detectable group(s). Preferably, the His-tag binding compound is substituted at the $R_1$ position of compounds of formulas I-V described above.

Inclusion of more than one detectable group is also within the scope of this invention. The selection of a detectable group may be made based on the ease of the protocol for engineering the detectable group into the compound, and on the end use of the compound.

Examples of detectable groups include fluorescent groups, phosphorescent groups, luminescent groups, spin labels, photosensitizers, photocleavable moieties, chelating centers, heavy atoms, radioactive isotopes, isotopes detectable by nuclear magnetic resonance, paramagnetic atoms, and combinations thereof.

Typically, a detectable group generates a detectable signal that can be readily monitored. Examples of detectable signals that can be monitored include fluorescence, fluorescence anisotropy, time-resolved luminescence, phosphorescence amplitude and anisotropy, electron spin resonance (ESR), singlet oxygen production, hydroxy radical-mediated protein inactivation, metal-ion sensing, X-ray scattering, radioactivity, nuclear magnetic resonance spectroscopy of the attached isotope, and enhanced relaxivity of protons in the immediate vicinity of a paramagnetic species.

Other modifying groups that aid in the use of the His-tag binding compound of the invention may also be incorporated. For example, the compound may be substituted at one or more positions to add a solid phase binding group or a cross linking group. Preferably, the compound is substituted with a solid phase binding group at the $R_1$ position of compounds of formulas XI-XVI described above. The compound may be further coupled to a solid phase. In some embodiments, the compound may be substituted at one or more positions to add an oligonucleotide of any length (e.g., DNA or RNA). Preferably, the compound is substituted with an oligonucleotide at the $R_1$ position of compounds of formulas XI-XVI described above.

The compound may be further coupled to another oligonucleotide which is bound to a synthetic agent, including but not limited to: drug, selective protein binder, fluorophore, etc.

In some embodiments, the His-tag binding compound is capable of traversing a biological membrane. The small size of the His-tag binding compound can contribute toward the ability of the His-tag binding compound to traverse a biological membrane.

A His-tag binding compound that is unable to traverse a biological membrane may be derivatized.

In some embodiments, a His-tag binding compound may be derivatized by addition of groups that enable or enhance the ability of the His-tag binding compound to traverse a biological membrane. In some embodiments, derivatization of the His-tag binding compound does not significantly alter the ability of the His-tag binding compound to subsequently react with the target sequence. In some embodiments, a His-tag binding compound may be derivatized transiently. In such instances, after traversing the membrane, the derivatizing group is eliminated to regenerate the original His-tag binding compound. Examples of derivatization methods that increase membrane traversability include esterification of phenols, ether formation with acyloxyalkyl groups, and reduction of chromophores to uncharged leuco compounds.

In some embodiments, the His-tag binding compound, engineered to comprise a detectable group, may be nearly or completely undetectable until it specifically reacts with a target sequence (i.e., with a His-tag peptide motif). Such engineered His-tag binding compound can be particularly useful because it provides a means to specifically and accurately detect the presence of the His-tag binding compound/target sequence complex with very little background signal.

Also within the scope of this invention is a His-tag binding compound that may be detectable before and after it specifically reacts with a target sequence to form the His-tag binding compound/target sequence complex. In such instances, it is preferable if the detectable signal of the His-tag binding compound can be differentiated from the detectable signal of the complex. For example, if the detectable signal of the His-tag binding compound is a fluorescent signal, it would be preferable if the fluorescence of the complex is red-shifted or blue-shifted relative to the detectable signal produced by the His-tag binding compound alone.

The His-tag binding compound may also lack a detectable signal, both before and even after specifically reacting with a target sequence. These His-tag binding compounds can be useful in many techniques that do not require a detectable signal, or that use other methods of detection. These His-tag binding compounds may be useful when the goal is to attach a polypeptide to a solid substrate, or cross-link two polypeptides.

In some embodiments, use of His-tag binding compounds according to this invention may provide a means to detect proteins of interest, wherein it may be advantageous to express these proteins of interest as His-tagged fusion proteins instead of expressing the protein as a fusion protein with a very large fluorescent protein (FP) attached to it. A His-tag binding compound of this invention, coupled to a synthetic agent and/or detectable group, (e.g. a fluorescent dye, or oligonucleotide), may then be used to target the protein of interest (See FIGS. 1 and 2, FIG. 32A, FIG. 41, and FIGS. 46-47 and 50-53B). Such His-tag targeted fluorescent agent is expected to fluoresce upon binding to the targeted His-tagged protein, which may serve as a genetically targeted probe, and/or as a turn-on fluorescent probe. In some embodiments, the His-tag binding compound is coupled to a protein surface receptor according to this invention. In some embodiments, the His-tag binding compound is coupled to a fluorescent dye. In some embodiments, the His-tag binding compound is coupled to a quinoline based cyanine dye (QBC). In some embodiments, the His-tag binding compound is coupled to an oligonucleotide.

In some embodiments, this invention is directed to a His-tag binding compound for use as a genetically targeted probe; or in some embodiments, for use as a fluorescent probe; or in some embodiments, for use as a turn on fluorescent probe; or in some embodiments, for use in imaging of a His-tagged polypeptide of interest within a cell; or in some embodiments, for use in the detection of a protein of interest (POI) in its native environment; or in some embodiments, for use in measuring gene expression of a His-tagged polypeptide of interest (POI) in a living and/or fixed cells; or in some embodiments, for the localization of a POI in a living and/or fixed cells; or in some embodiments, for use as an artificial receptor, capable of binding a His-tagged protein; or in some embodiments, for use in decorating a cell with a synthetic agent; or in some embodiments, for use in adhering a first cell to a second cell; or in some embodiments, for use in adhering a cell to a surface; or in some embodiments, for use in inducing luminescence in a cell; or in some embodiments, for use in binding a cell to a protein of interest (POI); each represents a separate embodiment according to this invention.

In some embodiments, the His-tag binding compound is coupled to a fluorescent dye. In some embodiments, the fluorescent dye is QBC. In some embodiments, the His-tag binding compound is coupled to a QBC. In some embodiments, the His-tag binding compound is coupled to an oligonucleotide. In some embodiments, the His-tag binding compound is coupled to a protein surface receptor. In some embodiments, the His-tag binding compound is a sensor according to this invention. In some embodiments, the His-tag binding compound is a fluorescent probe. In some embodiments, the His-tag binding compound is a turn-on fluorescent probe. In some embodiments, the His-tag binding compound is a genetically targeted probe.

In some embodiments, the fluorescently-tagged His-tag binding compound is a genetically targeted probe.

In some embodiments, said His-tag binding compound according to this invention is covalently linked to a fluorophore, directly or via a linker, thereby obtaining said fluorescently tagged His-tag binding compound. In some embodiments, said His-tag binding compound is linked to a fluorophore through the $R_1$ moiety of compounds of formulas XI-XVI. In some embodiments, said $R_1$ of compounds of formulas XI-XVI are linked to said fluorophore through a linker, wherein said linker is as described herein above for compounds according to this invention. In some embodiments, the fluorophore is a QBC.

In some embodiments, a fluorophore comprises a QBC. In some embodiments, a fluorophore comprises a solvatochromic dye. Solvatochromic fluorophores display sensitivity to the polarity of the local environment. These molecules exhibit a low quantum yield in aqueous solution but become highly fluorescent in nonpolar solvents or when bound to hydrophobic sites in proteins or membranes. In certain embodiments, solvatochromic fluorophores include 2-propionyl-6-dimethylaminonaphthalene (PRODAN) (Weber et al. *Biochemistry* 1979, 18, 3075-3078; Cohen et al. *Science* 2002, 296, 1700-1703), 4-dimethylamino phthalimide (4-DMAP) (Saroja et al. *J. Fluoresc.* 1998, 8, 405-410), and 4-amino-1,8-naphthalimide derivatives (Grabchev et al. *J. Photochem. Photobiol., A* 2003, 158, 37-43; Martin et al. *J. Lumin.* 1996, 68, 157-146). In some embodiments, the solvatochromic fluorophore is selected from: fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, Tamra, BODIPY, FITC, Thiazole orange, Quinoline blue, and Thiazole red. In some embodiments, said solvatochromic dye is dansyl.

In some embodiments, fluorescence emission is measured over time. In some embodiments, fluorescence emission is measure before and after a His-binding compound is incubated with a His-tagged polypeptide or a cell comprising a His-tagged polypeptide. In some embodiments, said measuring is of a live cell. In some embodiments, said measuring of is a fixed cell. In some embodiments, said measuring is of a cell supernatant.

In some embodiments, a cell is a mammalian cell. In some embodiments, a cell is a rat, a mouse, a dog, or a human cell. In some embodiments, a cell is a yeast cell. In some embodiments, a cell is a tissue culture cell-line cell. In some embodiments, a cell is a primary culture cell from a transgenic mammal. In some embodiments, a cell is a recombinant cell. In yet another embodiment, a cell comprises a nucleic acid encoding a His-tagged polypeptide of interest. In some embodiments, a cell expresses a His-tagged polypeptide of interest. In another embodiment a cell secretes a His-tagged polypeptide of interest. Each possibility comprises an embodiment of this invention.

In some embodiments, this invention is directed to a method for imaging a His-tagged polypeptide of interest (POI) within a cell, said method comprising the steps of:
a. expressing said His-tagged polypeptide in a recombinant cell;
b. incubating said recombinant cell with a fluorescent probe according to this invention; and
c. visualizing the fluorescence emission of said fluorescent probe.

In some embodiments, said recombinant cell is fixed using any method known in the art, prior to the incubating step. In some embodiments, the fluorescent probe passively crosses the plasma membrane of a live cell. In some embodiments, the fluorescent probe is micro-injected into a live cell. In some embodiments, the fluorescent probe is derivatized in a way that allows its crossing of the plasma membrane of a live cell. In some embodiments, said visualizing is observing under a microscope. In some embodiments, a fluorescent microscope is used to detect and localize the fluorescent signal. In some embodiments, a fluorescent microscope with a plate reader or the ability to record images at multiple locations over time is used to detect and localize the fluorescent signal. In some embodiments, the fluorescent probe is a genetically targeted sensor. In some embodiments, the fluorescent probe is a turn on probe. In some embodiments, the fluorescent probe is represented by formula XXI-XXV or XXXV-XXXVII. In some embodiments, the fluorescent probe is compound 408, 409, 410, 313, 314 or 315; each represents a separate embodiment according to this invention.

In some embodiments, this invention is directed to a method of labeling a protein of interest (POI) in complex environment using a fluorescent probe, said method comprises:
a. expressing a His-tagged POI in a complex environment;
b. incubating the His-tagged POI with a fluorescent probe according to this invention; and
c. measuring the fluorescence emission of said fluorescent probe:His-tagged P01 complex;
wherein detection of a fluorescent signal is dependent on the formation of said fluorescent probe:His-tagged POI complex.

In some embodiments, said fluorescent probe is a His-tag binding compound according to this invention coupled to a fluorescent dye or a fluorophore. In some embodiments, the fluorescent probe is a turn on probe. In some embodiments, the fluorescent probe is represented by formula XXI-XXV or XXXV-XXXVII. In some embodiments, the fluorescent probe is compound 408, 409, 410, 313, 314 or 315; each represents a separate embodiment according to this invention.

The term "complex environment" refers, In some embodiments, to an environment that comprises large proteins that tend to engage in non-specific interactions such as serum albumin (e.g., BSA and HSA).

In some embodiments, the complex environment comprises—, IgG, IgA, Avidine, Insulin, SAv, BSA, GST-P1, HSA, AGP or any combination thereof. In some embodiments, the complex environment is an environment that stabilizes the POI. In some embodiments, the complex environment is the native environment of the POI.

In some embodiments, this invention is directed to a method of identifying a protein of interest (POI) in complex environment using a fluorescent probe according to this invention, said method comprising:
a. expressing a His-tagged POI in a complex environment;
b. incubating the His-tagged POI with a fluorescent probe according to this invention; and
c. measuring the fluorescence emission of said fluorescent probe:His-tagged P01 complex;
wherein detection of a fluorescent signal is dependent on the formation of said fluorescent probe:His-tagged POI complex.

In some embodiments, the fluorescent probe is a turn on probe. In some embodiments, the fluorescent probe is represented by formula XXI-XXV or XXXV-XXXVII. In some embodiments, the fluorescent probe is compound 408, 409, 410, 313, 314 or 315; each represents a separate embodiment according to this invention.

In some embodiments, this invention is directed to a method of measuring gene expression of a His-tagged polypeptide of interest (POI) in a cell said method comprising the steps of:
a. expressing a His-tagged polypeptide of interest in a cell;
b. incubating the cell with a fluorescent probe according to this invention; and
c. measuring the fluorescence of said cell;
wherein detection of a fluorescent signal is dependent on the formation of a His-tagged polypeptide:fluorescent probe complex.

In some embodiments, the His-tagged polypeptide is a cell surface receptor and measuring comprising use of a fluorescent cell sorter. In some embodiments, the His-tagged polypeptide is secreted from the cells, and said measuring involves collecting the cell supernatant and measuring the fluorescence of the supernatant. In yet another embodiment, a method of measuring gene expressing comprises a further step of homogenizing a cell comprising a His-tagged polypeptide at a given time point, incubating the fluorescent probe with the cell homogenate, and measuring the resultant fluorescence. In some embodiments, a plate reader is used to measure the fluorescence of an array of cells. In some embodiments, a low-density array is used. Each possibility comprises an embodiment of the invention. Methods for measuring fluorescence are well known in the art. In some embodiments, the fluorescent probe is a turn on probe. In some embodiments, the fluorescent probe is represented by formula XXI-XXV or XXXV-XXXVII. In some embodiments, the fluorescent probe is compound 408, 409, 410, 313, 314 or 315; each represents a separate embodiment according to this invention.

In some embodiments, a His-tagged polypeptide comprises a polyhistidine tag. A "polyhistidine tag" (His-tag) according to this invention comprises at least 2, at least 3, at least 4, at least 5, at least 6, at least 7, at least 8, at least 9, at least 10 histidine residues. In some embodiments, a protein of interest (POI) comprises a polyhistidine tag of this invention, at its N-terminus. In some embodiments, a protein of interest (POI) comprises a polyhistidine tag of this invention, at its C-terminus. In some embodiments, a protein of interest (POI) comprises a polyhistidine tag of this invention, at an internal location of the contiguous amino acid sequence. In some embodiments, the His-tag comprises hexa-histidine peptide (6×His-tag). In some embodiments, the His-tag comprises deca-histidine peptide (10×His-tag).

Terms and Definitions

An "alkyl" or "alkylene" group refers, In some embodiments, to a saturated aliphatic hydrocarbon, including straight-chain and branched-chain. In some embodiments, the alkyl group has 1-20 carbons. In some embodiments, the alkyl has 1-12 carbons. In some embodiments, the alkyl group has 1-7 carbons. In some embodiments, the alkyl group has 1-5 carbons. In some embodiments, the alkyl group has 1-6 carbons. In some embodiments, the alkyl group has 1-4 carbons. The alkyl group may be unsubstituted or substituted by one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl. In some embodiments, the alkyl is-$(CH_2)_6$—. In some embodiments, the alkyl is-$(CH_2)_2$—. In some embodiments, the alkyl is-$(CH_2)_3$—. In some embodiments, the alkyl is-$CH_2$—. In some embodiments, the alkyl is-$CH_2$—CH($CH_2$—OH)—$(CH_2)_4$—. In some embodiments, the alkyl is-$CH_2$—CH($CH_2$—OH)—. In some embodiments the alkyl of this invention is optionally substituted and optionally interrupted by a heteroatom consisting of O, N, P, S or combination thereof.

A "haloalkyl" group refers, In some embodiments, to an alkyl group as defined above, which is substituted by one or more halogen atoms, e.g. by F, Cl, Br or I.

A "hydroxyl" group refers, In some embodiments, to an OH group. It is understood by a person skilled in the art that when $R_1$, $R_2$ or $R_3$ in the compounds of the present invention is OR, then R is not OH.

In some embodiments, the term "halogen" or "halo" refers to a halogen, such as F, Cl, Br or I.

An "alkynyl" refers to unsaturated hydrocarbon which comprises at least one carbon-carbon triple bond. In some embodiments, the alkynyl group has 2-20 carbons. In some embodiments, the alkynyl has 2-12 carbons. In some embodiments, the alkynyl has 2-6 carbons. In some embodiments, the alkynyl has 2 carbons.

An "arylalkyl" group refers to an alkyl bound to an aryl, wherein alkyl and aryl are as defined above. An example of an aralkyl group is a benzyl group.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In some embodiments, the aryl group is a 4-8 membered ring. In some embodiments, the aryl group is a 4-12 membered ring(s). In some embodiments, the aryl group is a 6 membered ring. In some embodiments, the aryl group is a 5 membered ring. In some embodiments, the aryl group is 2-4 fused ring system.

An "alkyl ether" of this invention refers to an alkyl as defined above interrupted by one or more oxygen atoms. In some embodiments, alkyl ether refers to a PEG (polyethylene glycol). In some embodiments, alkyl ether refers to —$[(CH_2)_2—O]_k$— wherein k is between 1 and 20. In some embodiments, the alkylether has 1-6 carbon atoms. In some embodiments, the alkylether has 1-12 carbon atoms. In some embodiments, the alkylether has 1-20 carbon atoms. In some embodiments, the alkylether has 3 carbon atoms. In some embodiments, the alkylether has 4 carbon atoms. In some embodiments, the alkylether has 2-5 carbon atoms. In some embodiments, the alkylether has 2 carbon atoms. In some embodiments, the alkylether is-$CH_2$—$CH_2$—O—$CH_2$—.

An "alkyl amine" of this invention refers to an alkyl as defined above which has an amine moiety within the carbon atom chain. In some embodiments, alkyl amine refers to $(CH_2)_n$—NH—. In some embodiments, the amine moiety is at one end of the carbon chain. In some embodiments, the amine moiety is within the backbone of the carbon chain. In some embodiments, the alkyl amine is a substituted or unsubstituted linear or branched alkyl of 1-6 carbon atoms which has an amine moiety at one end. In some embodiments, the alkyl amine is a substituted or unsubstituted linear or branched alkyl of 1-12 carbon atoms which has an amine moiety at one end. In some embodiments, the alkyl amine is a substituted or unsubstituted linear or branched alkyl of 1-3 carbon atoms which has an amine moiety at one end.

An "alkyl amide" of this invention refers to an alkyl as defined above which has an amide moiety at one end. In some embodiments, alkyl amide refers to $(CH_2)_n$—NHC(O). In some embodiments, alkyl amide refers to $(CH_2)_n$—C(O)NH wherein n is an integer between 1 and 10. In some embodiments, the alkyl amide is a substituted or unsubstituted linear or branched alkyl of 1-6 carbon atoms which has an amide moiety at one end. In some embodiments, the alkyl amide is a substituted or unsubstituted linear or branched alkyl of 1-12 carbon atoms which has an amide moiety at one end. In some embodiments, the alkyl amide is a substituted or unsubstituted linear or branched alkyl of 1-3 carbon atoms which has an amide moiety at one end. In some embodiments, the alkyl amide is-$(CH_2)_6$—NHC(O). In some embodiments, the alkyl amide is —$(CH_2)_2$—NHC(O). In some embodiments, the alkyl amide is-$CH_2$—NHC(O). In some embodiments, the alkyl amide is-$CH_2$—CH($CH_2$—OH)—$(CH_2)_4$—NHC(O). In some embodiments, the alkyl amide is-$CH_2$—CH($CH_2$—OH)—NHC(O).

An "alkyl di-amide" of this invention refers to an alkyl as defined above which is interrupted by two amide moieties. In some embodiments, alkyl di-amide refers to $(CH_2)_n$—NHC(O)—$(CH_2)_m$—NHC(O) wherein n is an integer between 1 and 10. In some embodiments, the alkyl di-amide is a substituted or unsubstituted linear or branched alkyl of 1-6 carbon atoms which has an amide moiety at one end of the carbon chain and another amide moiety inside the backbone of the chain. In some embodiments, the alkyl di-amide is a substituted or unsubstituted linear or branched alkyl of 2-12 carbon atoms which has two amide moieties within the carbon chain. In some embodiments, the alkyl di-amide is a substituted or unsubstituted linear or branched alkyl of 2-6 carbon atoms which has two amide moieties within the carbon chain. In some embodiments, the alkyl di-amide is a substituted or unsubstituted linear or branched alkyl of 1-20 carbon atoms which has two amide moieties within the carbon chain. In some embodiments, the alkyl di-amide is —$CH_2$—CH($CH_2OH$)—NHC(O)—$(CH_2)_2$—NHC(O)—. In some embodiments, the alkyl di-amide is-NHC(O)—$(CH_2)_2$—NHC(O)—.

An "alkyl triazole" of this invention refers to an alkyl as defined above which has a triazole moiety at one end. In some embodiments, alkyl triazole refers to $(CH_2)_n$-triazole wherein n is an integer between 1 and 10. In another embodiment n is 3. In some embodiments, the alkyl triazole is a substituted or unsubstituted linear or branched alkyl of 1-6 carbon atoms which has a triazole moiety at one end. In some embodiments, the alkyl triazole has 1-12 carbon atoms. In some embodiments, the alkyl triazole has 1-3 carbon atoms.

The term "substituted" refer to substitutions that include one or more groups selected from: halogen, hydroxy, hydroxyalkyl, alkoxy, haloalkyl, carbonyl, amido, alkylamido, dialkylamido, nitro, cyano, amino, alkylamino, dialkylamino, carboxyl, thiol, thioalkyl and the like.

In some embodiments, a "subject" refers to a mammal, a human, a female or a male.

The terms "comprises" and variations thereof do not have a limiting meaning where these terms appear in the description and claims.

Unless otherwise specified, "a," "an," "the," and "at least one" are used interchangeably and mean one or more than one.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The following examples are presented in order to more fully illustrate the preferred embodiments of the invention. They should in no way be construed, however, as limiting the broad scope of the invention.

EXAMPLES

Materials and Methods

All solvents and reagents were obtained from commercial suppliers and used without further purification. Dry solvents were purchased from Sigma Aldrich with the exception of dry DMSO, which was purchased from Arcos.

IgG from human serum, IgA from human serum, human serum albumin (HSA), human $\alpha_1$ acid glycoprotein (AGP) and calmodulin (CaM) from bovine testes were purchased from Sigma Aldrich. Human recombinant GST-P1-1, mouse recombinant His-calmodulin, human recombinant Drp1 (DAPK-related protein 1), and human recombinant CaMKII were obtained from the Israel Structural Proteomics Center (Weizmann Institute of Science). M13 and Bax BH3 peptide (55-74) wild type were purchased from Anaspec (Fremont, CA). Protein G protein fragment His-Tag was purchased from abeam. Recombinant human insulin from yeast, recombinant human B-cell lymphoma protein 2 alpha His-Tag (Bcl-2), recombinant streptavidin from *Streptomyces avidinii*, and avidin from hen's egg white were all purchased from ProSpec-Tany TechnoGene Ltd. (Ness Ziona, Israel). Bovine serum albumin (BSA) was purchased from MP biomedicals (Santa Ana, CA). Fmoc-L-2,3-diaminopropionic acid, cholesterol and paclitaxel were purchased from Chem-Impex International (Wood Dale, IL). $H_2N$-$PEG_3$-tBu, 4-Azidobutyric acid and tolbutamide were purchased from Chem-Impex International (Wood Dale, IL), ChemPep, Inc. (Wellington, FL), and Chiralix (Nijmegen, The Netherlands), respectively. Calmidazolium, Mastoparan, sodium salicylate, andrographolide, pioglitazone, DPC (fenamic acid), apigenin, aspirin, carbimazole, α-D-glucose-6-phosphate monosodium salt (α-G6P), angiotensin II human, 1,3-PB-ITU dihydrobromide, irsogladine maleate, and PP2 (4-amino-5-(4-chlorophenyl)-7-(t-butyl)pyrazolo [3,4-d]pyrimidine) were purchased from Santa Cruz Biotechnology. Dopamine, histamine dihydrochloride, ouabain octhahydrate, naringin, amikacin, biotin, digitoxin, estrone, glucose pentaacetate, podophyllotoxin, colchicine, neocuproine hydrate, and erythromycin were purchased from Sigma Aldrich. λ-protein phosphatase and CaMKII (phospho Thr305) antibody were purchased from New England Biolabs (UK) Ltd, and GeneTex (Irvine, CA), respectively. Anti-flag-tag antibody was purchased from Pierce thermo scientific (Rockford, IL). The $^1H$ NMR spectra were recorded on a Bruker Avance 300 MHz NMR instrument. Electronspray mass spectrometry was performed either with a Micromass Platform LCZ-4000 instrument at the Weizmann Institute of Science mass spectrometry facility or by using the LTQ Orbitrap Discovery hybrid FT mass spectrometer (Thermo Fisher Scientific, Inc.) equipped with an electrospray ionization ion source at the Faculty of Agriculture, Hebrew University of Jerusalem. The exact masses from elemental compositions were calculated using ChemDraw Ultra 12.0. Analytical reversed phase high-performance liquid chromatography (RP-HPLC) analysis was performed either on a Waters liquid chromatography system equipped with a 2487 dual wavelength UV detector, 600 gradient pump, and a 717 plus autosampler or an Agilent 1260 infinity quaternary pump LC system, maximum pressure 400 bar, equipped with a diode-array detector with max-light high-sensitivity cartridge cell.

Peptides were either synthesized manually (peptide P1, Table 1) or purchased from Synpeptide Co., Ltd. Shanghai, China (peptides P2 and P3, Table 1) or using an automated synthesizer (Advanced ChemTech, Apex 396) (peptides P4 and P5, Table 1). The azido-modified peptides (Table 1) and compounds $C_{10}$-$C_{19}$ (Table 1) were purified by RP-HPLC using a ThermoSeparation instrument (P200 pump, UV 100 detector), and a pre-packed Vydac $C_{18}$ column. Protein structures were produced using Discovery Studio Visualizer, version 2.5 (Accelrys, San Diego, CA). Structures of CaM, CaM($Ca^{+2}$), CaM-M13, CaMKII, and CaMKII/CaM ($Ca^{+2}$) were taken from the Protein Databank codes 1 CFD, 1CLL, 2BBM, 2VN9, 2WEL, respectively.

Fluorescence was measured using a BioTek synergy H4 hybrid multiwell plate reader, in black flat-bottom polystyrene NBS 384-well microplates (Corning). The same machine was used to calculate the concentration of the final sensors using clear flat-bottom polystyrene 384 well microplates (Corning). The concentrations of compounds 1-5 were determined by measuring the absorbance of dansyl at 330 nm and using an extinction coefficient s=4300 $M^{-1}cm^{-1}$. Protein concentrations were determined using a Nano-Drop ND-1000 spectrophotometer (Thermo Scientific).

Example 1

Synthetic Details for Various Compounds of the Invention

Figure 3:
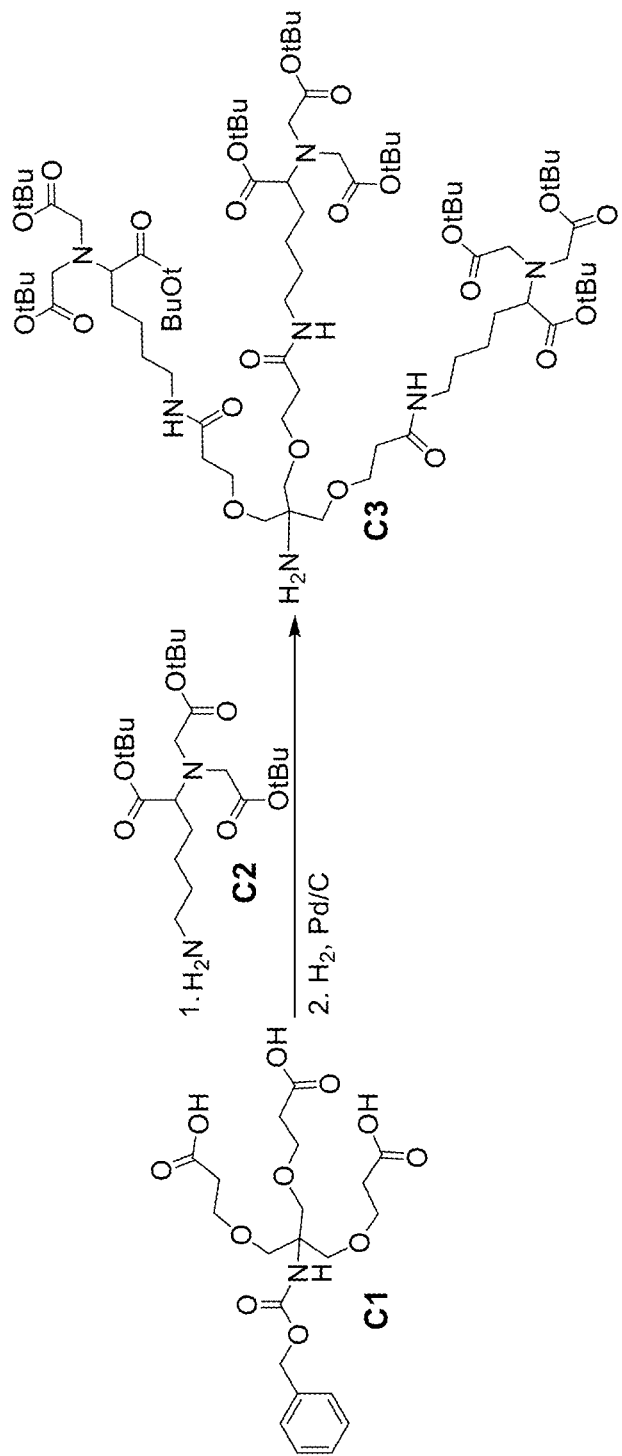
FIG. 3 depicts a synthetic scheme of the synthesis of a His-tag binder comprising tri-Nitrilotriacetic Acid (C3).

Fluorescent Molecular Sensor for Targeting Changes in Protein Surfaces
Synthesis of Tri-Nitrilotriacetic Acid (C3) (FIG. 3)
Compounds C1 and C2 were synthesized according to published procedures. The synthetic details of compounds C1 and C2 are described in Example 3 below.

Compound C1 (615 mg, 1.3 mmol), compound C2 (1.8 g, 4.18 mmol), EDC (996.8 mg, 5.2 mmol), HOBt (175.63 mg, 1.3 mmol), and triethyl amine (725.2 µL, 5.2 mmol) were mixed under argon in dry THF (40 mL) for 36 hours. The solvent was evaporated and the mixture was re-dissolved in diethyl ether and washed with HCl (0.5 M) and brine. After drying with $Na_2SO_4$, the product was purified by combiflash silica column chromatography using a gradient of 0-7% MeOH in DCM to afford the pure material (1.16 g, 52% yield).

$^1$H NMR (300 MHz, $CDCl_3$): δ=1.43 (s, 54H), 1.44 (s, 27H), 1.50-1.56 (m, 12H), 1.63-1.65 (m, 6H), 2.40 (t, J=5.7 Hz, 6H), 3.15-3.22 (m, 6H), 3.32 (t, J=7.4 Hz, 3H), 3.40-3.54 (m, 12H), 3.62 (s, 6H), 3.67 (t, J=5.6 Hz, 6H), 5.01 (s, 2H), 5.40 (s, 1H), 6.78-6.79 (m, 2H), 7.32-7.33 (m, 5H).

ESI$^+$-MS (m/z): calcd. for [M+Na]$^+$1732.04, found 1732.42, calcd. for [M+2Na]$^{+2}$ 877.01, found 877.40, calcd. for [M+3Na]$^{+3}$ 592.34, found 592.84.

This product was then hydrogenated using 10% Pd/C (86 mg) in methanol (20 mL) under $H_2$ atmosphere (1 atm) overnight. After complete removal of the benzyl group, as determined by TLC and ninhydrin staining, the palladium catalyst was filtered through cotton to afford a viscous oily product (925 mg, 87% yield).

$^1$H NMR (300 MHz, $CDCl_3$): δ=1.44 (s, 54H), 1.45 (s, 27H), 1.52-1.58 (m, 12H), 1.63-1.64 (m, 6H), 2.42-2.50 (m, 6H), 3.22-3.24 (m, 6H), 3.27-3.32 (m, 3H), 3.36-3.47 (m, 12H), 3.50-3.62 (m, 6H), 3.72-3.75 (m, 6H), 6.65-6.68 (m, 1H), 7.17 (br-s, 2H).

ESI$^+$-MS (m/z): calcd. for [M+H]$^+$ 1575.03 found 1575.29, calcd. for [M+2H]$^{+2}$ 788.01, found 788.40.

Figure 4:
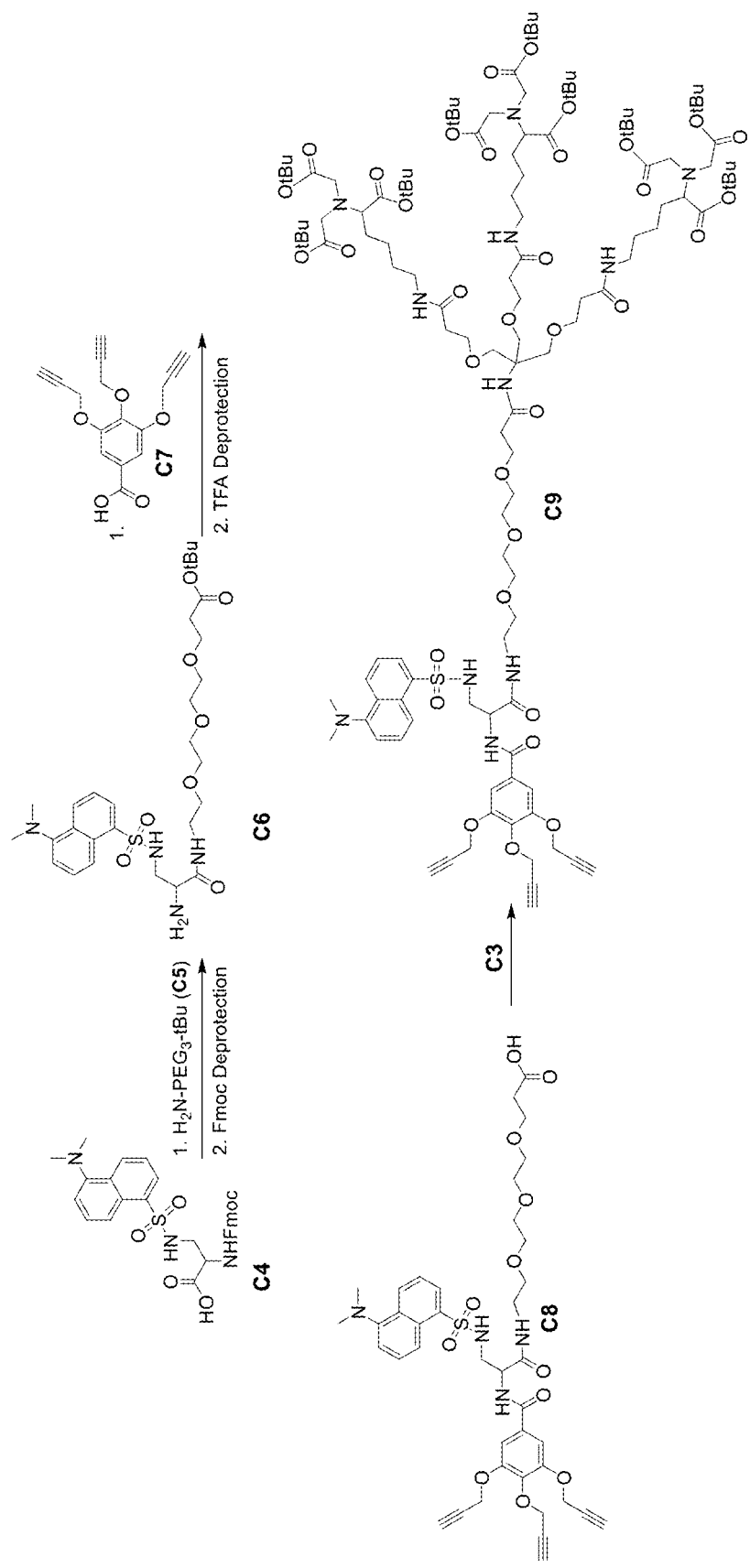
FIG. 4 depicts a synthetic scheme of the synthesis of compound C9.

Synthesis of Compound C9 (FIG. 4)

C4, C7 were synthesized according to previously published procedures.

Compound C6 (FIG. 4)

C4 (1.64 g, 2.9 mmol), C5 (805 mg, 2.9 mmol), DIPEA (1 mL, 5.8 mmol), and HATU (1.1 g, 2.9 mmol) were stirred in dry THF (50 mL) under argon at room temperature overnight. The reaction mixture was evaporated and then purified by combiflash silica column chromatography using a gradient of 0-8% MeOH in DCM to afford the Fmoc protected product (2.13 g, 89% yield).

$^1$H NMR (300 MHz, $CDCl_3$): δ=1.42 (s, 9H), 2.45 (t, J=6.6 Hz, 2H), 2.86 (s, 6H), 3.10-3.33 (m, 2H), 3.38-3.45 (m, 2H), 3.54-3.60 (m, 10H), 3.65 (t, J=6.5 Hz, 2H), 4.17-4.21 (m, 1H), 4.27 (m, 1H), 4.31-4.33 (m, 2H), 5.99-6.06 (m, 2H), 6.97 (br-s, 1H), 7.16 (d, J=7.5 Hz, 1H), 7.29-7.34 (m, 2H), 7.37-7.42 (m, 2H), 7.49-7.60 (m, 4H), 7.76 (d, J=7.5 Hz, 2H), 8.25-8.28 (m, 2H), 8.54 (d, J=8.4 Hz, 1H).

ESI$^+$-MS (m/z): calcd. for [M+Na]$^+$841.34, found 841.39.

Next, the Fmoc group of the residue (321 mg, 0.39 mmol) was deprotected by 20% piperidine in dry DMF (15 mL) for 1 hour. The solvent was then evaporated and the residue was further placed under high vacuum for 6 h. The product was purified by combiflash silica column chromatography using a gradient of 0-3.5% MeOH in DCM to afford C6 (170 mg, 65% yield).

$^1$H NMR (300 MHz, $CDCl_3$): δ=1.42 (s, 9H), 2.50 (t, J=6 Hz, 2H), 2.88 (s, 6H), 3.09 (dd, J=4.8, 13.5 Hz, 1H), 3.18-3.24 (m, 2H), 3.40-3.45 (m, 2H), 3.50 (t, J=5.3 Hz, 1H), 3.54-3.57 (m, 2H), 3.60-3.62 (m, 8H), 3.69 (t, J=6.2 Hz, 2H), 7.18 (d, J=7.5 Hz, 1H), 7.49-7.60 (m, 2H), 7.64-7.65 (m, 1H), 8.18-8.26 (m, 2H), 8.54 (d, J=8.4 Hz, 1H).

ESI$^+$-MS (m/z): calcd. for [M+H]$^+$ 597.29, found 597.40, calcd. for [M+Na]$^+$619.27, found 619.40.

Compound C8 (FIG. 4)

C6 (168 mg, 0.281 mmol), C7 (88.04 mg, 0.309 mmol), N,N-Diisopropylethylamine (DIPEA) (97.88 µL, 0.56 mmol), and HCTU (290.6 mg, 0.70 mmol) were stirred in 10 mL dry THF under argon at room temperature overnight. Then the solvent was evaporated and the residue was purified by combiflash silica column chromatography using a gradient of 0-5% MeOH in DCM. The fractions containing the product were collected, dissolved with ethyl acetate, and washed with 0.5M HCl, 0.5 M NaOH and brine, and then the organic layer was dried with $Na_2SO_4$. The tert-butyl protected product (130 mg) was obtained with a 53% yield.

$^1$H NMR (300 MHz, $CDCl_3$): δ=1.42 (s, 9H), 2.44-2.49 (m, 2H), 2.58-2.59 (m, 1H), 2.79 (s, 2H), 2.89 (s, 6H), 3.15-3.24 (m, 1H), 3.42-3.46 (m, 3H), 3.56 (br-s 6H), 3.60 (br-s 4H) 3.66 (t, J=6.5 Hz, 2H), 4.59-4.61 (m, 1H), 4.82-4.84 (m, 6H), 6.39-6.43 (m, 1H), 7.19 (d, J=7.5 Hz, 1H), 7.31 (t, J=5.3 Hz, 1H), 7.36 (s, 2H), 7.48-7.57 (m, 2H), 7.82 (d, J=6.9 Hz, 1H), 8.23-8.27 (m, 2H), 8.56 (d, J=8.4 Hz, 1H).

ESI$^+$-MS (m/z): calcd. for [M+Na]$^+$885.33, found 885.19, calcd. for [2M+Na]$^{+1}$ 1747.68, found 1747.50.

The tert-butyl protected product (120 mg) was then dissolved in a mixture of TFA/DCM (6 mL; 1:1) and stirred for 2 h. The reaction mixture was diluted with chloroform (50 mL) and evaporated 5 times and placed under high vacuum overnight to afford C8 in a quantitative yield.

$^1$H NMR (300 MHz, $CDCl_3$): δ=2.47 (t, J=2.1 Hz, 1H), 2.55-2.58 (m, 4H), 2.95 (s, 6H), 3.24-3.34 (m, 2H), 3.43-3.47 (m, 2H), 3.58-3.70 (m, 10H), 3.73-3.80 (m, 2H), 4.79-4.81 (m, 7H), 6.82 (t, J=6.2 Hz, 1H), 7.21-7.24 (m, 1H), 7.28 (s, 2H), 7.48-7.56 (m, 2H), 7.77-7.82 (m, 1H), 7.91 (d, J=7.5 Hz, 1H), 8.25 (d, J=7.2 Hz, 1H), 8.36 (d, J=8.7 Hz, 1H), 8.58 (d, J=8.4 Hz, 1H).

ESI$^+$-MS (m/z): calcd. for [M+Na]$^+$829.27, found 829.35, calculated for [M−H+2Na]$^+$851.25, found 851.41. ESI$^-$-MS (m/z): calcd. for [M−H]$^-$ 805.27, found 805.39.

Compound C9 (FIG. 4)

A solution of C8 (40 mg, 49.5 mol), C3 (186 mg, 118 µmol), HCTU (56.29 mg, 136 µmol), and DIPEA (23.6 µL, 135.5 mol) in 3 mL dry THF was stirred overnight under argon. The solvent was evaporated and the reaction was purified by combiflash silica column chromatography using a gradient of 0-4.8% MeOH in EtOAc to afford C9 (74 mg, 63% yield).

$^1$H NMR (300 MHz, $CD_3CN$): δ=1.40-1.42 (m, 81H), 1.56-1.61 (m, 18H), 2.29-2.31 (m, 11H), 2.82-2.84 (m, 6H), 2.90 (br-s, 1H), 3.09-3.11 (m, 6H), 3.25-3.32 (m, 8H), 3.36-3.41 (m, 10H), 3.45-3.48 (m, 11H), 3.58 (br-s, 13H), 4.42-4.46 (m, 1H), 4.74-4.76 (m, 2H), 4.80-4.81 (m, 4H), 6.66-6.67 (m, 1H), 6.83-6.85 (m, 3H), 7.16-7.21 (m, 3H), 7.49-7.58 (m, 2H), 7.68-7.70 (m, 1H), 8.17-8.24 (m, 2H), 8.47-8.52 (m, 1H).

ESI$^+$-MS (m/z): calcd. for [M+3Na]$^{+3}$ 810.75, found 810.84 calcd. for [M+2Na]$^{+2}$ 1204.63, found 1204.67.

Figure 5:
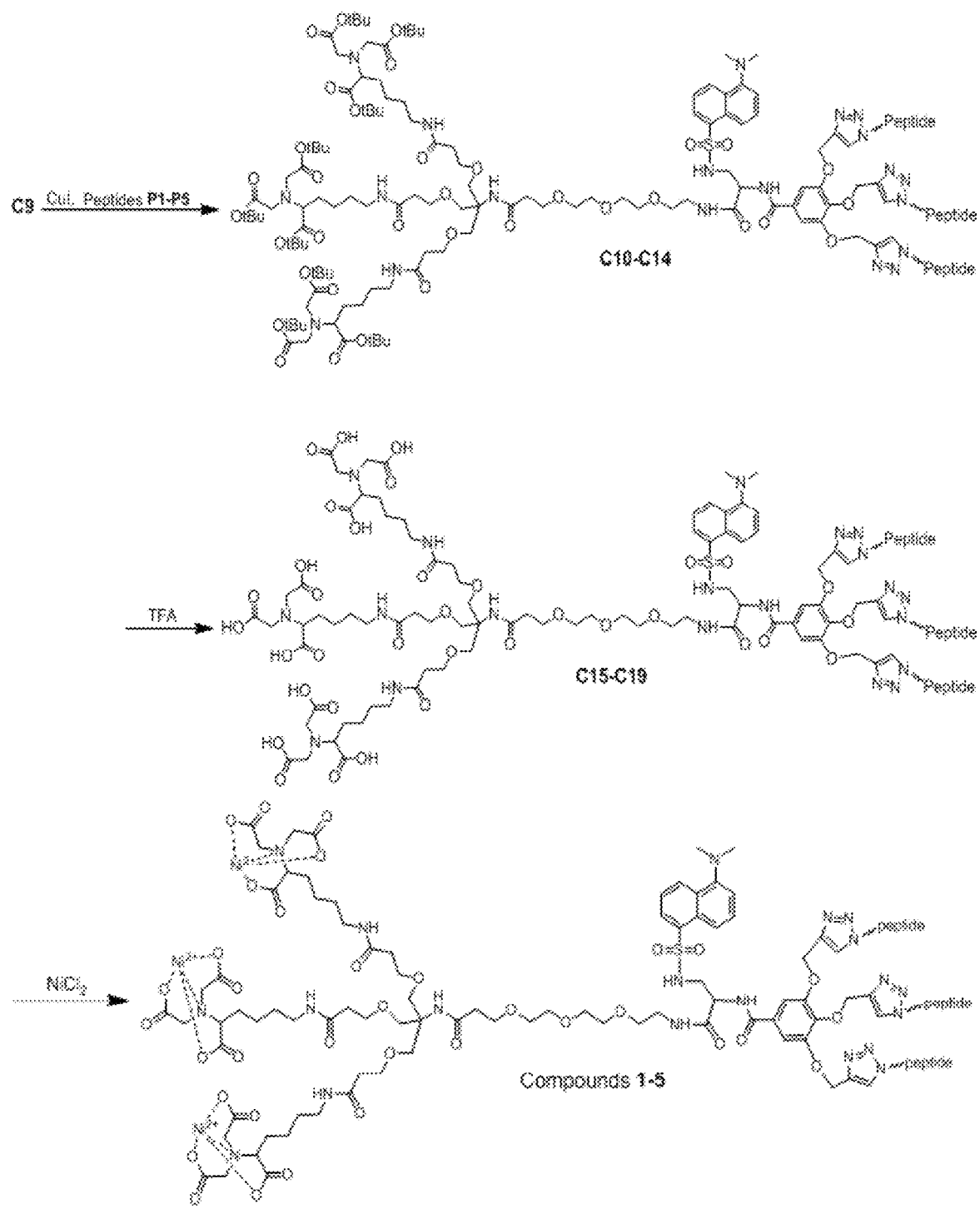
FIG. 5 depicts a synthetic scheme of the synthesis of compounds 1-5.
Figure 6:
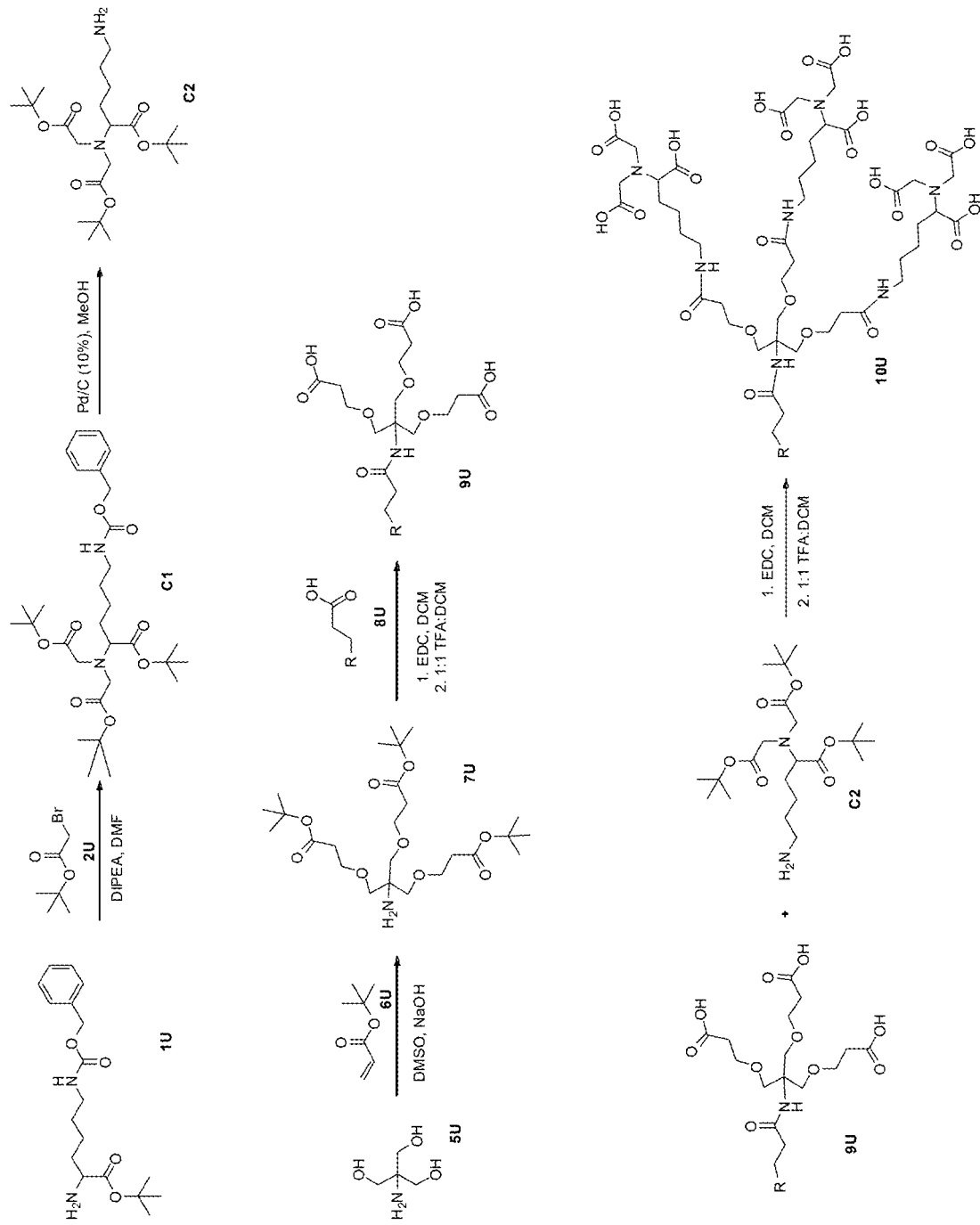
FIG. 6 depicts a synthetic scheme for preparing a variety of modified tri NTA compounds (10u) whose complex with Ni(II) can selectively bind His Tags.
Figure 14:
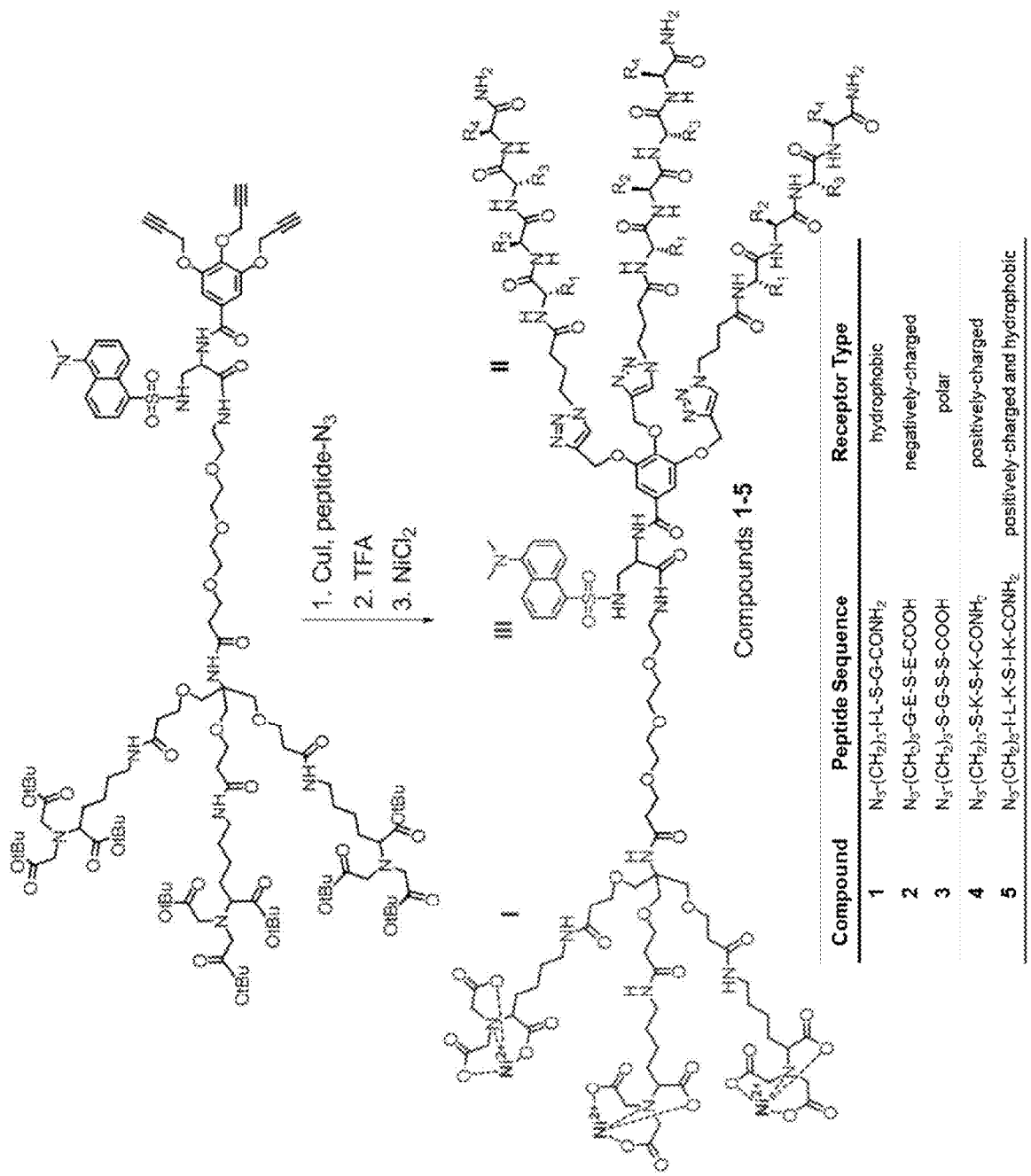
FIG. 14 depicts a method for preparing different protein surface sensors comprising a tri-Ni$^{+2}$-NTA complex (I), a tripodal peptide receptor (II), and a dansyl group (III), which serve as a His-tag binder, a protein surface receptor, and a solvatochromic probe, respectively.

Synthesis of Compounds 1-5. (FIGS. 5, 14)

TABLE 1

The sequences of the peptides used in this study.

| Compound | peptide | Peptide sequence |
|---|---|---|
| C10, C15 | P1 | $N_3$—$(CH_2)_3$—I-L-S-G-$CONH_2$ |
| C11, C16 | P2 | $N_3$—$(CH_2)_3$-G-E-S-E-COOH |
| C12, C17 | P3 | $N_3$—$(CH_2)_3$-S-G-S—S—COOH |
| C13, C18 | P4 | $N_3$—$(CH_2)_3$—S—K—S—K—$CONH_2$ |
| C14, C19 | P5 | $N_3$—$(CH_2)_3$—I-L-K—S—I—K—$CONH_2$ |

TABLE 1A

SEQ ID Nos. of the peptides used in this study.

| Peptide sequence | SEQ ID No. |
|---|---|
| I-L-S-G | SEQ ID No. 1 |
| G-E-S-E | SEQ ID No. 2 |
| S-G-S-S | SEQ ID No. 3 |
| S-K-S-K | SEQ ID No. 4 |
| I-L-K-S-I-K | SEQ ID No. 5 |

Compound C10 (FIG. 5)

C9 (6.52 mg, 2.76 µmol) and P1 (Table 1, 8.25 mg, 16.5 µmol) were dissolved in 200 µL DMSO and 2 mL acetonitrile under argon. Then 2,6-lutidine (3.82 µL, 33 mol), DIPEA (5.75 µL, 33 mol), and CuI (1.84 mg, 9.65 µmol) were sequentially added under argon. The reaction mixture was stirred overnight. The solvents were removed and the residue was purified using RP-HPLC. Yield: 22.5%.

HRMS-$ESI^+$ (m/z) calcd. for $[M+2Na]^{+2}$, 1952.5753 found, 1952.5712, calcd. for $[M+3Na]^{+3}$, 1309.3800 found 1309.3784.

Compound C11 (FIG. 5)

C9 (5.18 mg, 2.19 µmol) and P2 (7 mg, 13.1 µmol) were dissolved in 100 µL DMSO under argon. Then 2,6-lutidine (3.07 µL, 26.3 mol), DIPEA (4.58 µL, 26.3 mol), and CuI (5 mg, 26.3 µmol) were sequentially added under argon. The reaction mixture was stirred overnight. The reaction was purified using RP-HPLC. Yield 23%. C11 was used directly for the next step.

Compound C12 (FIG. 5)

C9 (3.64 mg, 1.54 µmol) and P3 (4.14 mg, 9.255 µmol) were dissolved in 100 µL DMSO under argon. Then 2,6-lutidine (2.15 µL, 18.5 µmol), DIPEA (3.22 µL, 18.5 mol), and CuI (3.52 mg, 18.5 µmol) were sequentially added under argon. The reaction mixture was stirred overnight. The reaction was purified using RP-HPLC. Yield 52.6%.

HRMS-$ESI^+$ (m/z) calcd. for $[M-2H]^{-2}$, 1851.8987 found 1851.8998, calcd. for $[M-3H]^{-3}$, 1234.2634, found 1234.2618.

Compound C13 (FIG. 5)

C9 (6.13 mg, 2.59 mol) and P4 (8.7 mg, 15.6 mol) were dissolved in 100 µL DMSO under argon. Then 2,6-lutidine (3.62 µL, 31.1 µmol), DIPEA (5.42 µL, 31.1 µmol), and CuI (5.93 mg, 31.1 µmol) were sequentially added under argon. The reaction mixture was stirred overnight. The reaction was purified using RP-HPLC. Yield 42%.

HRMS-$ESI^+$ (m/z) calcd. for $[M+3H]^{+3}$ 1347.4304, found 1347.4290, calcd. for $[M+4H]^{+4}$ 1010.8246, found 1010.8240, calcd. for $[M+5H]^5$ 808.8611, found 808.8604.

Compound C14 (FIG. 5)

C9 (3.93 mg, 1.66 µmol) and P5 (8.1 mg, 9.98 µmol) were dissolved in 100 µL DMSO under argon. Then 2,6-lutidine (2.32 µL, 19.9 µmol), DIPEA (3.46 µL, 19.9 mol), and CuI (3.79 mg, 19.9 µmol) were sequentially added under argon. The reaction mixture was stirred overnight. The reaction was purified using RP-HPLC. Yield 37%.

HRMS-$ESI^+$ (m/z) calcd. for $[M-3H]^{-3}$ 1597.6360, found 1597.6362

Compounds C15-C19 (FIG. 5)

Compounds C10-C14 were deprotected using 50% TFA in DCM (1 mL) for 6 h. The solvent and TFA were removed and the products were purified using RP-HPLC.

Compound C15: yield 40%, HRMS-$ESI^+$ (m/z) calcd. for $[M-3H+Na]^{-2}$ 1686.7864, found 1686.7852, calcd. for $[M-3H]^{-3}$ 1116.8612, found 1116.8598.

Compound C16: yield 32%, HRMS-$ESI^+$ (m/z) calcd. for $[M-2H]^{-2}$ 1725.1470, found 1725.1455, calcd. for $[M-3H]^{-3}$ 1149.7623, found 1149.7610.

Compound C17: yield 29%, HRMS-$ESI^+$ (m/z) calcd. for $[M-2H]^{-2}$ 1599.1153, found 1599.1142, calcd. for $[M-3H]^{-3}$ 1065.7411, found 1065.7411.

Compound C18: yield 38%, HRMS-$ESI^+$ (m/z) calcd. for $[M-2H]^{-2}$ 1766.3456, found 1766.3456, calcd. for $[M-3H]^{-3}$ 1177.2280, found 1177.2273.

Compound C19: yield 64%, HRMS-$ESI^+$ (m/z) calcd. for $[M-3H]^{-3}$ 1429.4482, found 1429.4482.

General Procedure for Peptide Synthesis

Peptide 1 (P1, Table 1) was synthesized manually on Rink amide resin using standard solid phase Fmoc method. Coupling reactions were run on a 0.2-mmol scale. The coupling was carried out using a twofold excess of each amino acid (coupling for 1 hour), PyBOP/NMM as the coupling reagents, and 25% piperdine in NMP for Fmoc deprotection. 4-azidobutyric acid (1.2 equiv.) was coupled overnight using the HOAT/DIC (1.2 equiv.) coupling reagents.

Peptides 2 and 3 (P2 and P3, Table 1), synthesized on Wang resin were purchased from Synpeptide Co., Ltd. Shanghai, China.

Peptides 4 and 5 (P4 and P5, Table 1) were synthesized using an automated synthesizer (Advanced ChemTech, Apex 396) on Rink amide resin. The coupling was carried out using a sixfold excess of each amino acid (coupling for 2×45 min), HCTU/DIPEA as coupling reagents, and 25% piperdine in NMP for Fmoc deprotection. 4-azidobutyric acid (1.2 equiv.) was coupled overnight using HOAT/DIC (1.2 equiv.) coupling reagents. The peptides were cleaved from resin by TFA/$H_2O$/triisopropylsilane (95:2.5:2.5) for 2 h. The peptides were purified using preparative RP-HPLC on a C18 column and characterized by electrospray mass spectrometry.

P1: $ESI^+$-MS (m/z): calcd. for $[M+H]^+$ 499.29, found 499.32, calcd. for $[M+Na]^+$ 521.28, found 521.26.

P2: $ESI^-$-MS (m/z): calcd. for $[M-H]^-$ 530.18, found 530.20

P3: ESI⁻-MS (m/z): calcd. for [M−H]⁻ 446.16, found 446.13.

P4: ESI⁺-MS (m/z): calcd. for [M+H]⁺ 559.33, found 559.43 calcd. for [M+Na]⁺581.31, found 581.36.

P5: ESI⁺-MS (m/z): calcd. for [M+H]⁺ 811.55, found 811.60.

Compounds 1-5 (FIG. 5)

An aqueous solution of $NiCl_2$ (final concentration, 79.2 µM) was added to a solution of compounds 1-5 (12 µM) in PBS buffer (4.1 mM, pH=7.3) and incubated for either 30 minutes or overnight.

Example 2

Synthetic Routes for Preparing Universal His-Tag Binding Compounds (Compound 10u) (FIGS. 6-10)

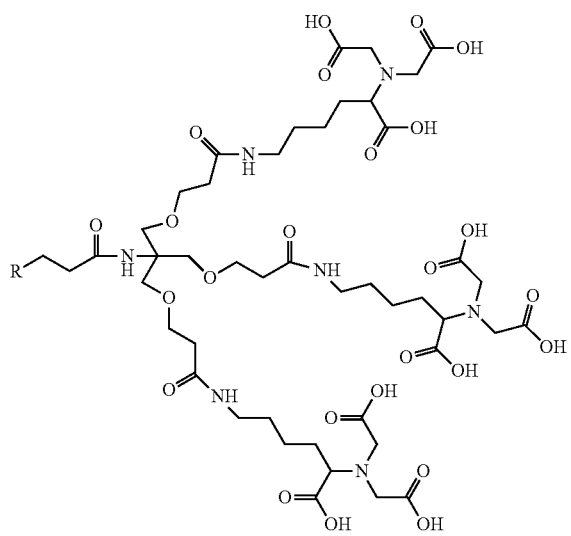

10u

The synthesis of 10u begins with N-alkylation of N-benzyloxycarbonyl-L-lysine tert-butyl ester (1u) with tert-butyl bromoacetate (2u), followed by benzyl deprotection to obtain an amino-modified NTA (C2), according to a literature procedure. A tripodal precursor molecule (9u) was also synthesized according to a reported procedure by 1,4-addition of 2-amino-2-hydroxymethyl-propane-1,3-diol (5u) to tert-butyl acrylate (6u), followed by coupling to a modified carboxylic acid (8u) and TFA deprotection. The final product (10u), whose complex with Nickel (II) can tightly bind His-tags, was obtained by coupling 9u to C2 using EDC and deprotecting the t-butyl groups by TFA.

Figure 7:
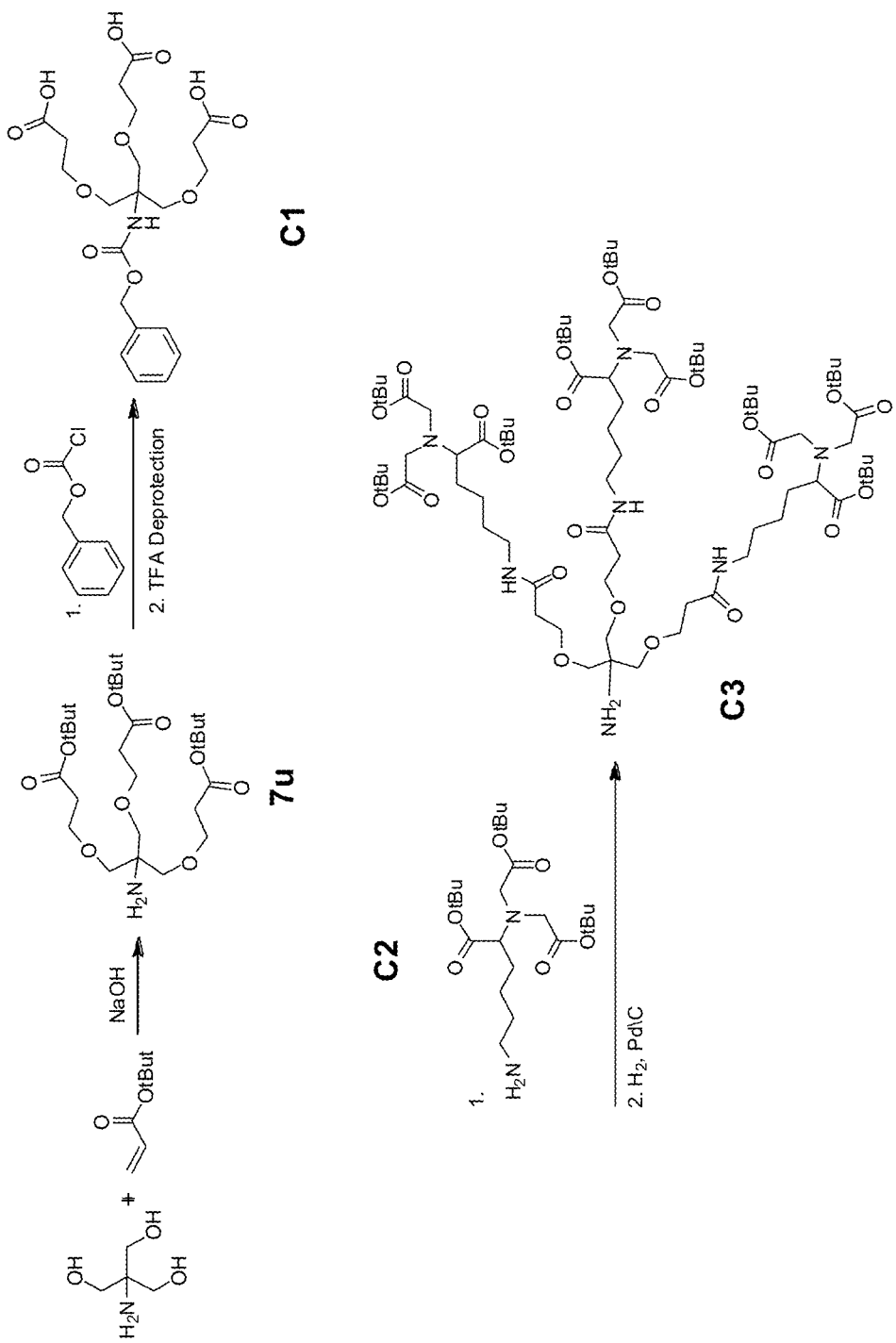
FIG. 7 depicts a synthetic scheme for preparing compound C3.

In order to afford an amine-modified and t-Bu-protected tri-NTA (C3), compound 7u can also be protected by Benzyl chloroformate followed by coupling to C2 and benzyl deprotection to afford compound C3 (FIG. 7).

Figure 8:
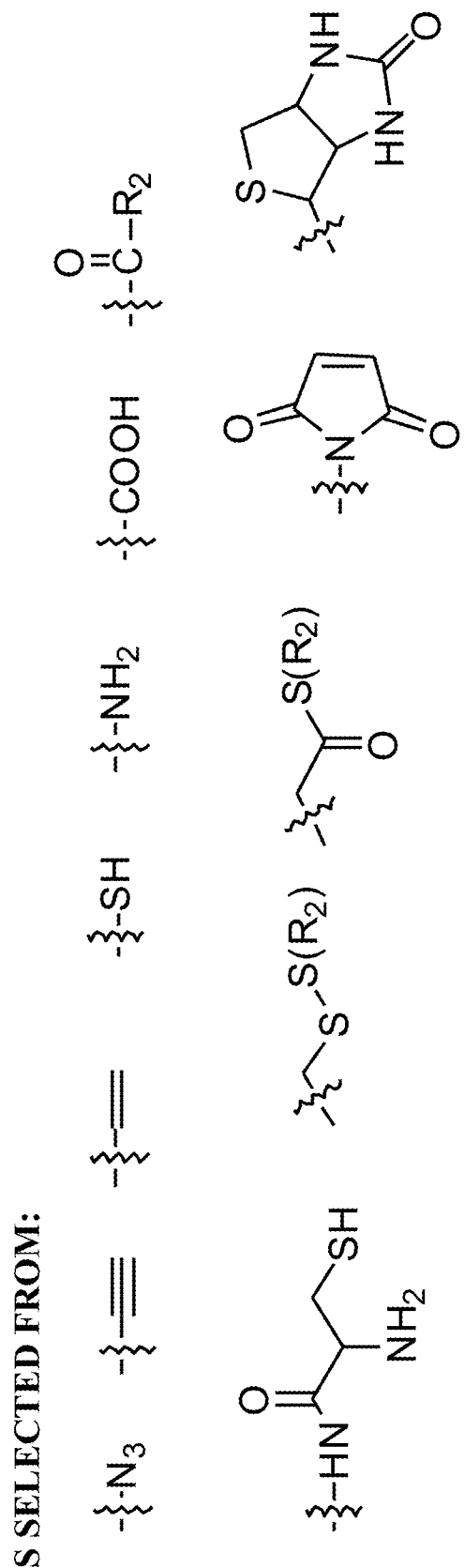
FIG. 8 depicts examples of various possible R groups for compound 8u [R(CH$_2$)$_x$COOH].

The modified carboxylic acid of compound 8u (FIG. 6) can be any $R(CH_2)_x$ COOH, where x represents the number of carbons and the R groups can consist of various functionalities, such as an azide, alkyne, thioester, disulfide, maleimide, and biotin (FIG. 8).

Figure 9:
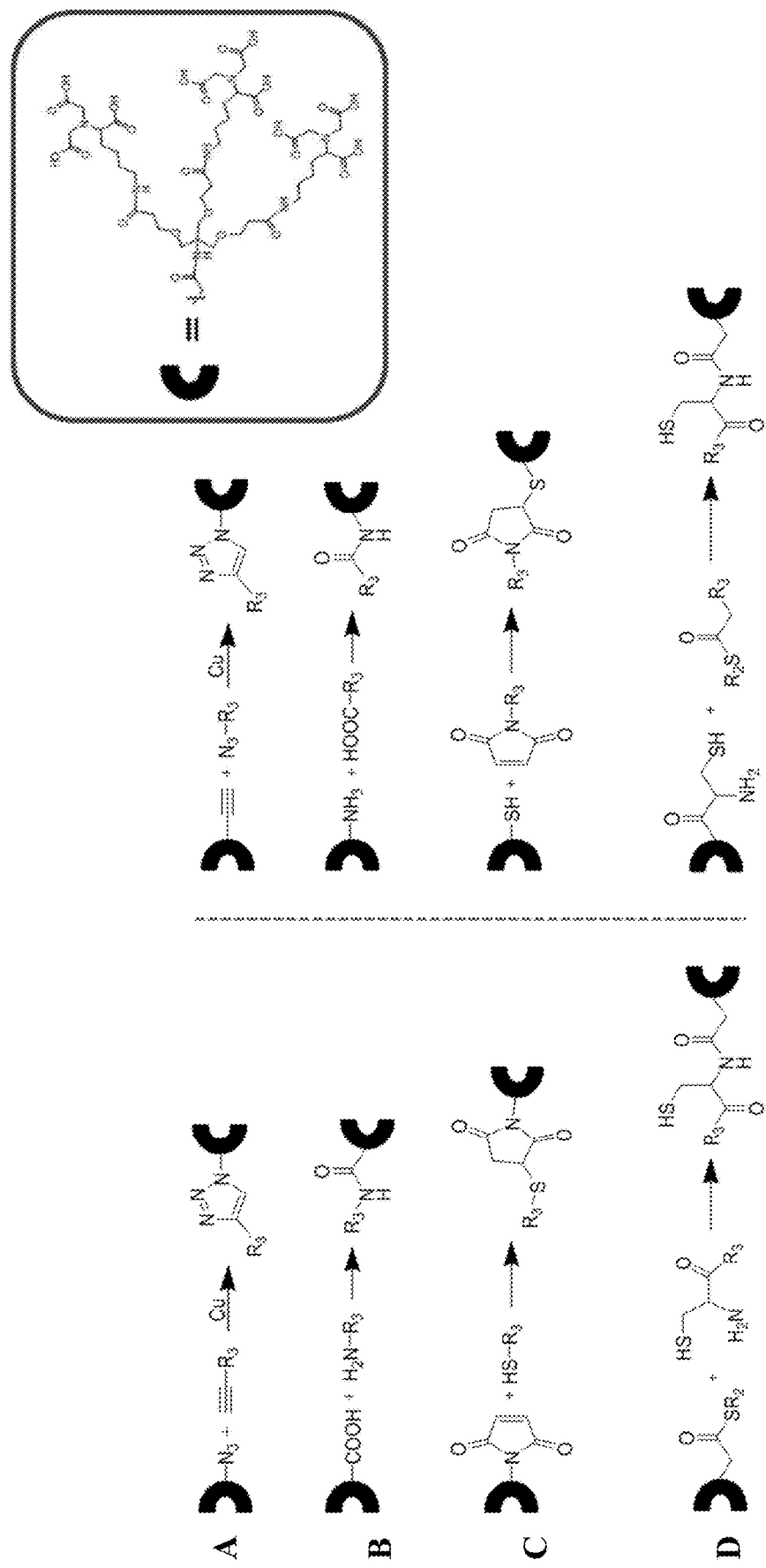
FIG. 9 depicts examples of different reactions that can be utilized to modify the His-tag binding compounds of the invention (the insert shows a specific His-tag binder) for a variety of linkers and compounds.

These functionalities, as well as various other functionalities, can be used to attach compound 10u (FIG. 6, and the insert in FIG. 9), as well as its t-Bu-protected precursor or compound C3 (FIG. 7) to a variety of compounds using the click reaction (FIG. 9A), carboxylic acid-amine coupling (FIG. 9B), thiol-malimide coupling (FIG. 9C), or native chemical ligation (FIG. 9D).

Figure 10:
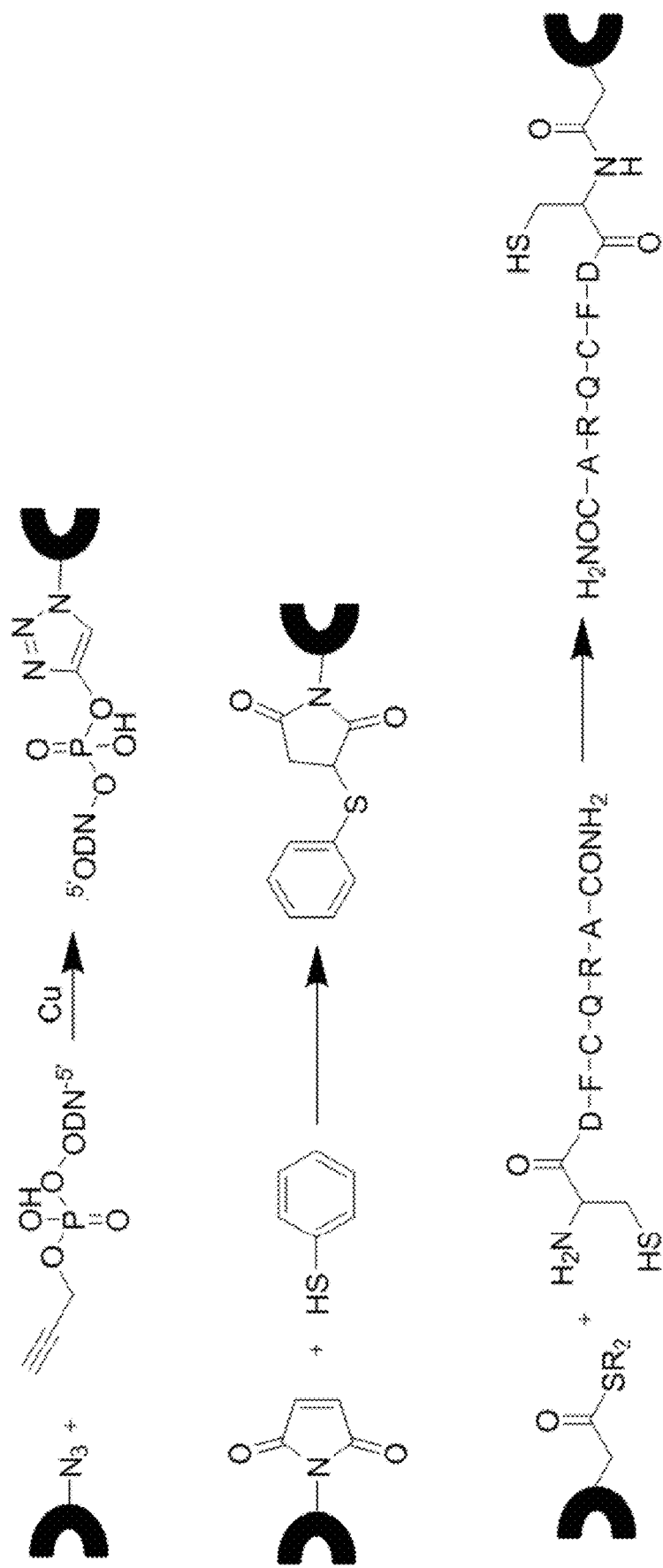
FIG. 10 depicts specific examples for modifying His-tag binding compounds of the invention to oligonucleotides (top), to small molecules (middle), and to peptides (bottom).

FIG. 10 shows specific examples of how modified tri-NTA compounds can be attached to DNA, small molecules, and peptides.

Figure 39:
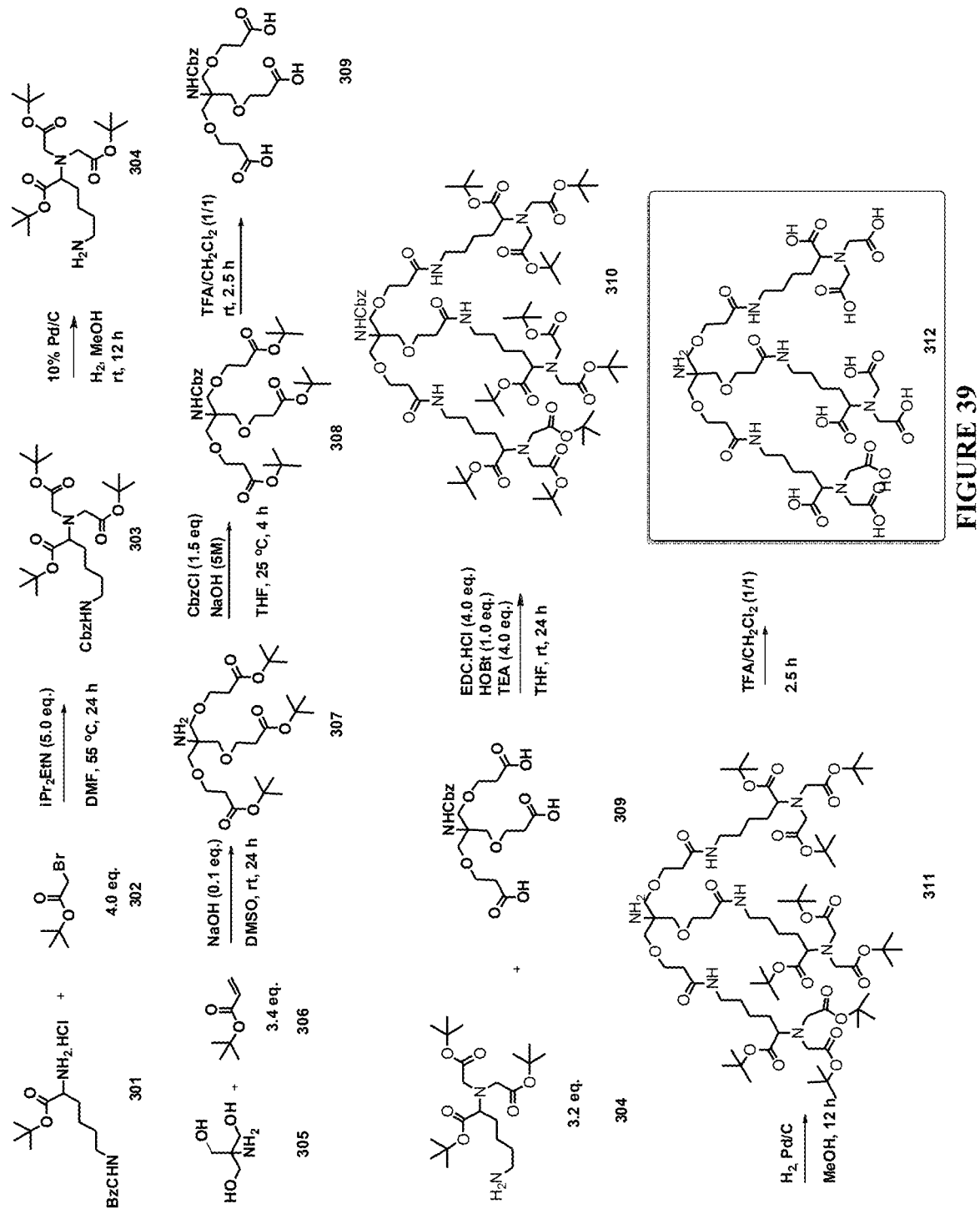
FIG. 39 shows the synthesis of a His-tag binding compound according to this invention.
Figure 40:
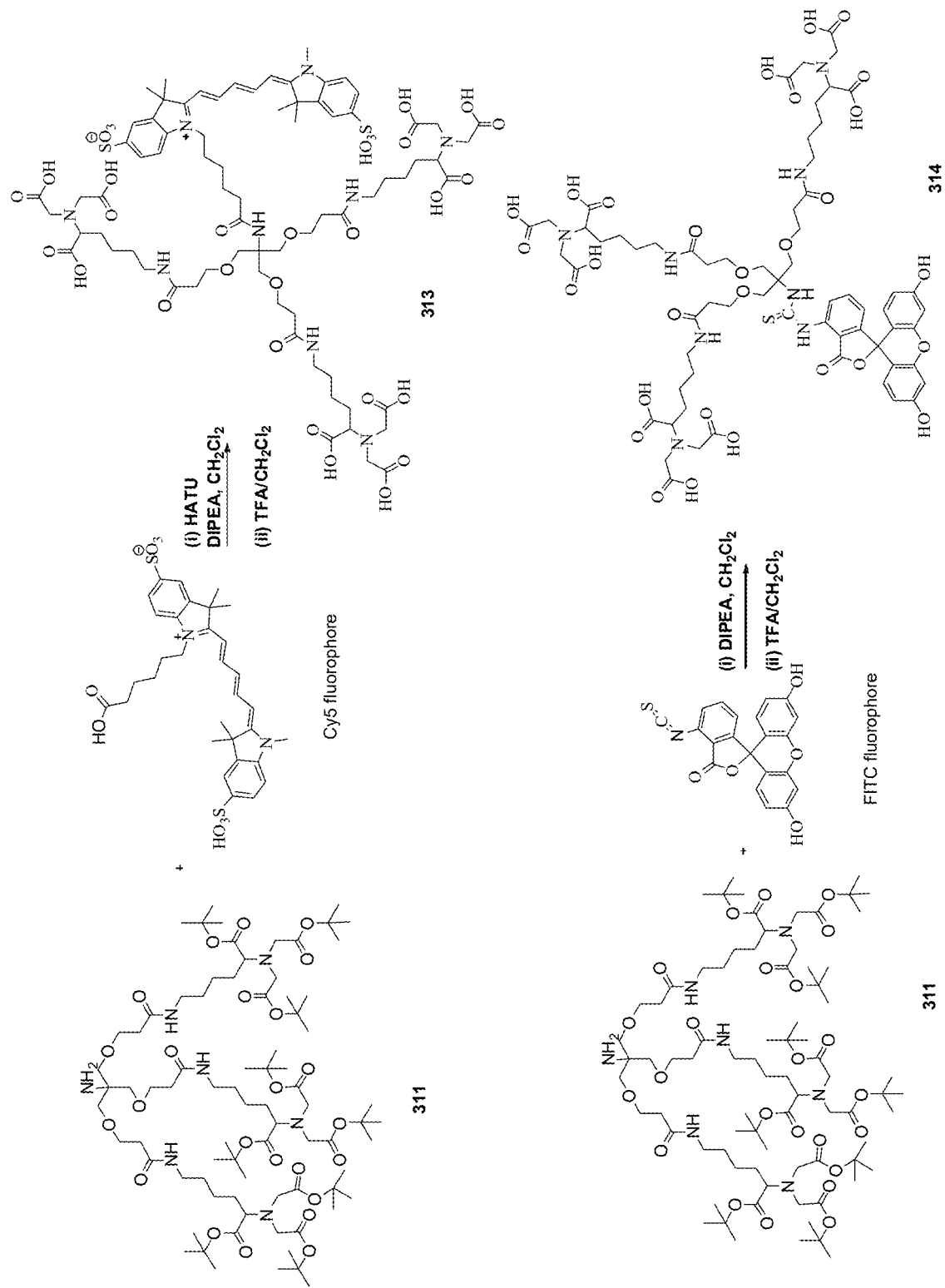
FIG. 40 shows the synthetic details of fluorophore coupling to His-tag binding compounds according to this invention.
Figure 41:
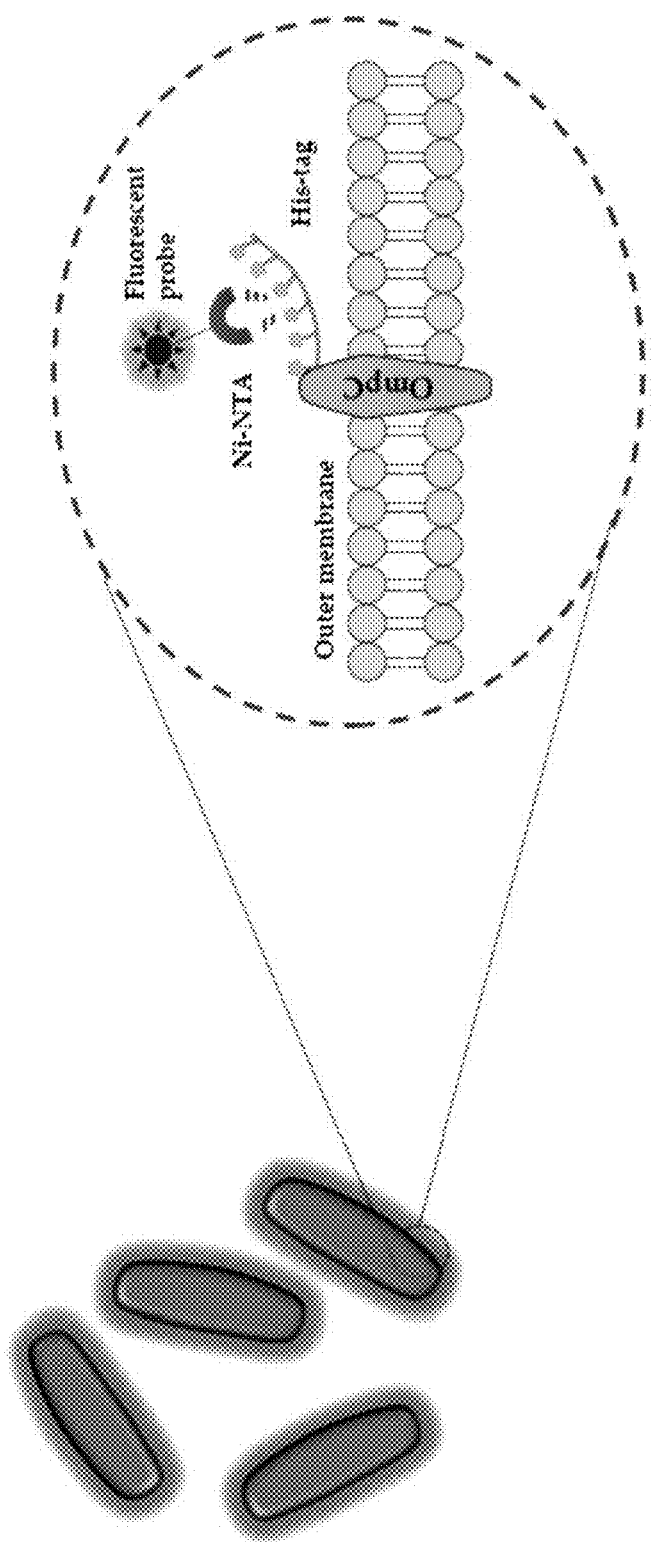
FIG. 41 shows a graphical illustration of the design of fluorescent probes comprising His-tag binding compounds according to this invention.
Figure 42:
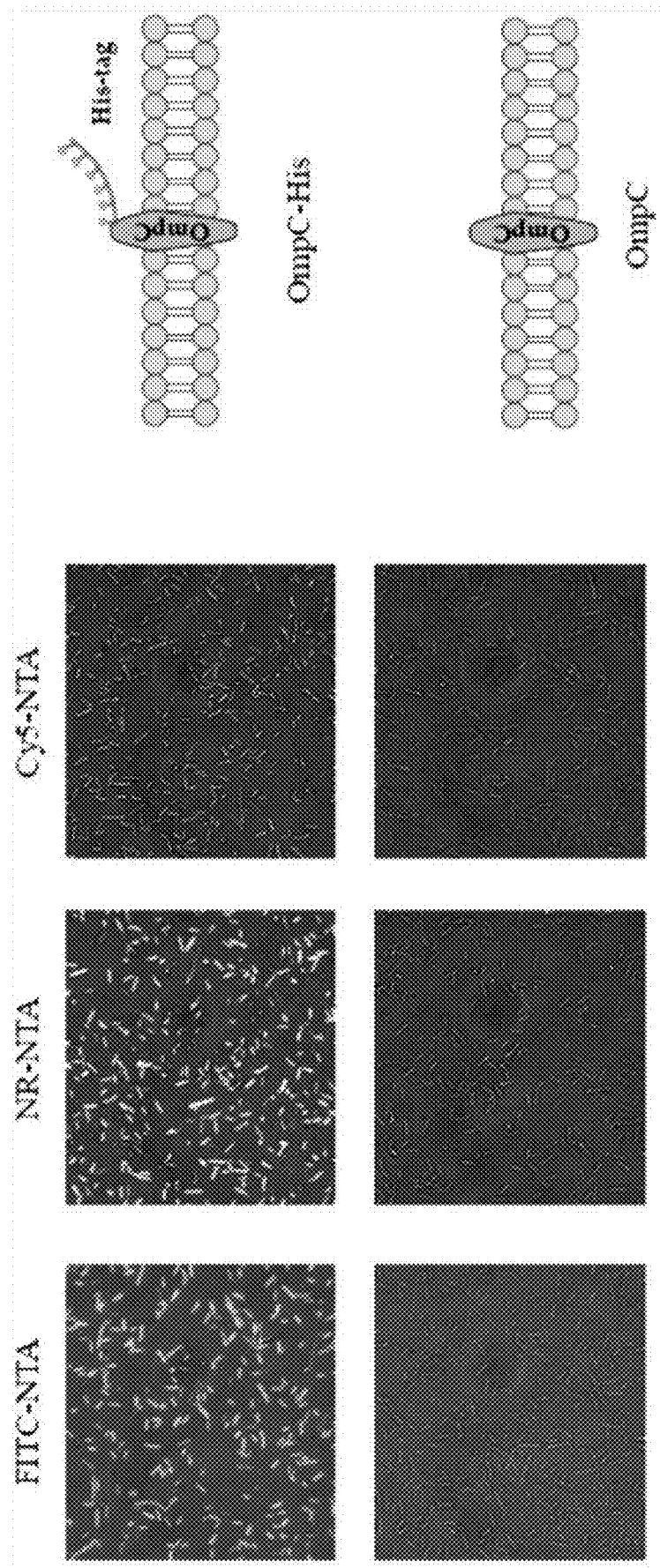
FIG. 42 shows fluorescence images of E. coli expressing His-OmpC (top) and OmpC (bottom) after incubation with 314 (FITC-NTA), 315 (NR-NTA) and 313 (Cy5-NTA).
Figure 43:
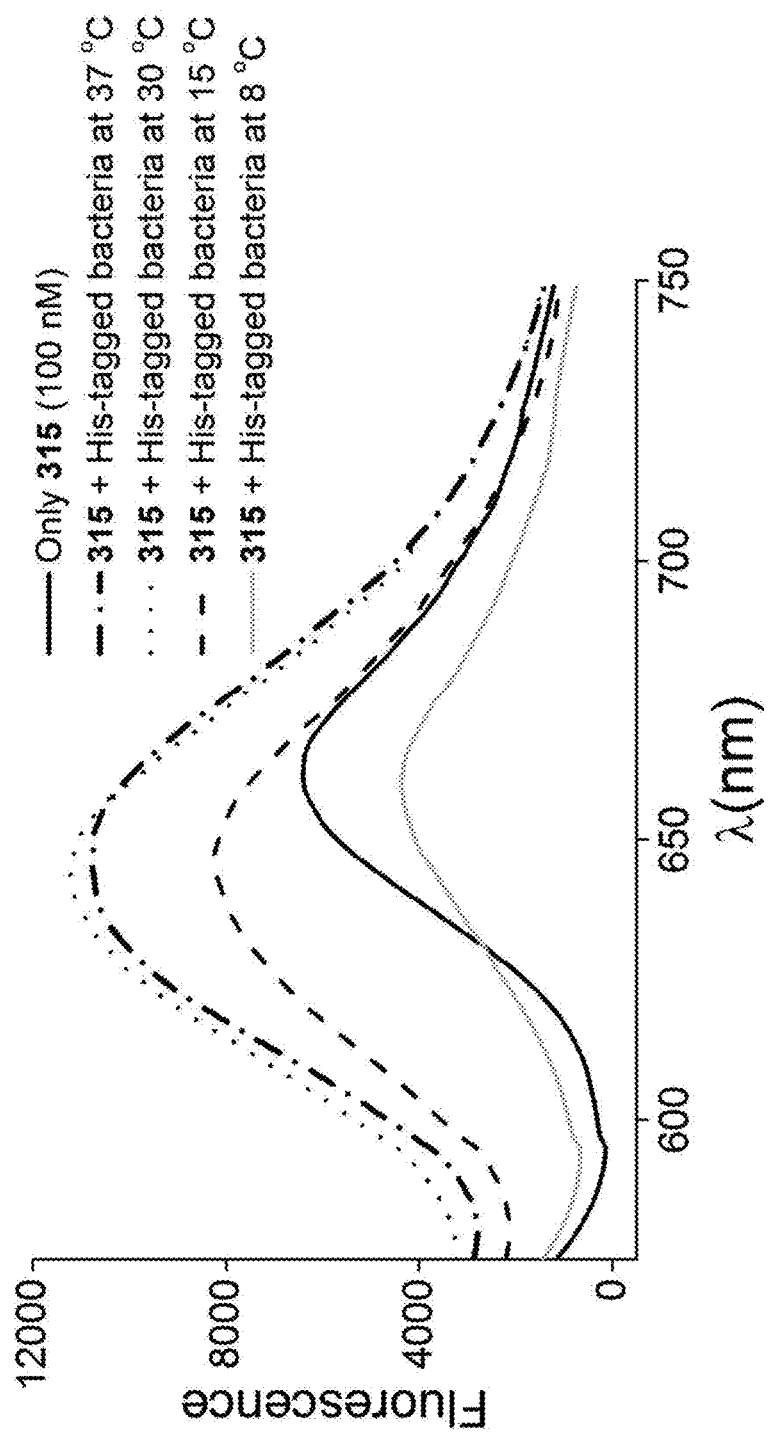
FIG. 43 shows the changes in the fluorescence response of a pre-incubated sample of 315 and $NiCl_2$ after addition of His-tagged bacteria expressed at different temperatures.
Figure 44:
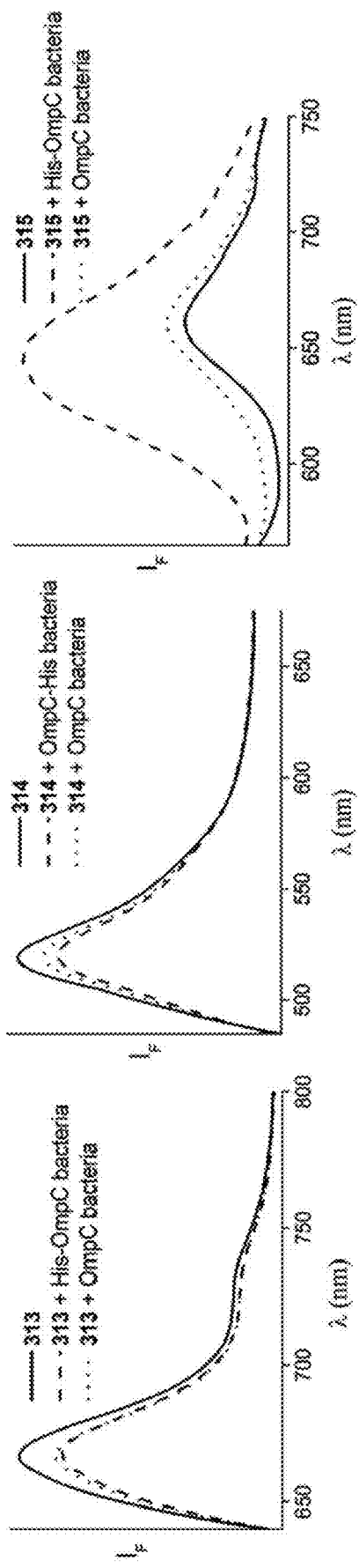
FIG. 44 shows fluorescence responses of probes 313-315 to His-OmpC and OmpC bacteria expressed at 30° C.
Figure 45:
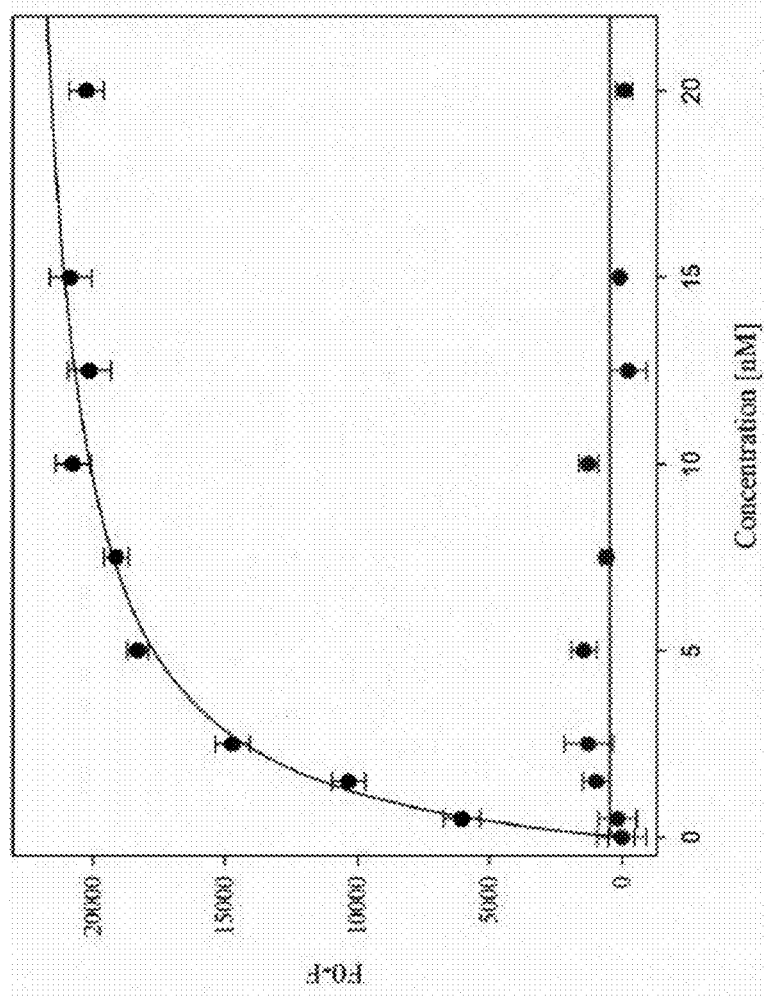
FIG. 45 depicts the changes in the fluorescence of a fluorescein-labeled His-tag peptide (5 nM) upon addition of increasing concentrations of NR-NTA (Compound 315). $NiCl_2$ was tested as a negative control.

Example 13 below, and FIGS. 39 and 40 describe alternative synthetic routes for the preparation of His-tag binding compounds (Compound 312, 313, 314, 315) and precursors (Compound 311) according to this invention.

Example 3

Figure 11:
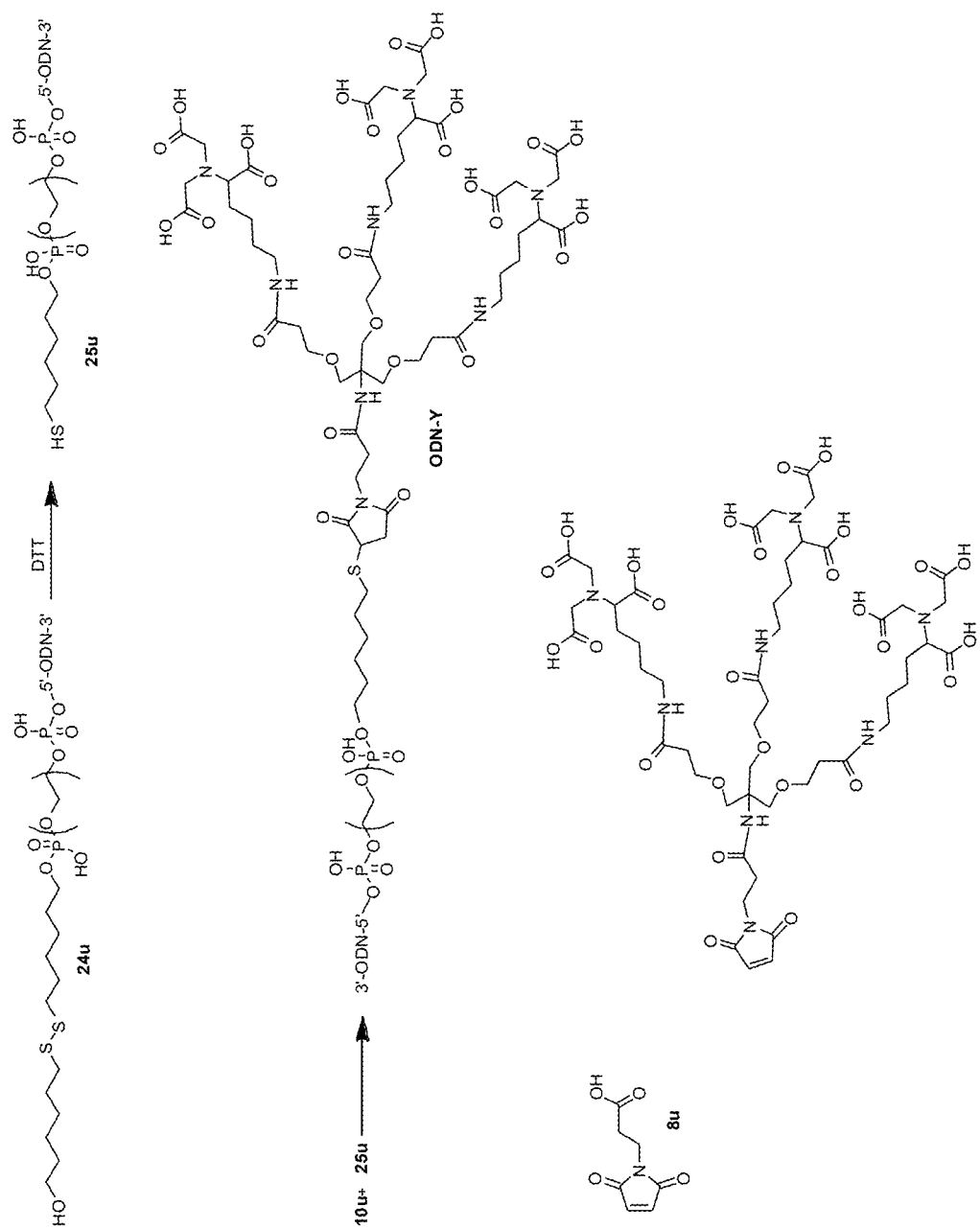
FIG. 11 depicts a synthetic scheme for an ODN modified with specific His-tag compound of the invention (ODN-Y), as well as the structures of a Maleimidopropionic acid (compound 8u), which was used to prepare the maleimide-modified His-tag binding compound (10u).
Figure 12:
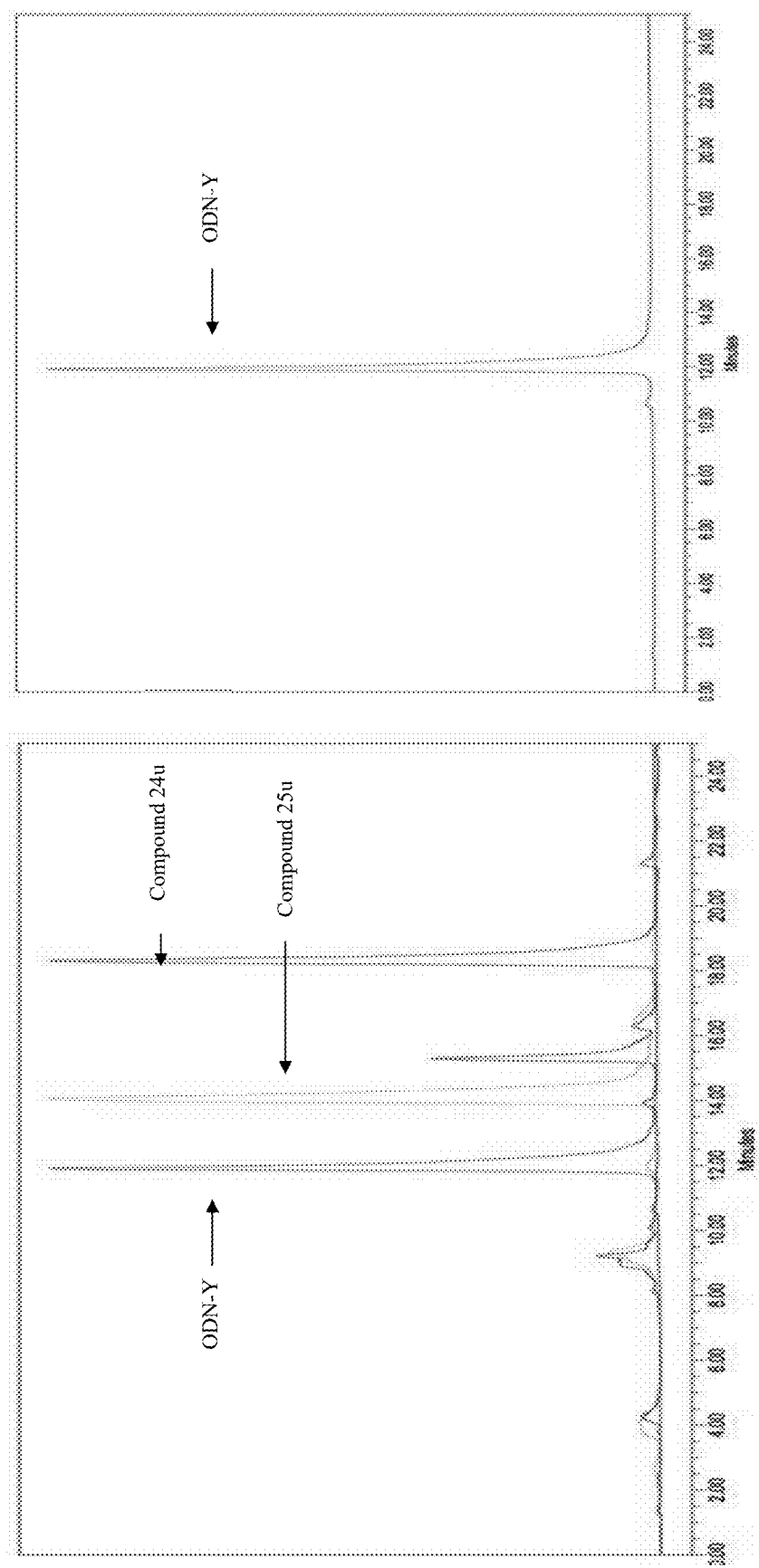
FIG. 12 depicts HPLC chromatogram of the reaction mixture (left) for preparing ODN-Y and of the pure product (ODN-Y, right).

Synthetic Procedures, Characterization, and Binding Studies of ODN Bound His-Tag Binders of the Invention An oligonucleotide (ODN) modified with a tri NTA group (FIG. 11, ODN-Y) was prepared by reducing a dithiol-modified ODN (24u) with DTT and reacting the resulting product (25u) with 10u via Michael addition. ODN-Y was purified using HPLC (FIG. 12) and characterized by MALDI-TOFF. Compound 10u was prepared according to the scheme presented in FIG. 6, where compound 8u is a Maleimidopropionic acid.

The synthesis procedures and the ¹H-NMR and MS characterization of the various products are described below:

di-tert-butyl-2,2'-((6-(((benzyloxy)carbonyl)amino)-1-(tert-butoxy)-1-oxohexan-2-yl)azanediyl)diacetate (C1)

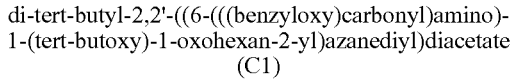

t-butyl bromo acetate (2.39 ml, 16 mmol) and DIPEA (3.5 ml, 20 mmol) were added to a solution of N-benzyloxycarbonyl-L-lysine tert-butyl ester (1.5 g, 4.02 mmol) in 25 ml DMF. The reaction was purged with argon and then heated to 55° C. and stirred overnight. The excess solvent was removed under high vacuum and 15 ml hexane:ethyl acetate 3:1 was added to the solidified mixture. The mixture was filtered over sinter glass and washed with the same solvent (3×10 ml). The filtrate was concentrated under reduced pressure and the residue was purified by column chromatography (80:20 hexane/EtOAc) to yield the purified product (2.2 g, 97% yield).

¹H NMR ($CDCl_3$, 300 MHz): δ 1.44 (s, 18H); 1.47 (s, 9H); 1.50 (m, 2H); 1.54 (m, 2H); 1.65 (m, 2H); 3.21 (m, 2H); 3.31 (t, J=6 Hz, 1H); 3.46 (dd, 4H); 5.09 (s, 2H); 7.33 (s, 5H).

ES-MS (m/z): Calcd: 564.34; Found: 587.32 (M+Na).

di-tert-butyl 2,2'-((6-amino-1-(tert-butoxy)-1-oxohexan-2-yl)azanediyl)diacetate (C2)

C1 (2.2 g, 3.92 mmol) was dissolved in 50 ml MeOH and purged with argon. 10% Pd/C (44 mg) was added and the reaction was stirred vigorously overnight under $H_2$. The mixture was filtered over colite and the solvents from the filtrate were removed under reduced pressure. Yield: 1.6 g, (3.8 mmol), 96%.

¹H NMR ($CDCl_3$, 300 MHz): δ 1.44 (s, 27H); 1.65 (m, 4H); 1.81 (m, 2H); 2.99 (t, J=9 Hz, 2H); 3.31 (t, J=6 Hz, 1H); 3.43 (dd, 4H).

ES-MS (m/z): Calcd: 430.3; Found: 431.35 (MH+), 453.42 (M+Na).

di-tert-butyl 3,3'-((2-amino-2-((3-(tert-butoxy)-3-oxopropoxy)methyl)propane-1,3-diyl)bis(oxy))dipropanoate (7u)

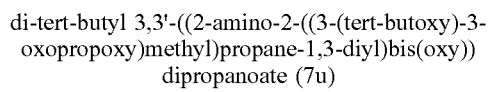

2-Amino-2-hydroxy ethyl-propane-1,3-diol (1.21 g, 10.0 mmol) was dissolved in 2.0 mL of DMSO and cooled to 15°

C. under argon. Then, 0.2 mL 5.0 M NaOH was injected, followed by dropwise addition of tert-butyl acrylate (5.0 mL, 34 mmol). The reaction mixture was brought to room temperature and stirred overnight. The excess regents and solvents were removed under high vacuum and the residue was purified by column chromatography (70:30 EtOAc/hexane+0.05% v/v NH$_4$OH) to yield colorless oil (1.01 g, 20% yield).

$^1$H NMR (CDCl$_3$, 300 MHz): δ 1.44 (s, 27H); 2.46 (t, J=6.0 Hz, 6H); 3.39 (s, 6H); 3.66 (t, J=6 Hz, 6H).

ES-MS (m/z): Calcd: 505.33; Found: 506.36 (MH+), 528.36 (M+Na).

di-tert-butyl 3,3'-((2-((3-(tert-butoxy)-3-oxopropoxy)methyl)-2-(3-(2,5-dioxo-2,5-dihydro-1H-pyrrol-1-yl)propanamido)propane-1,3-diyl)bis(oxy)) dipropanoate (intermediate product, 9u wherein R is maleimide)

600 mg (1.18 mmol) of 7u was dissolved in 30 ml dry DCM under argon and cooled to 0° C. in an ice bath. Thereafter, EDC (339 mg, 1.7 mmol, 1.5 eq) and DIPEA (413.7 µL, 2.32 mmol, 2 eq) were added and the reaction mixture was stirred for 30 min. 3-Maleimidopropionic acid (240.1 mg, 1.4 mmol, 1.2 eq) was added, and the solution was stirred overnight. Then 40 mL DCM was added and the solution was washed with water (10 mL) and brine (10 mL). The organic layer was dried with Na$_2$SO$_4$, filtered, and concentrated at high vacuum. Finally, the crude product was purified by column chromatography (97:3 DCM/MeOH) to yield a yellow oil (501.6 mg, 64%).

$^1$H NMR (CDCl$_3$, 300 MHz): δ 1.44 (s, 27H); 2.44 (t, J=6 Hz, 6H); 2.51 (t, J=6 Hz, 2H); 3.63 (t, J=6 Hz, 6H); 3.67 (s, 6H); 3.80 (t, J=6 Hz, 6H); 6.69 (s, 2H). ES-MS (m/z): Calcd: 656.35; Found: 657.44 (MH+), 679.31 (M+Na).

3,3'-((2-((2-carboxyethoxy)methyl)-2-(3-(2,5-dioxo-2,5-dihydro-1H-pyrrol-1-yl)propanamido)propane-1,3-diyl)bis(oxy))dipropanoic acid (9u)

Deprotection of the tert-butyl group was done with 50% trifluoroacetic acid in DCM (v/v) for 2.5 h. The product was washed repeatedly with DCM and then dried under high vacuum.

$^1$H NMR (D$_2$O, 300 MHz): 2.47 (t, J=6 Hz, 2H); 2.59 (t, J=6 Hz, 6H); 3.61 (s, 6H); 3.67-3.75 (m, 8H); 6.83 (s, 2H).

ES-MS (m/z): Calcd: 488.16; Found: 489.18 (MH+), 511.12 (M+Na) 977.03 (2M+H) 999.15 (2M+Na).

Tert-Butyl Protected Tri-NTA (Intermediate Product)

A solution of compound 9u (160 mg, 304.8 µmol) in 10 ml dry DCM was cooled to 0° C. in an ice bath and DIPEA (212 µL, 1.2 mmol, 4 eq), EDC (191 mg, 1 mmol, 3.3 eq), and HOBt (41 mg, 304.8 µmol, 1eg) were added consecutively. After 15 min, compound C2 (433 mg, 1 mmol, 3.3 eq) was added and the reaction was stirred overnight. Then 40 mL DCM was added and the solution was washed with water (10 mL). The organic layer was dried with Na$_2$SO$_4$, filtered, and concentrated at high vacuum. Finally, the crude product was purified by column chromatography (96:4 DCM/MeOH) to yield a colorless oil (96.6 mg, 18.3%).

$^1$H NMR (MeOD, 300 MHz): δ 1.50 (s, 54H); 1.55 (s, 27H); 1.71 (m, 18H); 2.42 (t, 6H); 2.49 (m, 2H); 3.20 (t, 6H); 3.31 (m, 12H); 3.55-3.74 (m, 17H); 6.84 (s, 2H).

ES-MS (m/z): Calcd: 656.35; Found: 657.44 (MH+), 679.31 (M+Na).

Maleimide-Modified Tri-NTA (10u)

Deprotection of the tri-NTA t-butyl groups was done with 50% trifluoroacetic acid in DCM (v/v) for 2.5 h. The product was washed repeatedly with DCM and then dried under high vacuum. $^1$H NMR (MeOD, 300 MHz): δ 1.47 (m, 6H); 1.53 (m, 6H); 1.91 (m, 6H); 2.43 (m, 8H); 3.17 (m, 6H); 3.58-3.65 (m, 15H); 4.1 (m, 14H); 6.82 (s, 2H). ES-MS (m/z): Calcd: 1220.48; Found: 1221.53 (MH+), 1243.39 (M+Na).

Following the successful preparation of 10u, a His-tag binding strand (ODN-Y, FIG. 11) was also prepared by reducing a dithiol-modified ODN (24u) with DTT and reacting the resulting product (25u) with 10u via Michael addition. ODN-Y was purified using HPLC (FIG. 12) and characterized by MALDI-TOFF.

Example 4

Determination of the Dissociation Constant for the His-Tag-ODN-Y Interaction

Figure 13:
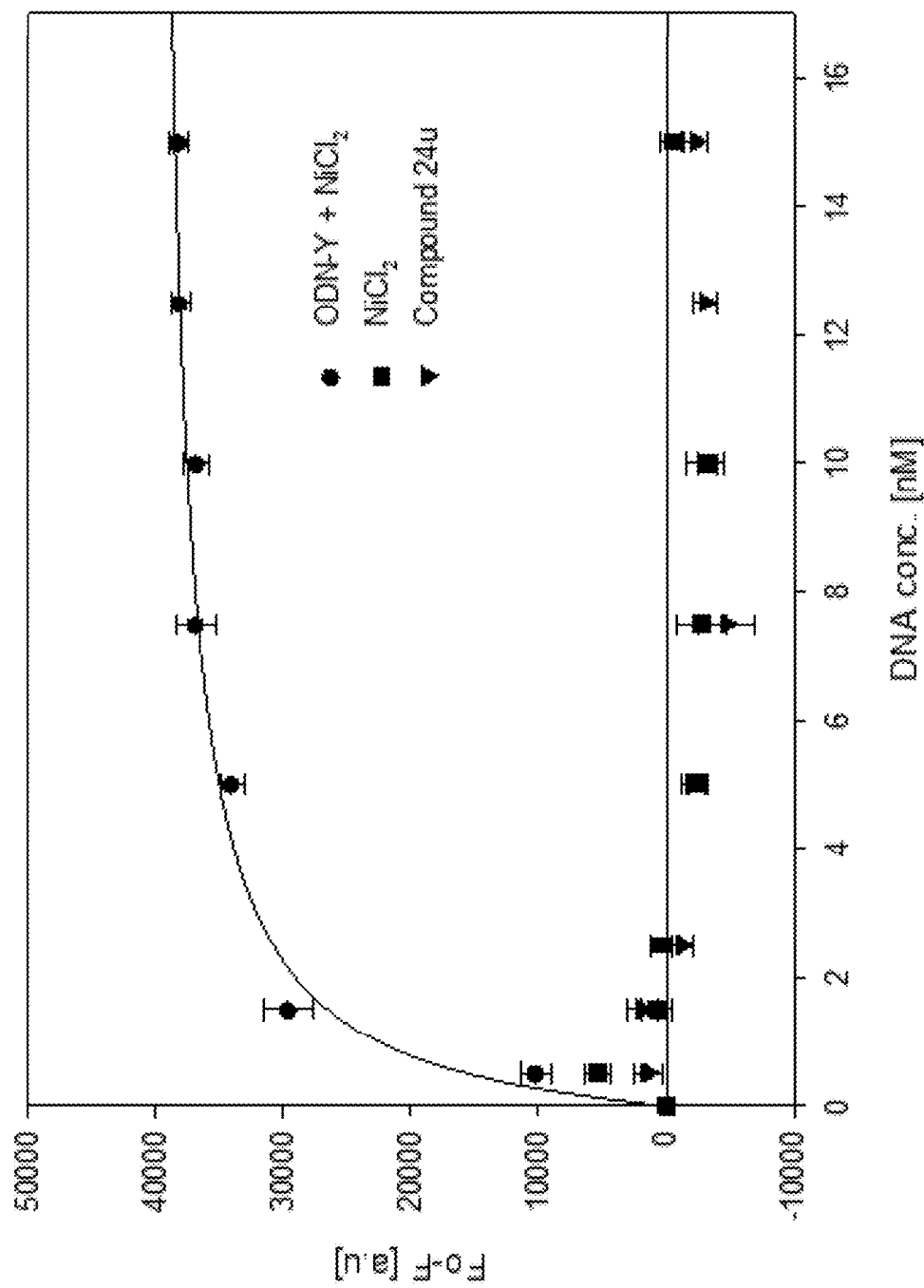
FIG. 13 depicts His-tag compound binding assay. Changes in the fluorescence of a fluorescein-labeled His-tag peptide (5 nM) upon the addition of increasing concentrations of ODN-Y—Ni(II) in PBS. Compound 24u (FIG. 11) and NiCl$_2$ were tested as negative controls.

ODN Y was incubated with nickel chloride and the binding of the resulting complex to His-tag was confirmed by following the decrease in the emission signal of a fluorescein-labeled His6 peptide upon incremental addition of ODN-Y—Ni$^{+2}$ (FIG. 13). The dissociation constant ($K_d$) was determined by subtracting the fluorescence signal of the complex from the signal of the His6 peptide alone. The binding curve fitting and $K_d$ calculation were done using SigmaPlot software. The Kd value was found to be 3.2±0.4 nM.

Example 5

Binding Measurements of Sensors of the Invention to His-Tagged Protein

Figure 2:
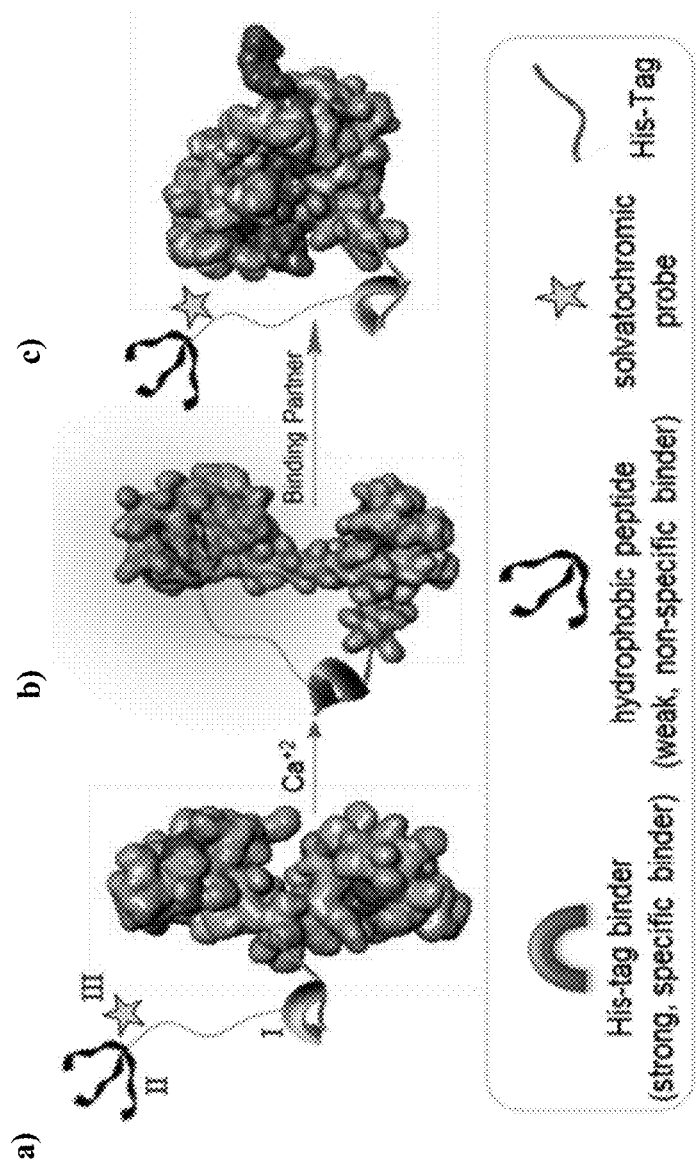
FIG. 2 depicts the operating principles of a targeted protein surface sensor consisting of a His-tag binder (I), a protein surface receptor (II), and a solvatochromic probe (III). The binding of calcium ions to His-CaM (a) promotes the exposure of a hydrophobic cleft on the surface of His-CaM($Ca^{+2}$) and a consequent interaction with the sensor's hydrophobic receptor (b). Changes in the molecular environment of the solvatochromic probe result in enhanced emission. A binding partner, such as the M13 peptide, can also be sensed by the system owing to the formation of a His-CaM($Ca^{+2}$)-M13 complex (c), which triggers the release of the protein-bound receptor.

His-tagged calmodulin (His-CaM) (FIG. 2, state a) was selected as the first protein of interest (POI) for testing this approach because, upon binding to Ca$^{+2}$ ions, this calcium-binding protein exposes a large hydrophobic cleft that can potentially accommodate a complementary synthetic receptor (FIG. 2, state b). In addition, this hydrophobic patch is involved in various binding interactions, which should enable testing the suitability of the technique for identifying binding partners (FIG. 2, state c).

Five compounds were prepared, which share the same His-tag binder and fluorophore, but differ in their appended receptors (FIG. 14). Compound 1, which possesses a hydrophobic receptor, was designed to interact with the hydrophobic surface of His-CaM(Ca$^{+2}$) (FIG. 2, State b). In contrast, the other compounds, which possess negatively charged (2), polar (3), positively charged (4), as well as positively charged and hydrophobic (5) receptors were designed to serve as control compounds, which would not respond to changes in the surface of His-CaM.

In principle, compounds 2-5 could also be used to sense changes in the surfaces of other His-tag-labeled proteins. In all compounds (1-5), complexation of tri-nitrilotriacetic acid (tri-NTA) ligand (I) with nickel ions forms the His tag binder, which is connected via a tri-ethylene glycol spacer to a tripodal peptide (II) and a dansyl group (III), which serve as a protein surface receptor, and a solvatochromic probe, respectively.

Figure 15:
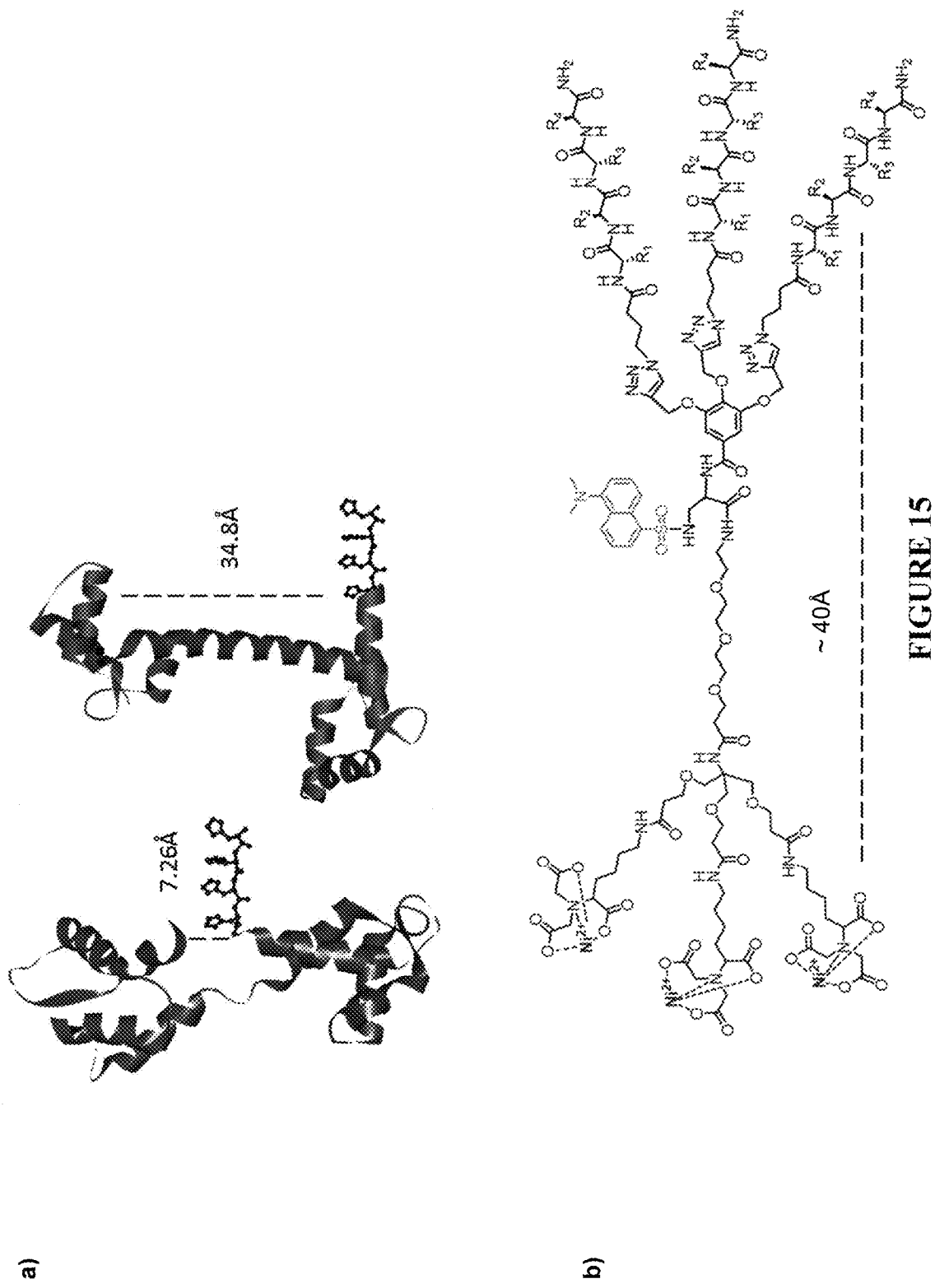
FIG. 15 depicts (a) Visualization of CaM in the calcium-free (left panel) and calcium-bound (right panel) conformations, showing the distance between the N' and C' termini. The proteins' images were generated with Discovery Studio Visualizer 2.5, which was also used to calculate the distance. (b) Approximate length of the sensor 1.

A modeling program showed that the length of the spacer is sufficient to bind various locations of CaM's surface and, in particular, to allow simultaneous binding of the sensor to both the His-tag and the hydrophobic patch on His-CaM (Ca$^{+2}$) (FIG. 15).

Prior to measuring the sensor's performance, it was confirmed that 1 can bind to His-CaM in each of its states, namely, before (FIG. 2a) and after the subsequent binding to Ca$^{2+}$ (FIG. 2b) and binding partners (FIG. 2c). Fluorescence binding studies were performed first, to confirm that 1 can bind His-tag with nanomolar affinity ($K_d$(approx)=157 nM±21, FIG. 17), akin to other multivalent NTA ligands.

Figure 16:
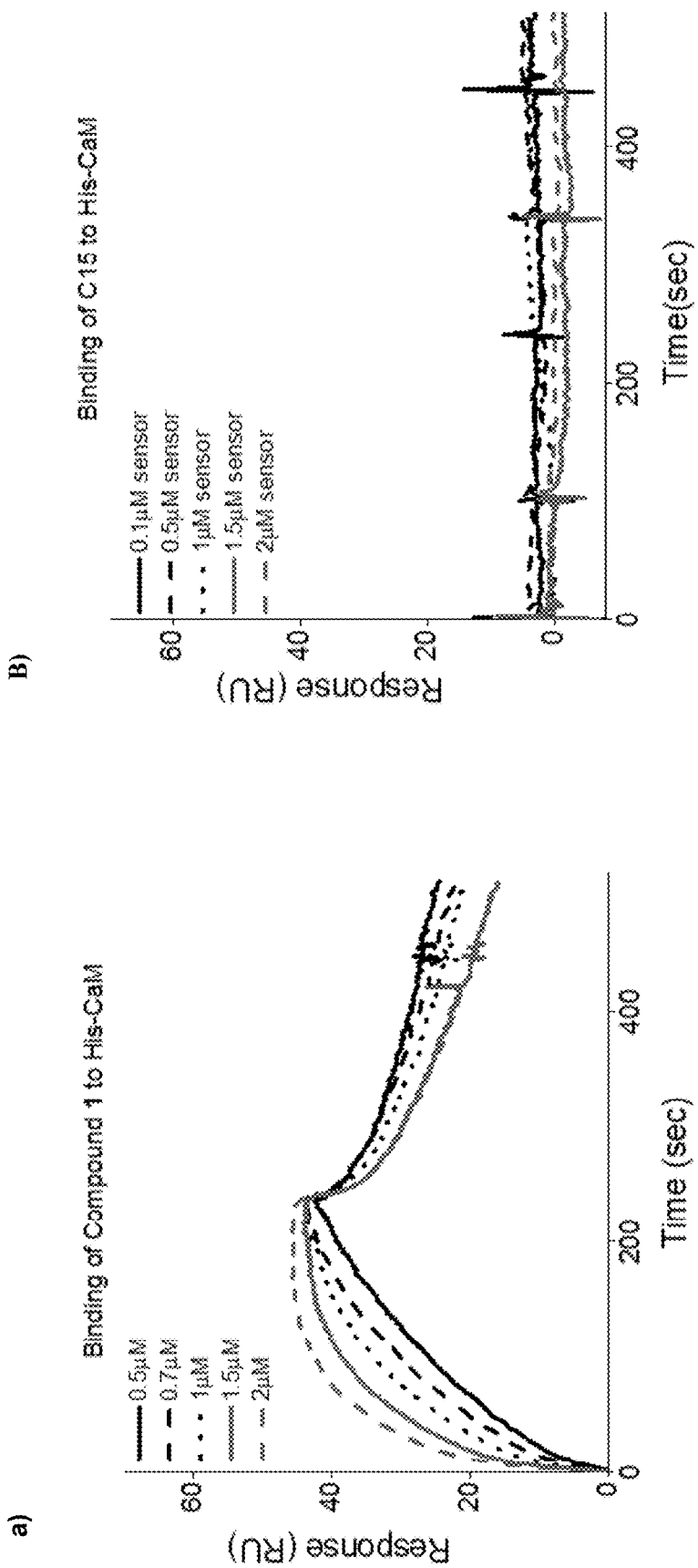
FIG. 16 depicts SPR sensorgrams recorded for the (a) 1-His-CaM and (b) C$_{15}$-His-CaM interactions.
Figure 18:
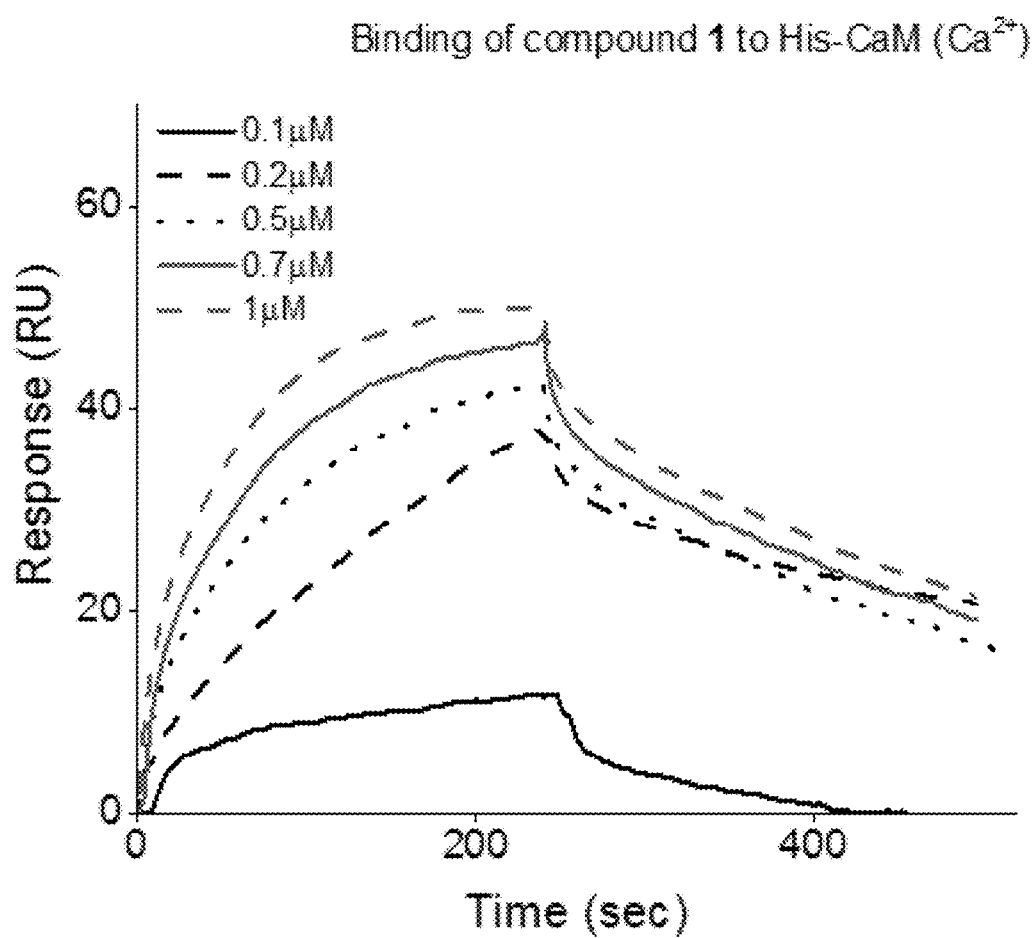
FIG. 18 depicts SPR sensorgrams recorded for the 1-His-CaM($Ca^{2+}$) interaction.
Figure 19:
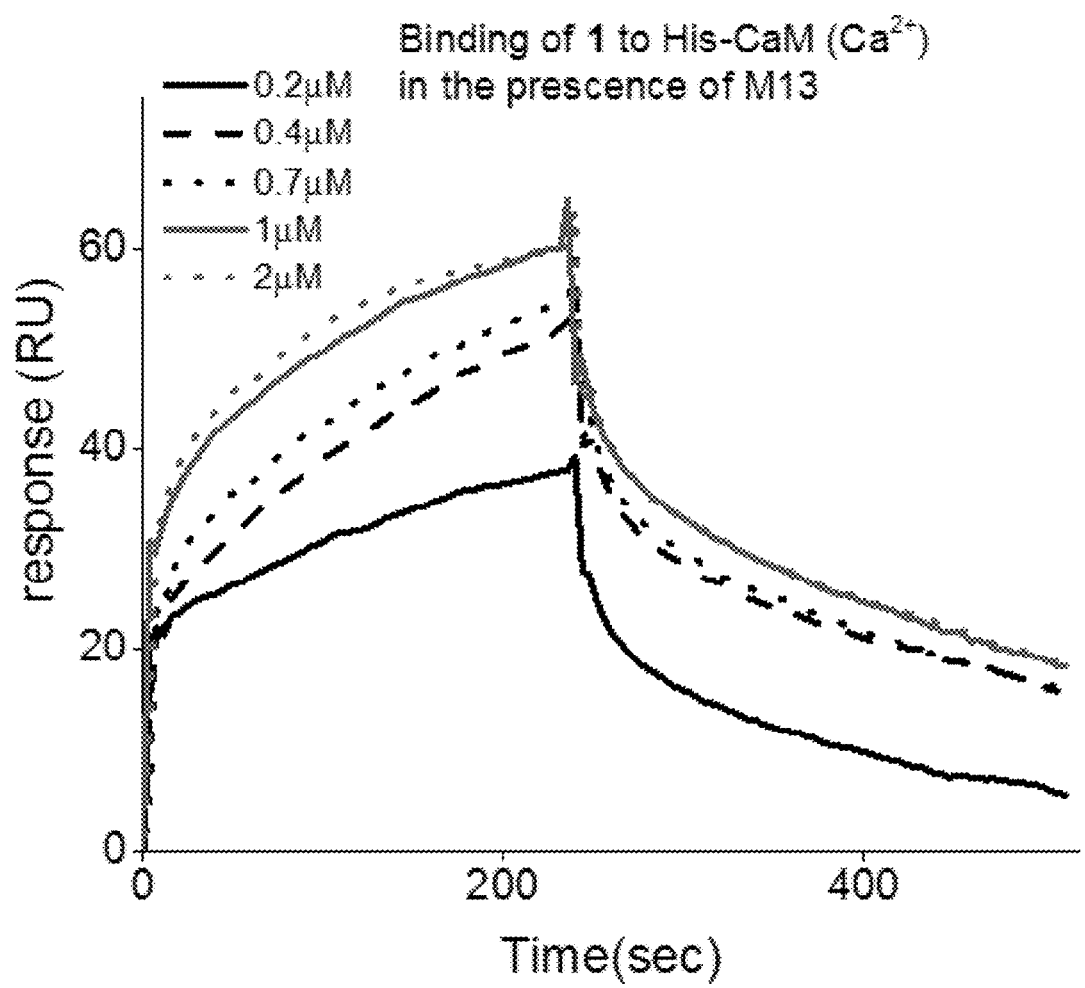
FIG. 19 depicts SPR sensorgrams recorded for the 1-His-CaM($Ca^{2+}$) interaction in the presence of excess M13.

In the next step, surface plasmon resonance (SPR) measurements were performed (FIG. 16) to ensure that 1 also binds His-CaM ($K_d$(approx)=176 nM, FIG. 16, left panel) and His-CaM(Ca$^{2+}$) ($K_d$ (approx)=134 nM, FIG. 18) with similar affinities. SPR also showed 1 also binds His-CaM (Ca$^{2+}$) in the presence of excess of known binding partner M13 (FIG. 19), which bind to His-CaM(Ca$^{2+}$) with low nanomolar affinity. Similar measurements performed in the absence of nickel ions confirmed that apo 1 does not interact with His-CaM (FIG. 16, left panel) indicating the weak affinity of the tripodal receptor toward the surface of His-CaM. Taken together (FIGS. 16 and 18, 19, and Table 2) the SPR studies show that possible interactions between tripodal receptor of 1 and the CaM's surface (FIG. 2, state b) could only be induced by the strong interactions between the tri-NTA-Ni$^{2+}$ complex and the His tag of CaM.

TABLE 2

Summary of dissociation constants that were obtained using SPR experiments.

| Entry | Analyte | Dissociation constant (μM) |
| --- | --- | --- |
| 1 | 1-His CaM | 176 |
| 2 | 1-His CaM (Ca$^{2+}$) | 134 |
| 3 | 1-His CaM (Ca$^{2+}$)-M13 | 231 |
| 4 | 1-His CaM (Ca$^{2+}$)-Mastoparan | 244 |
| 5 | C15- His CaM | — |
| 6 | M13-His CaM (Ca$^{2+}$) | 0.0088 |
| 7 | Mastoparan- His CaM (Ca$^{2+}$) | 0.0012 |

Example 6

Fluorescence Measurements: Sensing Protein Surface Changes with Compounds 1-5

The ability of sensor 1 (200 nM) to detect the Ca$^{+2}$-induced conformational change of His-CaM was tested (FIG. 20a), by following the change in the emission upon the sequential addition of 1) His-CaM (200 nM), 2) CaCl$_2$ (0.3 mM), and 3) EGTA (1.2 mM). As expected from the design, a strong enhancement in dansyl's emission was observed only when calcium ions were added to the solution and this fluorescence was immediately decreased upon the addition of EGTA. Similar fluorescence responses were observed with higher concentrations of sensor and protein, however, the concentrations, which were used in these measurements, were selected after screening for various different conditions (FIG. 21) and selecting the minimal concentrations (200 nM) that can provide strong and reproducible emission signals.

Figure 20:
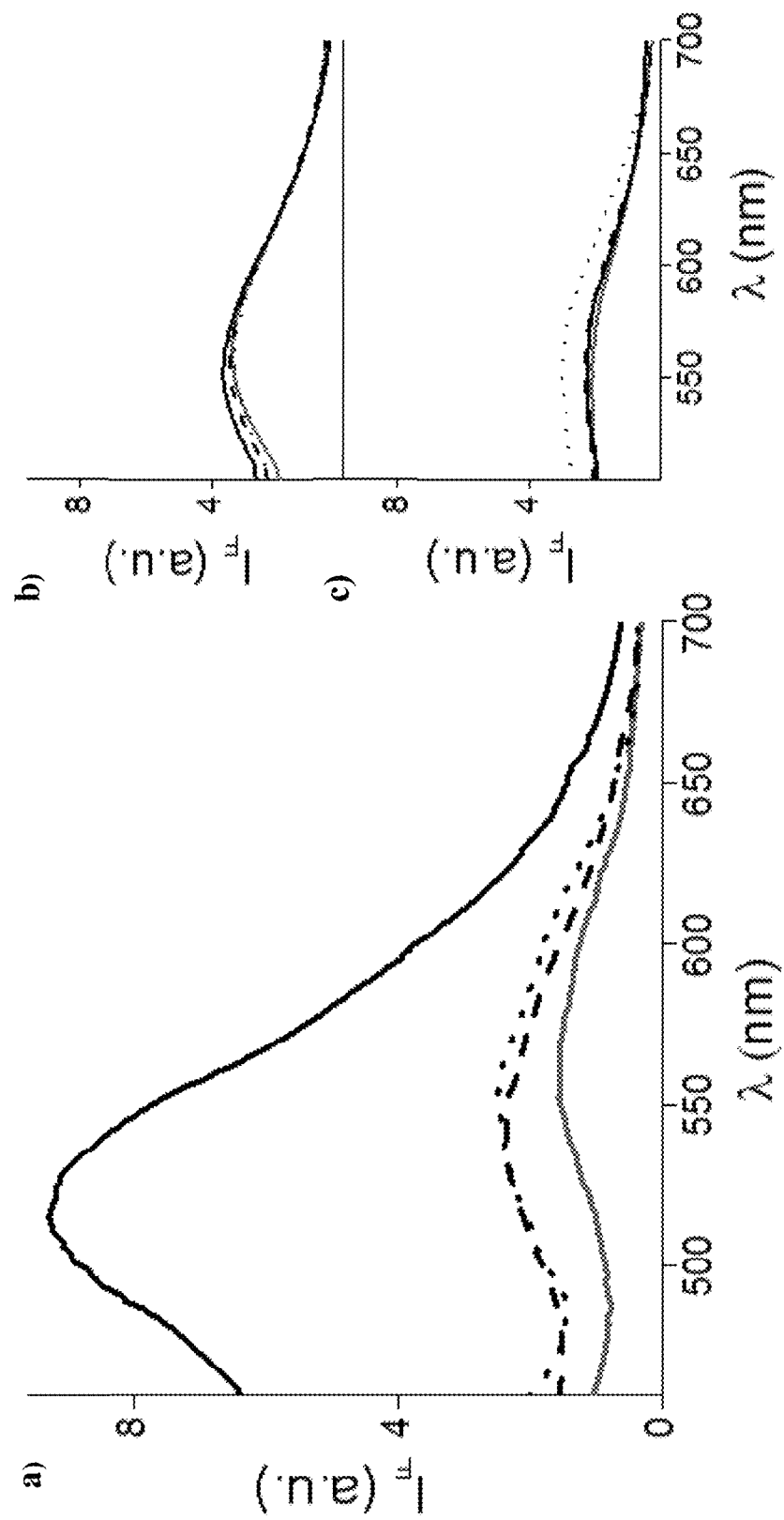
FIG. 20 depicts (a) Fluorescence spectra of 1 (200 nM) before (solid grey line) and after the sequential addition of 200 nM His-CaM (dashed line), 0.3 mM CaCl$_2$ (solid black line), and 1.2 mM EGTA (dotted line). (b) A similar experiment performed in the absence of $Ni^{+2}$ ions. (c) A similar experiment performed with CaM lacking a His-tag. Excitation: 330 nm.
Figure 22:
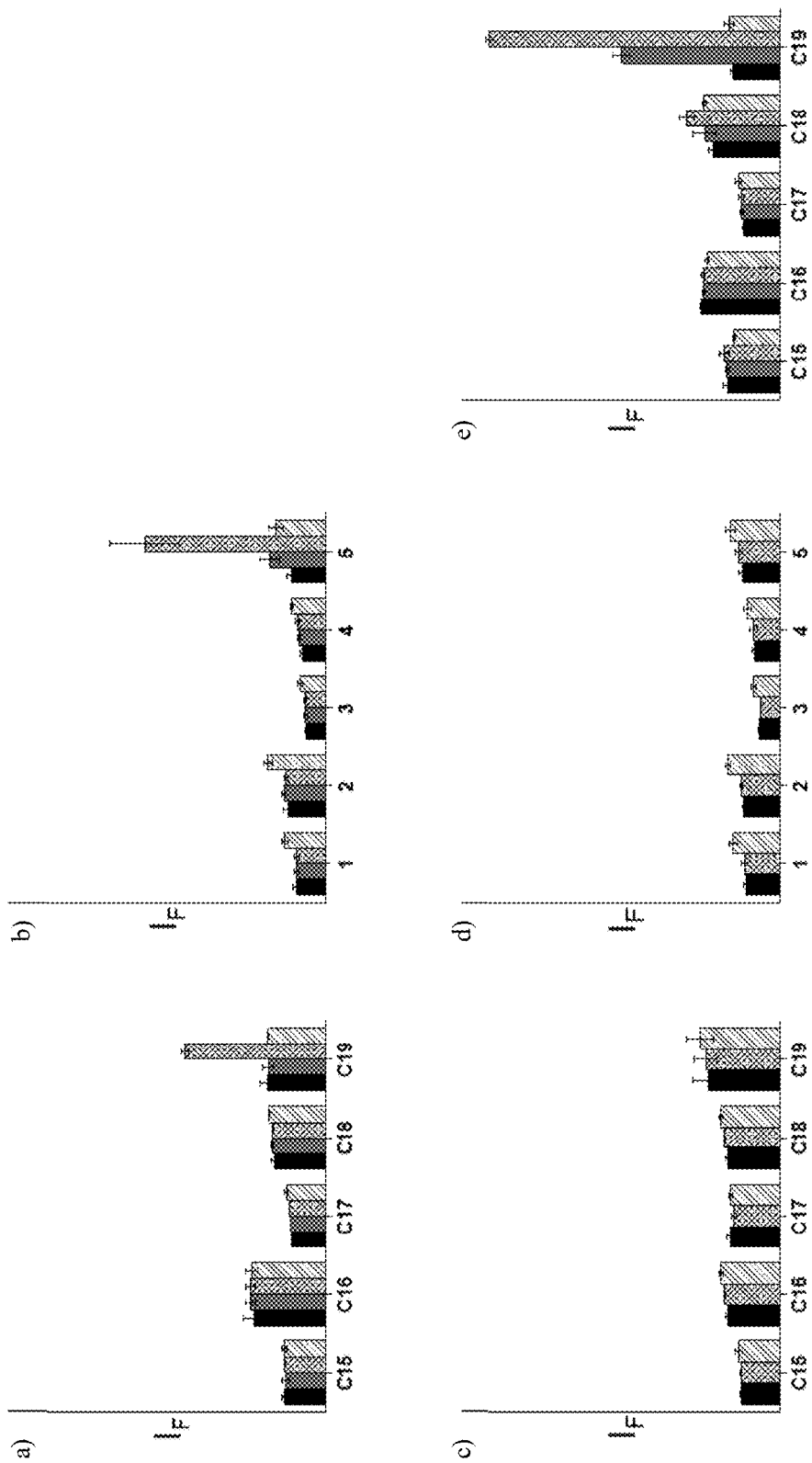
FIG. 22 depicts the fluorescence response of (a) (■) compounds C15-C19 (200 nM) and (b) (■) compounds 1-5 (200 nM) to the sequential addition of (■) CaM (200 nM), (▨) $Ca^2$ (0.3 mM), and (▨) EGTA (1.2 mM). (c) Fluorescence response of (■) compounds C15-C19 (200 nM) and (d) (■) compounds 1-5 to the sequential addition of (▨) $Ca^{2+}$ (0.3 mM) and (▨) EGTA (1.2 mM) (e) Fluorescence response of (■) compounds C15-C19 (200 nM) to the sequential addition of (■) His-CaM (200 nM), (▨) $Ca^{2+}$ (0.3 mM), and (▨) EGTA (1.2 mM).

To further confirm that the fluorescence enhancement did not result from non-specific interactions between His-CaM (Ca$^{+2}$) and the tripodal receptor, or from the presence of excess of calcium ions in the medium, several control experiments were performed (FIGS. 20 and 22). For example, no change in the emission signal was observed when the experiment was repeated in the absence of nickel ions (FIG. 20b), or with CaM that lacks the His-tag (FIG. 20c). Similarly, sensor 1 did not respond to the addition of Ca$^{+2}$ only (FIG. 22). Taken together with the SPR measurements (FIG. 16, right panel), these control experiments confirm the proposed sensing mechanism, in which the simultaneous binding of sensor 1 to both the His-tag and the hydrophobic surface of His-CaM(Ca$^{+2}$) (FIG. 2, state b) is crucial for obtaining the observed effect.

Example 7

The Effect of the Peptide Character on the Fluorescence Response of Sensors of the Invention.

Figure 23:
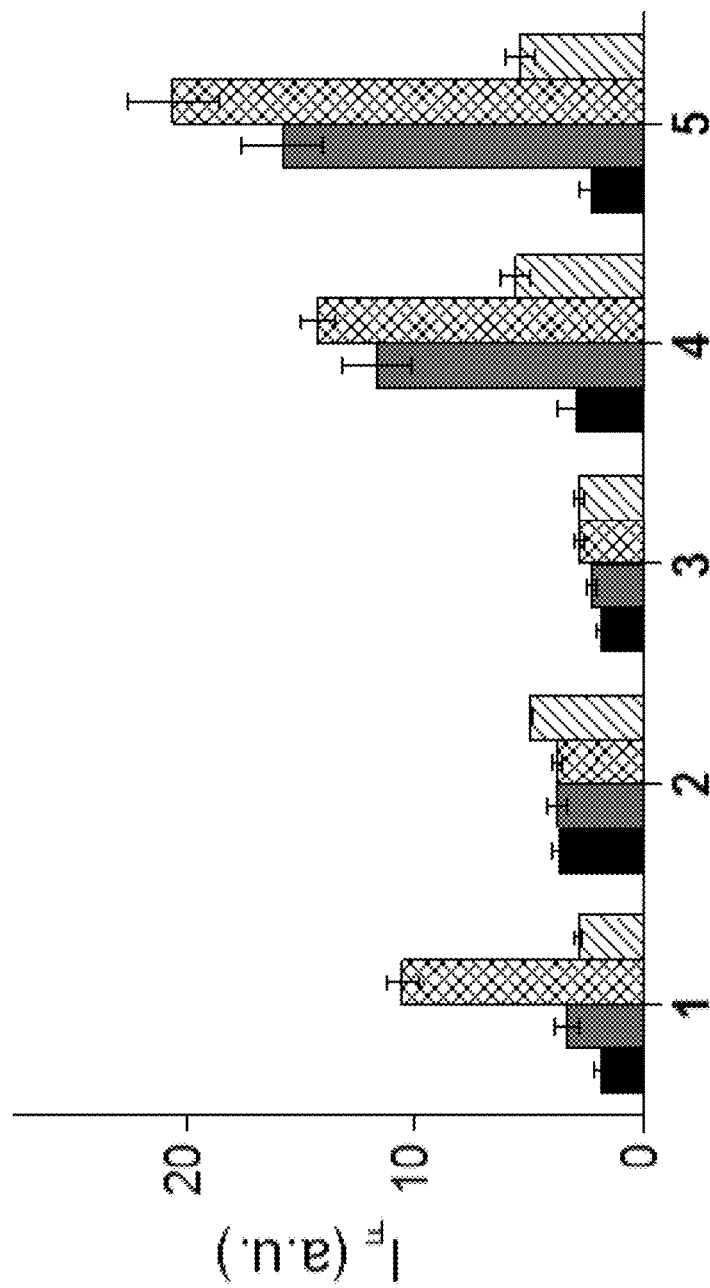
FIG. 23 depicts a Fluorescence response of compounds 1-5 (■) to the sequential addition of His-CaM (■), $Ca^{+2}$ (▨), and EGTA (▨).

As noted before, an important aspect of the proposed approach is the ability to "tune" the properties of the tripodal peptide, in such a way that would enable the receptor to interact primarily with a specific region (or a modification) on the protein's surface (FIG. 2, state b). This principle was validated by repeating the above experiments with the four additional control compounds (2-5, FIG. 23), which do not contain hydrophobic receptors. As shown in FIG. 23, a simple alteration in the sequence of the appended peptides had a dramatic effect on the fluorescence response. Specifically, the emission of compounds with negatively charged (2) or polar (3) receptors was not enhanced by the sequential addition of His-CaM and calcium ions, indicating that these sensors do not interact with the surface of His-CaM or His-CaM(Ca$^{+2}$). In contrast, sensors with positively charged (4) or hydrophobic and positively charged (5) receptors generated high fluorescence signals both in the presence and absence of calcium ions, which most likely result from electrostatic interactions with negatively charged side chains on the surface of this acidic protein (pI=3.9-4.3). This experiment also indicates that structural activity relationship (SAR) studies could be used to further improve the efficiency of such systems.

Example 8

Figure 24:
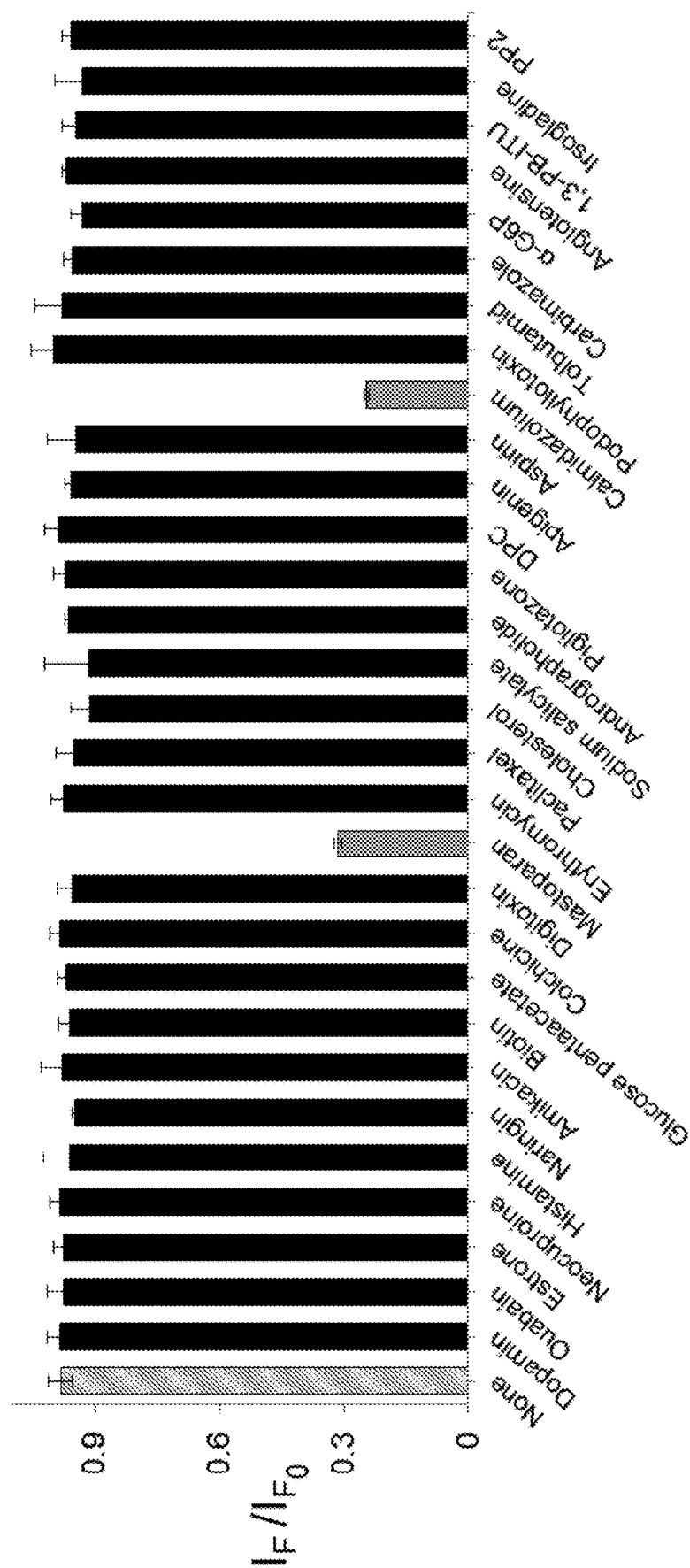
FIG. 24 depicts Fluorescence emission generated by the His-CaM($Ca^{+2}$)-1-complex (200 nM) in the absence (▨) and presence of 1.6 M of randomly selected drugs (■), and known CaM inhibitors calmidazolium and mastoparan (■).

The Fluorescence Response of Sensor of the Invention to the Addition of a Variety of Randomly Selected Drugs The ability to detect changes in protein surfaces opens up new possibilities for using such sensors to identify binding partners (FIG. 2, state c). Unlike enzyme inhibitors that can be readily detected by enzymatic assays, identifying molecules that interact with protein surfaces is generally complicated by the need to use antibodies and stepwise protocols, or special techniques such as fluorescence anisotropy or surface plasmon resonance (SPR) (FIG. 16). To determine whether synthetic molecules that bind to the CaM surface can be identified by our system, we followed the fluorescence response of the His-CaM(Ca$^{+2}$)-1 complex (FIG. 2, state b) to the addition of a variety of randomly selected drugs, as well as the known CaM inhibitors calmidazolium and mastoparan (FIG. 24). A decrease in the fluorescence emission was observed only in the presence of the CaM inhibitors, which is expected from the release of the protein-bound receptor upon the formation of the His-CaM(Ca$^{+2}$)-drug complex (FIG. 2, state c).

Example 9

The Fluorescence Response of Sensor of the Invention to the Addition of Natural Binding Partners The ability of sensor 1 to detect natural binding partners was tested. This is a more challenging goal to achieve because the sensor must be inert to the presence of large proteins that may also possess hydrophobic patches on their surfaces and/or proteins that tend to engage in non-specific interactions such as serum albumin (e.g., BSA and HSA). Accordingly, the His-CaM(Ca$^{+2}$)-1 complex was incubated with 12 different proteins (FIG. 25), among which CaMKII and Drp1 are known to be CaM binding partners, whereas M13 is the binding fragment (26 aa peptide) of the skeletal muscle myosin light chain kinase (sk-MLCK). The response of the system to the known binding partners and, most importantly, the recovery of emission by the addition of a competing CaM (that lacks His-tag) provide evidence for the ability of the system to identify specific protein partners.

Example 10

Figure 26:
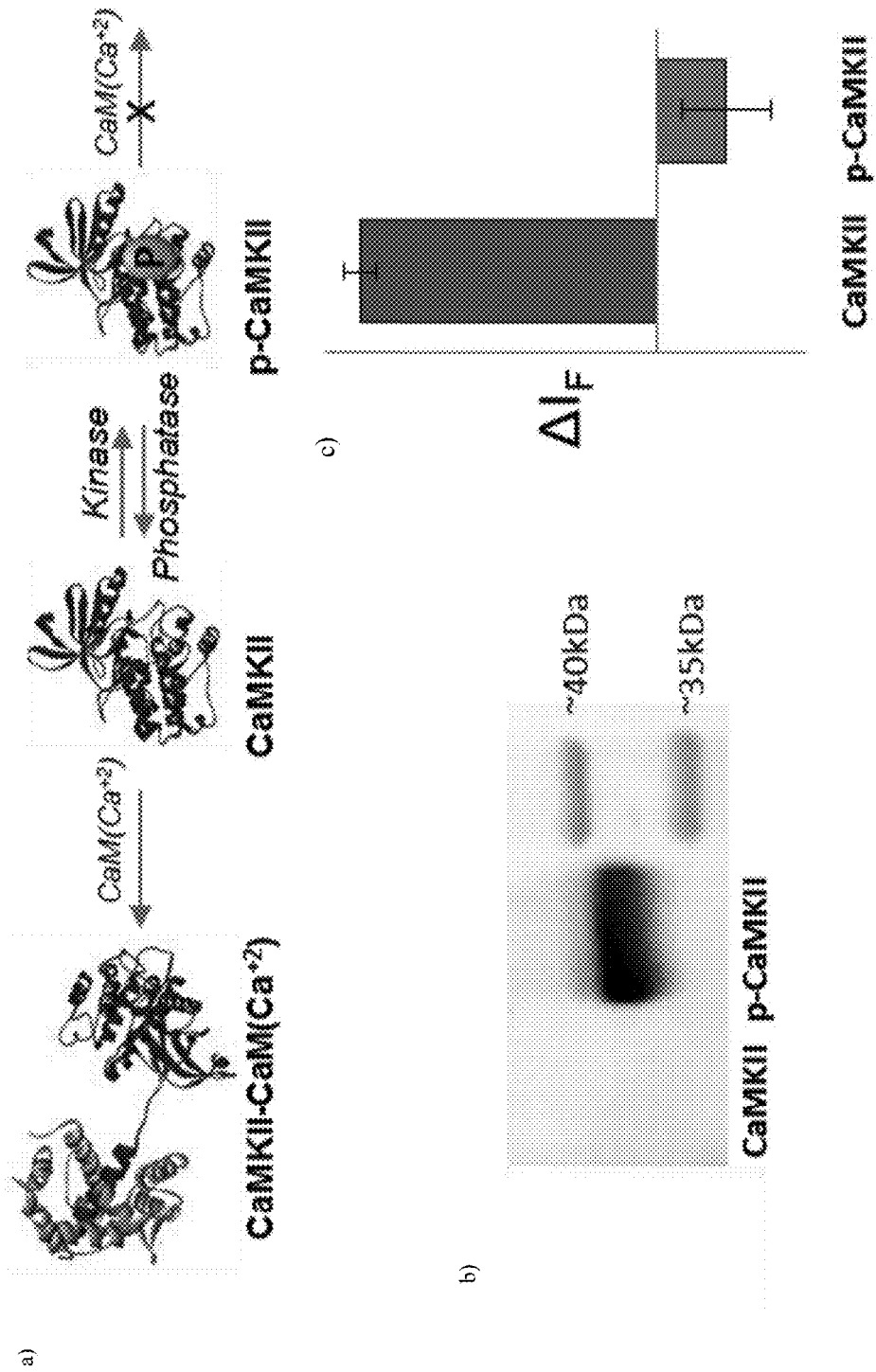
FIG. 26 depicts (a) Schematic illustration showing the preferential binding of CaM($Ca^{+2}$) to a non-phosphorylated CaMKII. The phosphate group on p-CaMKII is denoted as (Ⓟ) (b) Determining the phosphorylation state of CaMKII by a conventional western blot technique. (c) Determining the phosphorylation state of CaMKII (800 nM) by recording the fluorescence response of His-CaM($Ca^{+2}$)-1 (200 nM) to addition of CaMKII and p-CaMKII.

Detection of Surface Modifications in Unlabeled Proteins by Sensors of the Invention The system was also probed to detect surface modifications of unlabeled proteins. As a proof-of-principle, the phosphorylation state of calmodulin-dependent protein kinase II was determined (CaMKII, FIG. 26) using the His-CaM(Ca$^{+2}$)-1 complex. CaM(Ca$^{+2}$) is known to bind only the dephosphorylated state of this enzyme (FIG. 26$a$) and hence, it was expected that a decrease in the fluorescence signal will be observed only in response to a dephosphorylated CaMKII. Accordingly, p-CaMKII was treated with phosphatase to obtain CaMKII (see experimental details in Example 19 below) and the phosphorylation state of samples containing p-CaMKII or CaMKII was initially determined by conventional western blot analysis (FIG. 26$b$). Although this technique can be used to distinguish between the samples, it is a laborious process that normally takes 1-2 days, in which proteins are separated using SDS-PAGE and transferred to a membrane to allow the binding of primary and secondary antibodies. This approach also requires multiple incubation and washing steps, and a specific antibody for each modification. In contrast, this system could determine the phosphorylation state of each sample within seconds, simply by incubating the protein with a solution containing the His-CaM(Ca$^{+2}$)-1 complex (FIG. 26$c$).

Example 11

Figure 27:
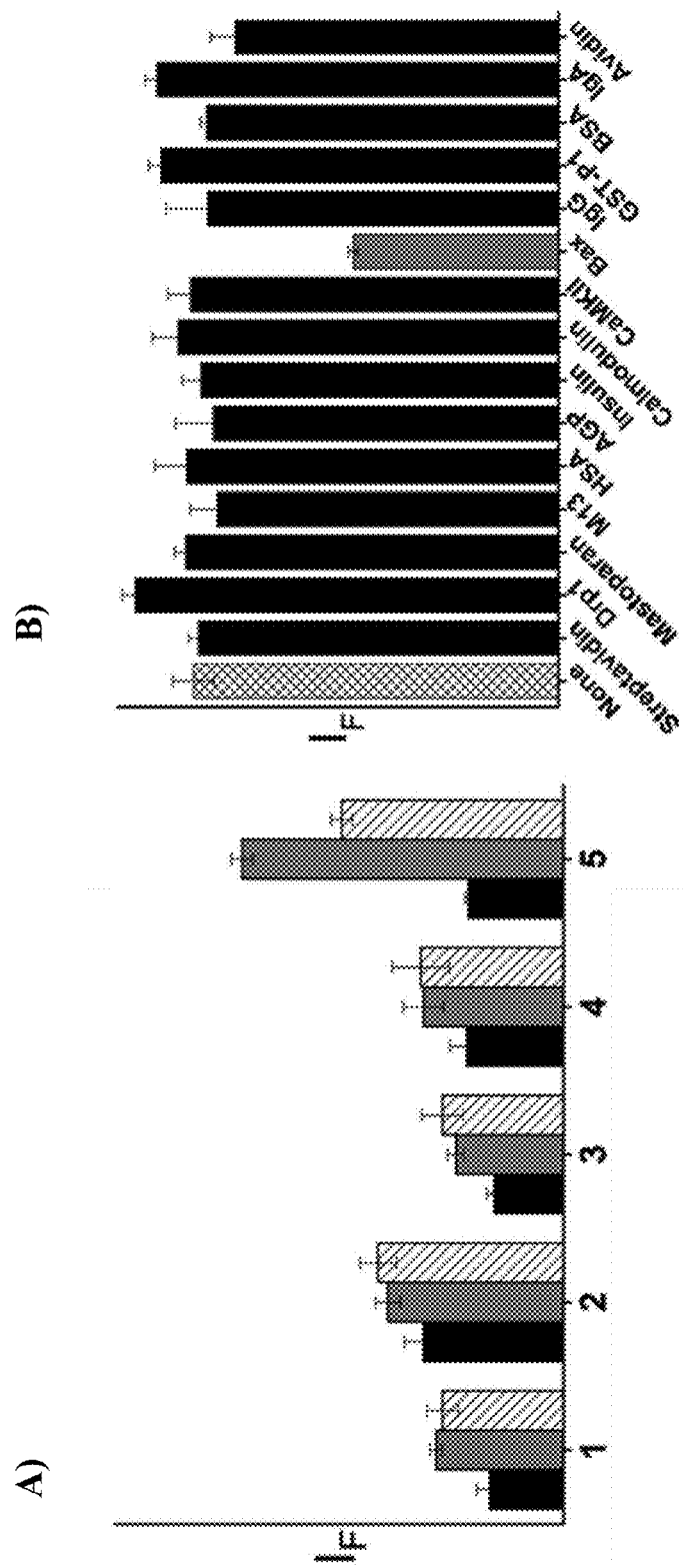
FIG. 27 depicts fluorescence response of a) (■) compounds 1-5 (200 nM) to the sequential addition of (■) His-Bcl-2 (200 nM) (▨) Bax-BH3 (1.6 mM). b) Fluorescence of the His-Bcl-2-5 complex (200 nM) before (▨) and after the addition of 800 nM of randomly selected proteins (■), as well as the known Bcl-2 binding partner: Bax BH3 (■).

Detection of Binding Interactions Between Bcl-2 and BAX by Sensors of the Invention The sensing of His-CaM's surface by the tripodal receptor of 1 supports previous studies, in which it was shown that bringing a non-specific synthetic receptor in the vicinity of a protein, is likely to promote interactions between this receptor and the surface of the protein target. It was therefore expected that even a small sensor library, consisting of only five different receptors (FIG. 23, compounds 1-5), would be sufficient for identifying sensors that can detect surface modifications of His-tag labelled proteins, which are not related to CaM. The ability of compounds 1-5 to detect the interactions between Bcl-2 and Bax was tested. These proteins belong to Bcl-2 family, which plays an important role in regulating apoptosis. The interaction between Bcl-2 and an amphipathic alpha helical peptide of Bax (Bax-BH3), in particular, prevents Bax from triggering apoptosis. As shown in FIG. 27$a$, of the different compounds tested, the emission of the amphipathic sensor 5, was most significantly enhanced upon binding to His-Bcl-2 and this emission was decreased when the Bax-BH3 peptide was added. Other proteins, as well as M13 and mastoparan that were previously detected by the His-CaM(Ca$^{+2}$)-1-complex (FIG. 24), did not change the emission signal generated by the His-Bcl-2-5 complex. In addition, no change in the emission signal was observed in the absence of nickel ions (FIG. 28), which further demonstrate the selectivity and binding mechanism of such sensors.

Example 12

Experimental Details

Fluorescence Response of Compounds 1-5 to CaM Surface Modifications

Figure 21:
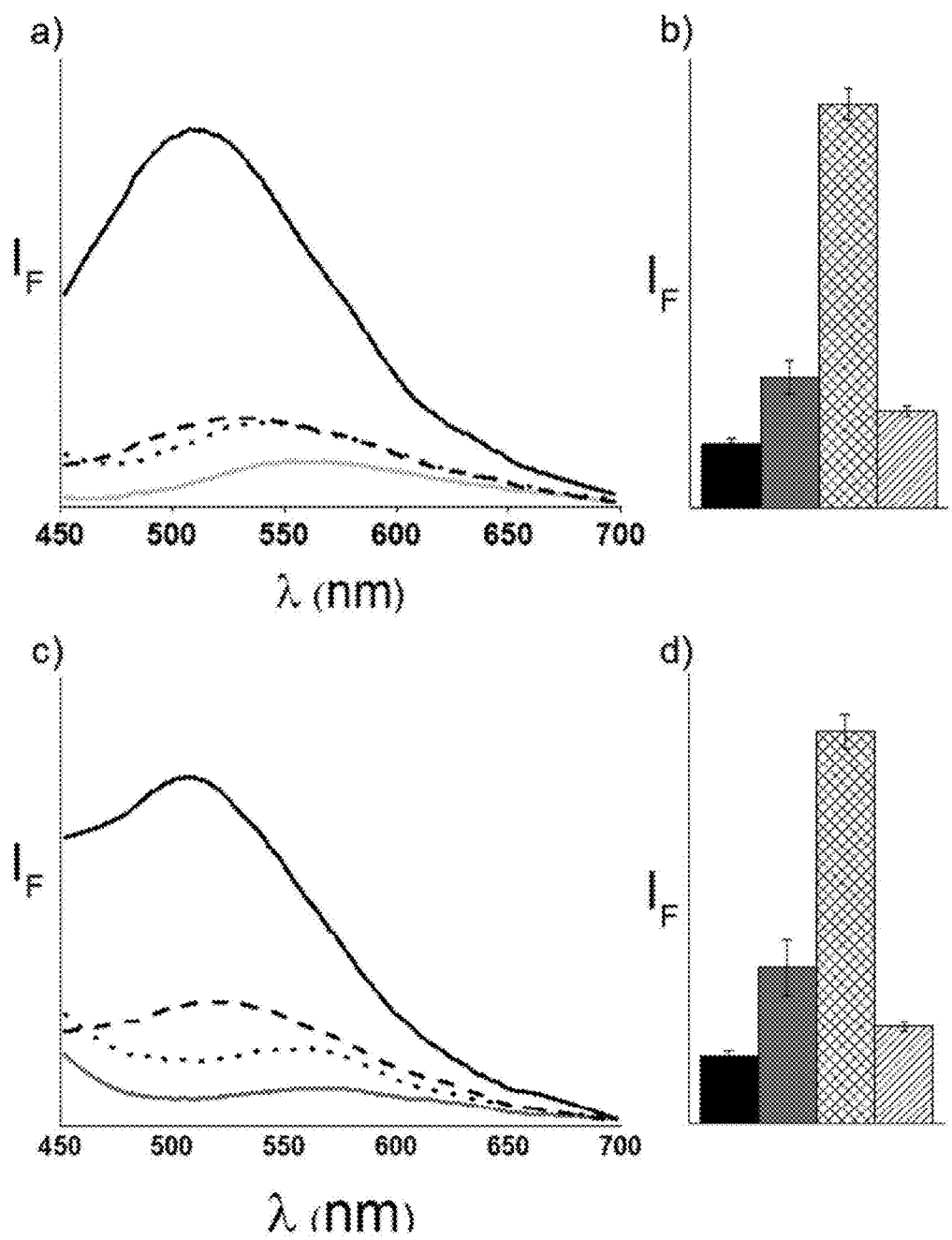
FIG. 21 depicts the fluorescence spectra of 1 (200 nM) before (solid grey line) and after the sequential addition of (a) 400 nM His-CaM (dashed line) or (c) 600 nM His-CaM (dashed line), 0.3 mM $CaCl_2$ (solid black line), and 1.2 mM EGTA (dotted line). The fluorescence response of (■) compound 1 (200 nM) to the sequential addition of (b) (■) His-CaM (400 nM) or (d) (■) His-CaM (600 nM), (▨) $Ca^{2+}$ (0.3 mM), and (▨) EGTA (1.2 mM).

Compounds 1-5 (50 µL, 12 µM) in phosphate buffer (4.1 mM, pH=7.3) were dispensed into a 384-well plate and fluorescence intensities were recorded with an excitation wavelength of 330 nm. His-CaM (final concentration, 200 nM), CaCl$_2$ (final concentration, 0.3 mM), and EGTA (final concentration, 1.2 mM) were subsequently added to each well and the fluorescence intensity values were recorded again (FIGS. 22 and 20). The emission values correspond to the maximal intensities recorded either at $\lambda_{em}$=510 nm or at $\lambda_{em}$=560 nm. Fluorescence was measured in triplicate. Data shown in FIGS. 20 and 22 are the average of the triplicates and error bars represent standard deviation. Control experiments were performed in a similar manner (FIGS. 22$a$-$e$) and with higher His-CaM concentrations (FIG. 21).

Fluorescence Response of Compounds 1-5 to Protein G Surface Modifications

Compounds 1-5 (50 µL, 10 µM) in phosphate buffer (4.1 mM, pH=7.3) are dispensed into a 384-well plate and fluorescence intensities are recorded with an excitation wavelength of 330 nm. His-Protein G (final concentration, 200 nM) and IgG (final concentration, 800 nM) are subsequently added to each well and the fluorescence intensity values are recorded again. The emission values obtained, correspond to the maximal intensities recorded either at $\lambda_{em}$=530 nm or at $\lambda_{em}$=560 nm. Fluorescence is measured in triplicate. Control experiments are performed in a similar manner.

Fluorescence Response of Compounds 1-5 to Bcl-2 Surface Modifications

Figure 28:
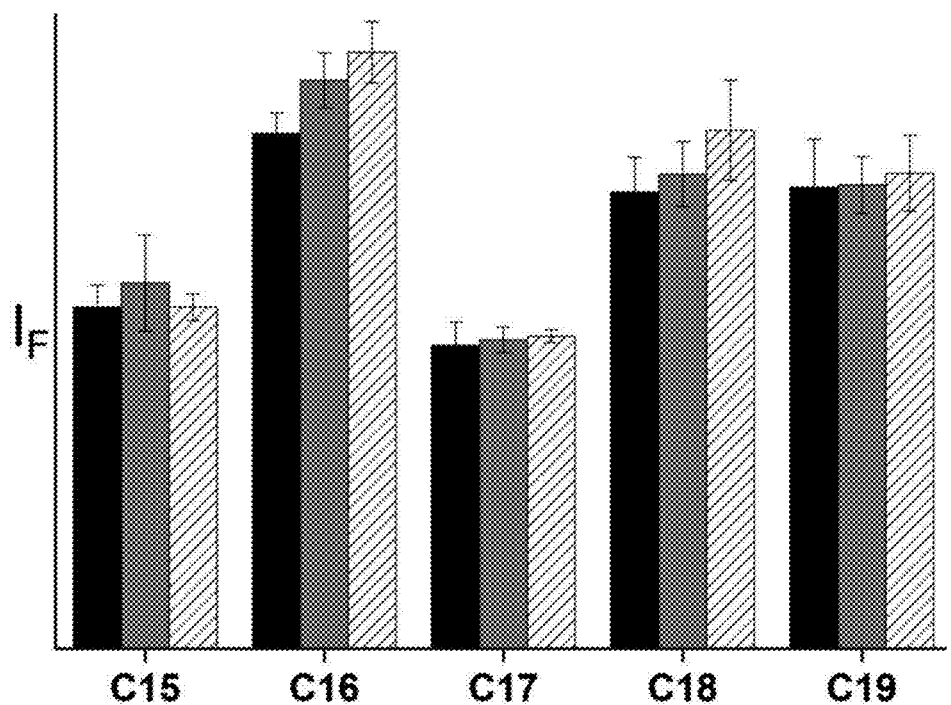
FIG. 28 depicts fluorescence response of (■) compounds C15-19 (200 nM) to the sequential addition of (■) His-Bcl-2 (200 nM) (▨) Bax BH3 (1.6 mM).

Compounds 1-5 (50 L, 10 µM) in phosphate buffer (4.1 mM, pH=7.3) were dispensed into a 384-well plate and fluorescence intensities were recorded with an excitation wavelength of 330 nm. His-Bcl-2 (final concentration, 200 nM) and Bax BH3 (final concentration, 1.6 µM) were subsequently added to each well and the fluorescence intensity values were recorded again. The emission values correspond to the maximal intensities recorded either at $\lambda_{em}$=530 nm or at $\lambda_{em}$=560 nm. Fluorescence was measured in triplicate. Data shown in FIG. 27 is the average of the triplicates and error bars represent standard deviation. Control experiments were performed in a similar manner (FIG. 28).

Screening Assay with Different Small Molecules and Peptide Inhibitors

A mixture of compound 1 (200 nM), His-CaM (400 nM), and CaCl$_2$ (0.3 mM) in PBS buffer (4.1 mM, pH=7.3) was dispensed into a 384-well microplate, and fluorescence emission spectra were recorded. Then various drugs (1.6 M)

and peptides (1.6 M) were added and the fluorescence emission was again recorded. Fluorescence measurements were performed in triplicate and the emission intensities before the addition of each drug were normalized to 100% (FIG. 24).

Screening Assay for Protein Interactions Using Surface Sensors.

Probing Protein Interactions for Calmodulin

Figure 25:
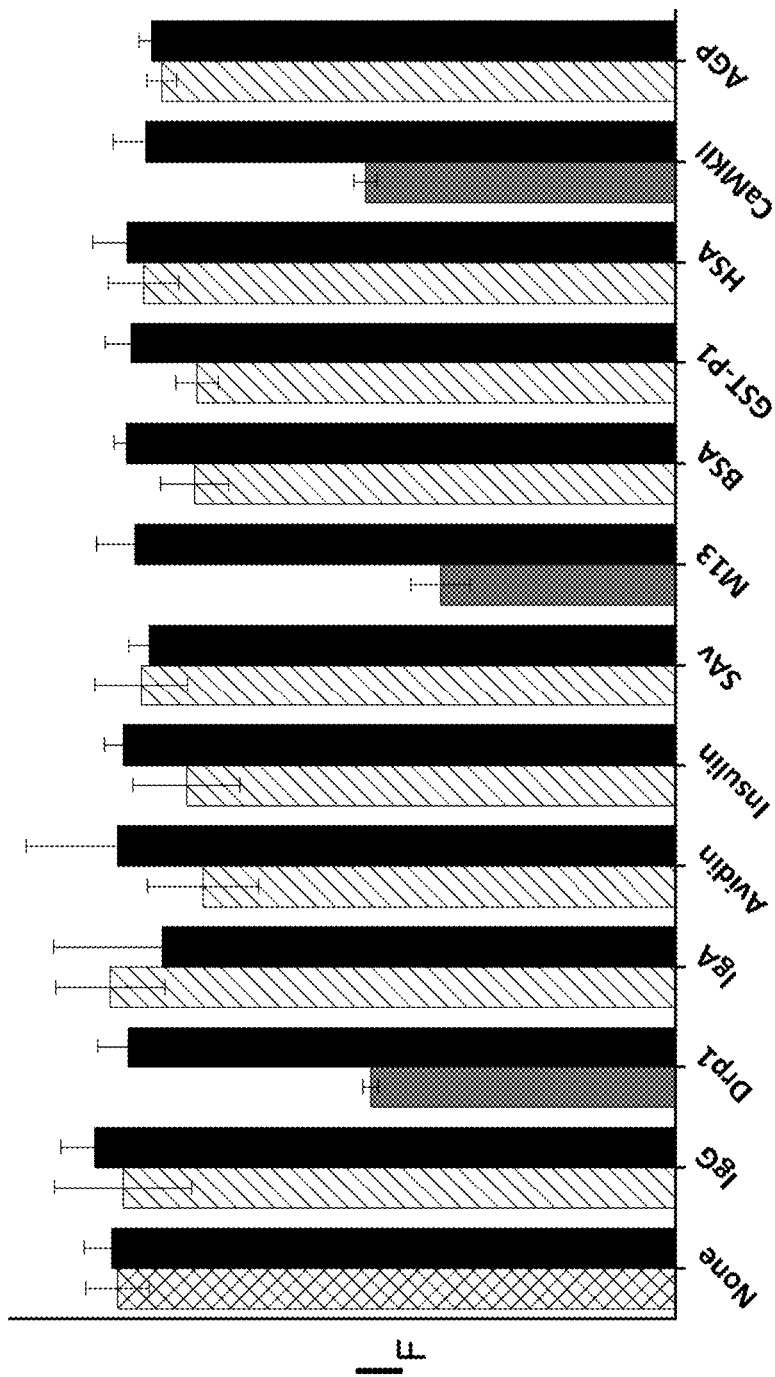
FIG. 25 presents the fluorescence of the His-CaM($Ca^{+2}$)-1-complex (200 nM) before (▨) and after the addition of 800 nM of randomly selected proteins (▨), as well as known CaM binding partners: CaMK-II, M13, and Drp1 (■). The black bars correspond to emissions recorded in the presence of a competing CaM, which lacks a His-tag (1.6 μM).

A mixture of compound 1 (200 nM), His-CaM (200 nM), and $CaCl_2$ (0.3 mM) in PBS buffer (4.1 mM, pH=7.3) was dispensed into a 384-well microplate, and the fluorescence emission spectra were recorded. Various proteins (0.8 M) and M13 peptide (0.8 M) were added and the fluorescence emission was again recorded. As a competing binding partner CaM (1.6 M) was added. Fluorescence measurements were performed in triplicate. The emission intensities before the addition of each protein were normalized to 100% (FIG. 25).

Probing Protein Interactions for Protein G

A mixture of compound 5 (200 nM) and His-protein G (200 nM) in PBS buffer (4.1 mM, pH=7.3) is dispensed into a 384-well microplate, and the fluorescence emission spectra are recorded. Various proteins (0.8 μM) and IgG (0.8 μM) are added and the fluorescence emission is again recorded. Fluorescence measurements are performed in triplicate. The emission intensities before the addition of each protein are normalized to 100%.

Probing Protein Interactions for Bcl-2

A mixture of compound 5 (200 nM) and His-Bcl-2 (200 nM) in PBS buffer (4.1 mM, pH=7.3) was dispensed into a 384-well microplate, and the fluorescence emission spectra were recorded. Various proteins (0.8 μM) and Bax BH3 peptide (0.8 μM) were added and the fluorescence emission was again recorded. Fluorescence measurements were performed in triplicate. The emission intensities before the addition of each protein were normalized to 100% (FIG. 27b).

Dissociation Constant.

The approximate dissociation constant for the sensor 1-His tag interaction was determined using a carboxyfluorescein-labeled hexa-histidine peptide. Carboxyfluorescein-labeled hexa-histidine peptide (60 L, 10 nM) in PBS buffer (4.1 mM, pH=7.3) was dispensed into a 384-well microplate and the fluorescence data were recorded using excitation and emission filters of 485/20 and 580/20, respectively, and a 510 nm cut-off mirror. Then, various concentrations of 1 (final concentrations ranging from 0-650 nM) were added to the wells and the fluorescent intensities were recorded again. The complexation of the labeled peptide with compound 1 leads to strong fluorescence quenching, by the chelated transition $Ni^{+2}$ ions. Fluorescence data were collected in triplicate. The data was normalized to 100% for labeled peptide before the addition of sensor 1 and the relative quenching percentages were plotted against the sensor's concentration. The data was then analyzed by fitting to a non-linear regression for single-site saturation ligand binding $$(y = \frac{B_{max}x}{K_d + x},$$

Figure 17:
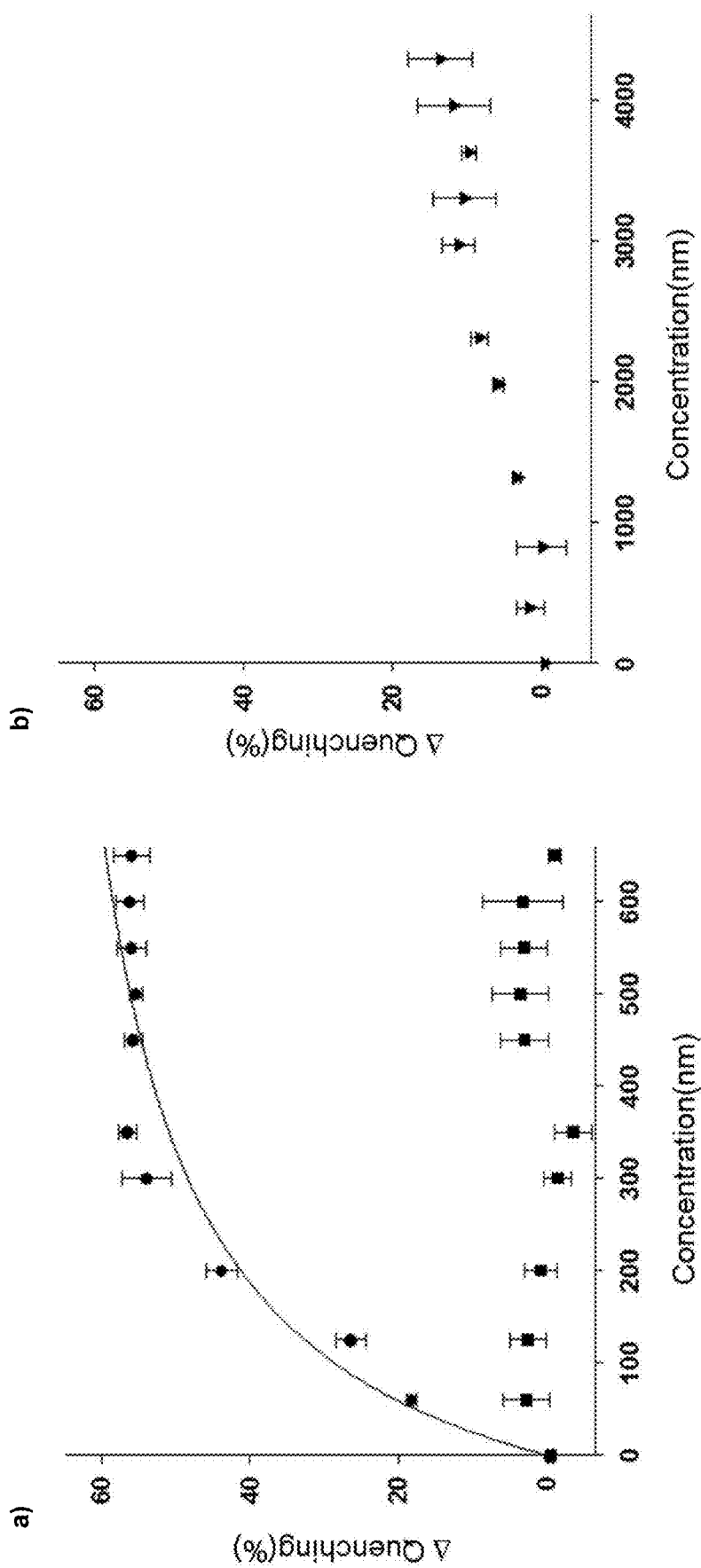
FIG. 17 depicts (a) Binding curves obtained for compound 1 (●) by the addition of increasing amounts of compound 1 to a carboxyfluorescein-labeled hexa-histidine peptide ($K_d$=157±21 nM, $R^2$=0.96). Control experiments (a,b) were performed with C15 (■) and NiCl$_2$(▼).

$B_{max}$=maximum specific binding is 73.82±3) using Sigma-Plot 9.0, which resulted in a $K_d$ value of 157±21 nM. The control experiments were performed with C15 and only $NiCl_2$ (FIG. 17).

Surface Plasmon Resonance Experiments.

SPR experiments were performed to assess the dissociation constant between His-CaM and the compound 1 in the presence/absence of $Ca^{2+}$ ions and other ligands. His-CaM was diluted in 180 μL PBS buffer (4.1 mM, pH=7.3) and 20 μL sodium acetate (1M, pH=3) to reach a final concentration of 20 μg/mL and then immobilized on a Biacore sensor chip CM5 through EDC/NHS chemistry. Flow cells were activated for 5 min by injecting 50 μL mixture of 50 mM NHS:200 mM EDC. Then 50 μL of His-CaM (20 g/mL) was injected at a rate of 10 μL/min followed by injection of ethanolamine (1 M) to block the remaining surface-activated groups. Various analytes (Table 1) were injected in different concentrations, ranging from 0.1-2 μM for (20 μL/min, 80 μL injection with a delay of 180 s wash) (Table 1). Between consecutive analyte injections, the surface was regenerated with 2 mM NaOH (20 μL at 10 μL/min) followed by PBS buffer (60 μL at 10 μL/min). Non-derivatized dextran matrix flow cells served as reference cells. For determination of dissociation constants in the presence of M13 or Mastoparan (entries 3 and 4), first 80 μL M13 or Mastoparan (3 μM, 20 μL/min) were injected and after dissociation began 80 μL compound 1 (concentration range of 0.2-2 μM, 20 μL/min) was injected. $CaCl_2$ (0.3 mM) was pre-incubated with the analyte before injections. For the control compound C15 (entry 5), prior to each injection, the chip was washed with 20 μL EDTA (50 mM, 20 μL/min) followed by PBS buffer (20 μL at 20 μL/min) to remove any traces of $Ni^{2+}$. The data were globally fitted using BiaEvaluation software 3.2.

CaMKII Assays.

CaMKII Dephosphorylation

CaMKII was dephosphorylated according to a previously published procedure. 0.787 nmol p-CaMKII was incubated with λ-phosphatase (600 U) and $MnCl_2$ (50 mM) at 4° C. overnight. Then the mixture was buffer exchanged into HEPES buffer (20 mM, 0.3 M NaCl, 1 mM $CaCl_2$, pH=7.5) using a 3 kDa cutoff centrifugal filter (Amicon Ultra, Millipore) at 4° C.

CaMKII Western Blot Analysis

Figure 29:
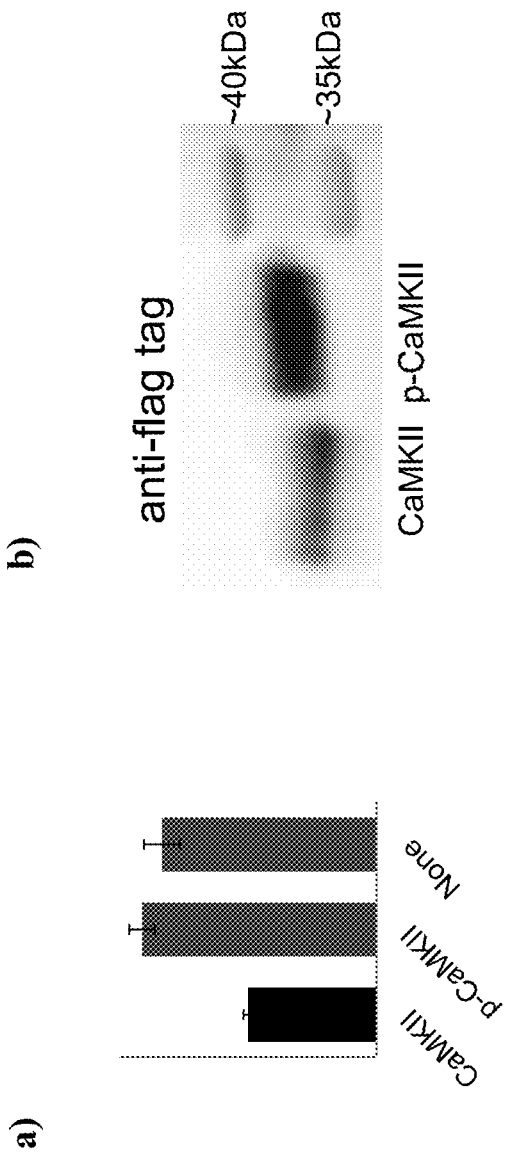
FIG. 29 depicts (a) Fluorescence of the His-CaM ($Ca^{+2}$)-1 complex (200 nM) before (none) and after the addition of 0.8 □M CaMKII and p-CaMKII. (b) Western blot detection of CaMKII and p-CaMKII with anti-flag-tag antibody. Both CaMKII and p-CaMKII are detected by an anti-flag tag antibody whereas only p-CaMKII is detected by phospho-specific antibody, as shown in (b).
Figure 30:
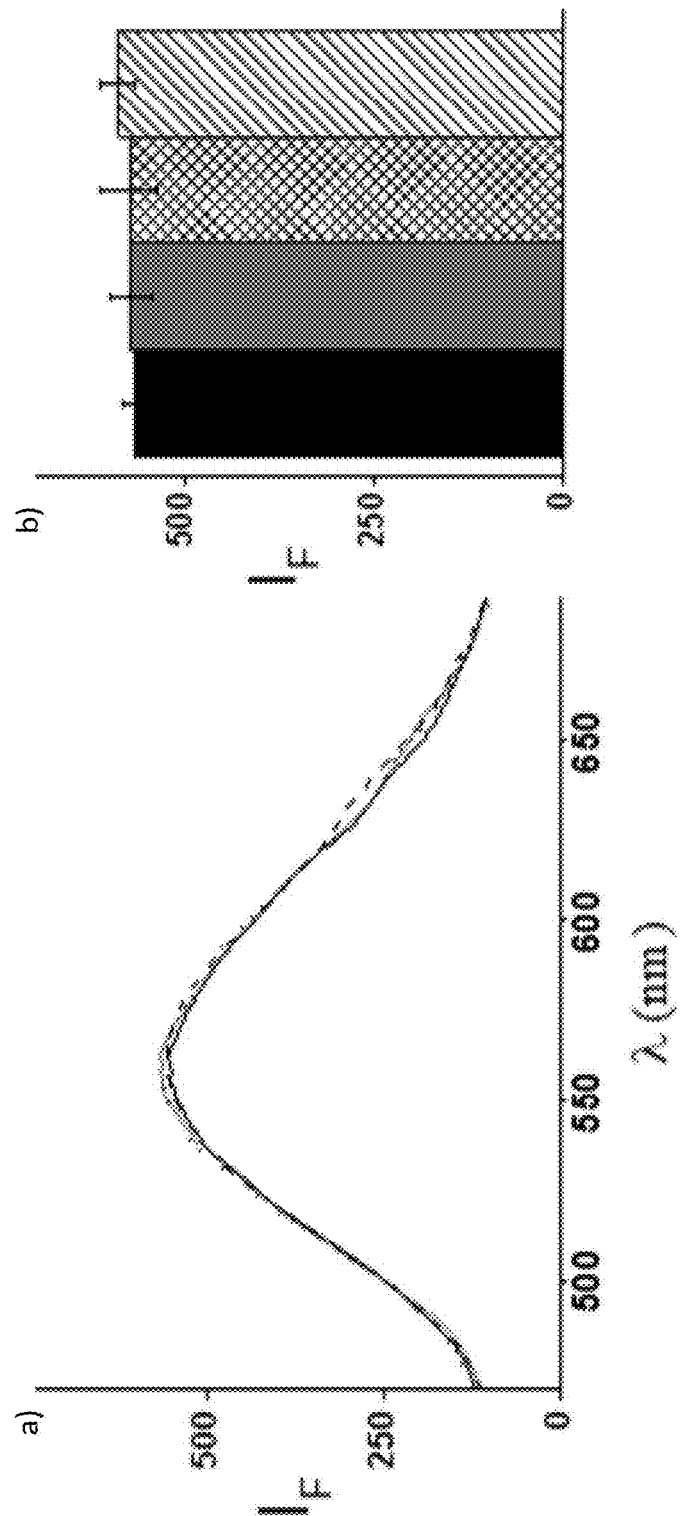
FIG. 30 depicts a-b) Fluorescence response of (■) compounds C15 (2 □M) to the sequential addition of (■) His-CaM (200 nM), (▨) $Ca^{2+}$ (0.3 mM), and (▨) EGTA (1.2 mM).
Figure 31:
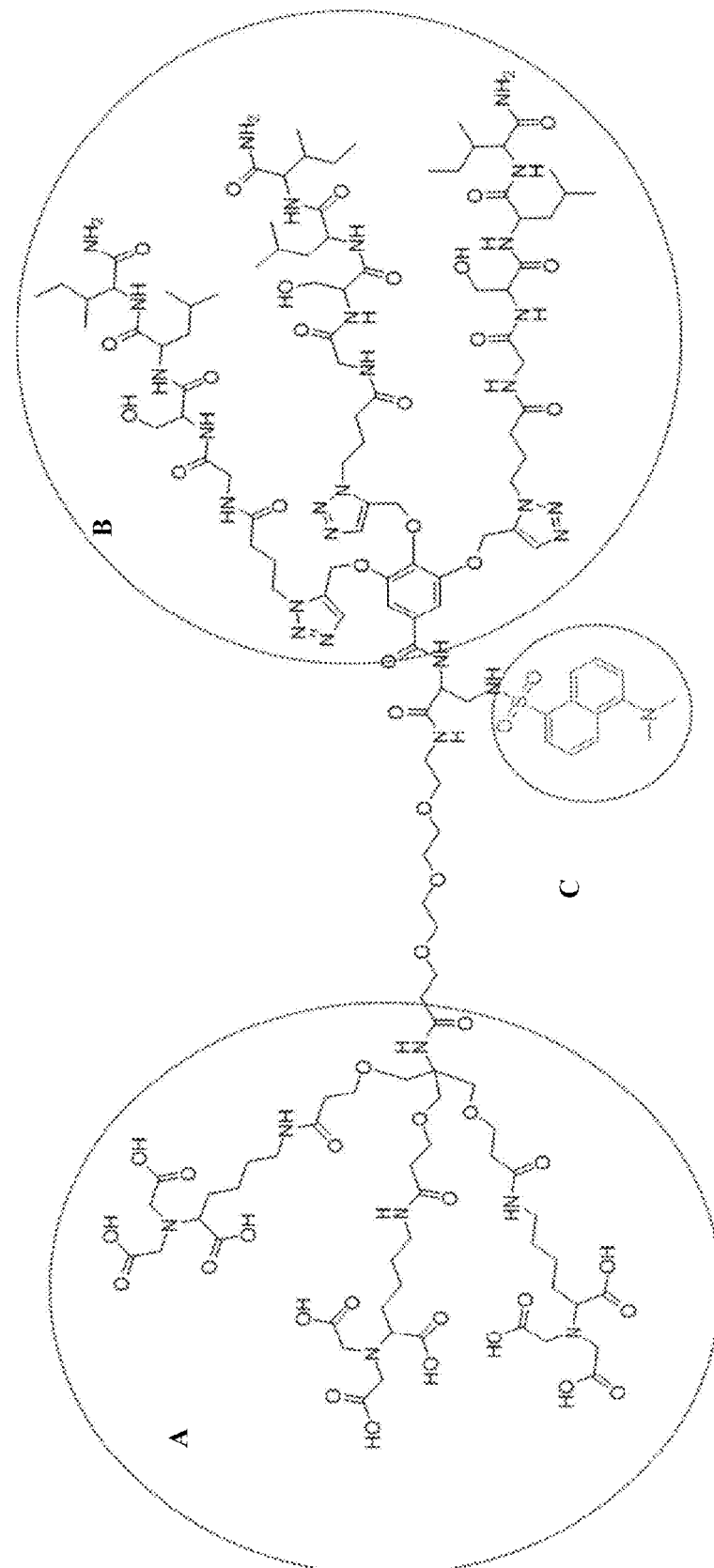
FIG. 31 depicts the protein surface sensor consists of three components. A: A bis-NTA unit for specific His-tag binding. B: A tripodal hydrophobic peptide that serves as a non-selective protein surface receptor. C: A Dansyl group as the solvatochromic fluorophore.

Approximately 2 g of p-CaMKII and 1 g of CaMKII were loaded in each western blot run. Proteins were resolved on a 10% SDS-PAGE gel and transferred to a membrane, blocked with 5% BSA in PBST buffer (0.1% Tween), and probed with either antibody specific for p-CaMKII (at a dilution of 1:1000) or anti-flag tag (at a dilution of 1:1000 dilution) as primary antibodies. Intermediate washing between steps was done with PBST buffer. HRP-conjugated goat anti-rabbit was used as secondary antibody (at a dilution of 1:10000). CaMKII is expressed with anti-flag tag, which permits performing loading control analysis. Using the primary antibody that is specific for flag tag, a signal for both p-CaMKII and CaMKII (phosphatase treated) was obtained using BIORAD ChemiDoc™ XRD+ (FIGS. 26 and 29).

Example 13

Synthetic Details of ODN Bound His-Tag Binders of the Invention

Materials and Methods

All reagents and solvents were obtained from commercial suppliers. Oligonucleotides were obtained from W. M. Keck Foundation Biotechnology at Yale University, which were synthesized using standard automated solid-phase synthesis. Aluminum-backed silica plates (Merck silica gel 60 F254)

were used for thin layer chromatography (TLC) to monitor solution-phase reactions. The $^1$H-NMR spectra were recorded using a 300 MHz Bruker Avance NMR spectrometer. Chemical shifts are reported in ppm on the δ scale down field from TMS as the internal standard. The following abbreviations were used to describe the peaks: s-singlet, d-doublet, t-triplet, q-quartet, quin-quintet, and m-multiplet. Electrospray mass spectrometry was performed with a Micromass Platform LCZ-4000 instrument at the Weizmann Institute of Science mass spectrometry facility. Matrix-assisted laser desorption ionization time-of-flight (MALDI-TOF) mass spectrometry was performed on an AB SCIEX 5800 system, equipped with an Nd: YAG (355 nm) laser with a 1 KHz pulse (Applied Biosystems), at the Weizmann Institute of Science mass spectrometry facility. The purification of oligonucleotides was carried out on a Waters 2695 separation module HPLC system with a 2994 photodiode array detector using either a Waters XBridge™ OST C18 column (2.5 µM, 4.6 mm×50 mm) or an XBridge™ OST C18 column (2.5 µM, 10 mm×50 mm). Oligonucleotide samples were desalted using illustra MicroSpin G-25 Columns (GE Healthcare) according to the supplier's instructions. Concentrations of the oligonucleotides were quantified based on their respective electronic absorption at 260 nm and the molar extinction coefficient of the oligonucleotide at this wavelength. Cell images were acquired using an Olympus IX51 fluorescent microscope equipped with a U-MNIBA3 fluorescence filter cube (excitation and emission filters of 470-495 nm, and 510-550 nm, respectively), a U-MNG2 fluorescence filter cube narrow-band (excitation and emission filters of 530-550 nm, and 590 nm, respectively) and a U-MF2 fluorescence filter cube (excitation and emission filters of 620-660 nm, and 700-775 nm, respectively).

Synthetic Procedures

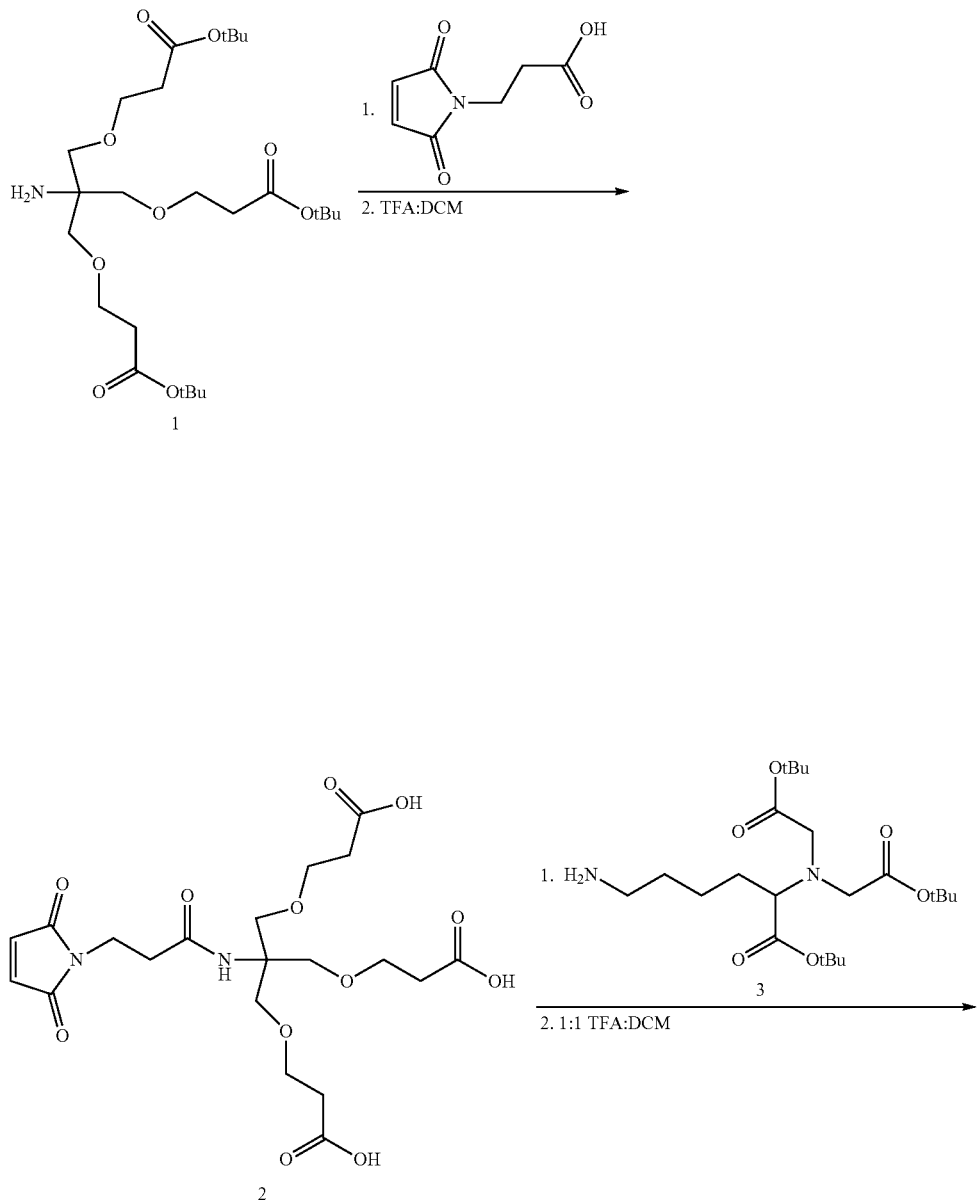

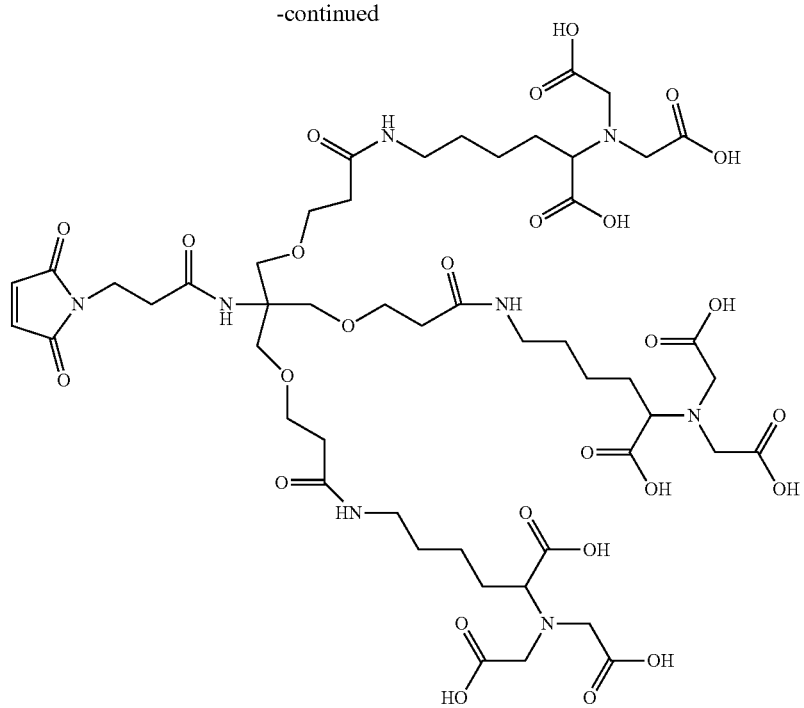

4

Compounds 1 and 3 of scheme 1 were synthesized according to previously reported procedures (Cardona, C. M. An improved synthesis of a trifurcated newkome-type monomer and orthogonally protected two-generation dendrons. J. Org. Chem. 67, 1411-1413 (2002); Huang, Z. Facile synthesis of multivalent nitrilotriacetic acid (nta) and nta conjugates for analytical and drug delivery applications. Bioconjugate Chem. 17, 1592-1600 (2006).

Compound 2 of scheme 1: Compound 1 (600 mg, 1.18 mmol) was dissolved in dry DCM (30 ml) under argon and cooled to 0° C. Then, EDC (339 mg, 1.7 mmol) and DIPEA (413.7 μl, 2.32 mmol) were added and the reaction mixture was stirred for 30 min at room temperature. 3-Maleimidopropionic acid (240.1 mg, 1.4 mmol) was added, and the solution was stirred overnight. Then 40 ml DCM was added, and the solution was washed with water (10 ml), and brine (10 ml). The organic layer was dried with Na$_2$SO$_4$, filtered, and concentrated under high vacuum. Finally, the crude product was purified by column chromatography (DCM/MeOH, 97:3) to yield a yellow oil (501.6 mg, 64%).

$^1$H NMR (CDCl$_3$, 300 MHz): δ 1.44 (s, 27H); 2.44 (t, J=6 Hz, 6H); 2.51 (t, J=6 Hz, 2H); 3.63 (t, J=6 Hz, 6H); 3.67 (s, 6H); 3.80 (t, J=6 Hz, 6H); 6.69 (s, 2H). ESI-MS (m/z): calcd. for (M+H): 657.35, found 657.44; calcd. for (M+Na): 679.35, found 679.31.

The tert-butyl groups were then deprotected using a 1:1 (v/v) mixture of TFA: DCM for 2.5 h. After removing the solvents, the excess of TFA was co-evaporated 4 times with DCM and then the product was dried under high vacuum.

$^1$H NMR (D$_2$O, 300 MHz): δ 2.47 (t, J=6 Hz, 2H); 2.59 (t, J=6 Hz, 6H); 3.61 (s, 6H); 3.67-3.75 (m, 8H); 6.83 (s, 2H). ESI-MS (m/z): calcd. for (M+H): 489.16, found 489.18; calcd. for (M+Na): 511.16, found 511.12; calcd. for (2M+H): 977.32, found 977.03; calcd. for (2M+Na): 999.32, found 999.15 (2M+Na).

Compound 4 of scheme 1: A solution of compound 2 (160 mg, 304.8 μmol) in dry DCM (10 ml) was cooled to 0° C. in an ice bath and DIPEA (212 μl, 1.2 mmol), EDC (191 mg, 1 mmol), and HOBt (41 mg, 304.8 μmol) were added consecutively. After 15 min, compound 3 (433 mg, 1 mmol) was added and the reaction was stirred overnight. Then DCM (40 ml) was added and the solution was washed with water (10 ml). The organic layer was dried with Na$_2$SO$_4$, filtered, and concentrated at high vacuum. Finally, the crude product was purified by column chromatography (DCM/MeOH, 96:4) to yield a colorless oil (96.6 mg, 18.3%). $^1$H NMR (MeOD, 300 MHz): δ 1.50 (s, 54H); 1.55 (s, 27H); 1.71 (m, 18H); 2.42 (t, J=6 Hz, 6H); 2.49 (m, 2H); 3.20 (t, J=6 Hz, 6H); 3.31 (m, 12H); 3.55-3.74 (m, 17H); 6.84 (s, 2H). ESI-MS (m/z): calcd. for (M+Na): 1749.13, found 1748.72; calcd. for (M+2Na): 886.06, found 886.27; calcd. for (M+3Na): 598.37, found 598.52. The tert-butyl groups were then deprotected using a 1:1 (v/v) mixture of TFA: DCM for 2.5 h. After removing the solvents, the excess of TFA was co-evaporated 4 times with DCM and then the product was dried under high vacuum $^1$H NMR (MeOD, 300 MHz): δ 1.47 (m, 6H); 1.53 (m, 6H); 1.91 (m, 6H); 2.43 (m, 8H); 3.17 (m, 6H); 3.58-3.65 (m, 15H); 4.1 (m, 14H); 6.82 (s, 2H). ESI-MS (m/z): calcd. for (M+H): 1221.48, found 1221.53; calcd. for (M+Na): 1243.48, found 1243.39. HRMS.

General Procedure for the Synthesis of the ODN-1 Strands:

Scheme 2.

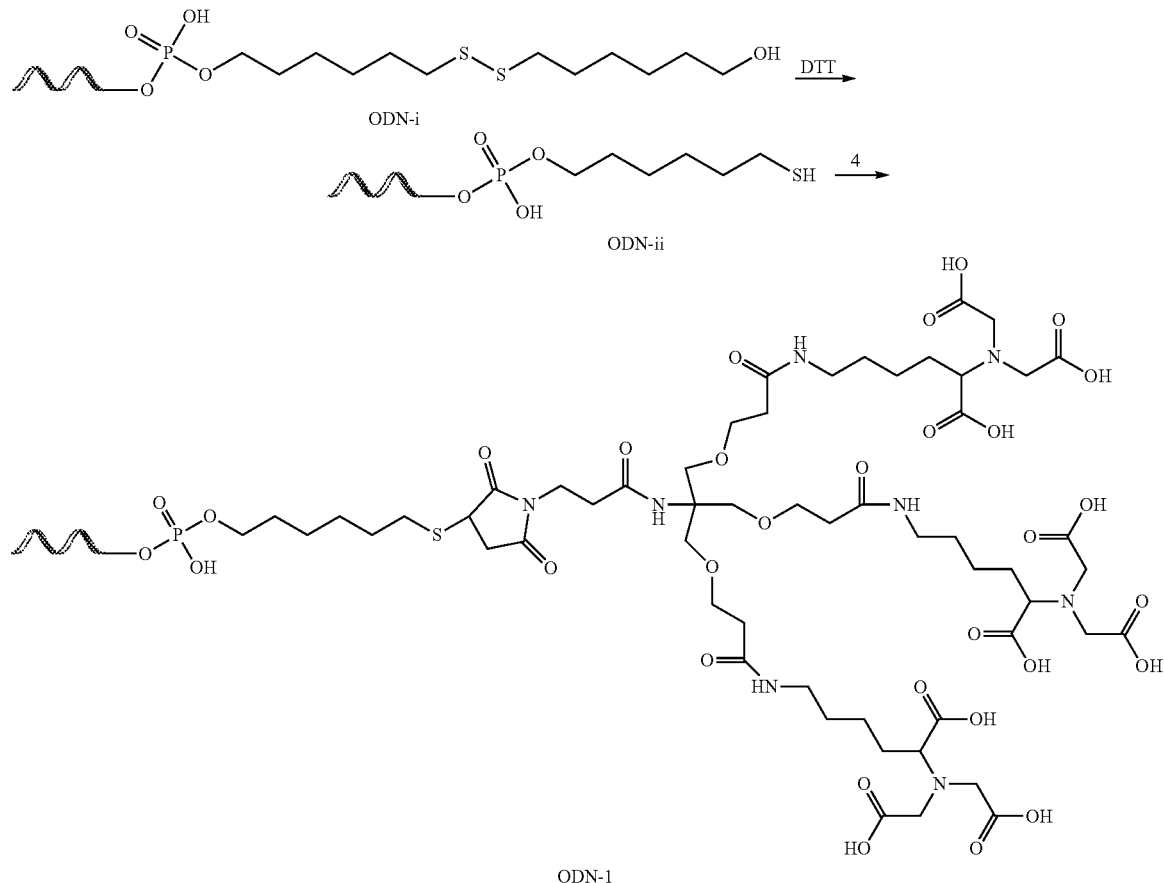

ODN-i of scheme 2 (200 nmol) was treated with 400 μl of a DTT solution (50 mM DTT in 50 mM Tris buffer, pH 8.3) for 1 hour. The reduced oligonucleotide (ODN-ii) was then desalted on Sephadex™ G-25 and dried under reduced pressure. ODN-ii was added to a solution of 4 (8 mg) in concentrated PBS x 10, pH 7. The reaction was stirred overnight. The product was purified using RP-HPLC. MALDI-TOF MS (m/z): X-ODN-1: calcd. 6319.6, found 6334.2; ODN-1: calcd. 8876.1, found 8893.3; Compound 101: calcd. 11453.6, found 11454.3; Compound 103: calcd. 9139.8, found 9139.2; Compound 104: calcd. 9119.9, found 9115.9.

Compounds 100-104 where synthesized according to the general synthesis described hereinabove.

Synthesis of Folate-ODN-2 (Compound 206):

Scheme 3.
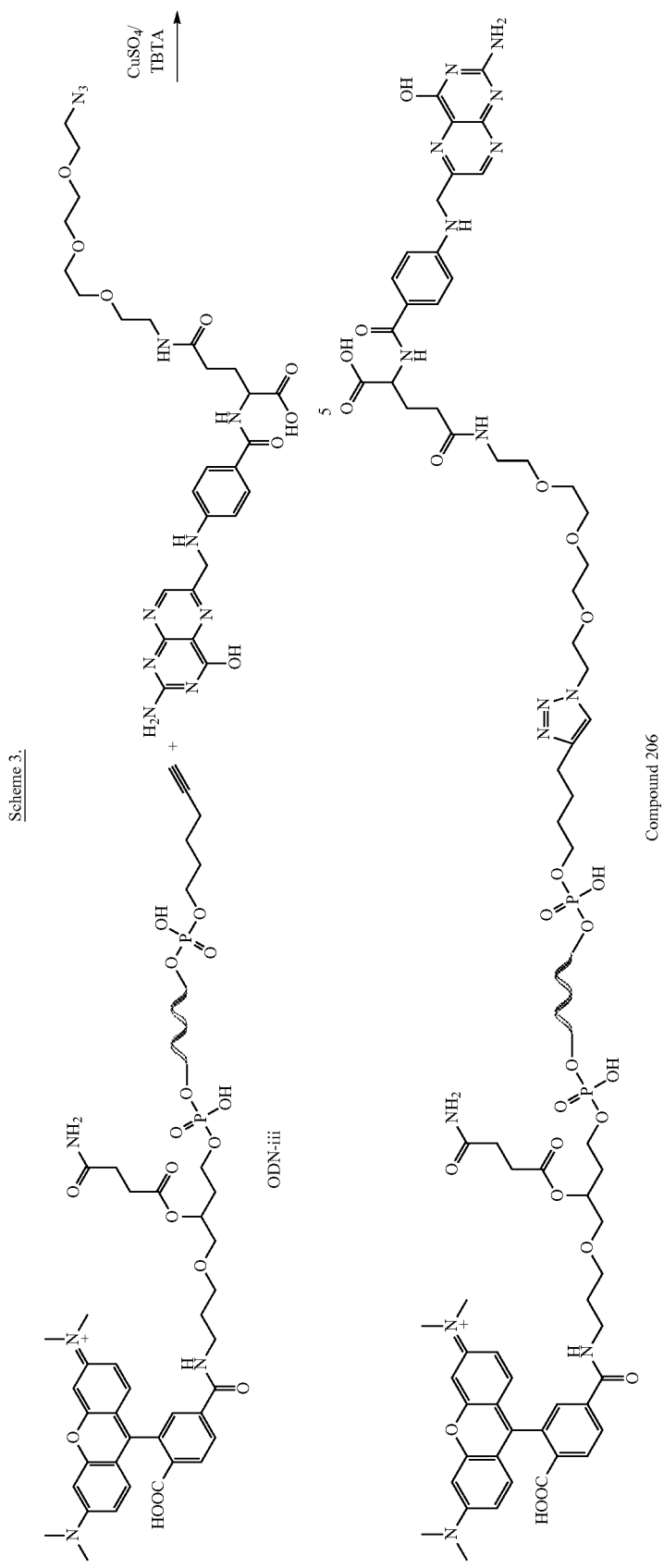
Compound 206

Folate azide 5 of scheme 3, was prepared according to a previously published procedure. ODN-iii of scheme 3 (150 nmol) was dissolved in 160 µl MQ water, followed by the addition of compound 5 (1.5 µmol), ascorbic acid (20 µl, 0.9 µmol), TEAA buffer (40 µl, 2 M, pH=7), and DMSO (200 µL). After degassing with argon, Cu-TBTA (80 µL, 0.9 µmol) was added, and the mixture was stirred for 12 h. The product was purified using RP-HPLC to afford Compound 206. MALDI-TOF MS (m/z): calcd. 9940, found 9941.

OmpC Construction and Expression

OmpC construction. E. coli outer membrane protein C (OmpC) was isolated by PCR, amplified from E. coli ASKA library and cloned into pET21 using RF cloning OmpC_F-pET21: TTTGTTTAACTTTAAGAAGGAGATATA-CATATGAAAGTTAAAGTACTGTCCCTC (SEQ ID No.: 11) and OmpC_RpET21: TTCCTTTCGGGCTTTGT-TAGCAGCCGG ATCTTAGAACTGGTAAACCAGACCC (SEQ ID No.: 12). The resulting plasmid was a His-tag less construct. Polyhistidine-linker sequences were inserted in the predicted 7$^{th}$ loop of the OmpC. OmpC-(6His)i contains 11 amino acid (Aa) sequence: SAGHHHHHHGT (SEQ ID No.: 13) was constructed by Inverse PCR using the following 2 primers: OmpC_His1 F:CATCATCACCATGGTAC-CTCTAAAGGTAAAAACCTGGGTCGTGGCTAC (SEQ ID No.: 14), and OmpC_His1R: ATGGTGATGATGAT-GATGACCCGCGGAGGTAC CATGGTGATGATGGT-GATGACCCGCGGA (SEQ ID No.: 15). The resulting plasmid served as a template for introducing a second His-linker to obtain OmpC-(6His)$_2$ 22 Aa sequence: SAGHHHHHIHGTSAGHHHITHGT (SEQ ID No.: 16) by using the following 2 primers: OmpC_His2FInverse: CAC-CATCACGGTACCTCTAAAGGTAAAAAC CTGGGT-CGTG (SEQ ID No.: 17) and OmpC_His2RInverse: GTGATGGTGACCC GCGGAGGTACCATGGTGAT-GATGGTGATG (SEQ ID No.: 18). An additional third His-linker was introduced to OmpC-(6His)$_2$ by using the following 2 primers: OmpC_His3FInverse: CATCAT-CATGGTACCTCTAAAGGTAAAAACCTGGGTCGTG (SEQ ID No.: 19) and OmpC_His3RInverse: ATGAT-GATGACCCGCG GAGGTACCGTGATGGTGGT-GATGGTG (SEQ ID No.: 20). The resulting construct OmpC-(6His)$_3$ contains 33 Aa His-linker: SAGHHHHfHGTSAGHHIHIHGT SAGHHHIHGT (SEQ ID No.: 21) in the same position at the predicted 7$^{th}$ loop of OmpC. For the Inverse PCR cloning reactions one primer of each set of primers had to be phosphorylated.

Purification of OmpC. The expression of OmpC was tested in the whole cell extracts (WCE) and in the membrane fraction. Cultures expressing OmpC, and His-OmpC were harvested, resuspended in Na$_2$HPO$_4$ (10 mM, pH 7.3) and lyzed by sonication. A sample from each culture was analyzed by SDS-PAGE for the expression of OmpC in the WCE. Following sonication, the supernatant was separated by centrifugation at 13800 g for 10 min. The membrane fraction was recovered by centrifugation of the supernatant at 13800 g for 30 min., resuspended in 10 mM Na$_2$HPO$_4$, pH 7.3, 2% Triton X-100 and incubated at 37° C. for 30 min. The insoluble fraction was recovered by centrifugation at 13800 g for 30 min., washed and resuspended in 10 mM Na$_2$HPO$_4$ pH 7.3. Proteins from the membrane fractions were analyzed by SDS-PAGE.

Oligonucleotides

The oligonucleotides used in the experiments are detailed in Table 1.

TABLE 1

Oligonucleotides (ODNs)

| Description | Sequence | SEQ ID No. |
|---|---|---|
| Compound 100 | 5'GCGGCGAGGCAGC3' | 1 |
| Compound | 3'ATCCTAGTCCGTCGATACTGCACTG5' | 2 |
| ODN-1 and Compound 102 | 3'ATCCTAGTCCGTCGATACT5' | 3 |
| Compound 103 | 3'GATGACAGCTAGCAGATCAACATGG5' | 4 |
| Compound 104 | 3'CGCGCGAAAAAAAAAAAAGCAACGC5' | 5 |
| Compound 200 | 5'TAGGATCAGGCAGCTATGACGTGAC3' | 6 |
| Compound 201 | 3'CAGTGCAGTATCGACGGACTAGGAT5' | 7 |
| Compound 202 and FAM-ODN-2 | 3'CAGTGCAGTATCGACGGACTAGGAT5' | 7 |
| Compound 203 | 3'CCATGTTGATCTGCTAGCTGTCATC5' | 8 |
| Compound 204 | 3'GCGTTGCTTTTTTTTTTTCGCGCG5' | 9 |
| Compound 205 | 3'CAGTGCAGTATCGACGGACTAGGAT5' | 7 |
| Compound 206 | 3'CAGTGCAGTATCGACGGACTAGGAT5' | 7 |
| Compound 207 | 3'CAGTGCAGTATCGACGGACTAGGAT5' | 7 |
| ODN-3 | 5'GTCACGTCATAGCTGCCTGATCCTA3' | 10 |

Bacterial Strains and Growth Conditions

E. coli K-12 strain KRX (Promega) was used for protein expression. Transformed bacteria with the different OmpC constructs (OmpC or His-OmpC) were cultured to saturation in LB medium supplemented with 100 g/ml of ampicillin at 30° C. 40 µl of the pre-cultured cells were then diluted into 4 ml of fresh LB medium supplemented with ampicillin and incubated until the OD$_{600}$ reaches ~0.6. Protein expression was then induced by the addition of 0.1% Rhamnose and 20 M isopropyl-b-D-1-thiogalactopyranoside (IPTG) and cultures were allowed to grow at 30° C. for 18 h.

General Procedure for Decorating Bacteria with the Oligonucleotides

The bacterial cells (OmpC or His-OmpC) were collected by centrifugation at 6000 g for 4 min. The pellet was washed twice with PBS x 1 buffer and resuspended in the same buffer to an OD$_{600}$ of 0.3. To a 100 µl sample of the bacteria suspension, a preincubated sample of DNA (500 nM) and NiCl$_2$ (2.5 M) was added, and the cells were incubated at room temperature for 1 h. Then the bacterial sample were washed twice with PBS, resuspended in 100 µl PBS and placed on a glass-bottom dish (P35G-1.5-14-C; MatTek) precoated with poly-l-lysine (Sigma Aldrich) and left to adhere for 1 h. Finally, the wells were washed vigorously with PBS three times and imaged using an Olympus IX51 fluorescent microscope. The samples were imaged using 60× or 100× objective lenses.

Treatment of the Modified Bacteria with EDTA

Bacterial samples decorated with Compound 100 were incubated with various concentration of EDTA (0, 5, 10 mM) for 1 h. Cells were then collected (6,000 g, 4 min) and washed twice with 200 µl PBS buffer. Cells were resuspended in 100 µl PBS buffer and added to poly-l-lysine-coated slides for imaging.

Flow Cytometry

Bacteria were decorated with Compound 101 according to the procedure described above. The samples were analyzed using BD FACS Aria Fusion instrument (BD Biosciences, San Jose, CA, USA) equipped with 488 nm (blue), 561 nm (green), and 640 nm (red) lasers. Sorting was performed using a 100-μm nozzle equipped with BD FACS Diva software v8.0.1 (BD Biosciences). Data was analyzed using FlowJo software.

Bacterial Cell Growth

His-OmpC bacteria decorated with Compound 101 was incubated for 30 min in M9 minimal medium containing 2% glucose. The sample was spun down at 6,000 g for 2 min and the supernatant was discarded. After washing the pellet with M9 minimal medium, the cells were diluted to $OD_{600}$=0.05 in M9 medium in a 96-well plate. Growth kinetics was monitored by recording $OD_{600}$ under shaking at 30° C. for 24 h. Bacteria expressing His-OmpC was used as a control. The ability of the modified His-tagged bacteria to grow and divide was also demonstrated using fluorescence microscopy. For these experiments, the bacteria were prepared using a similar procedure. After diluting the sample to $OD_{600}$=0.3, it was allowed to grow at 30° C. 100 μl samples were withdrawn at different time intervals and plated on poly-l-lysine-coated glass bottom dishes and imaged by fluorescent microscopy.

Introducing Posttranslational Modifications' to the Bacteria

Bacterial cells were decorated with ODN-1 according to the procedure described above. After washing the sample with PBS, the following ODNs were added sequentially: Compound 200, ODN-3, Compound 201, ODN-3, Compound 202, and ODN-3. After each incubation step, cells were washed twice with PBS and a sample was taken for imaging before the addition of the subsequent strand. Fluorescently labeled ODN-2 strands were added at a concentration of 500 nM and incubated for 30 min, while ODN-3 strand was added at a concentration of 2 μM and incubated for 2 h.

Mixed Population of Bacteria

Three samples of His-OmpC bacteria (100 μl each) were separately labeled with Compound 102, Compound 103, or Compound 104. Each sample was washed twice with PBS. Then, an equal ratio (30 μl each) of the three samples were combined and Compound 202, Compound 203 and Compound 204 (500 nM) were added to the mixture and incubated for 10 min. The bacterial cells were centrifuged at 6,000 g for 2 min, washed twice with PBS and imaged by fluorescent microscopy using 488, 561, and 647 nm excitation lasers and 488/50, 610/60, and 685/50 emission filters. For flow cytometry analysis, the samples were not washed after addition of ODN-2 strands.

Bacteria-Streptavidin Interaction

His-tagged bacterial cells were decorated with a duplex consisting of ODN-1 and Compound 205 duplex according to a similar procedure described above. For binding with streptavidin, cells were incubated with Alexa-647 streptavidin conjugate (500 nM) in PBS x 1 for 1 h, and after washing twice with PBS were imaged by fluorescent microscopy. The fluorescent signal was abolished when bacterial cells were treated with ODN-3 (3 M) for 1 h. The control experiment was performed similarly using bacteria decorated with a duplex containing ODN-1 and the complementary strand.

Bacteria-KB Cell Interaction

KB cells were maintained in folate-depleted RPMI supplemented with 10% fetal bovine serum (FBS), 1% L-glutamine, and 1% penicillin/streptomycin. Cells (12,500 cells/well) were seeded onto glass bottom culture dishes (Mattek) and allowed to adhere overnight. Cells were then washed twice with PBS and incubated with 100 μl His-tagged bacteria decorated with ODN-1: Compound 206 duplex for 30 min. The medium was removed and cells were rinsed three times with PBS. Cells were then imaged using a fluorescence microscope and a 60× objective lens. A control experiment was performed similarly using bacteria decorated with a duplex lacking the folate moiety (ODN-1 and ODN-iii). To show the reversibility of interaction, the bacteria bound KB cells were incubated with ODN-3 (5 M) for 15 min. After washing twice with PBS buffer, cells were imaged again.

Adhesion to the Solid Support

The gold substrates were prepared by electron-beam evaporation of an adhesion layer of chromium (3 nm), followed by a 20 nm layer of gold (99.99% purity) onto high precision cover glasses (170±5 μm, Marienfeld-Superior, Germany). A solution of (11-mercaptoundecyl)tetra(ethylene glycol)[9] (2 mM in ethanol) were added to the gold coated substrates and incubated for 2 h. After removing the solution, the slides were washed four times with ethanol. Bacteria samples decorated with a duplex consisting of Compound 102 and Compound 207 were washed twice with PBS, resuspended in 100 μl phosphate buffer (pH=3.8), and then incubated on gold surfaces for 15 min. The solution containing bacteria was removed, and the slides were rinsed three times with PBS, and twice with water. Finally, they were imaged using an Olympus IX51 microscope.

Super-Resolution Microscopy

Super-resolution images were collected on a Vutara SR200 STORM (Bruker) microscope based on the single-molecule localization biplane technology. His-tagged bacteria was decorated with ODN-1:Compound 201 duplex according to the procedure described in above. The bacteria were imaged using 647 nm excitation laser and 405 nm activation laser in an imaging buffer composed of 5 mM cysteamine, oxygen scavengers (7 M glucose oxidase and 56 nM catalase) in 50 mM Tris, 10 mM NaCl and 10% glucose at pH 8.0. Images were recorded using a 60×NA 1.2 water immersion objective (Olympus) and Evolve 512 EMCCD camera (Photometrics) with gain set at 50, frame rate at 50 Hz, and maximal power of 647 and 405 nm lasers set at 6 and 0.05 $kW/cm^2$, respectively. Total number of frames acquired was 8000. Data was analyzed by the Vutara SRX software.

Example 14

Design Principles of a Dynamic Artificial Receptor System

Objective: To produce an artificial receptor fulfilling the following requirements: (1) the artificial receptor is easily modifiable by molecular signals in their environment, (2) the artificial receptor is capable of attaching different bioactive molecules, labeling molecules, and synthetic agents, (3) the artificial receptor does not perturb desirable cell functions, (4) the artificial receptor can be reversibly modified.

Figure 32A:
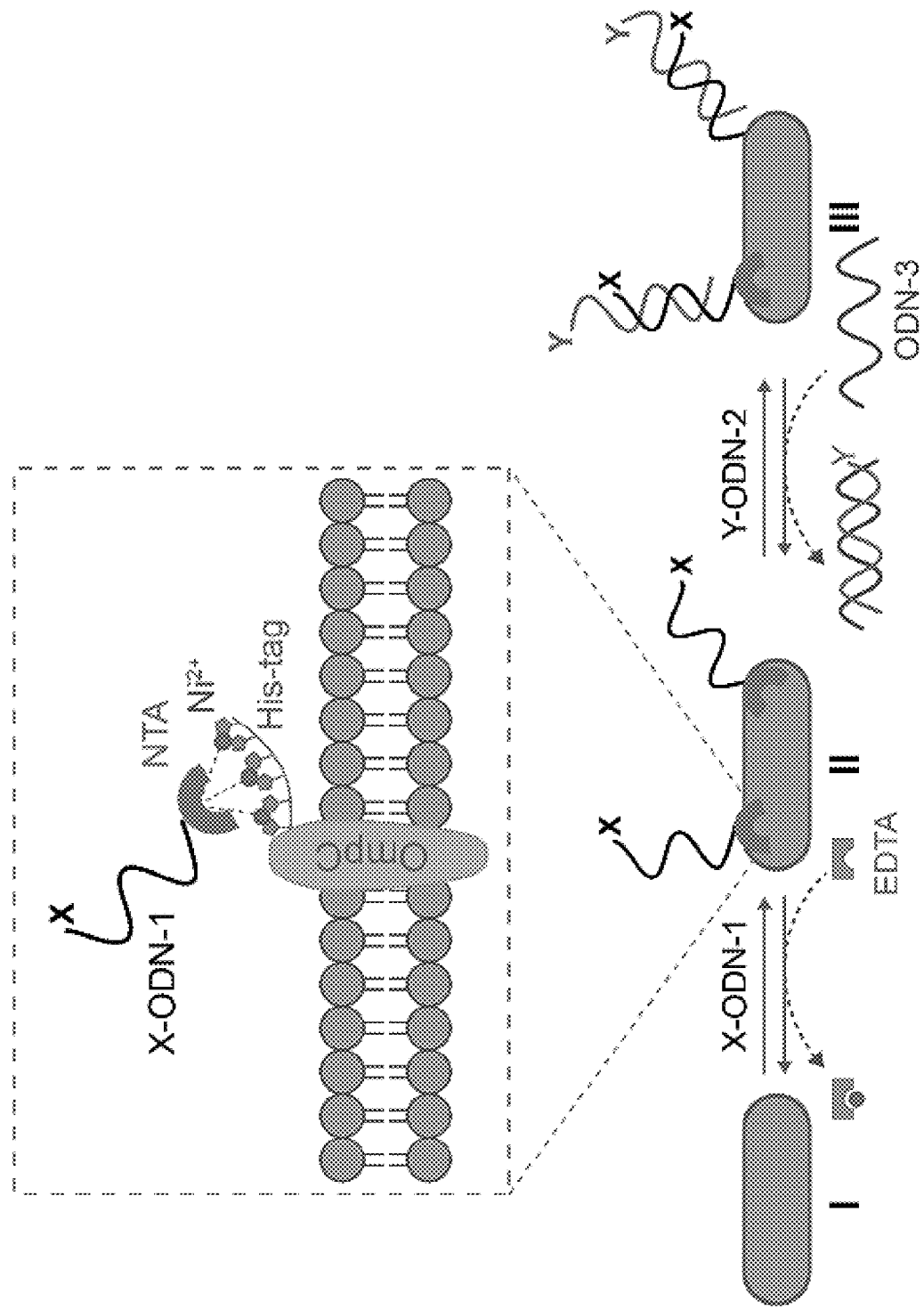
FIGS. 32A-32B show the design of an artificial receptors system.

FIG. 32A shows the design and operation principles of an embodiment of the synthetic receptor system presented herein. The system comprises: A first polypeptide, said polypeptide comprising a membranal anchoring domain and an extracellular binding domain. In the examples shown herein, the membranal anchoring domain used is outer membrane protein C (OmpC) and the extracellular binding domain is hexa-histidine tag (His-tag). The first compound is sometimes termed His-OmpC in the Examples.

Figure 32B:
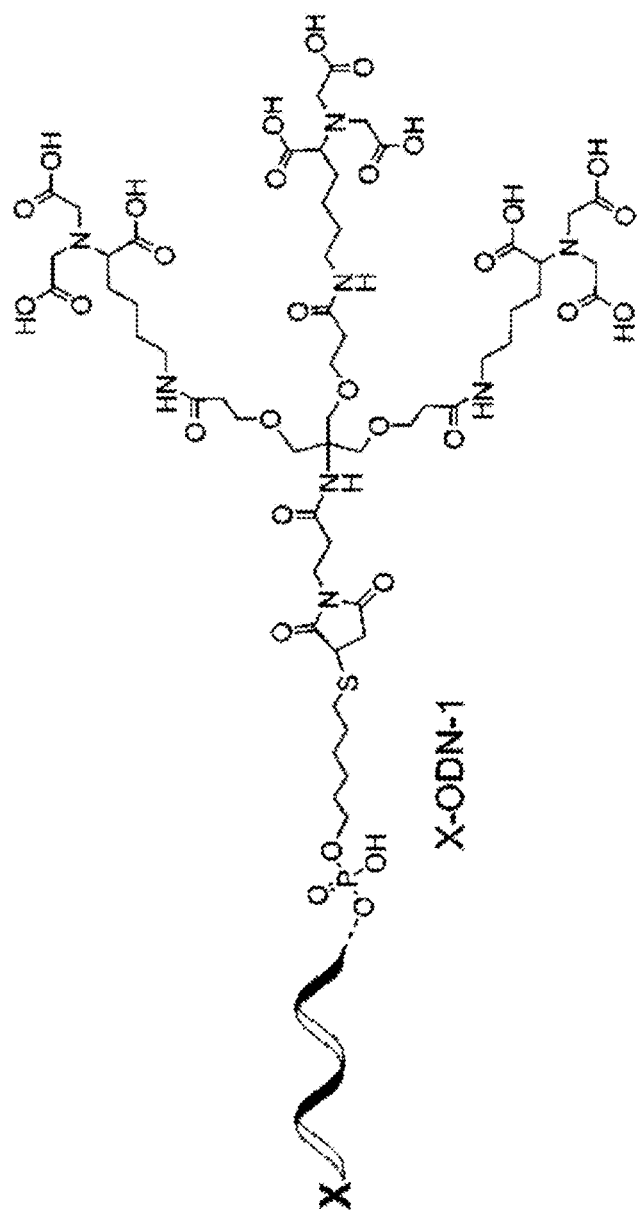

The first compound, comprises a first oligonucleotide (ODN-1) bound to a binder, said binder comprises affinity to said extracellular binding domain. The first compound is sometimes termed X-ODN-1 in the Examples, wherein ODN-1 denotes the first oligonucleotide, and X denotes an optional labeling moiety. In the examples shown herein, the binder is a three nitrilo acetic acid (Tri-NTA) conjugate, which binds His-tag. FIG. 32B shows an embodiment of X-ODN-1.

The second compound comprises a second oligonucleotide (ODN-2) bound to a synthetic agent on its end. The second compound is sometimes termed Y-ODN-2 in the Examples, wherein ODN-2 denotes the second oligonucleotide, and Y denotes the synthetic agent on its end. The oligonucleotide ODN-2 is complementary to the first oligonucleotide ODN-1. However, Y-ODN-2 bears also a short overhang region, termed a toe-hold region. Such toe-hold region can be used to initiate strand displacement and detachment of Y-ODN-2 from X-ODN-1 by an oligonucleotide complementary to the whole ODN-2 oligonucleotide.

The system optionally comprises a third compound, comprising a third oligonucleotide (ODN-3).

The oligonucleotide ODN-3 is complementary to the whole ODN-2 sequence, i.e., both to the toe-hold region and to the region bound to ODN-1. Cells can be optionally incubated with ODN-3, which produces strand displacement. In a first step, ODN-3 binds to Y-ODN-2 toe hold region. In a second step, ODN-3 competes with ODN-1 for binding with ODN-2, until eventually it detaches Y-ODN-2 from X-ODN-1.

The artificial receptor system described above was used for decorating a cell surface according to at least two approaches. In the first approach, cells expressing His-OmpC were incubated with X-ODN-1 in the presence of Ni (II) (FIG. 1, steps I and II). X-ODN-1 was efficiently bound to His-OmpC in such conditions. The effect of the synthetic agent was terminated by detaching X-ODN-1 from His-OmpC, for example by incubating the cells with a Ni (II) chelator as EDTA.

In the second approach, cells expressing His-OmpC were first incubated with X-ODN-1 in the presence of Ni (II) (FIG. 1, steps I and II). Then, cells were incubated with Y-ODN-2, which bound to X-ODN-1 (FIG. 1, steps III). Optionally, addition of ODN-3 terminated the effect of the synthetic agent of Y-ODN-2 (FIG. 1, steps III and II).

The artificial receptor system developed and disclosed herein present a number of advantages. First, the receptors are non-covalently anchored to the cellular membrane. Such non-covalent anchoring allows controlling the number of receptors on the cell membrane and surface by external molecular signals (e.g., X-ODN-1, EDTA, Y-ODN-2, and ODN-3). Second, the anchoring domain of the receptors is stably inserted into the cell membrane, and an extracellular domain can bind different synthetic agents. Thus, different synthetic agents can be bound to the extracellular domain without re-engineering the cells. Third, the anchoring domain has a minimal size and is present only at specific locations on the bacteria membrane. Thus, the anchoring domain does not perturb cellular function. Fourth, the synthetic receptors can be to reversible modified. This allows dynamically altering their structure while they are attached to the bacterial membrane, resembling post-translational modifications that occur on natural receptors.

Example 15

Decorating Bacteria with Artificial Receptors and Controlling the Receptors Functioning Objective: To decorate bacterial membranes with an artificial receptor.

Methods: His-tagged OmpC was expressed in *E. coli*, which was then incubated with an X-ODN-1 appended either with a Cy5 dye or TAMRA (Compounds 100-101) in the presence of nickel ions and EDTA.

Methods and protocols are detailed in Example 1.

Figure 33A:
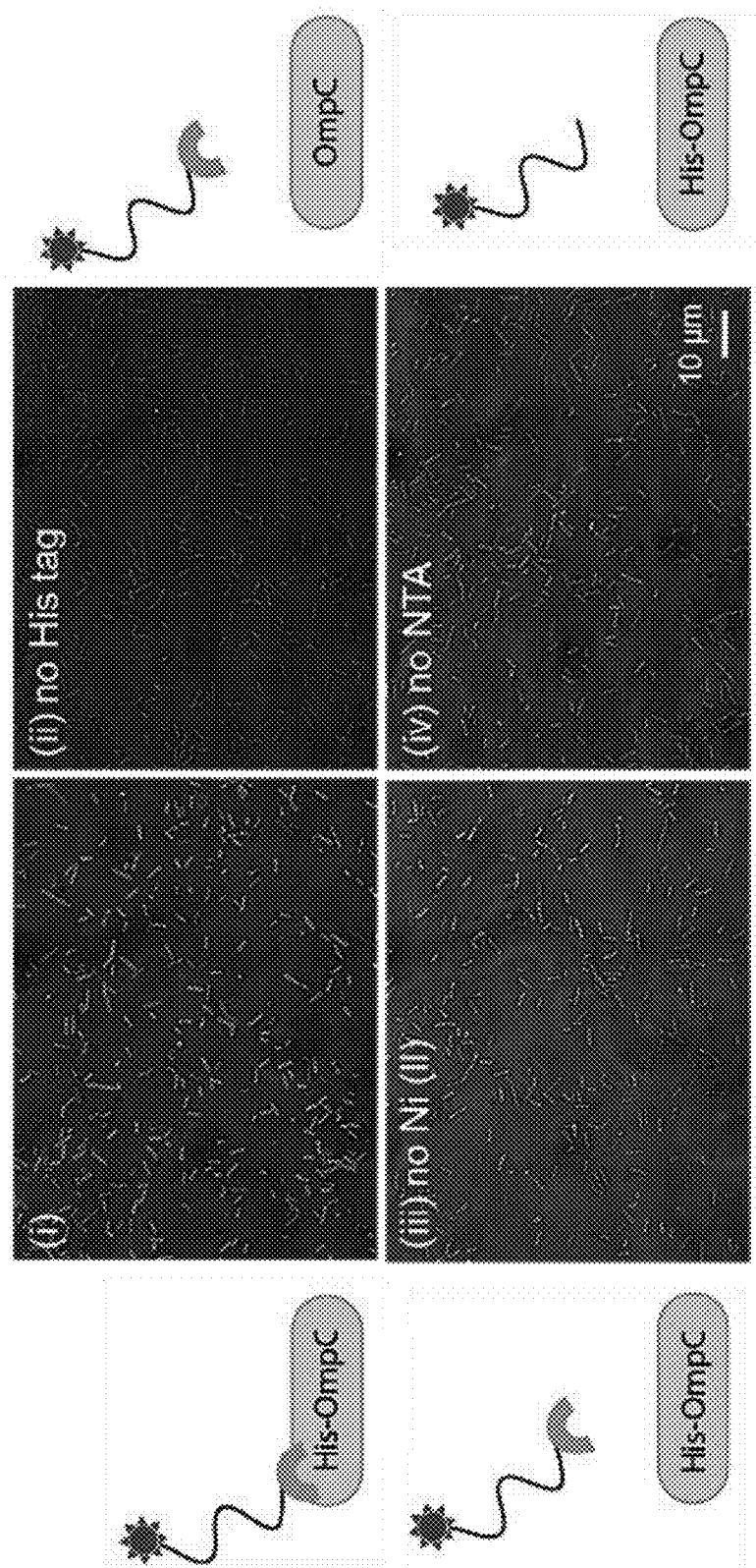
FIGS. 33A-33E show reversible, non-covalent modification of bacterial membrane with a synthetic receptor.

Results: Fluorescence imaging revealed that His-tagged OmpC engineered bacteria incubated with Compound 100 were successfully decorated with the Cy5 fluorophore (FIG. 33A, i). To confirm that the labeling did not result from a non-specific interaction between Compound 100 and the bacteria surface, Compound 100 was also incubated with native bacteria lacking His-OmpC (FIG. 33A, ii), as well as with the His-tagged bacteria in the absence of nickel ions (FIG. 33A, iii). Additionally, His-tagged bacteria was incubated with a Cy5-labeled ODN lacking atri-NTA group (FIG. 33A, iv). No fluorescence was observed in any of these controls, confirming the selectivity of ODN-1 to membrane bound His-tags.

Figure 33B:
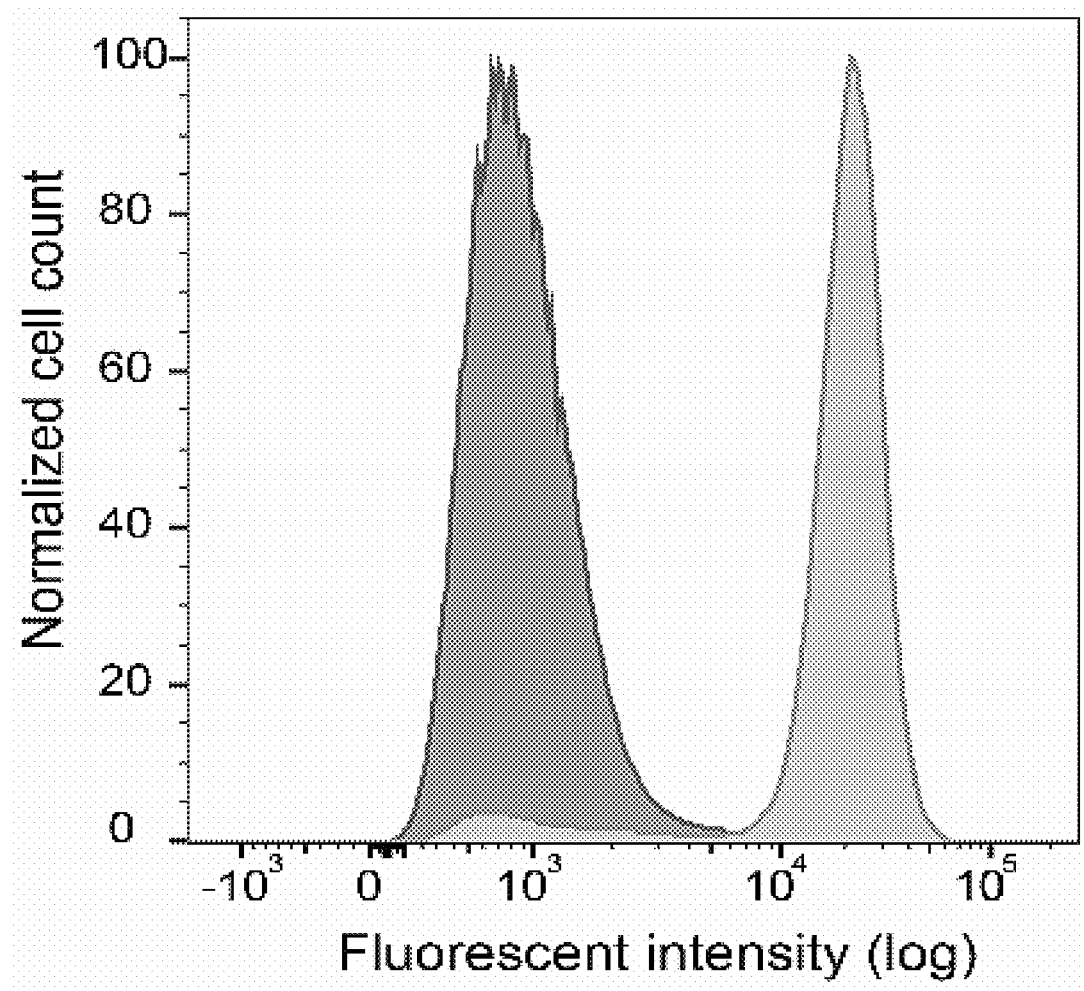

The selectivity and degree of labeling were further analyzed by flow cytometry. 90.9% of His-tagged modified bacteria and 1% of native bacteria were labeled by Cy5 (FIG. 33B).

Figure 33C:

The ability of the system to control the activity levels of the artificial receptors by external signals was further tested. Bacteria were exposed to increased concentrations of EDTA, which resulted in a decrease in surface coverage with Compound 100. 10 mM of EDTA completely removed Compound 100 from the cell surface. Detached Compound 100 could be washed from the medium and bacteria could be re-decorated with other molecules (FIG. 33C).

Figure 33D:
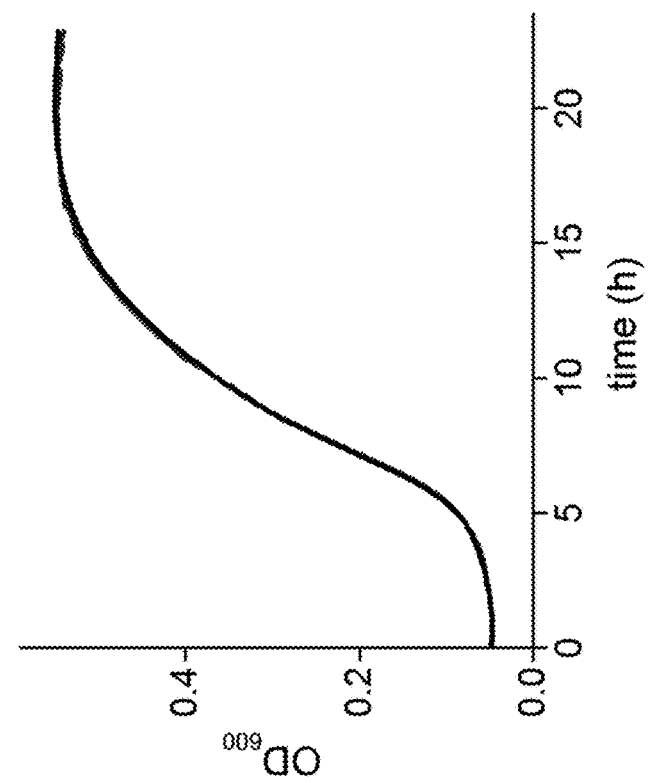

To confirm that attachment of X-ODN-1 does not affect the ability of the bacteria to grow and divide, the growth of TAMRA-ODN-1 (Compound 101) decorated bacteria was measured by optical density (OD) and compared to that of bare His-tagged bacteria. The growth kinetic curves were not affected by Compound 101 binding (FIG. 33D) indicating that the biomimetic cellular surface protein system does not affect cell division and survival.

Figure 33E:
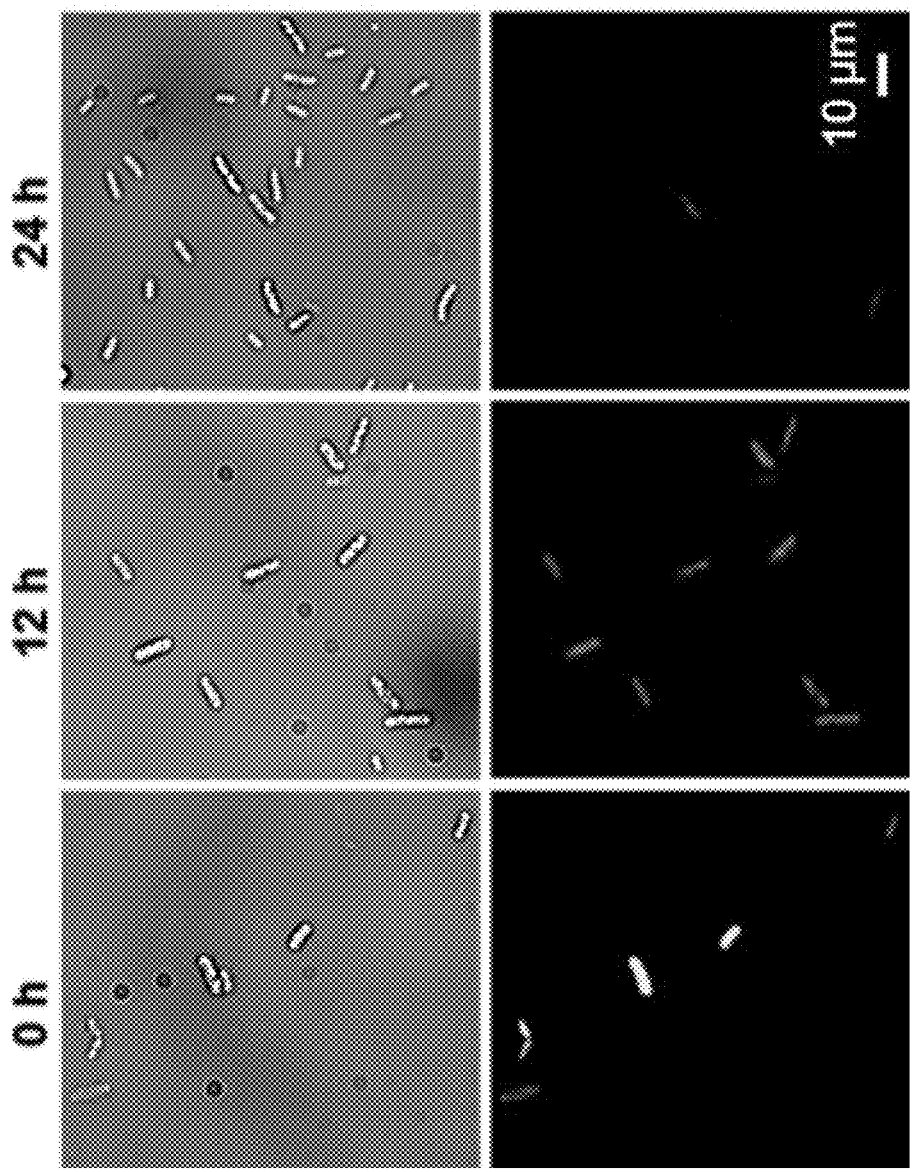

The ability of Compound 101 decorated bacteria to grow and divide was further demonstrated using fluorescence microscopy. Fluorescence microscopy revealed that the number of Compound 101 labeled cells increased with time, but that the fluorescence recorded in each cell decreased (FIG. 33E). These results were interpreted as a consequence of the Compound 101 molecules being divided between the daughter cells in each division.

Example 16

Reversible Modification of Membrane-Bound Synthetic Receptors Using Complementary Strands Objective: To reversibly modify the synthetic receptors by external molecules.

Figure 34A:
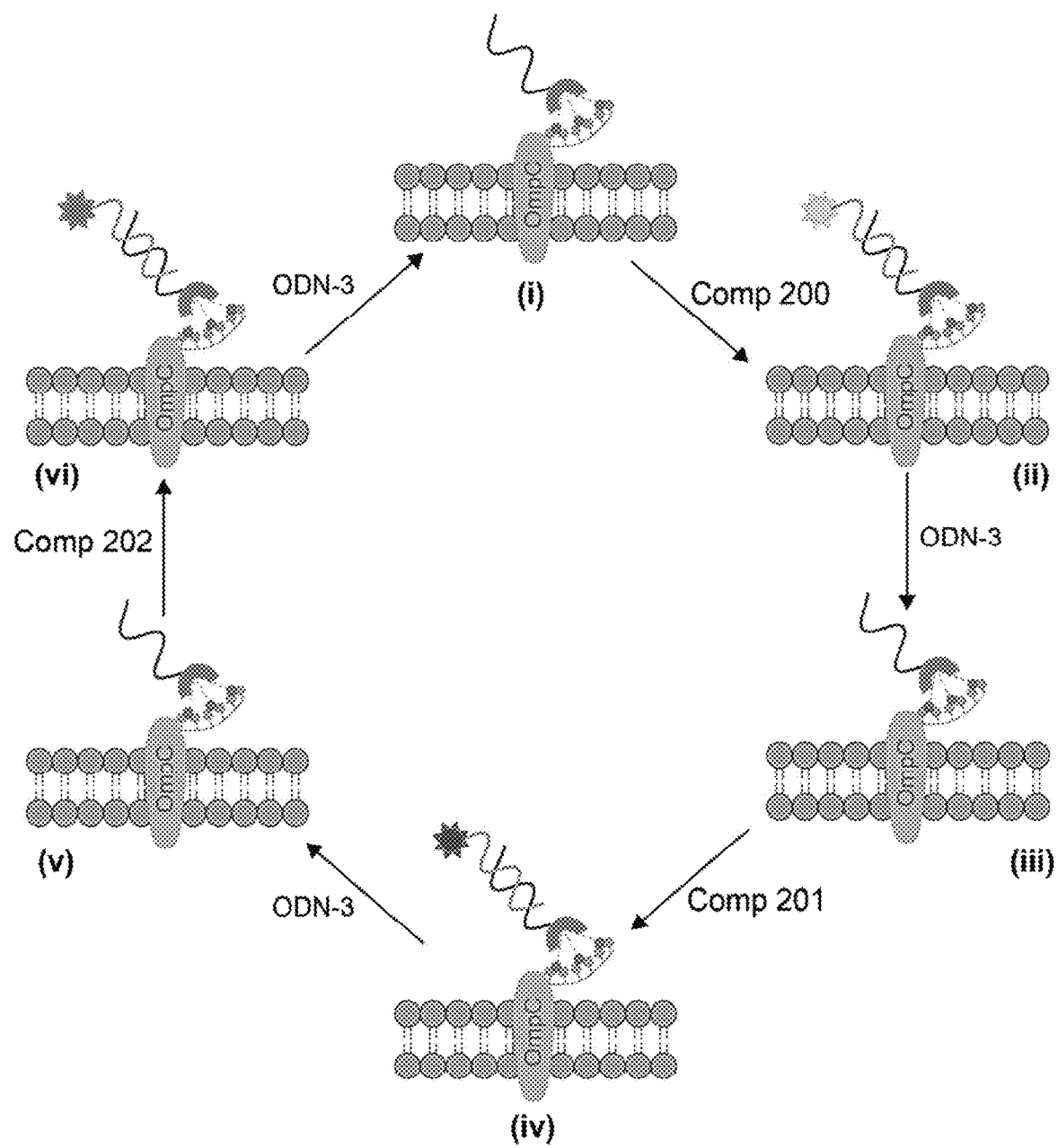
FIGS. 34A-34B show the reversible modification of membrane-bound synthetic receptor using complementary strands.

Methods: FIG. 34A schematically illustrates the experiments detailed herein. *E. Coli* ectopically expressing His-OmpC were first incubated with oligonucleotide X-ODN-1 (FIG. 34A, step (i)). Afterwards cells were incubated with a Compound 200, wherein ODN-2 is an oligonucleotide complementary to ODN-1 (FIG. 34A, step (ii)). Cells were then incubated with an ODN-3 oligonucleotide complementary to ODN-2 (FIG. 34A, step (iii)). Then cells were incubated with a Compound 201 (FIG. 34A, step (iv)). Next, cells were again incubated with an ODN-3 oligonucleotide (FIG. 34A, step (v)). Cells were finally incubated with a Compound 202 (FIG. 34A, step (vi)). Fluorescence was measured in all steps assessing the binding of TAMRA, Cy5, and FAM to the cell membranes.

Figure 34B:
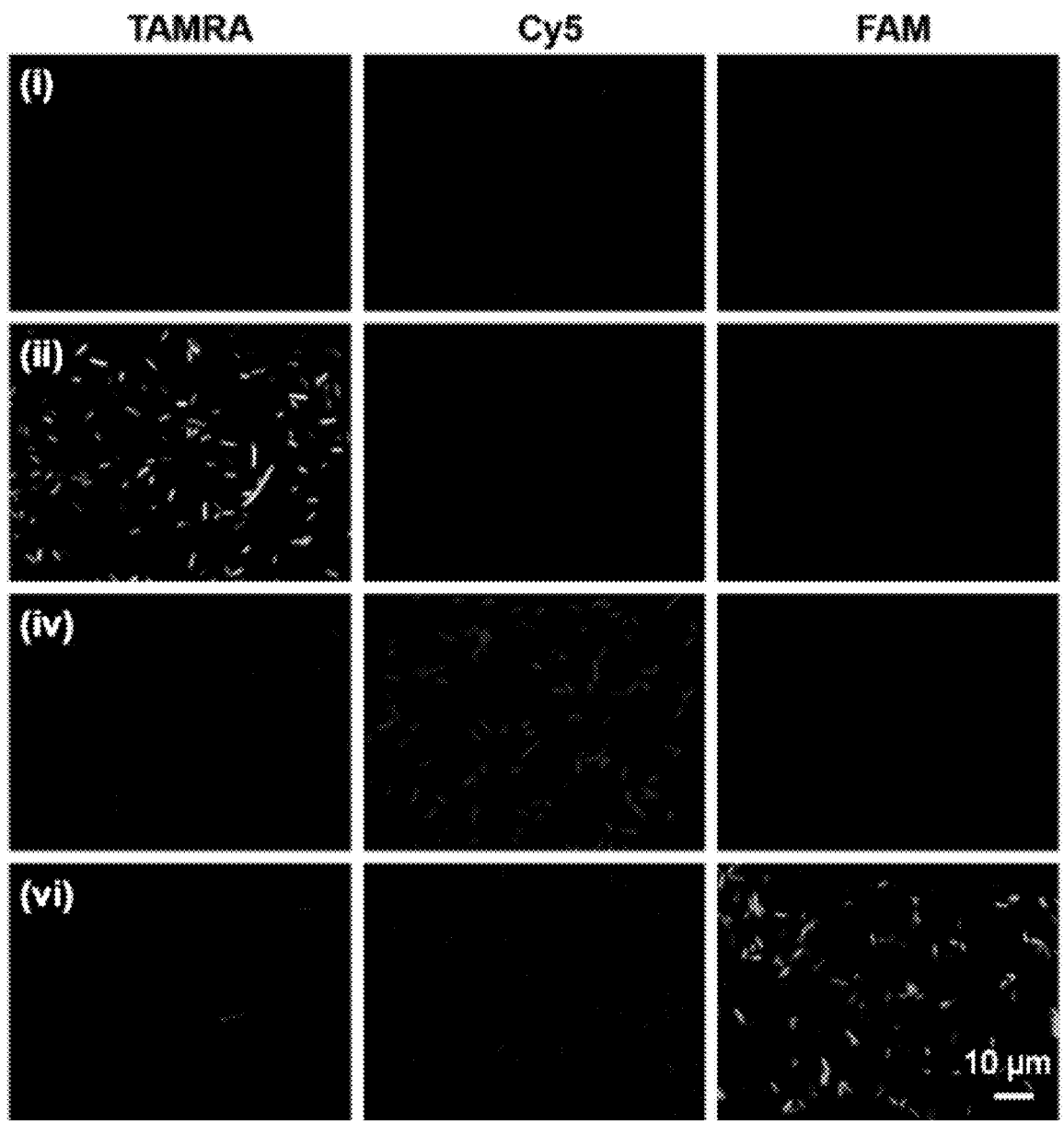

Results: Fluorescence microscopy revealed the presence of the corresponding dye (TAMRA, Cy5, and FAM) after bacteria were incubated with it. Further, the fluorescent emission disappeared after each time bacteria were incubated ODN-3 (FIG. 34B).

Example 17

Decorating Populations of Heterogenous Bacteria with Different Artificial Receptors Objective: To create a mixed population of bacteria, where each subpopulation bears a different sequences of ODN-1 and is modified by a different X-ODN-2 molecule.

Figure 35A:
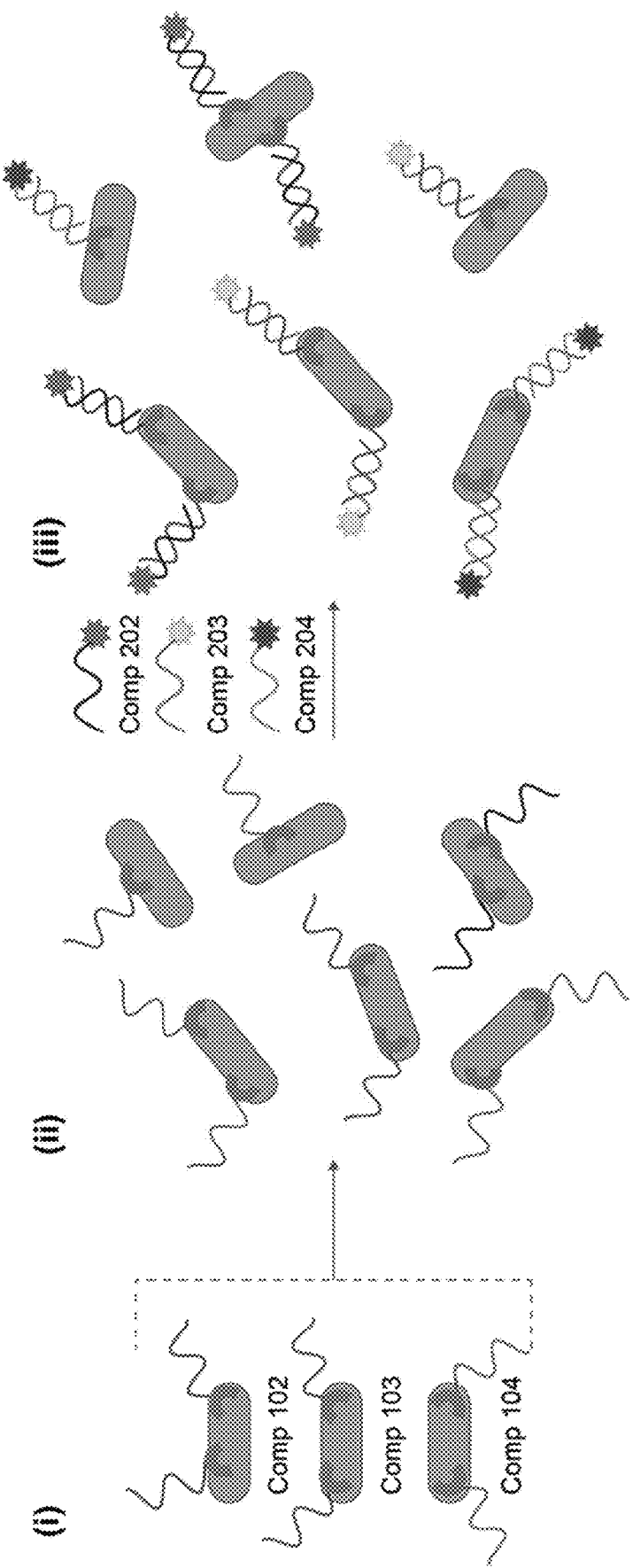
FIGS. 35A-35D show experimental modifications of bacterial cell surface luminescence.

Methods: Three populations of His-tagged *E. coli* were incubated with three different types of ODN-1 (Compound 102, Compound 103, and Compound 104; Compound 102, 103 and 104 respectively), which bared the same tri-NTA types but differed in their oligonucleotide sequences. Then, the three samples were combined and incubated with a mixture of three types of dye-labeled ODN-2 (Compound 202, Compound 200, and Compound 201 respectively); each of which was complementary to only one of the bacteria-bound ODN-1s (FIG. 35A). Bacteria were then analyzed by fluorescent microscopy and FACS.

Figure 35B:
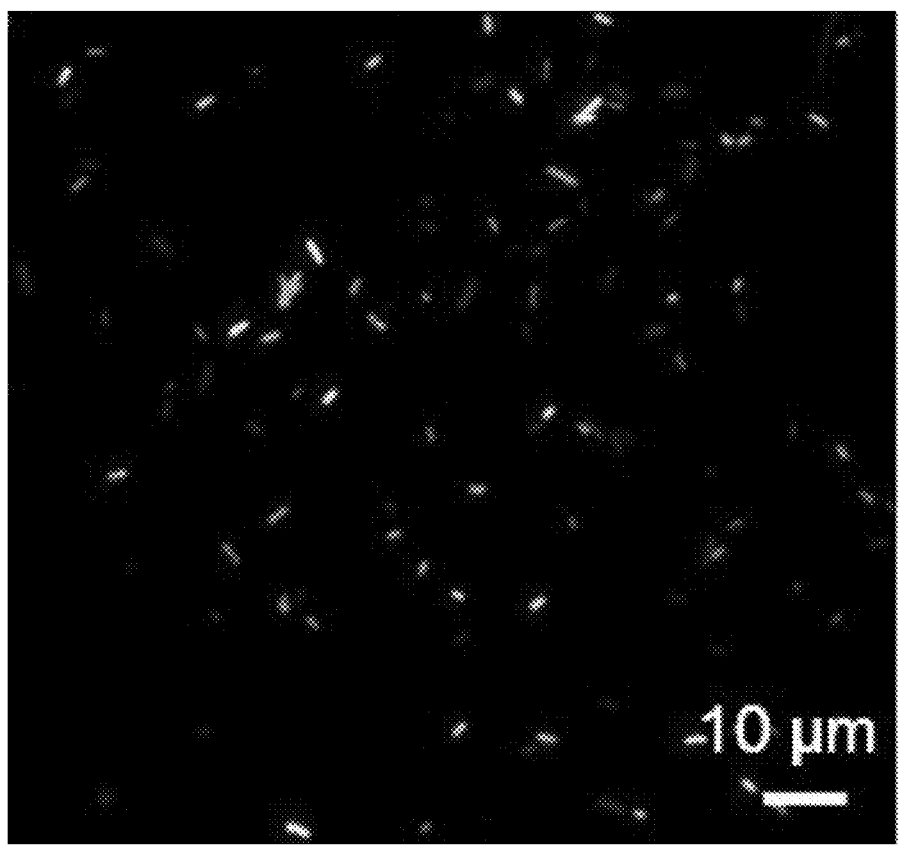
Figure 35C:
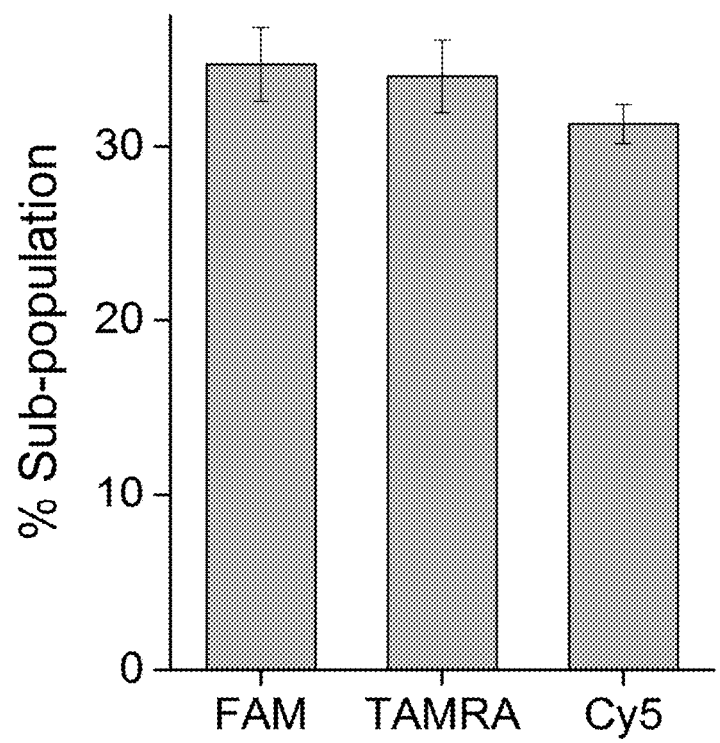
Figure 35D:
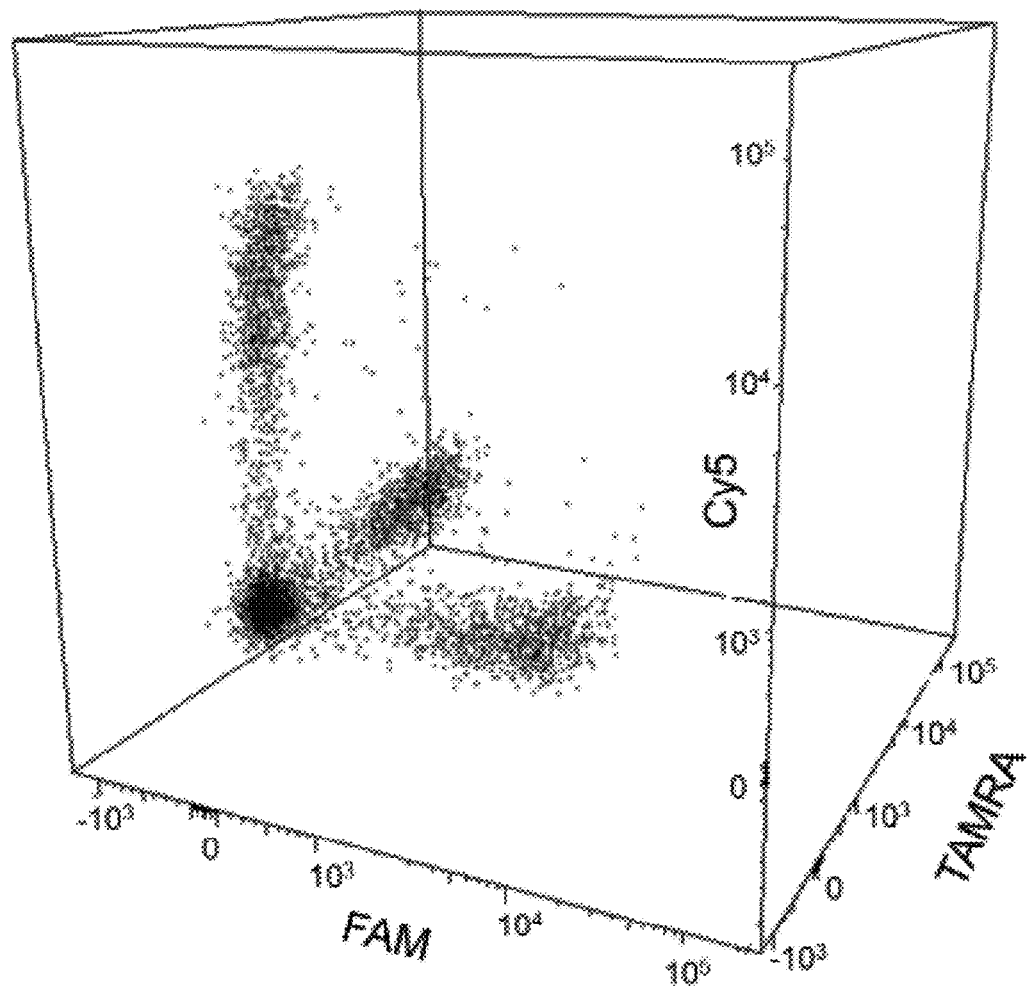

Results: Fluorescence microscopy (FIG. 35B) and FACS analysis (FIG. 35C) revealed the presence of three distinct groups of bacteria, each labeled with only one dye. Calculating the percentage of each population out of the total number of bacteria revealed a 1:1:1 ratio between the three sub-populations. (FIG. 35D) indicating that there is no strand swap between the three populations and that the sub-population modification occurs with very high selectivity.

Discussion: This experiment demonstrates a means to selectively label His-tagged proteins with different colors. Hence, one practical application that can be achieved with this approach is using the synthetic receptors to image specific proteins or cellular compartments in living cells. The advantage of using this method, over using other fluorescent probes that can bind and label short fusion peptides in living cells is the simplicity by which the fluorescent dye can be changed. Specifically, when DNA duplex-based fluorescent probes are used for live cell imaging there is no need to synthetize a new probe for each application. Instead, various different fluorescent dyes can be used for imaging, simply by preparing a wide range of fluorescently labeled ODN-2s from commercially available phosphoramidites and by using an automated DNA synthesizer.

Example 18

Endowment of New Properties to Bacteria by Artificial Receptors

Objective: To endow bacteria with unnatural and potentially useful properties by using the artificial receptor system.

Figures 36A, 36B, 36C:
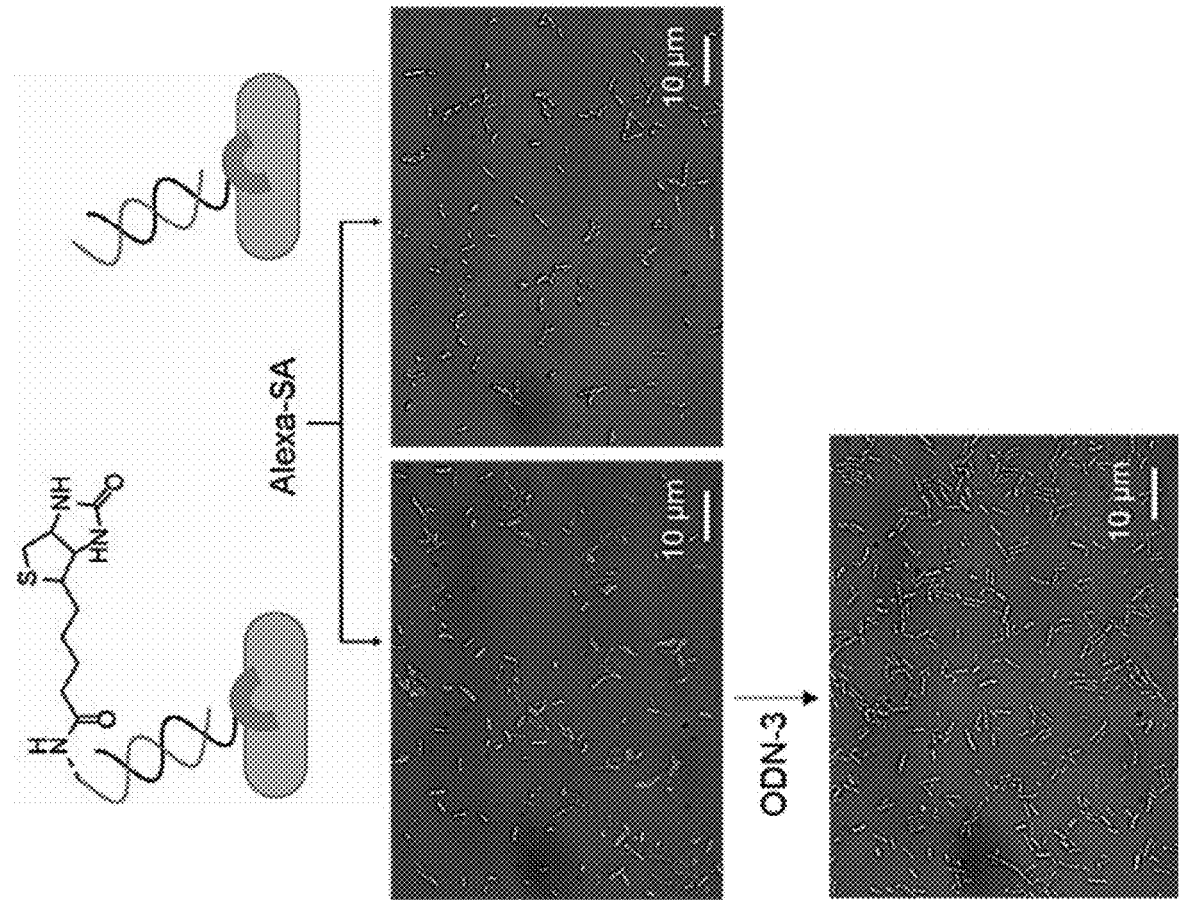
FIGS. 36A-36G show bacteria decorated to interact with proteins and cancer cells.

Methods: His-tagged *E. coli* were incubated with an ODN-1 molecule and afterwards with a biotin-ODN-2 molecule (Compound 205). Then, the cells were incubated with an Alexa 647-modified streptavidin (FIG. 36A). To verify specificity, the same experiment was performed with an ODN-2 molecule lacking biotin (FIG. 36A). Cells were then incubated with ODN-3 to detach ODN-2 from the cell membranes.

Results: Fluorescent microscopy revealed that bacteria became fluorescent only when Compound 205 was incorporated in the synthetic receptor (FIG. 36B), indicating specific binding of the protein to the bacterial membrane. The fluorescent signal disappeared when ODN-3 was added (FIG. 36C), indicating the reversibility of this process, and suggesting the possibility of regulating unnatural cell-protein-interactions using synthetic molecular signals as Compound 205 and ODN-3.

Example 19

Induction of Unnatural Cell-Cell Interactions by Artificial Receptors

Objective: To test whether synthetic receptor-protein interactions can mediate unnatural cell-cell interactions in general, and interactions resembling bacterial-mammalian cell interactions in particular.

Figures 36D, 36E, 36F:
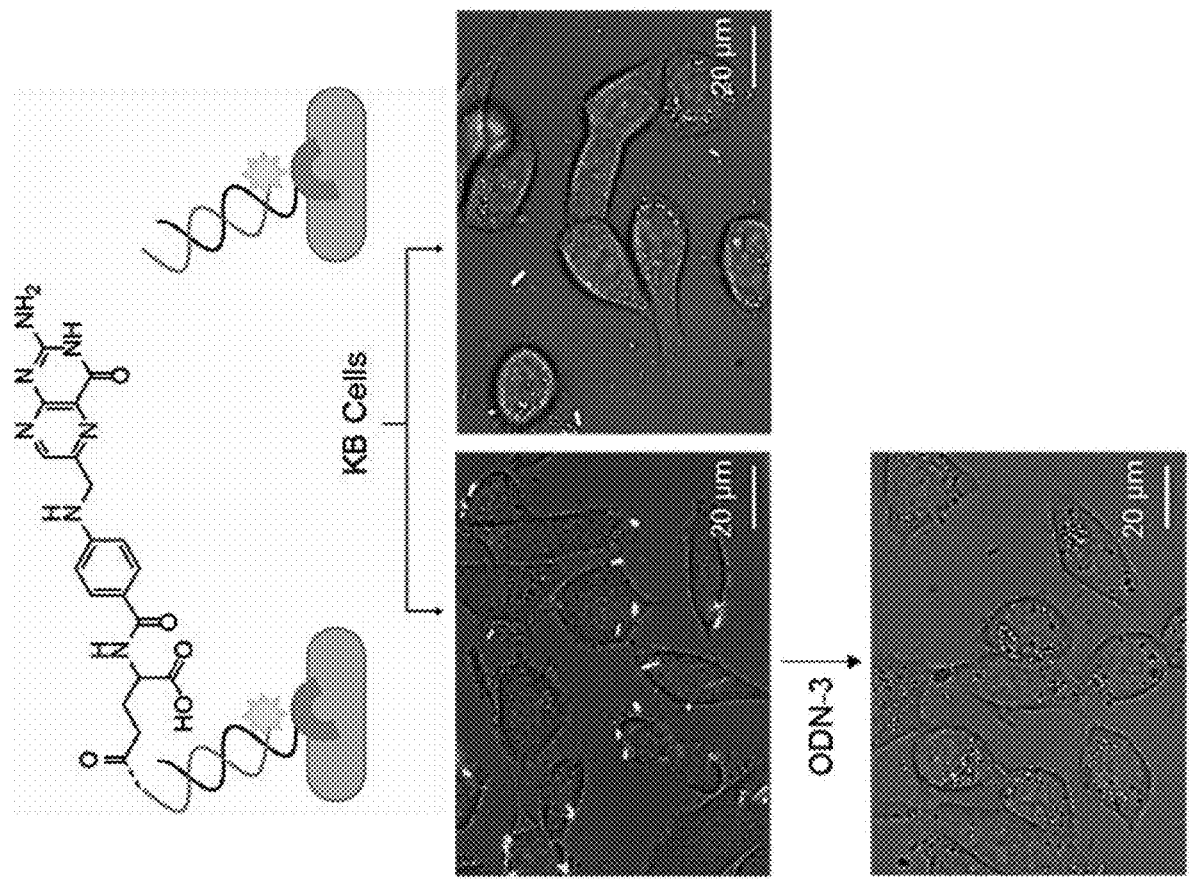

Methods: His-tagged bacteria were decorated with a DNA duplex containing Compound 101 and a folate-modified ODN-2 (compound 206). Then, bacteria were incubated with human epidermoid carcinoma KB cells overexpressing an extracellular folate receptor (FIG. 36D). As a control, KB cells were incubated with bacteria decorated with a similar TAMRA-labeled DNA duplex lacking the folate group (FIG. 36D). Cells were then incubated with ODN-3 to detach compound 206 from bacteria membranes.

Results: Fluorescent imaging revealed KB cells were labeled with glowing bacteria when incubated with compound 206 bound bacteria, but not with control bacteria (FIG. 36E). Incubation with ODN-3 fully detached compound 206 from the bacteria, thus releasing the bacteria from the KB cells (FIG. 36F).

Figure 36G:
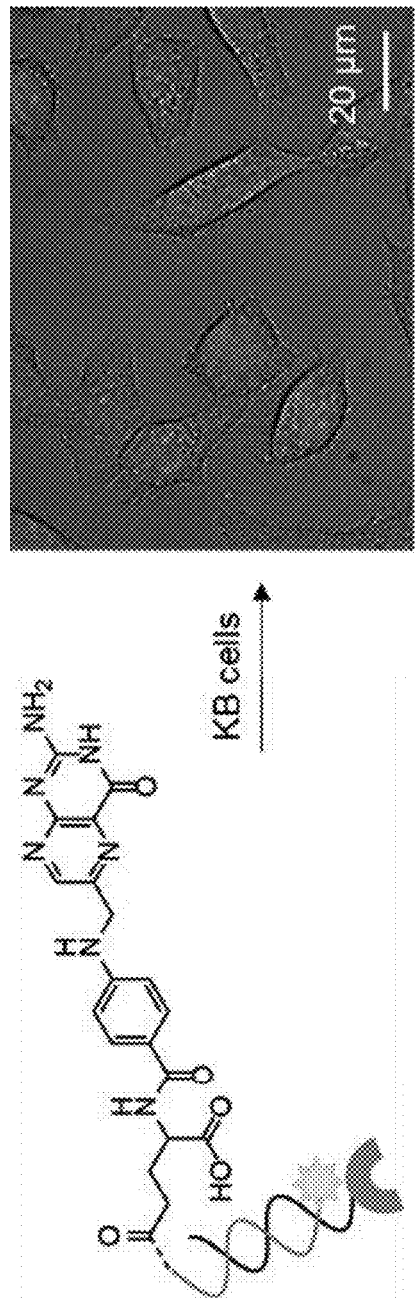

Incubation of KB cells with the DNA duplex alone (without His-tagged bacteria) did not result in fluorescent cancer cell labeling (FIG. 36G). This observation indicates that the bacteria scaffold itself plays a critical role in the interaction of folate with the folate receptor. One contribution of the bacteria to effective cell labeling is an increased avidity, which results from multivalent interactions between natural folate receptors on the KB cell and the folate-modified DNA duplexes on the surface of *E. Coli*. The second contribution is that each bacterial cell is decorated with multiple fluorophores, leading to a bright fluorescent labeling and consequently, to sensitive detection.

Discussion: These experiments provide evidence that unnatural cell-cell interactions can be both induced and disrupted using a biomimetic receptor system that responds to external molecular signals, such as compound 206 and ODN-3, respectively.

These experiments also demonstrate the relevance of this study to cell-based therapy. Here it is shown the ability to program bacterial cells to target cancer cells with increased avidity and selectively, by using synthetic cell-surface receptors to guide therapeutic cells to their targets. Further, the disruption of bacteria-cancer cell interactions with ODN-3 suggests that this approach can be used as an antidote to this class of therapeutics.

Example 20

Induction of Bacterial Adhesion to Abiotic Surfaces by Artificial Receptors

Objective: To test whether synthetic receptor can provide bacteria with the ability to interact selectively with solid substrates.

Figure 37A:
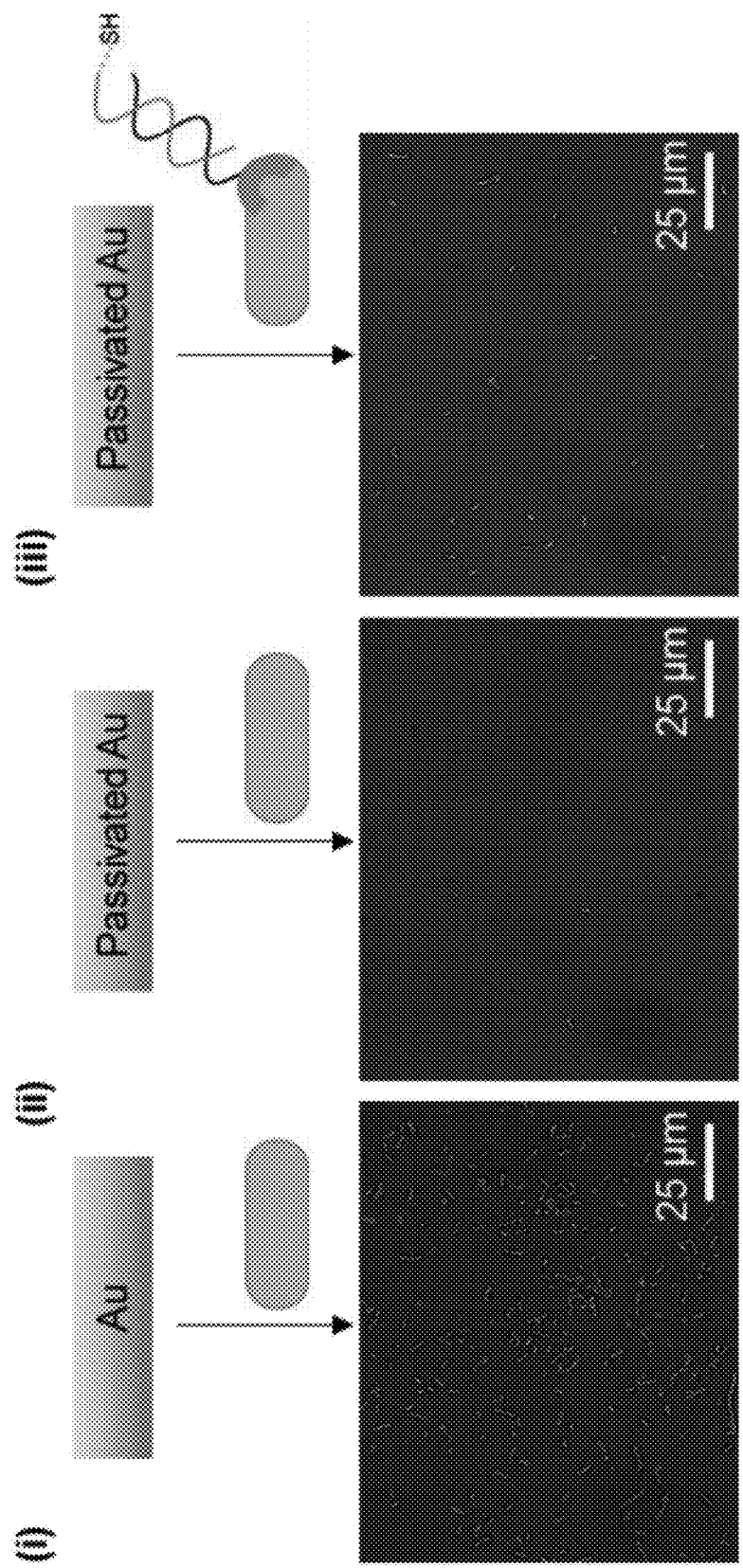
FIGS. 37A-37B show bacteria decorated to interact to a non-biological surface.

Methods: His-tagged bacteria were decorated with a duplex assembled from ODN-1 and HS-ODN-2 (Compound 207), namely, an ODN-2 that is appended with a thiol group. HS is known to have high affinity to gold. In the following step, unmodified His-tagged bacteria and thiol-modified His-tagged bacteria (FIG. 37A) were incubated with a gold substrate that was previously passivated with (11-mercaptoundecyl)tetra(ethylene glycol) to prevent non-specific bacterial adhesion. Gold surfaces were observed after 15 min incubation. Cells were then incubated with ODN-3 to detach Compound 207 from bacteria membranes.

Figure 37B:
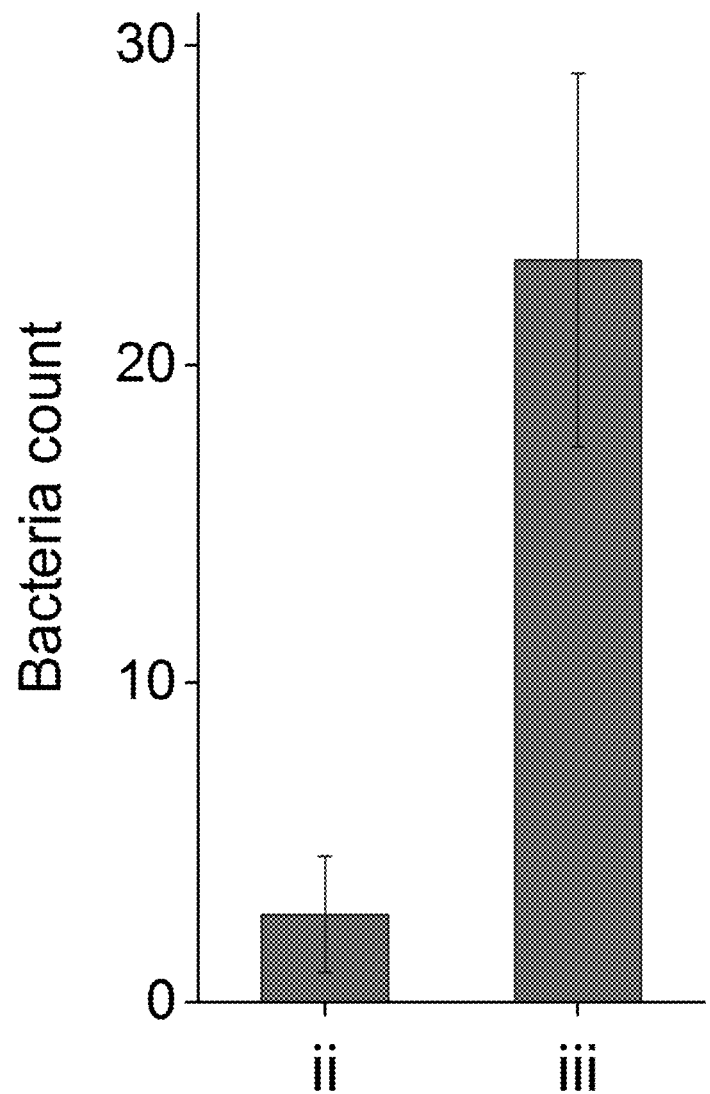

Results: Microscopy revealed an increase of about 8.5-fold in the attachment of thiol-modified bacteria to the gold substrate compared with the control (FIG. 37B). This indicates that the ODN-1:Compound 207 duplex acts as an unnatural adhesin that can mediate specific binding of bacteria to solid support. The selectivity of these synthetic adhesin to gold was further demonstrated by incubating the thiol-modified bacteria with the gold substrate in the presence of ODN-3, which led to a significant decrease in the number of surface-bound His-tagged bacteria.

Discussion: In the context of biomimicry, disruption of adhesion owing to changes that occur on the synthetic receptors resembles the way post-translational modification of natural adhesins are used by bacteria to disrupt adhesion processes. The unnatural adhesins presented herein can be used to have a precise control of the way bacteria are attached to solid supports. For example, changing the length of the DNA linkers or attaching the modified bacteria to more complex DNA architectures (such as DNA Origami/nanotechnology type structures) on the surface may alter the binding properties of the bacteria. Further, the approach presented herein can be used to generate engineered living materials (ELMs) made of controlled bacterial assemblies.

Example 21

Induction of Luminescence in Bacteria by Artificial Receptors

Background: Reversible switching of luminescence in response to the binding of cell surface proteins to extracellular molecular signals is a fundamental property of serval bacterial strains. A key principle underlying natural bacterial luminescence processes is the selective interaction between peptide autoinducers (AI) and their protein receptors, which enables them to trigger the emission of specific bacterial strains in complex biological mixtures. According to this invention, the ability to selectively label specific bacteria (modified with a unique ODN-1) in complex mixtures is described.

Objective: To control bacterial cell luminescence using biomimetic receptor systems (using super resolution microscopy).

Figure 38B:
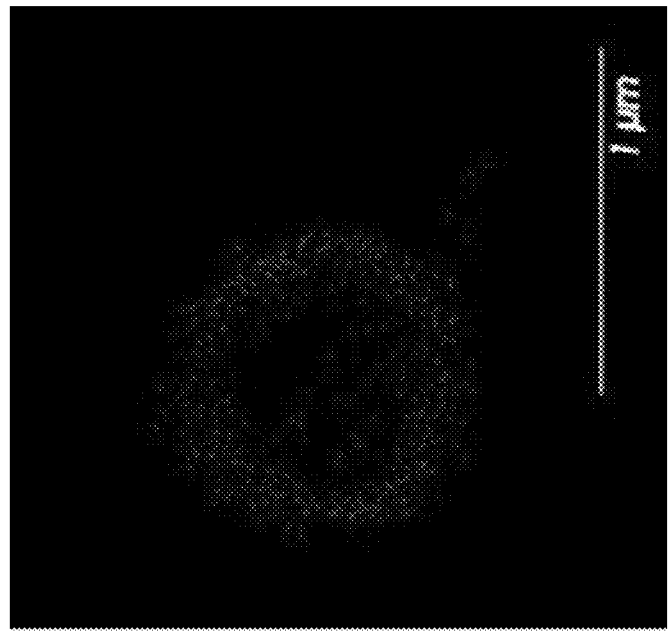
FIGS. 38A-38B show super-resolution images of His-tagged bacteria decorated with an ODN-1:Compound 201 duplex.
Figure 38A:
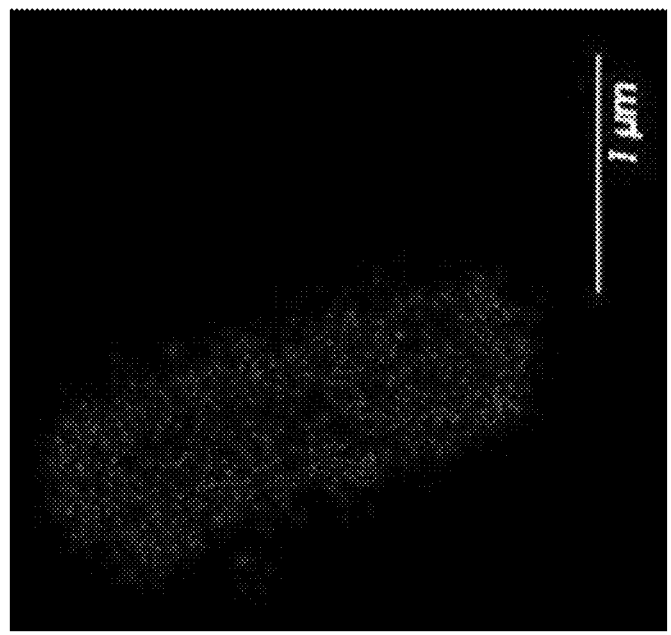

Methods: Due to the small size of bacteria, super resolution (SR) microscopy was used to visualize E. Coli's membrane with super resolution (SR). This was achieved by combining ODN-1 with a commercially available ODN-2 (Cy5-ODN-2; Compound 201) bearing a Cy5 dye, which is compatible with stochastic optical reconstruction microscopy (STORM). SR images of individual bacteria revealed that DNA duplex-based label clearly outlines the bacterial cell's borders (FIG. 38A). Imaging of the transverse cut of the bacteria confirms that only the outer membrane of the bacteria is labeled, namely, that the synthetic receptors are exposed on the bacterial surface and are not internalized (FIG. 38B).

Example 22

Discussion

The Examples disclosed above show a number of unexpected advantages as shown in the following examples: 1) The His-OmpC molecule can be stably expressed in E. coli. 2) The hexa-histidine moiety does not perturb the function of cell or of the synthetic agent due to its small size. 3) The His-tag can be efficiently targeted by NTA-Ni (II) complexes, including complexes of ODN-NTA conjugates. 4) The binding of His-OmpC to X-ODN-1 can be efficiently released by incubating the cells with a Ni (II) chelator, as EDTA. 5) The use of Y-ODN-2 circumvents the complexity of synthesizing the oligonucleotide X-ODN-1 which is attached on one end to the Tri-NTA moiety, and on the other to a synthetic agent. 6) The activity of the synthetic agent of Y-ODN-2 can be effectively terminated by incubating the cells with ODN-3.

The advantages of using ODN-small molecule conjugates as synthetic protein binders include the ability to precisely control the orientation, distances and valency of their binding units, as well as the ability to dynamically change their structure, which provides a means to regulate protein functions in real time. The Examples provided herein show that when synthetic proteins binders of this class are attached to cell's surfaces, their regulatory effect can be extended from the protein level to the cellular level. Specifically, on the cell' membrane such systems can act as artificial cell surface receptors that can be reversibly modified and hence, can provide the cells with 'programmable' properties. In this model system, metal coordination and DNA-hybridization were used to direct the formation of artificial receptors on a short peptide tag fused to an outer membrane protein on the surface of E. coli. Owing to the high selectivity and reversibility of the self-assembly processes, a biomimetic cell surface receptor system with unique features was obtained. For example, the ability to control reversibly the type of membrane-bound receptors and their local concentration levels with external molecular signals demonstrates the possibility of imitating dynamic processes that occur of cell surface proteins, such as changes in their expression level or post-translational modification. It was also shown that these changes can provide the bacteria with new properties such as an ability to glow with different colors, adhere to surfaces, and interact with proteins or cells; properties that may eventually be used in developing cell imaging methods, living materials and devices, or cell-based therapeutics, respectively. In light of these potential applications, the studies presented herein guide the development of additional biomimetic cell surface receptors, with which living cells could be 'programed' to preform diverse sets of functions.

Example 23

Figure 46A:
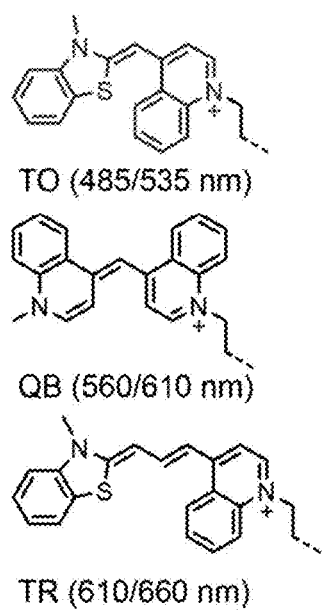
FIG. 46A depicts the structures of the dyes constituting the turn-on fluorescent probes: Thiazole Orange (TO), Quinoline Blue (QB) and Thiazole Red (TR).
Figure 46B:
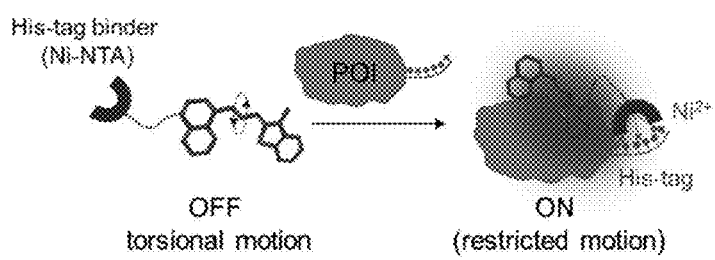
FIG. 46B and FIG. 46C illustrate the general structure of the probes and their mechanism of sensing.
Figure 46C:
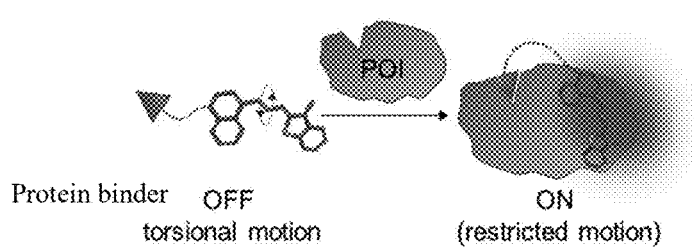

Turn-on Fluorescence Response of Quinoline Based Cyanine Dyes (QBC) Based Probes According to this Invention Turn-on fluorescent probes for protein detection were generated by attaching Thiazole orange (TO), Quinoline blue (QB), and Thiazole red (TR) (FIG. 46A) to a specific protein binder (FIGS. 46B and 46C, green triangle or a horseshoe). Such probes are designed to detect and image engineered proteins (FIG. 46B), namely, proteins modified with a recognition domain for probe binding, or native proteins (FIG. 46C). For example, the probes that were developed (compounds 408-410) can selectively bind the well-known hexa-histidine tag (His-tag, FIG. 46B), which can be fused to any protein. In addition, the probes can also be designed for detection and imaging of native (non-engineered) proteins (FIG. 46C).

This can be achieved by conjugating a quinoline based cyanine dye such as: TO, QB, or TR, to a synthetic agent that is known to bind a specific site on the native POI, for example, an inhibitor that binds an enzyme active site (compounds 401-407). According to the design provided herein, the interaction of the probe's specific binder with the POI promotes the binding of the cyanine dye to the POI's surface, which disrupts the dye's torsional motion and leads to an enhanced emission signal (FIGS. 46B and 46C).

Ten different probes (compounds 401-410) were synthesized and characterized. Probes 408-410 were designed to sense His-tagged labeled proteins, whereas probes 401-406 were designed to sense native (non-engineered) proteins. To generate probes 408-410, TO, QB, and NR were conjugated to a tri-nitriloacetic acid (tri-NTA) unit (His-tag binder according to this invention, as described hereinabove); these probes were shown to bind His-tagged labeled proteins with low nanomolar affinity. Probes 401-406, which were designed to sense glycogen synthase kinase-3 (GSK-3), were generated by attaching TO, QB, and NR to a known GSK-3 inhibitor (i.e., AR-A014418). Probe 407, which integrates QB and a known LDHA inhibitor, was designed to detect lactate dehydrogenase A (LDHA). Additional sensors for LDHA based on TO and NR can similarly be prepared and tested based on the information provided herein for the preparation and analysis of probes 401-407.

Figure 47:
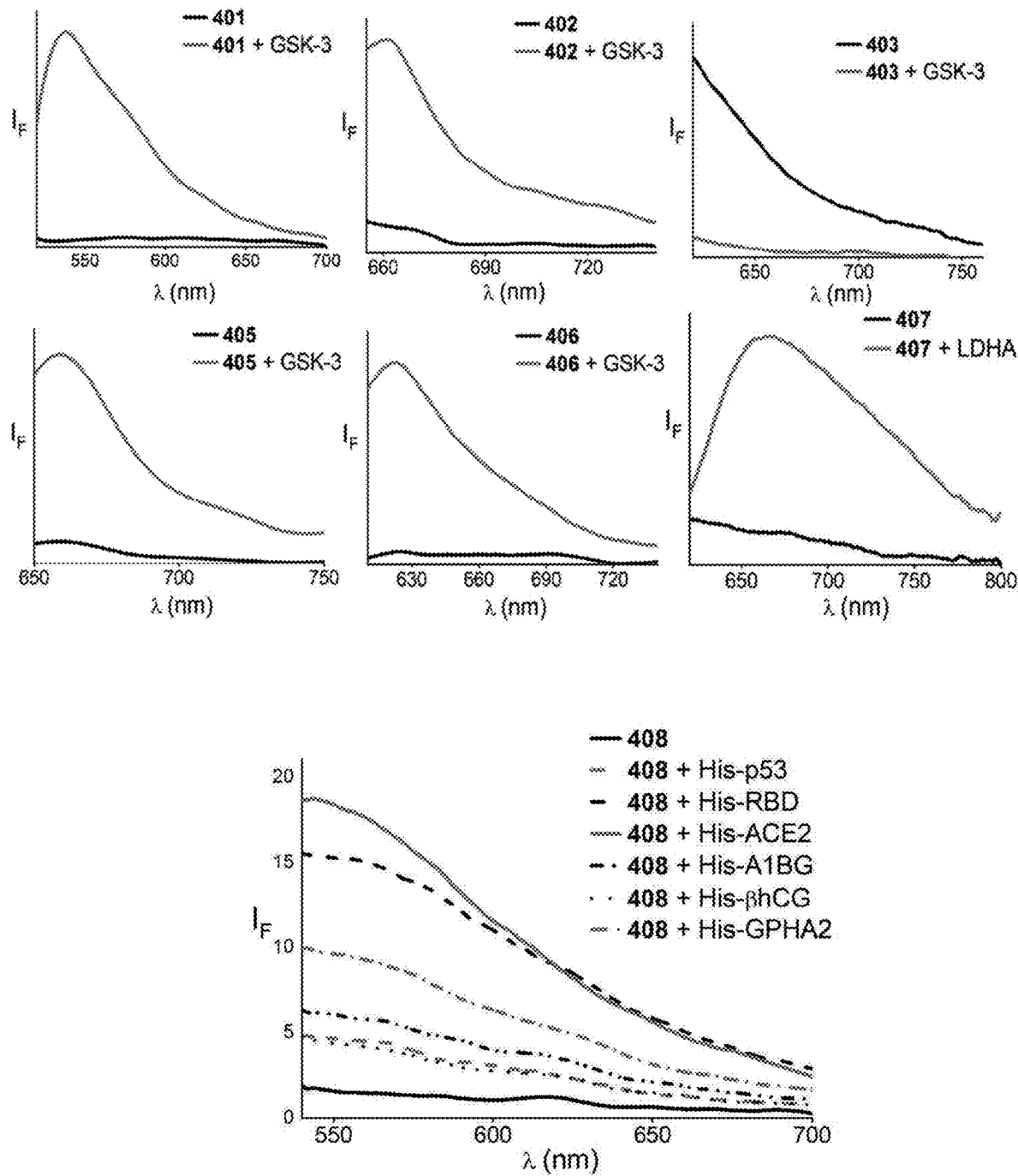
FIG. 47 shows the fluorescence responses of turn on fluorescent probes 401-408 of the invention. The fluorescence enhancement in the emission of all probes, upon incubation with their protein targets, provides compelling evidence that this technology is general.

FIG. 47 shows the fluorescence response of various sensors according to this invention to their target proteins. The advantage of using probes 408-410, which target a His-tag, is that they can be utilizes for a wide range of His-tagged proteins. This provides means to examine the generality of the design of this invention. The fluorescence enhancement in the emission of all tested probes, upon incubation with their protein targets (FIG. 47), provides compelling evidence that the technology provided herein is general.

Namely, that attaching quinoline based cyanine dyes (e.g., TO, QB, and TR) to specific protein binders, affords fluorescent molecular sensors whose emission turns on in the presence of the target proteins.

Example 24

Wash-Free Detection and Imaging of the Proteins in Living Cells by Turn-on Fluorescent Probes One advantage of using turn-on fluorescent probes over other methods for detecting and imaging proteins (e.g., immunofluorescence) is their ability to sense their targets without washing steps; this enables fast detection of the POI in vitro and in living cells. Efficient, wash-free detection becomes possible, owing to the relatively high signal-to-noise (S/N) detection ratio that such probes can afford (FIG. 47). The low initial fluorescence of the probes minimizes the emission generated by an excess of unbound probes in the medium and by the cell's autofluorescence.

Example 25

Screening for Compounds that Inhibit the Activity of Native Proteins In Vitro and in Living Cells.

Figure 50:
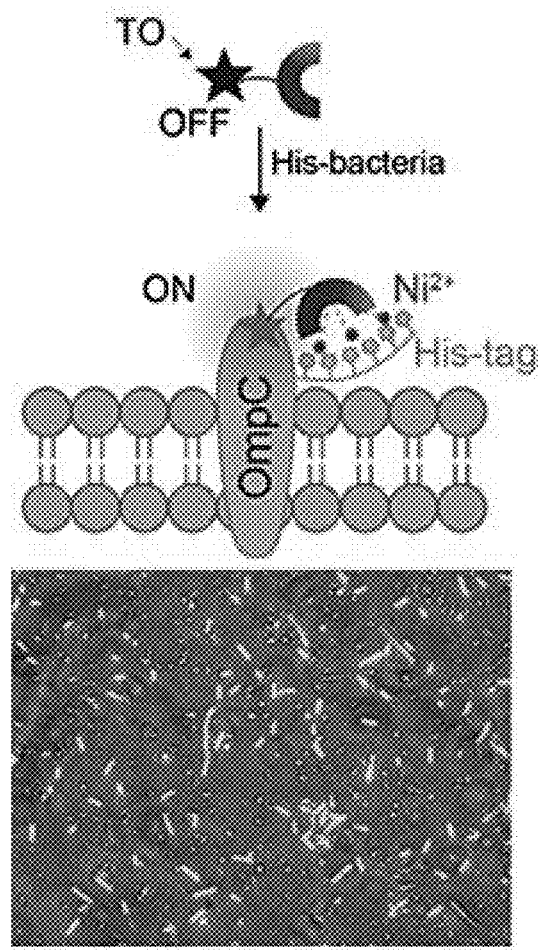
FIG. 50 depicts fluorescence images of bacteria expressing His-OmpC following incubation with probe 408 and subsequent washing.
Figure 51:
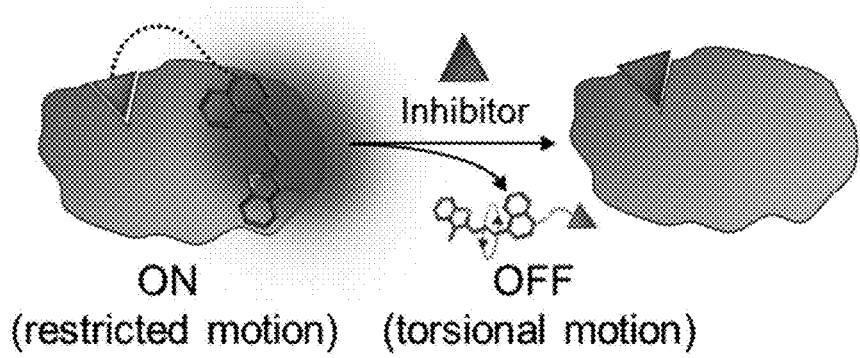
FIG. 51 depicts an illustration of the mechanism underlying an inhibitor detection with a TR probe of the invention.
Figure 52:
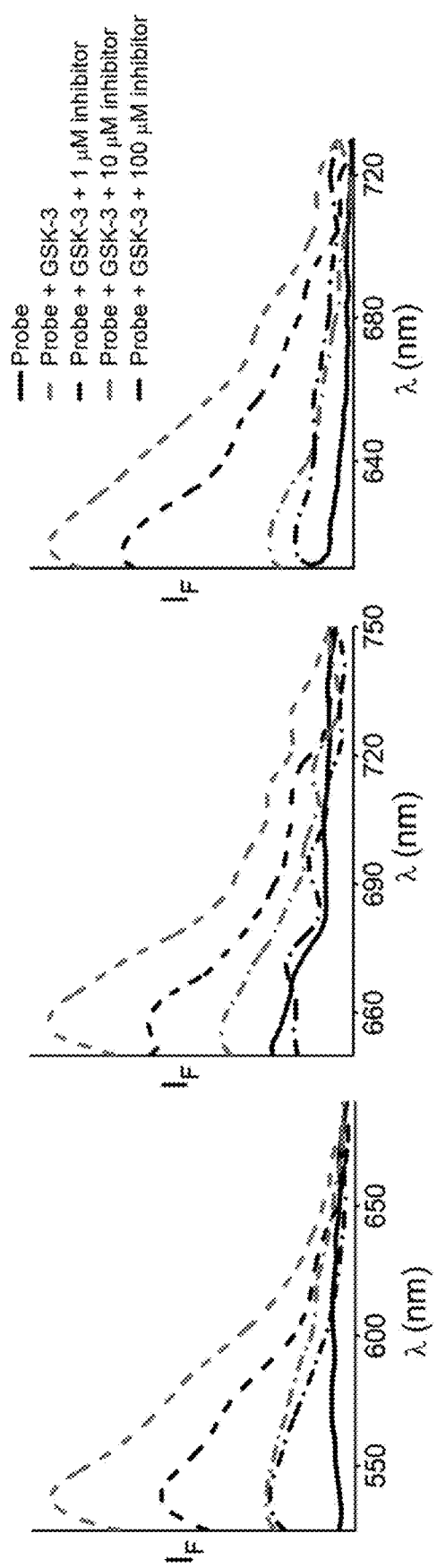
FIG. 52 depicts a detection of GSK-3 inhibitors in vitro using probes 401 (left), 402 (middle), and 403 (right), respectively.

FIG. 50 demonstrates the use of turn-on probes according to this invention with native proteins, for screening for new inhibitors.

Figure 53A:
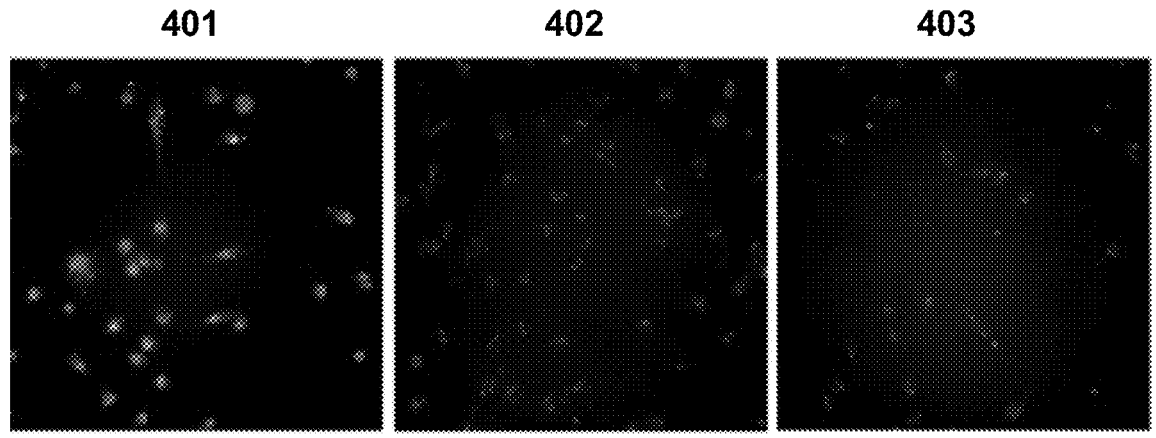
FIGS. 53A-53B depict a detection of GSK-3 inhibitors in living cells using probes 401, 402 and 403.
Figure 53B:
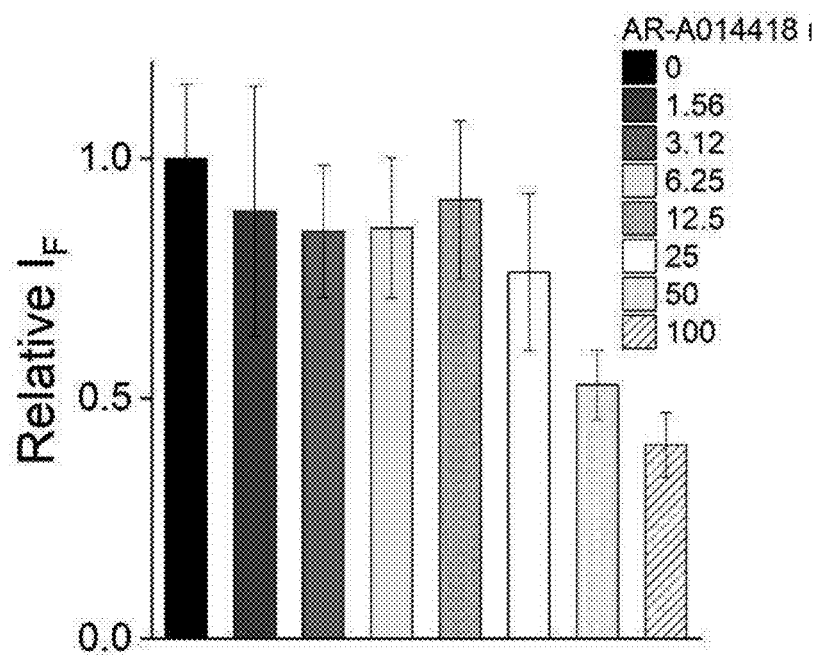
Figure 54:
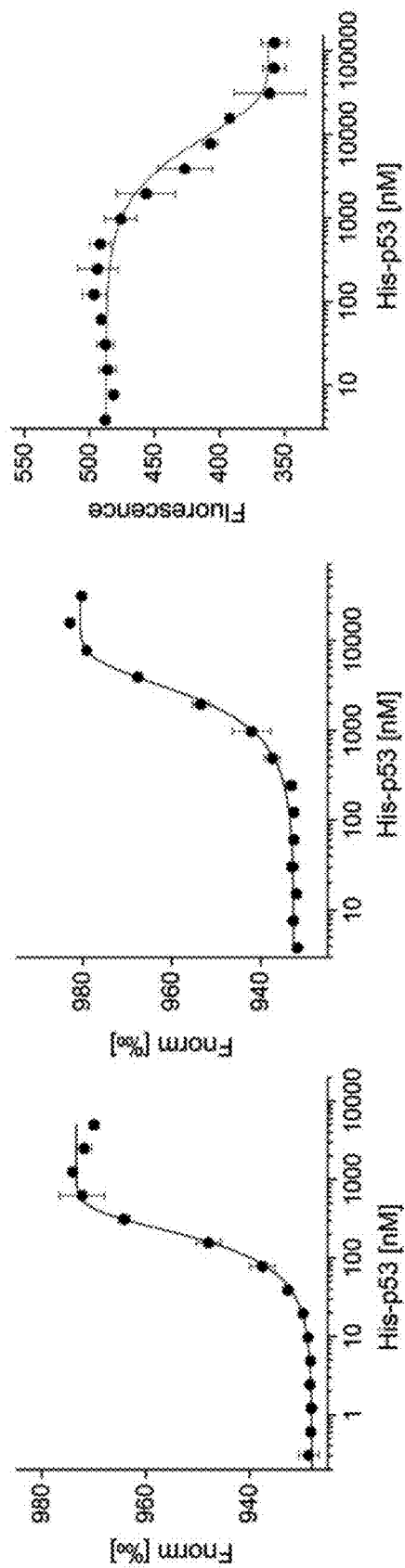
FIG. 54 depicts the MST analysis. Dose-response curves of compounds 402 (left), 404 (middle), and 405 (right) interacting with $His_6$-p53.
Figure 55:
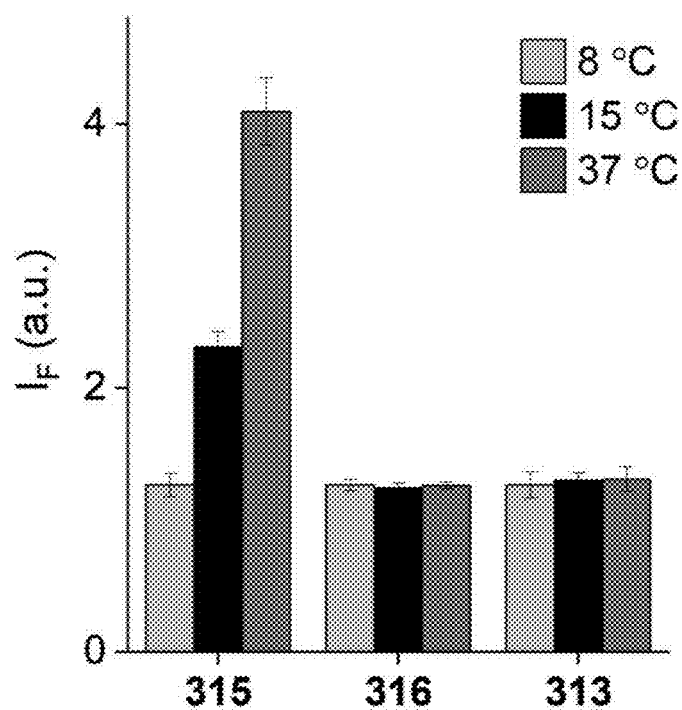
FIG. 55 depicts the fluorescence enhancement of probes 401, 402, and 403 in response to bacteria expressing His-OmpC bacteria cultured at different temperatures. These experiments were performed in triplicate.

Rapid, wash-free detection of inhibitors is achieved by following the reduction in the emission of the probes (i.e., the turn-off signal) when competing inhibitors displace them. The relevance of this technology to drug discovery was demonstrated by the ability of probes 401-406 to detect an inhibitor of glycogen synthase kinase-3 (GSK-3) (FIGS. 52 and 53A and 53B), a cytoplasmic serine/threonine kinase that regulates a number of signaling pathways. Because many of these pathways are involved in the development of diseases such as diabetes, cancer, and neurodegenerative disorders, GSK-3 has emerged as a prominent drug target. The results show that quinoline based cyanine dye probes 401-406 were able to detect the known GSK-3 inhibitor in vitro (FIG. 52) and in living cells (FIGS. 53A-53B).

Example 26

Synthesis of Compounds 401-410

Figure 48:
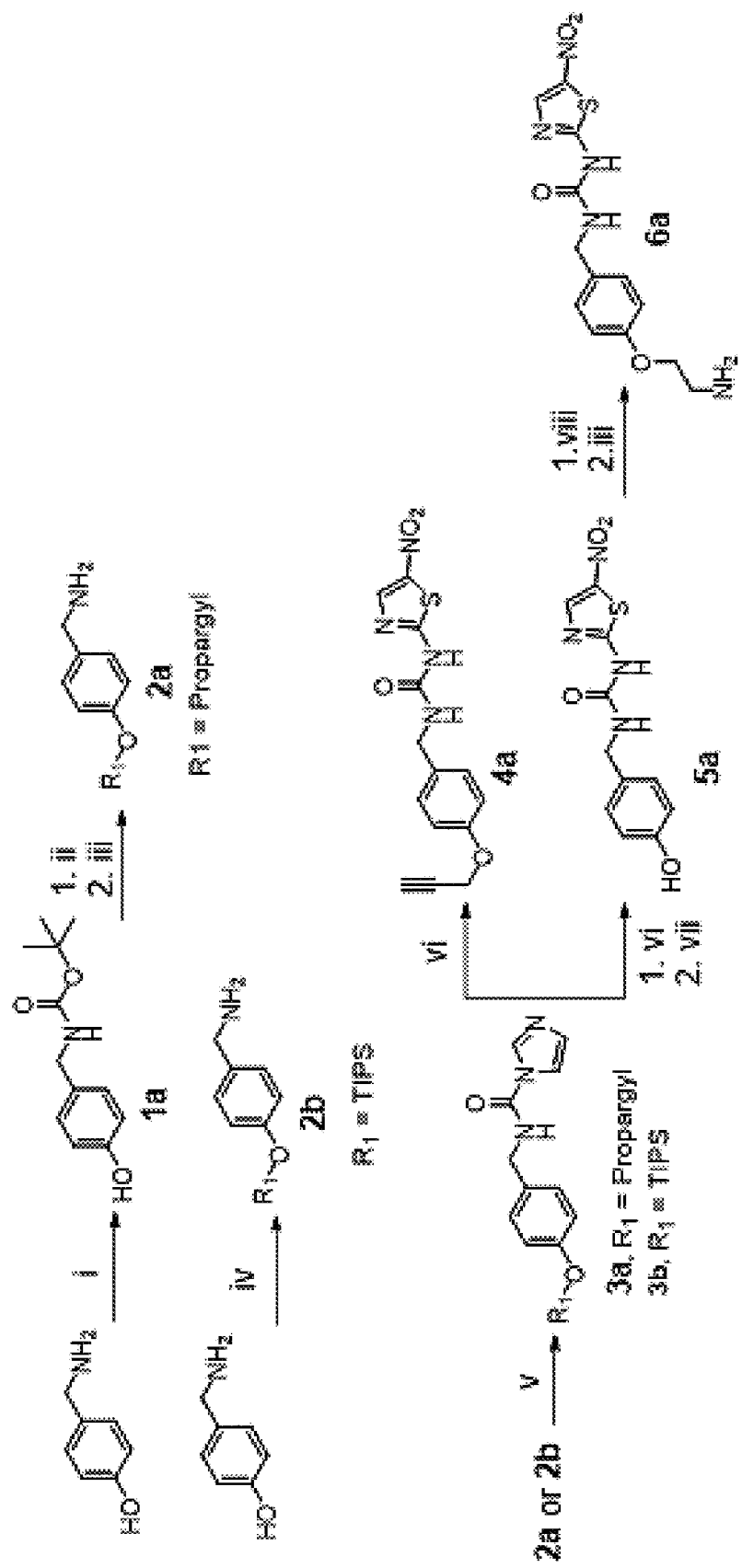
FIG. 48 depicts the synthetic scheme of the synthesis of turn on fluorescent probes 401-406. Synthetic steps for preparing probes 401-406. i) methyl iodide, ACN, 55° C.; ii) 3-iodopropanoic acid, ACN, 55° C.; iii) methyl iodide, DMF, 80° C.; iv) $EtN_3$, DCM; v) N,N'-diphenylformamidine, $Ac_2O$; vi) 2-azidoethan-1-amine, DIPEA, HATU, and DMF; vii) DIPEA, HATU, DMF; and viii) 1:1 $H_2O$/DMSO, $CuSO_4$, ascorbic acid.
Figure 49:
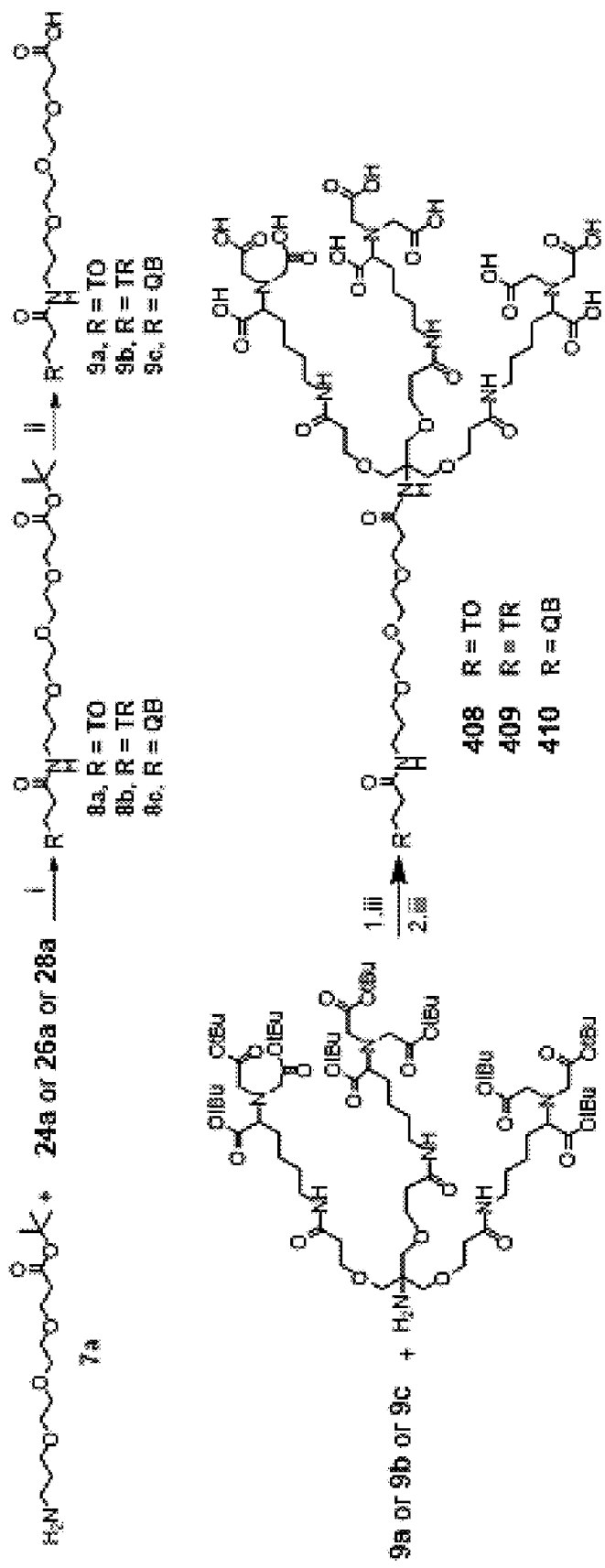
FIG. 49 depicts a synthetic scheme of the synthesis of turn on fluorescent probes 408-410. Synthetic steps for preparing probes 408-410: i) HATU, DIPEA, and DMF; ii) 20% TFA in DCM; iii) HATU, DIPEA, and DMF; iv) 50% TFA in DCM.

The synthesis of compounds 401-410 is described in FIGS. 48 and 49.

Synthetic steps for preparing probes 401-407. i) methyl iodide, ACN, 55° C.; ii) 3-iodopropanoic acid, ACN, 55° C.; iii) methyl iodide, DMF, 80° C.; iv) EtN$_3$, DCM; v) N,N'-diphenylformamidine, Ac$_2$O; vi) 2-azidoethan-1-amine, DIPEA, HATU, and DMF; vii) DIPEA, HATU, DMF; and viii) 1:1 H$_2$O/DMSO, CuSO$_4$,ascorbic acid.

Synthetic steps for preparing probes 408-410. i) HATU, DIPEA, and DMF; ii) 20% TFA in DCM; iii) HATU, DIPEA, and DMF; iv) 50% TFA in DCM.

Example 27

Synthesis of Compounds 313, 314 and 315

Materials and Methods

All solvents and reagents were obtained from commercial suppliers and used without further purification. Dry solvents were purchased from Sigma Aldrich. Deuterated solvents were purchased from Cambridge Isotope Laboratories, Inc. (Andover, MA). Sulfo-Cyanine5 carboxylic acid was obtained from Lumiprobe Corporation. The $^1$H NMR and $^{13}$C NMR spectra were recorded on a Bruker Advance 300, 400, or 500 MHz spectrometer. The chemical shifts are represented in ppm on the δ scale down field from TMS as the internal standard. The following abbreviations were used to describe the peaks: br-broad, s-singlet, d-doublet, t-triplet, td-triplet of doublets, q-quartet, quin-quintet, and m-multiplet. Electrospray mass spectrometry was performed either with a Micromass Platform LCZ-4000 instrument at the Weizmann Institute of Science mass spectrometry facility or by using the LTQ Orbitrap Discovery hybrid FT mass spectrometer (Thermo Fisher Scientific, Inc.) equipped with an electrospray ionization ion source at the Faculty of Agriculture, Hebrew University of Jerusalem. The analytical reversed phase high-performance liquid chromatography (RP-HPLC) analysis was performed on an Agilent Technologies 1260 Infinity quaternary pump LC system, equipped with a diode-array detector using a C18 column.

Preparative HPLC was carried out using an Agilent 218 purification system, equipped with an autosampler, a UV-Vis dual wavelength detector, and a 440-LC fraction collector operating under OpenLab ChemStation software. The elution phases consisted of 10% ACN and 0.10% TFA in $H_2O$ (eluent A) and 90% acetonitrile and 0.10% TFA in $H_2O$ (eluent B). Fluorescence was measured using a BioTek synergy H4 hybrid multiwall plate reader, in black flat-bottom polystyrene NBS 384-well microplates (Corning).

Abbreviations

Acetonitrile (ACN), dichloromethane (DCM), N,N'-diisopropylethylamine (DIPEA), N,N'-dimethylformamide (DMF), dimethyl sulfoxide (DMSO), 1-Ethyl-3-(3-dimethylaminopropyl) carbodiimide (EDC), fluorescein isothiocyanate (FITC), 1-[bis(dimethylamino)methylene]-1H-1,2,3-triazolo[4,5-b]pyridinium3-oxid hexafluorophosphate (HATU), hydroxybenzotriazole (HOBt), methanol (MeOH), MicroScale Thermophoresis (MST), nitrilotriacetic acid (NTA), polyacrylamide gel electrophoresis (PAGE), Phosphate buffer saline (PBS), reverse phase high-performance liquid chromatography (RP-HPLC), sodium dodecyl sulfate (SDS), Sulfo-Cyanine5 (SCy5), trifluoroacetic acid (TFA)

Synthesis of tri-NTA (scheme 4)

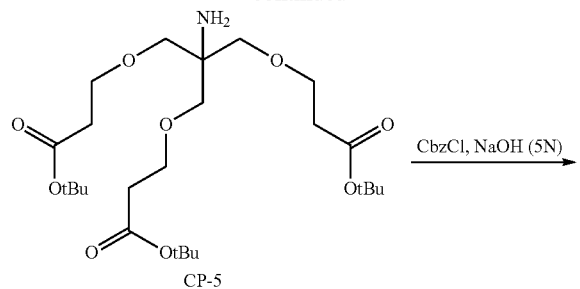

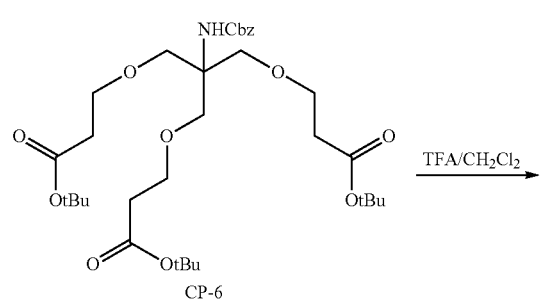

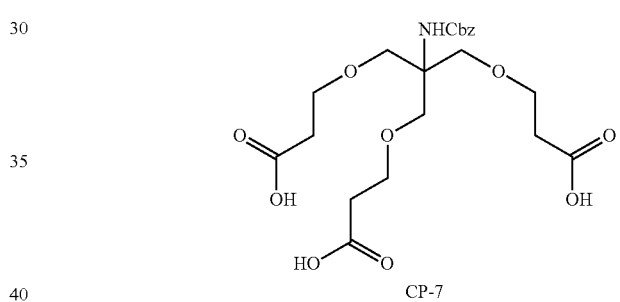

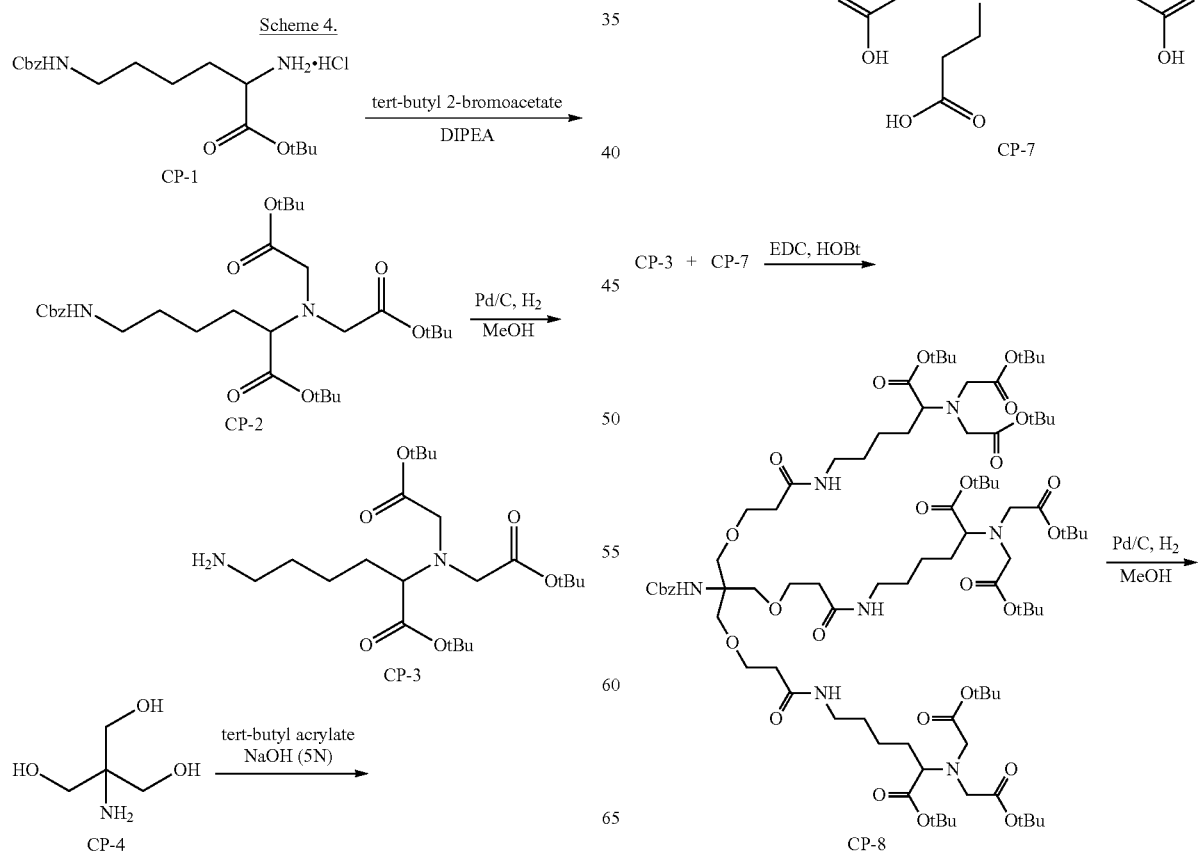

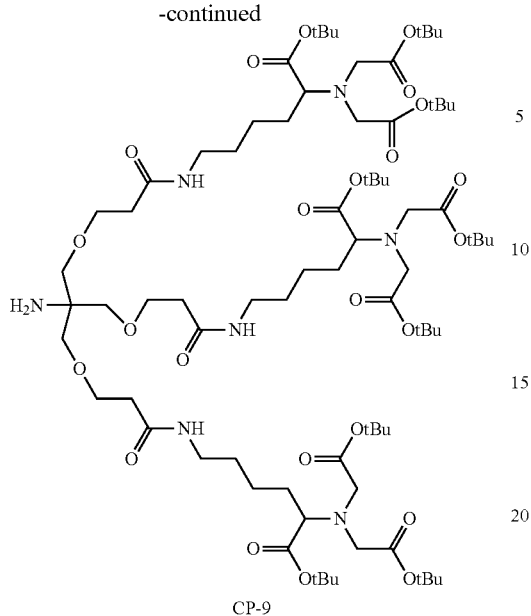
CP-9
The tri-NTA (CP-9) was synthesized following the earlier reported procedure. [Y. Nissinkorn, N. Lahav-Mankovski, A. Rabinkov, S. Albeck, L. Motiei and D. Margulies, *Chem. Eur. J*, 2015, 21, 15981].
Synthesis of Tri-NTA Appended with Nile Red (Compound 315) as Shown in Scheme 5
Scheme 5.
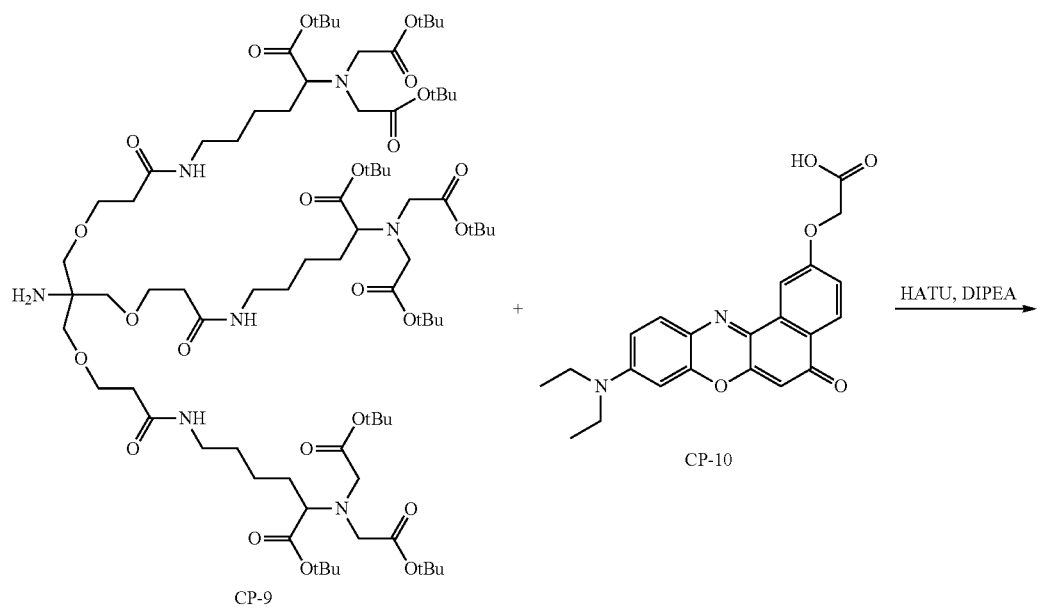

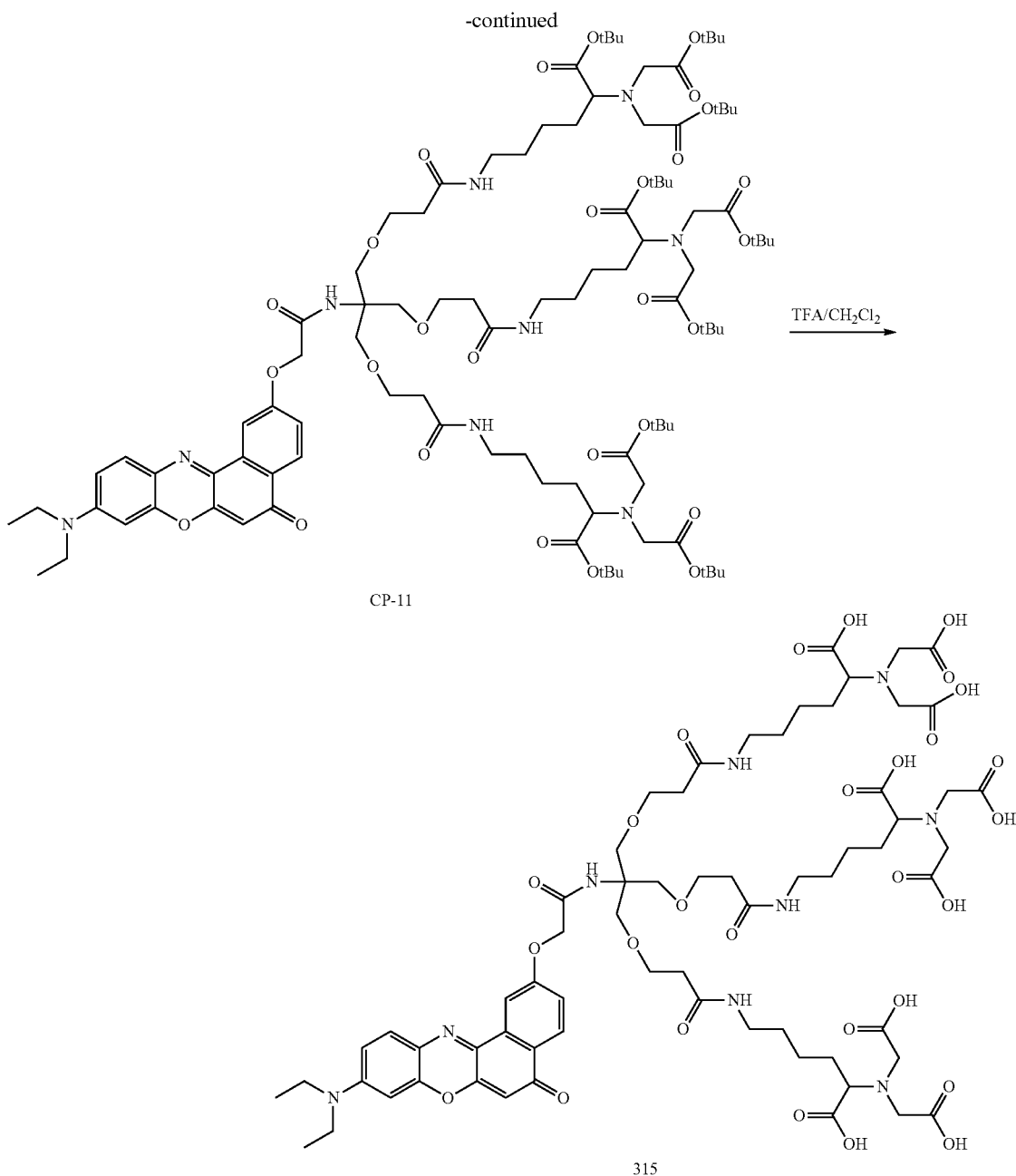

Synthesis of CP-11: DIPEA (0.01 mL, 0.06 mmol) and HATU (24.00 mg, 0.06 mmol) were sequentially added to a solution of Nile Red (CP-10) (12.00 mg, 0.03 mmol) in $CH_2Cl_2$ (2 mL), and the reaction mixture was stirred for 15 minutes. Then compound CP-9 (47.00 mg, 0.03 mmol), dissolved in $CH_2Cl_2$ (1.00 mL), was added dropwise and the reaction mixture was stirred at room temperature for 12 h under argon and dark conditions. After consumption of the starting materials (as monitored by TLC), $CH_2Cl_2$ was removed in vacuum and the residue was purified by RP-HPLC to afford CP-11 (30.00 mg, 78%) as a dark purple solid. $^1H$ NMR (400 MHz, $CDCl_3$): δ 1.44 (s, 56H), 1.45 (s, 27H), 1.67-1.47 (m, 12H), 1.87 (s, 4H), 2.26 (t, J=7.0 Hz, 6H), 2.40 (t, J=5.8 Hz, 6H), 3.15-3.30 (m, 9H), 3.40-3.50 (m, 16H), 3.65-3.75 (m, 12H), 4.6 (s, 2H), 6.31 (s, 1H), 6.46 (d, J=2.6 Hz, 1H), 6.71-6.65 (m, 4H), 7.03 (s, 1H), 7.24 (d, J=2.6 Hz, 1H), 7.61 (d, J=6.4 Hz, 1H), 8.07 (d, J=2.6 Hz, 1H), 8.25 (d, J=8.7 Hz, 1H). $^{13}C$ NMR (100 MHz, $CDCl_3$): δ 12.6, 23.1, 28.1, 29.7, 30.0, 36.6, 39.6, 45.1, 53.8, 59.7, 65.1, 67.5, 69.2, 80.6, 80.7, 96.3, 105.3, 107.3, 109.8, 118.1, 124.7, 126.6, 128.1, 131.2, 134.1, 139.4, 146.9, 150.9, 152.2, 159.7, 167.3, 170.7, 171.0, 172.3, 182.9. HRMS-ESI (m z): calcd. for $[M+Na]^+$ 1971.1349; found 1971.1340

Synthesis of Compound 315: The tert-butyl ester group was deprotected by adding TFA (1.00 mL) to a solution of CP-11 (30.00 mg, 15.00 μmol in DCM (2 mL) at 0° C. and under dark conditions. The reaction mixture was warmed up to the room temperature and stirring was continued for another 3.5 h. After the reaction was completed, DCM and TFA were evaporated. The traces of TFA were removed by co-evaporation with DCM. The crude compound was washed thrice with cold diethyl ether, followed by dissolution in 3 mL ACN/H₂O (1:1), freezing with liquid nitrogen, and lyophilization under high vacuum to afford a purple powder as a product (17.00 mg, 77%). ¹H NMR (500 MHz, DMSO-d₆): δ 1.09 (t, J=7.0 Hz, 6H), 1.17 (t, J=7.0 Hz, 6H), 1.30-1.41 (m, 6H), 1.49-1.60 (m, 6H), 2.29 (t, J=6.2 Hz, 6H), 2.92-3.05 (m, 6H), 3.31 (t, J=7.4 Hz, 3H), 3.38 (q, J=7.0 Hz, 4H), 3.41-3.54 (m, 14H), 3.54-3.59 (m, 6H), 3.61 (br s, 4H), 4.69 (s, 2H), 6.21 (s, 1H), 6.62-6.69 (m, 1H), 6.84 (dd, J=2.2, 9.2 Hz, 1H), 7.30 (dd, J=2.4, 8.7 Hz, 1H), 7.39 (s, 1H), 7.63 (d, J=9.1 Hz, 1H), 7.79 (t, J=5.2 Hz, 3H), 7.96 (d, J=2.2 Hz, 1H), 8.06 (d, J=8.7 Hz, 1H). ¹³C NMR (100 MHz, DMSO-d₆): δ 12.4, 23.1, 28.8, 29.2, 35.9, 38.4, 44.5, 53.2, 59.7, 64.2, 66.9, 67.4, 68.3, 96.0, 104.1, 106.8, 110.2, 115.7, 118.1, 118.7, 124.0, 125.4, 127.2, 131.0, 133.6, 138.1, 146.5, 150.9, 151.8, 160.2, 166.8, 169.8, 173.1, 173.9, 181.4. HRMS-ESI (m z): calcd. for [M]²⁻ 720.7836; found: 720.7853.

Synthesis of Tri-NTA Appended with Fluorescein (Compound 314), as Shown in Scheme 6

Scheme 6.

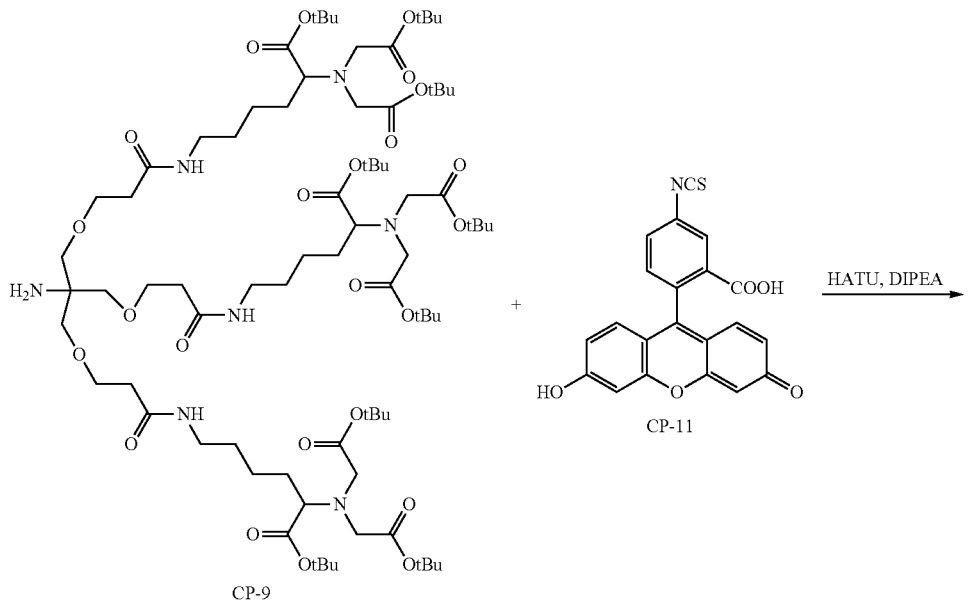

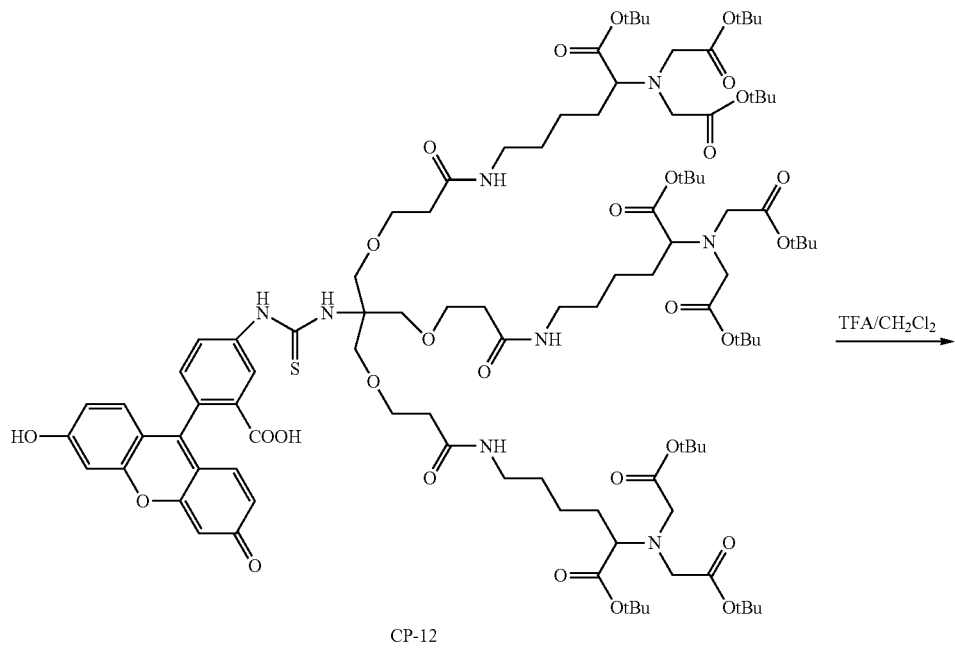

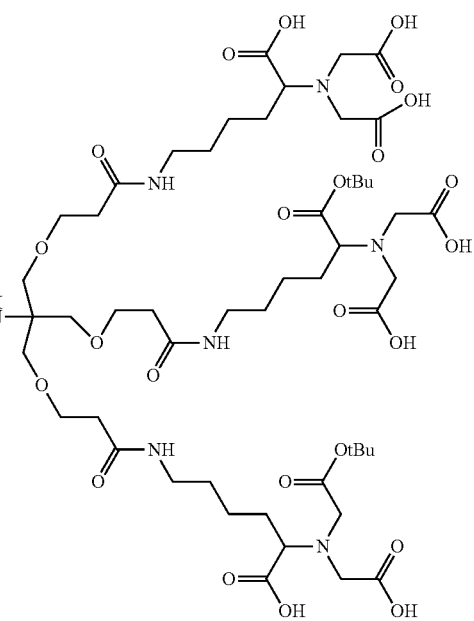

314

Synthesis of CP-12: Compound CP-9 (50.00 mg, 0.032 mmol) was dissolved in CH$_2$Cl$_2$ (5 mL) and the solution was basified with DIPEA (0.012 mL, 0.064 mmol). Then fluorescein isothiocyanate (CP-11, 12.00 mg, 0.032 mmol) was added to the above solution and the resulting reaction mixture was stirred at room temperature for 12 h under argon and dark conditions. The solvent was removed in vacuum and the residue was dissolved in DCM (20 mL) and washed with water (2×10 mL). The organic layer was dried over anhydrous sodium sulfate, filtered, and evaporated to dryness. Finally, the residue was purified by RP-HPLC to afford CP-12 (40.00 mg, 62%) as a bright yellow solid. $^1$H NMR (400 MHz, CDCl$_3$): δ 1.42 (br s, 87H), 1.69-1.46 (m, 12H), 2.47 (br s, 6H), 3.10-3.30 (m, 9H), 3.35-3.50 (m, 16H), 3.60-3.90 (m, 8H), 6.55 (d, J=8.0 Hz, 2H), 6.60 (br d, 2H), 6.74 (s, 2H), 6.96 (br s, 2H), 7.02 (d, J=8.0 Hz, 1H), 7.12 (br s, 1H), 7.90 (br s, 1H), 8.11 (s, 1H). $^{13}$C NMR (100 MHz, CDCl$_3$): δ 23.2, 28.1, 28.2, 28.6, 29.9, 36.4, 39.57, 54.2, 65.2, 67.9, 69.4, 81.4, 81.6, 81.8, 102.9, 111.8, 114.7, 115.3, 117.6, 119.4, 120.4, 127.0, 128.9, 130.7, 131.8, 142.1, 157.7, 160.6, 161.0, 161.4, 161.7, 167.1, 169.5, 171.2, 172.5, 180.7. HRMS-ESI (m/z): [M+Na]+1986.0440; found: 1986.0448.

Synthesis of Compound 314: The tert-butyl ester group was deprotected by adding TFA (1.00 mL) to a solution of CP-12 (40.00 mg, 0.02 mmol) in DCM (2.00 mL) at 0° C. and under dark conditions. The reaction mixture was warmed up to room temperature and stirring was continued for another 3.5 h. After the reaction was completed, DCM and TFA were evaporated. The traces of TFA were removed by co-evaporation with DCM. The crude compound was washed thrice with cold diethyl ether, followed by dissolution in 3.00 mL ACN/H$_2$O (1:1), freezing with liquid nitrogen, and lyophilization under a high vacuum to afford a bright yellow powder as a product (10.00 mg, 68%). $^1$H NMR (500 MHz, DMSO-d$_6$): δ 1.19-1.38 (m, 12H), 1.48-1.69 (m, 6H), 2.34 (br s, 6H), 2.95-3.07 (m, 6H), 3.26-3.46 (m, 5H), 3.45-3.55 (m, 14H), 3.63 (t, J=6.0 Hz, 4H), 3.69 (t, J=6.2 Hz, 2H), 3.86 (br s, 2H), 6.52-6.63 (m, 4H), 6.68 (br s, 2H), 7.18 (d, J=8.3 Hz, 1H), 7.27 (d, J=8.1 Hz, 1H), 7.37 (br s, 1H), 7.67-7.77 (m, 1H), 7.84 (d, J=4.7 Hz, 3H), 8.02-8.19 (m, 1H), 8.30 (s, 1H), 10.11 (br s, 1H). $^{13}$C NMR (100 MHz, DMSO-d$_6$): δ 23.1, 28.8, 29.2, 35.9, 38.4, 40.4, 53.3, 61.9, 64.2, 67.5, 68.1, 102.2, 109.7, 112.6, 115.2, 118.1, 124.0, 126.4, 129.0, 129.8, 141.3, 151.9, 159.5, 169.8, 169.9, 173.1, 173.9, 179.7. HRMS-ESI (m/z): [M]$^{-2}$ 728.2381; found: 728.2396.

Synthesis of Tri-NTA Appended with SCy5 (Compound 313) as Shown in Scheme 7
Scheme 7.
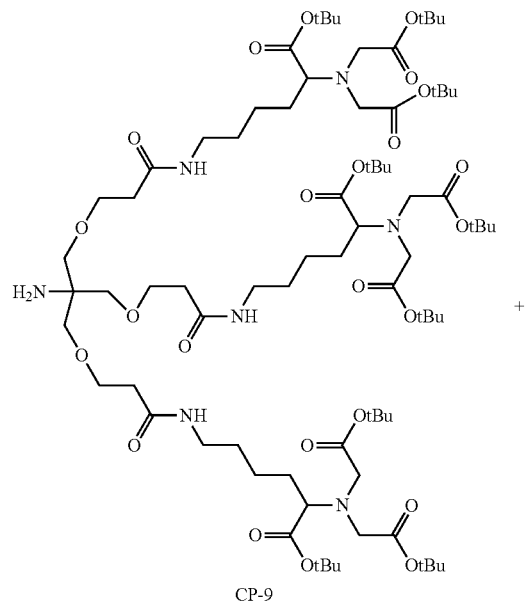
CP-9 +
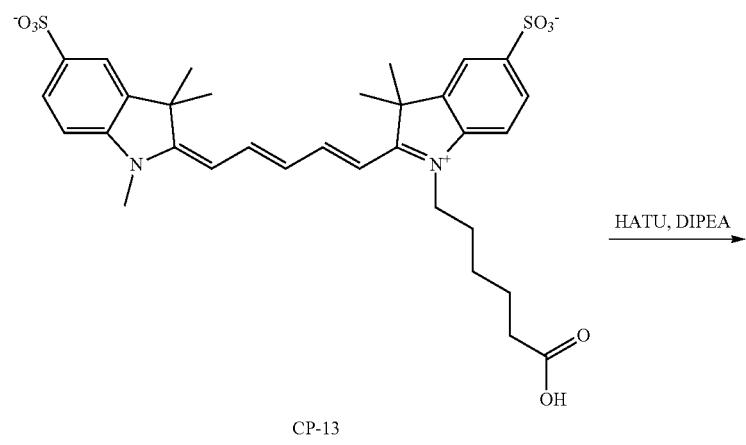
CP-13 →HATU, DIPEA

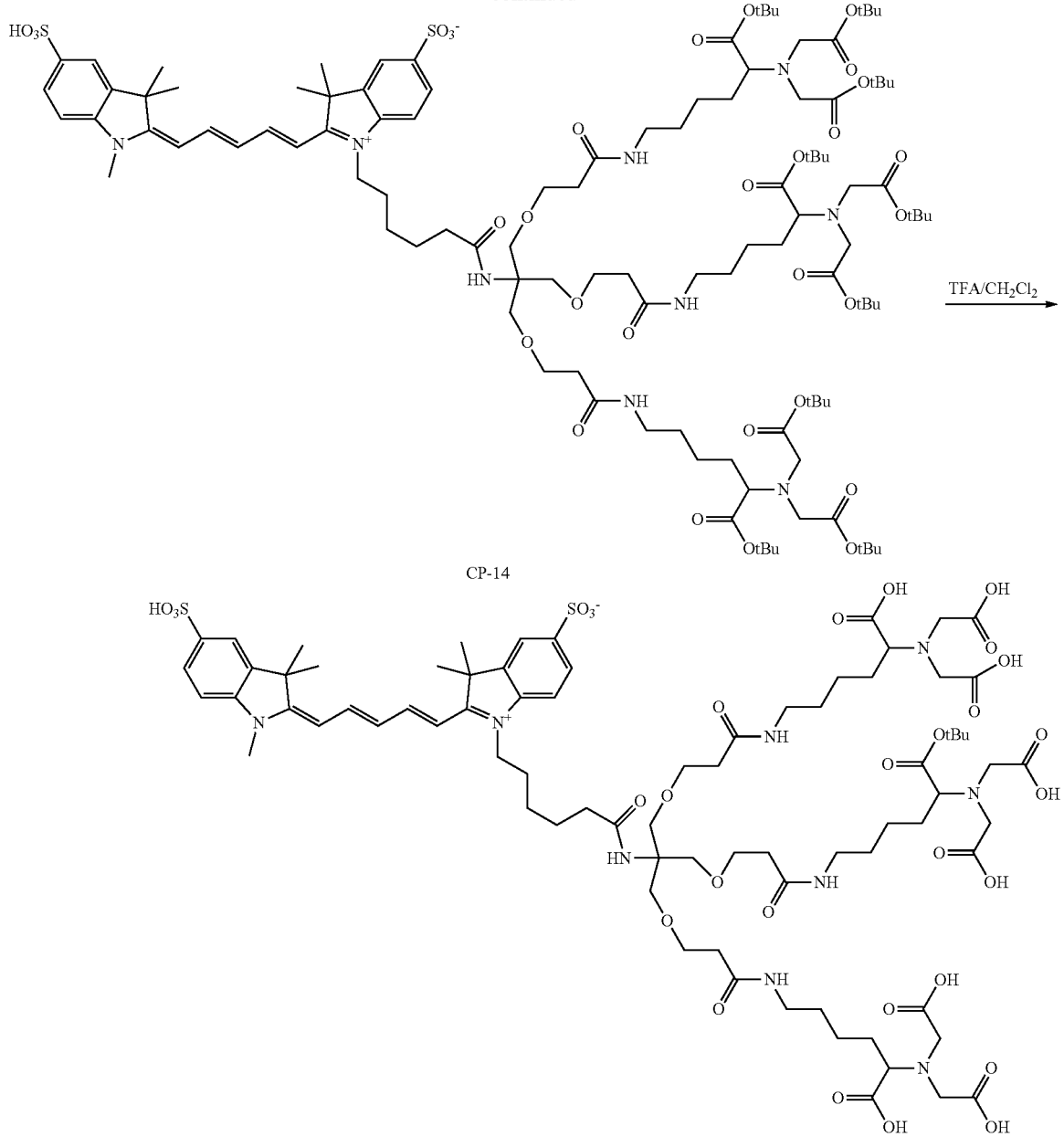

Synthesis of CP-14: DIPEA (3.80 µL, 21.80 µmol) and HATU (9.00 mg, 21.80 µmol) were sequentially added to a solution of the Scy5 carboxylic acid (CP-13, 7.00 mg, 10.90 µmol) in $CH_2Cl_2$ (2.00 mL). The reaction mixture was stirred for 15 minutes. Then compound CP-9 (17.00 mg, 10.90 µmol), dissolved in $CH_2Cl_2$ (1.00 mL), was added dropwise and the reaction mixture was stirred at room temperature for 12 h under argon and dark conditions. Finally, the solvent was removed in vacuum and the residue was purified by RP-HPLC to afford CP-14 (9.00 mg, 75%) as a blue solid. $^1$H NMR (400 MHz, DMSO-$d_6$): δ 1.23 (s, 8H), 1.37 (s, 55H), 1.44 (s, 30H), 1.49 (s, 12H), 1.68 (s, 12H), 2.06 (s, 2H), 2.25 (s, 6H), 2.98 (s, 6H), 3.21 (t, J=6.9 Hz, 3H), 3.31-3.59 (m, 27H), 4.06 (s, 2H), 6.27 (t, J=14.4 Hz, 2H), 6.55 (t, J=11.8 Hz, 1H), 7.03 (d, J=13.0 Hz, 2H), 7.16 (s, 1H), 7.32 (s, 2H), 7.63 (s, 1H), 7.80 (s, 4H), 8.35 (t, J=13.0 Hz, 2H). $^{13}$C NMR (100 MHz, DMSO-$d_6$): δ 13.9, 17.2, 22.0, 22.9, 24.5, 24.8, 25.7, 26.7, 26.9, 27.0, 27.5, 28.5, 28.7, 28.9, 29.0, 29.7, 30.1, 31.2, 31.3, 33.6, 35.5, 35.9, 38.4, 43.4, 48.4, 48.8, 53.2, 59.4, 64.5, 67.3, 68.2, 69.7, 79.9, 80.2, 103.2, 103.5, 110.0, 115.7, 118.7, 119.8, 119.9, 125.6, 129.9, 126.0, 140.3, 140.4, 141.9, 142.7, 145.1, 145.3, 154.2, 157.4, 157.7, 158.0, 158.3, 169.8, 170.0, 171.5, 172.1, 172.7, 173.6. HRMS-ESI (m z): calcd. for $[M+H]^+$ 2199.2227, found 2199.2283.

Synthesis of Compound 313: TFA (1.00 mL) was added to a solution of CP-14 (9.00 mg, 4.09 µmol) in DCM (2.00 mL) at 0° C. and under dark conditions. The reaction mixture was warmed up to room temperature and stirring was continued for another 3.5 h. After the reaction was completed, DCM and TFA were evaporated. Then the traces of TFA were removed by co-evaporation with DCM. Finally, the crude compound was washed thrice with cold diethyl ether, followed by dissolution in 3.00 mL ACN/H$_2$O (1:1), freezing with liquid nitrogen, and lyophilization under high vacuum to afford a blue powder as a product (5.00 mg, 73%). $^1$H NMR (400 MHz, DMSO-d$_6$): δ 1.18-1.36 (m, 14H), 1.44-1.61 (m, 10H), 1.69 (s, 12H), 2.07 (t, J=6.6 Hz, 2H), 2.27 (t, J=5.9 Hz, 6H), 2.99 (d, J=5.5 Hz, 6H), 3.33 (t, J=7.3 Hz, 3H), 3.40-3.56 (m, 23H), 3.59 (s, 3H), 4.07 (br s, 2H), 6.18-6.38 (m, 2H), 6.49-6.66 (m, 1H), 7.01 (s, 1H), 7.25-7.36 (m, 2H), 7.64 (d, J=8.4 Hz, 2H), 7.81 (br s, 5H), 8.35 (t, J=12.8 Hz, 2H). $^{13}$C NMR (100 MHz, DMSO-d$_6$): δ 23.2, 27.0, 27.2, 28.9, 29.3, 34.4, 36.0, 38.4, 48.9, 48.9, 53.4, 54.9, 59.5, 64.3, 67.4, 68.3, 110.2, 112.8, 115.8, 118.8, 119.8, 119.9, 125.8, 125.8, 126.0, 126.1, 126.2, 140.5, 140.5, 142.2, 142.8, 144.9, 145.1, 154.2, 154.3, 170.0, 172.4, 172.8, 173.3, 173.8, 174.0. HRMS-ESI (m z): calcd. for [M]$^{-2}$ 845.8184; found 845.8195.

Synthesis of Bis-NTA Appended with Fluorescein

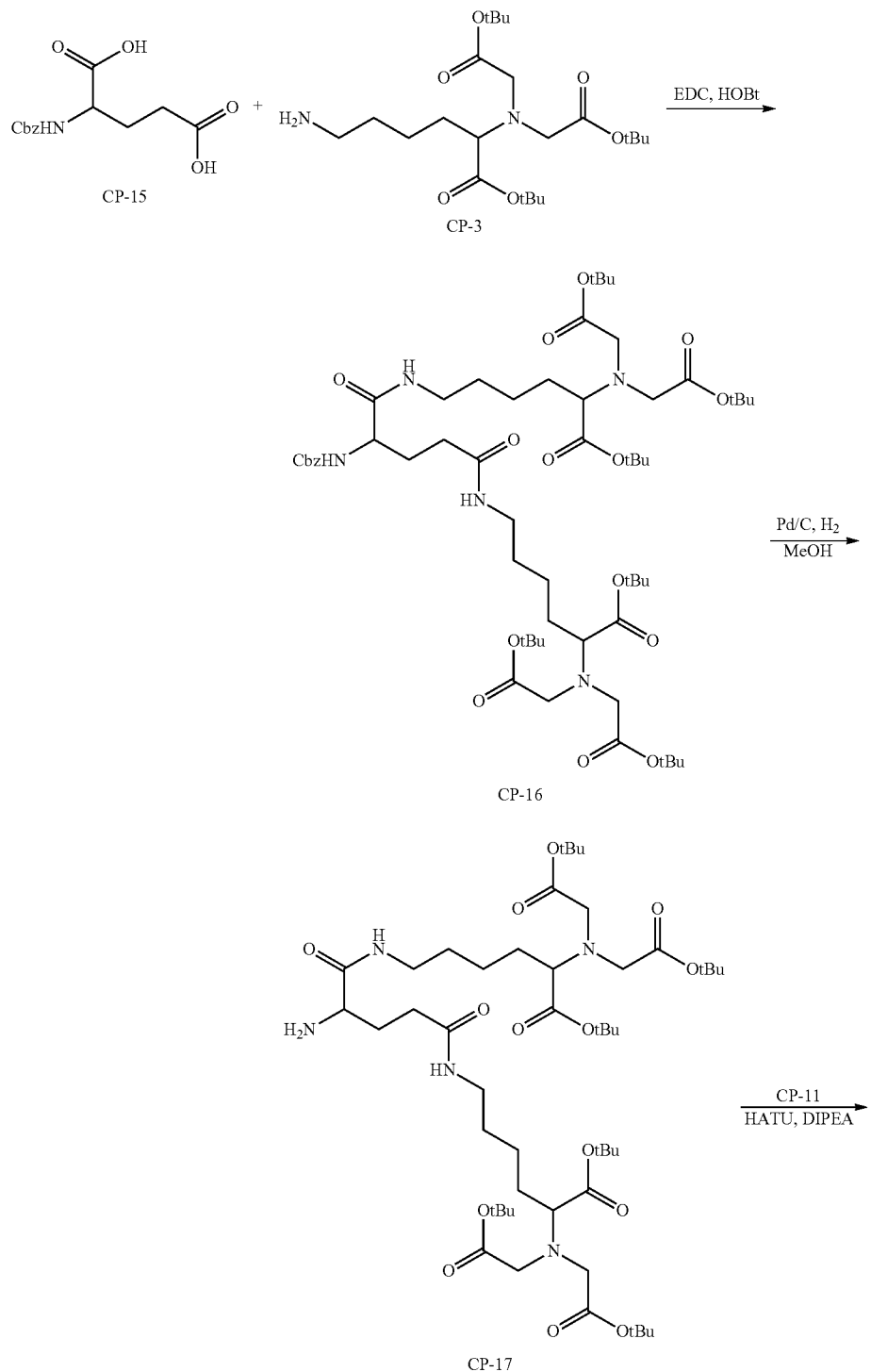

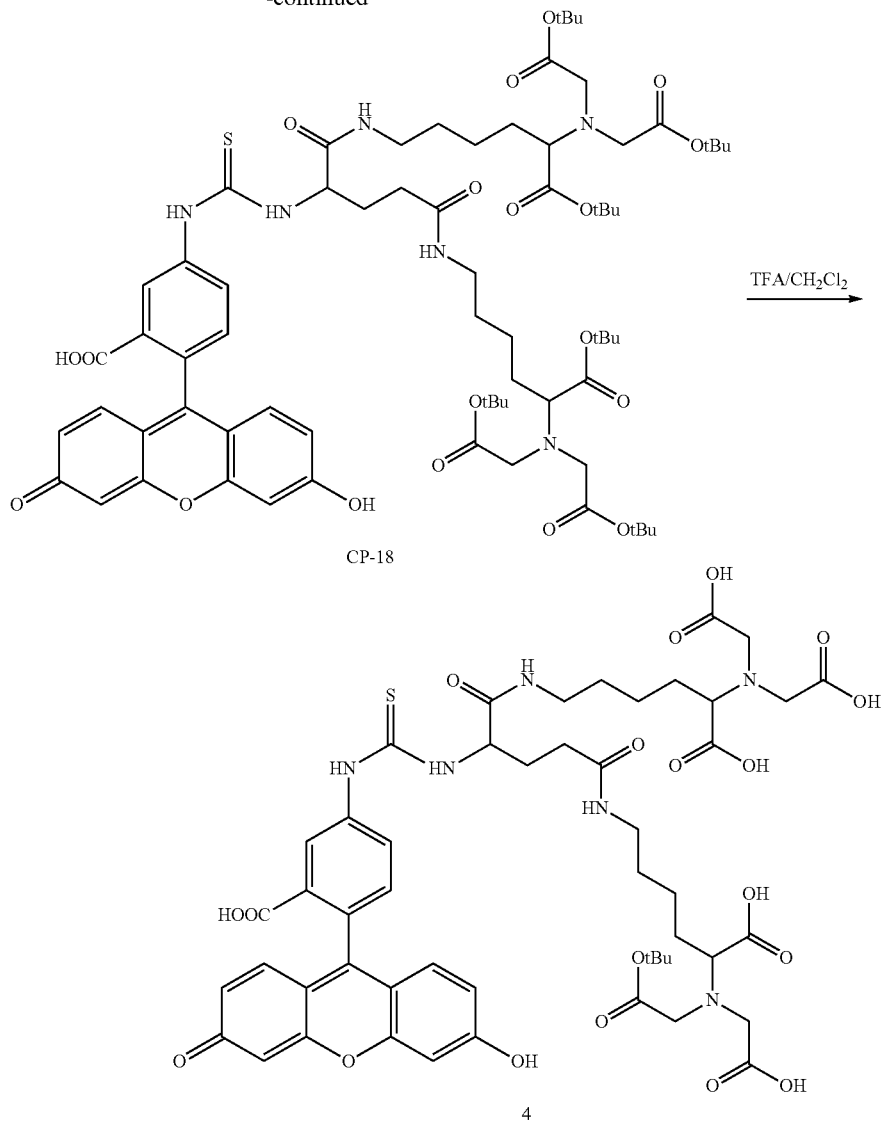

Synthesis of CP-16: Compound CP-15 (30.00 mg, 0.11 mmol) was dissolved in dry THF (7 mL), and then EDC·HCl (60.00 mg, 0.32 mmol) and HOBt (14.00 mg, 0.11 mmol) were sequentially added. The solution was basified to pH 7-8 with Et$_3$N (0.04 mL, 0.32 mmol). Next, the reaction mixture was stirred for 15 minutes at room temperature under argon and thereafter, compound CP-3 (100.00 mg, 0.23 mmol), dissolved in dry THF (3.00 mL), was added to the above solution. Stirring was continued for 24 h under argon and dark conditions. After completion of the reaction, as monitored by TLC, the solvent was removed in vacuum and the residue was purified by RP-HPLC to afford CP-16 (16.00 mg, 84%) as a light yellow solid. $^1$H NMR (400 MHz, acetonitrile-d$_3$) δ: 1.36-1.44 (m, 4H), 1.52 (s, 36H), 1.53 (m, 18H), 1.60-1.75 (m, 4H), 1.91-2.10 (m, 4H), 1.27-2.32 (m, 4H), 3.17-3.22 (m, 4H), 3.36 (td, J=1.7 Hz, 7.5 Hz, 2H), 3.43-3.55 (m, 8H), 4.07 (td, J=5.3, 7.5 Hz, 1H), 5.15 (s, 2H), 6.60-6.65 (m, 2H), 6.96 (t, J=5.5 Hz, 1H), 7.41-7.47 (m, 5H). ESI-MS (m/z): calcd. for [M+H]$^+$ 1106.68; found 1106.68.

Synthesis of CP-17: Compound CP-16 (0.60 g, 0.54 mmol) was dissolved in 30.00 mL MeOH and purged with argon. Next, 10% Pd/C (30.00 mg, 0.027 mmol) was added and the reaction was stirred overnight under H$_2$ (836 Torr). The mixture was filtered over Celite and the solvent was removed under reduced pressure. Yield: 0.50 g (95%). $^1$H NMR (500 MHz, DMSO-d$_6$) δ: 1.17-1.27 (m, 2H), 1.39 (s, 54H), 1.45-1.69 (m, 6H), 1.69-1.81 (m, 1H), 1.84 (br s, 1H), 1.96-2.12 (m, 2H), 2.91-3.09 (m, 4H), 3.22 (t, J=7.1 Hz, 2H), 3.32-3.37 (m, 5H), 3.39-3.48 (m, 4H), 7.71 (d, J=4.8 Hz, 1H), 7.77 (d, J=5.2 Hz, 1H). $^{13}$C NMR (125 MHz, DMSO-d$_6$) δ: 22.9, 27.8, 28.9, 29.0, 29.0, 29.2, 29.7, 29.8, 31.4, 32.1, 32.2, 34.4, 38.1, 38.2, 38.3, 53.2, 54.5, 54.9, 63.7, 64.5, 79.9, 80.3, 170.0, 171.5, 171.6, 171.7, 173.4, 174.6. ESI-MS (m/z): calcd. for [M+H]$^+$ 972.65; found 972.63.

Synthesis of CP-18: Compound CP-17 (100.00 mg, 102.98 μmol) was dissolved in DCM (1.00 mL) and the solution was basified to pH 7-8 with DIPEA (35.94 μL, 205.97 μmol). Then a solution of fluorescein isothiocyanate (CP-11, 44.00 mg, 113.27 μmol) in DCM (1.00 mL) was added to the above solution and the reaction mixture was stirred at room temperature for 7 h under argon and dark conditions. The solvent was removed in vacuum and the residue was purified by RP-HPLC to afford CP-18 (80.00 mg, 57%) as a light yellow solid. $^1$H NMR (500 MHz, Acetonitrile-d$_3$): d 1.43 (s, 27H), 1.44 (s, 27H), 1.56 (d, J=6.7 Hz, 4H), 1.58-1.71 (m, 12H), 2.87-2.96 (m, 1H), 2.97-3.05 (m, 1H), 3.31-3.34 (m, 2H), 3.37 (s, 4H), 3.39 (br.s., 4H), 3.45-3.47 (m, 2H), 6.55-6.58 (m, 1H), 6.59 (t, J=2.6 Hz, 1H), 6.61 (d, J=2.6 Hz, 1H), 6.67-6.75 (m, 6H), 7.16 (d, J=8.2 Hz, 1H), 7.29 (d, J=8.2 Hz, 1H), 7.70 (dd, J=8.2, 1.7 Hz, 1H). ESI-MS (m/z): calcd. for [M+H]$^+$ 1361.68, found 1361.69.

Synthesis of 4: TFA (1.00 mL) was added to a cooled solution (0° C.) of CP-18 (11.00 mg, 8.09 µmol) in DCM (2.00 mL) under dark conditions. The reaction mixture was warmed up to room temperature and stirring was continued for another 3.5 h. After the reaction was complete, DCM and TFA were evaporated. The traces of TFA were removed by co-evaporation with DCM. The crude compound was washed thrice with cold diethyl ether, followed by dissolution in 3.00 mL ACN/H$_2$O (1:1), freezing with liquid nitrogen and lyophilization under high vacuum to afford a light yellow fluffy powder as a product (8.00 mg, 96%). $^1$H NMR (500 MHz, DMSO-d$_6$): δ 1.31-1.38 (m, 4H), 1.47-1.68 (m, 7H), 1.90-1.99 (m, 1H), 2.06-2.24 (m, 4H), 2.72-2.80 (m, 2H), 3.00 (q, J=6.3 Hz, 2H), 3.35 (td, J=7.4, 3.3 Hz, 2H), 3.42-3.56 (m, 9H), 6.53-6.58 (m, 2H), 6.60 (d, J=8.7 Hz, 3H), 6.67 (d, J=2.3 Hz, 2H), 7.19 (d, J=8.4 Hz, 1H), 7.62 (br s, 1H), 7.77 (d, J=8.5 Hz, 1H), 7.87 (br s, 1H), 8.32 (d, J=7.6 Hz, 1H), 8.38 (s, 1H), 10.15 (s, 1H). ESI-MS (m/z): calcd. for [M+H]$^+$ 1025.30, found 1025.33.

3.6: Synthesis of Mono-NTA Appended with Fluorescein

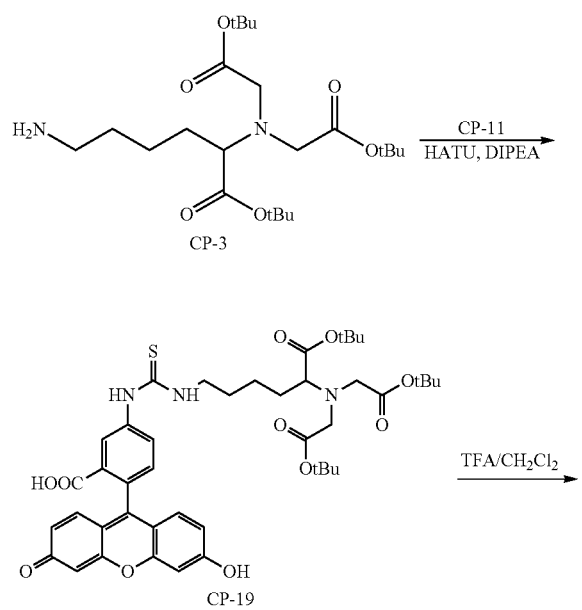

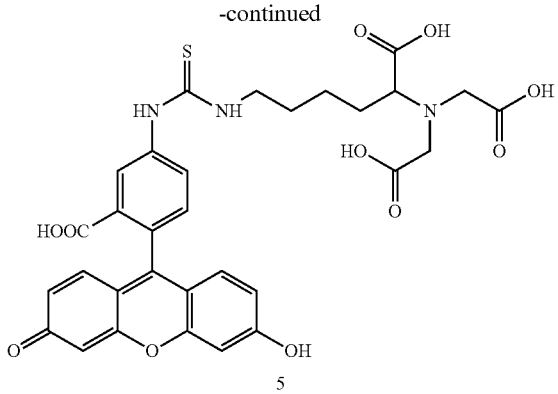

The mono-NTA appended with fluorescein was synthesized according to a previously reported procedure (S. Arai, S. I. Yoon, A. Murata, M. Takabayashi, X. Wu, Y. Lu, S. Takeoka and M. Ozaki, *Biochem. Biophys. Res. Commun.*, 2011, 404, 211).

Synthesis of CP-19: CP-3 (100.00 mg, 0.23 mmol) was dissolved in DCM (1 mL) and the solution was basified to pH 7-8 with DIPEA (0.04 mL, 0.23 mmol). Then fluorescein isothiocyanate (CP-11, 100.00 mg, 0.26 mmol) in DCM (1.00 mL) was added to the above solution and the reaction mixture was stirred at room temperature for 7 h under argon and dark conditions. The solvent was removed in vacuum and the residue was purified using RP-HPLC to afford CP-19 (0.16 g, 84%) as a dark yellow solid. $^1$H NMR (500 MHz, acetonitrile-d$_3$,): δ 1.46 (s, 18H), 1.48 (s, 9H), 1.50-1.58 (m, 2H), 1.67 (quin, J 7.0 Hz, 2H), 1.73-1.90 (m, 2H), 3.57-3.65 (m, 2H), 3.74 (d, J=17.1 Hz, 3H), 3.83 (d, J=17.1 Hz, 2H), 6.60 (dd, J=2.3, 8.7 Hz, 2H), 6.69-6.76 (m, 3H), 7.10 (br s, 1H), 7.14 (d, J=8.3 Hz, 1H), 7.71 (d, J=7.7 Hz, 1H), 8.14 (s, 1H). ESI-MS (m/z): calcd. for [M+H]$^+$ 820.35; found: 820.35.

Synthesis of 5: TFA (1.00 mL) was added to a pre-cooled (0° C.) solution of CP-19 (0.16 g, 0.195 mmol) in DCM (2.00 mL) under dark conditions. The reaction mixture was warmed up to room temperature and stirring was continued for another 3.5 h. After completion of the reaction, DCM and TFA were evaporated. The traces of TFA were removed by co-evaporation with DCM. The crude compound was washed thrice with cold diethyl ether, followed by dissolution in 3.00 mL ACN/H$_2$O (1:1), freezing with liquid nitrogen and lyophilization under high vacuum to afford a light yellow fluffy powder as a product (0.11 g, 87%). $^1$H NMR (400 MHz, DMSO-d$_6$): δ 1.27-1.49 (m, 2H) 1.55 (br s, 1H), 1.57-1.74 (m, 3H), 3.36-.43 (m, 2H), 3.45-3.52 (m, 5H), 6.54-6.59 (m, 3H), 6.59-6.63 (m, 3H), 6.67 (d, J=2.2 Hz, 3H), 7.17 (d, J=8.4 Hz, 1H), 7.74 (d, J=7.5 Hz, 1H), 8.05 (br s, 1H), 8.23 (br s, 1H), 9.87 (br s, 1H). $^{13}$C NMR (100 MHz, DMSO-d$_6$): δ 23.2, 28.1, 29.2, 53.2, 53.3, 64.4, 102.3, 102.3, 102.3, 109.8, 112.6, 112.6, 112.6, 112.7, 126.5, 126.5, 129.1, 151.9, 152.0, 158.2, 158.5, 159.5, 168.6, 172.9, 173.0, 173.7; ESI-MS (m/z): calcd. for [M+H]$^+$ 652.16; found: 652.17.

Example 28

Experimental Methods

Bacterial Strains and Growth Conditions.

*E. coli* K-12 strain KRX (Promega) was used for protein expression. The details of the expression of 3 copies of hexahistidine-tag at the 7th loop of the OmpC are described in Mankovski et. al. (*Nat. Commun.*, 2020, 11, 1299). Transformed bacteria with different OmpC constructs (OmpC or His-OmpC) were cultured overnight in LB medium containing ampicillin (100 g/ml) at 30° C. The next day, the bacterial cells were diluted 100-fold in fresh LB medium supplemented with ampicillin and incubated until the $OD_{600}$ reached ~0.6. Protein expression was then induced by the addition of 0.10% Rhamnose and 20 M isopropyl-b-D-1-thiogalactopyranoside (IPTG), and cultures were incubated overnight on a shaking plate (230 rpm) set at the desired temperatures of 8° C., 15° C., or 37° C. The bacterial cells were collected by centrifugation at 6000×g for 4 min. Pellets were washed twice with PBS×1 buffer (100 L) and then re-suspended in 100 μL in the same buffer to an $OD_{600}$ of 0.3.

General Procedure for Fluorescence Measurements

A sample of a probe (20 μM) and $NiCl_2.6H_2O$ (60 μM) were mixed in Tris buffer (10 mM, pH=7.5) and allowed to stand at room temperature for 30 minutes. Meanwhile, the bacterial cells (OmpC or His-OmpC) ($OD_{600}$=3.0) were transferred to Eppendorf tubes and centrifuged (6,000 g) for 4 minutes. After removing the LB medium, the pellet fraction was washed twice with Tris buffer (200 μL) and finally re-suspended in 200 μL Tris buffer. Then a probe, at a final concentration of 100 nM, was added to the bacterial suspension (60 L), and the emission spectrum was immediately recorded. The fluorescence responses of Compound 313, 315 and 314 were measured using excitation wavelengths of 545 nm, 465 nm, and 620 nm, respectively. These experiments were performed in triplicate for bacterial samples cultured at 8° C., 15° C., and 37° C.

Fluorescence Imaging Experiments

To a 100 μL sample of the bacteria suspension, a preincubated sample of each probe, 1-5 (500 nM) and $NiCl_2$ (2.5 M) was added, and the cells were incubated at room temperature for 1 h. Then each sample was washed twice with PBS, resuspended in 200 μL PBS, and placed on a glass-bottom dish (P35G-1.5-14-C; MatTek) precoated with poly-l-lysine (Sigma Aldrich) and left to adhere for 1 h. Finally, the wells were washed with PBS three times and imaged using an Olympus IX51 fluorescent microscope. The samples were imaged using 100× objective lenses.

Super-Resolution Imaging

Super-resolution images were obtained using a Vutara SR200 STORM (Bruker) microscope based on single-molecule localization biplane technology. His-tagged bacteria decorated with compound 3 were imaged using a 647 nm excitation laser and a 405 nm activation laser in an imaging buffer composed of cysteamine (5 mM), 7 M glucose oxidase, 56 nM catalase, and 10% glucose in 50 mM Tris, 10 mM NaCl, at pH 8.0. Images were recorded using a ×60 NA 1.2 water immersion objective (Olympus) and an Evolve 512 EMCCD camera (Photometrics) with gain set at 50, the frame rate at 50 Hz, and a maximal power of 647, and 405 nm lasers were set at 6 and 0.05 kW/cm2, respectively. The total number of frames acquired was 8000. Data were analyzed by Vutara SRX software.

Microscale Thermophoresis (MST)

The affinity of the tri-NTA (2), bis-NTA (4), and mono-NTA (5) probes to a His-tagged protein ($His_6$-P53) was measured using MST on a micro MST Monolith NT.115 instrument (NanoTemper Technologies, Munich, Germany). The concentrations of probes 2, 4, and 5 were kept constant. Each probe was separately incubated with $NiCl_2$ (5, 4, and 2 eq., respectively) for 30 min in PBST buffer (137 mM NaCl, 2.5 mM KCl, 10 mM $Na_2HPO_4$, 2 mM $KH_2PO_4$, at pH 7.4, 0.05% Tween-20). His tagged P53 was serially diluted in twofold dilutions and then each probe sample was added to the dilution series. The resulting protein-probe samples were centrifuged at 21,000 g at 4° C. for 10 minutes. After ensuring that there was no precipitation of the protein, the samples were loaded into Monolith NT.115 MST premium-coated capillaries. For probe 2 and 4, MST measurements were conducted at 20% LED power and 20% MST power. For probe 5, changes in the initial fluorescence were measured to determine the dissociation constant (M. J. Willemsen, C. J. Wienken, D. Braun, P. Baaske, and Stefan Duhr, *Assay Drug Dev. Technol.*, 2011, 9, 342). The experimental data were analyzed using NT analysis and MO affinity analysis (version 2.2.7) software, and were fitted according to the following equation;

$$\frac{[LP]}{[P]} = \frac{([L]+[P]+K_d) - \sqrt{(([L]+[P]+K_d)^2 - 4[L][P])}}{2[P]}$$

where [L] is the probe concentration that is kept constant, [P] is the concentration of the protein, [LP] is the concentration of a bound complex of L and P, and $K_d$ is the dissociation constant.

Gel Electrophoresis

The bacterial cells ($OD_{600}$ of 2) were collected by centrifugation at 6,000 g for 4 min. The supernatant was discarded and the pellet was washed with 1 mL of lysis buffer (10 mM $Na_2HPO_4$, pH=7.2), followed by centrifugation at 6,000 g for 10 min. The cell pellets were resuspended in 1 mL of lysis buffer containing a 2% protease inhibitor cocktail, and lysed by sonication for 2 min. The resulting cell lysate was centrifuged for 2 min at 12,000 rpm and the pellet was discarded. The supernatant was further centrifuged at 12,000 rpm for 30 min, and the resulting pellet was washed with the buffer and re-suspended in 170 μL of buffer. Next, 60 μL of the sample was run on Mini-PROTEAN TGX gels, 8-16% gradient gels (BioRad, Hercules, CA) at 120V for 90 min. The gels were stained with Instant Blue Coomassie Protein Stain and imaged using a BioRad Chemi-Doc XRS+ imager.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A compound represented by the structure of Formula XXXV:

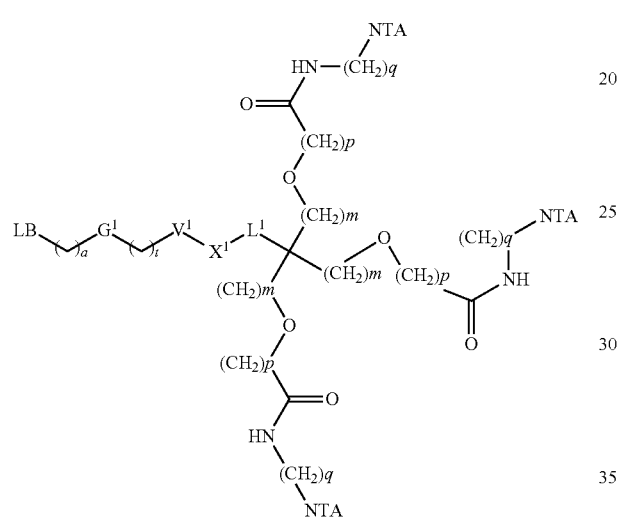

XXXV wherein a and t are each independently an integer between 0 and 15;

$G^1$ is selected from the group consisting of: a bond, carbamate, an amide [—C(O)NH or —NHC(O)], amine, $C_1$-$C_{12}$ alkyl amine, ester, ketone, O, N, S, carbonate, —O-alkyl-NH-carbamoyl phosphate and phosphate;

$V^1$ is selected from the group consisting of: a bond, a triazole, an amide [—C(O)NH or —NHC(O)], —C(O)O—, —OC(O)—, O, NH, N-alkyl, S, —PO$_4$H—, alkyl ether, —NH-alkyl-NH—, —O-alkyl-NH—, and —NH-alkyl-O— wherein said alkyl is optionally substituted, wherein said alkyl is optionally interrupted by an heteroatom consisting of O, N, P, S, or combination thereof;

$X^1$ is selected from the group consisting of: a bond or $C_1$-$C_{12}$ alkyl, an amide [—C(O)NH or —NHC(O)], —C(O)O—, —OC(O)—, O, NH, N-alkyl, S, —PO$_4$H—, $C_1$-$C_{12}$ alkyl ether, $C_1$-$C_{12}$-alkyl-NH, -alkyl-NHC(O)-alkyl, -alkyl-C(O)NH-alkyl, —NH-alkyl-NH—, —O-alkyl-NH—, and —NH-alkyl-O— wherein said alkyl is optionally substituted, wherein said alkyl is optionally interrupted by an heteroatom consisting of O, N, P, S, or combination thereof;

$L^1$ is selected from the group consisting of: a bond or $C_1$-$C_{12}$ alkyl, C(O), an amide [—C(O)NH or —NHC(O)], —C(O)O—, —OC(O)—, O, NH, $C_1$-$C_{12}$—N-alkyl, S, —PO$_4$H, —PO$_4$H—PO$_4$H—{[(CH$_2$)$_y$O]$_x$}$_z$—PO$_3$H—, wherein y is between 1-5, x is between 1-10 and z is between 1-10, —PO$_4$H—PEG, $C_1$-$C_{12}$ alkyl ether, $C_1$-$C_{12}$ alkylamine, $C_1$-$C_{12}$ alkyl-NH, —C(O)NH-alkyl, —NHC(O)-alkyl, NH-alkyl-NH—, —O-alkyl-NH—, and —NH-alkyl-O—, wherein said alkyl is optionally substituted, wherein said alkyl is optionally interrupted by an heteroatom consisting of O, N, P, S, or combination thereof;

m, p and q are each independently an integer between 1 and 8;

NTA is selected from the group consisting of: nitrilotriacetic acid, nitrilotriacetic acid complexed with at least one metal ion, and a protected derivative thereof; and LB is a quinoline-based cyanine dye, or a quinoline-based cyanine dye derivative (QBC);

or a suitable salt thereof.

2. The compound of claim 1, wherein m is 1; p is 2; q is 4; a is 1 or 2; t is 2; $G^1$ is an amide; $V^1$ is alkyl ether, preferably —[(O—CH$_2$—CH$_2$)$_k$]—, wherein k is an integer between 1 and 6, preferably 3; $X^1$ or $L^1$ is a bond or an amide; LB is Thiazole Orange (TO), Thiazole Red (TR) or Quinoline Blue (QB); said salt is a tosylate, iodide, chloride, bromide, fluoride, TFA or a PF$_6$ salt; or any combination thereof.

3. The compound of claim 1, wherein the compound represented by the structure of Formula XXXVI:

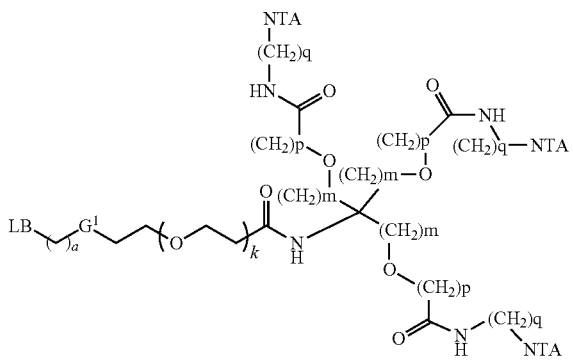

XXXVI wherein k is an integer between 0 and 8; or wherein the compound represented by the structure of Formula XXXVII:

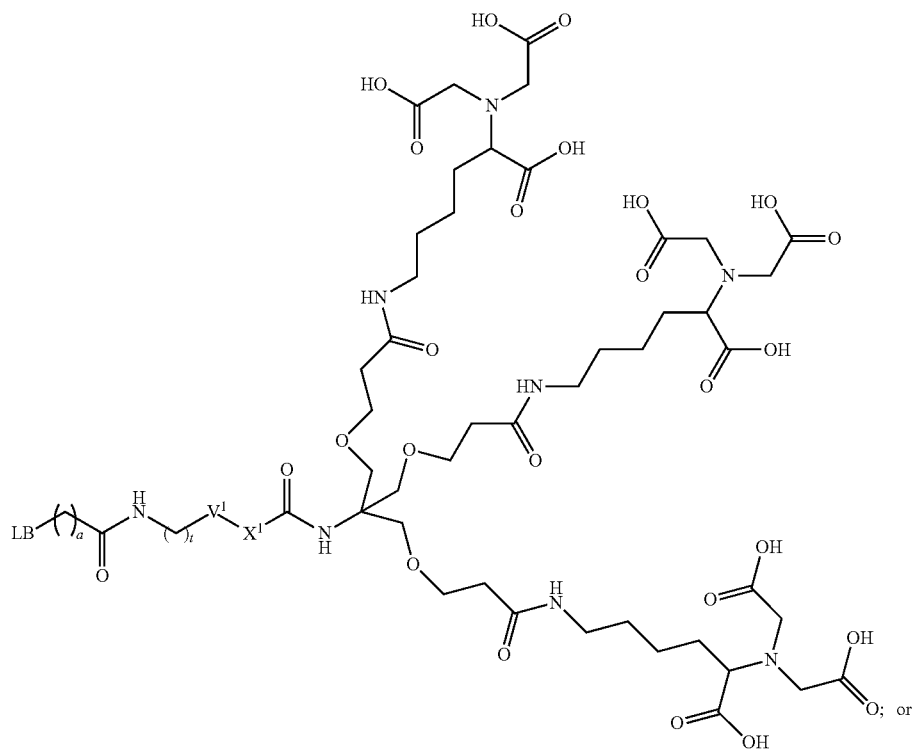
XXXVII
wherein the compound is represented by the structure of any one of compounds 408-410:
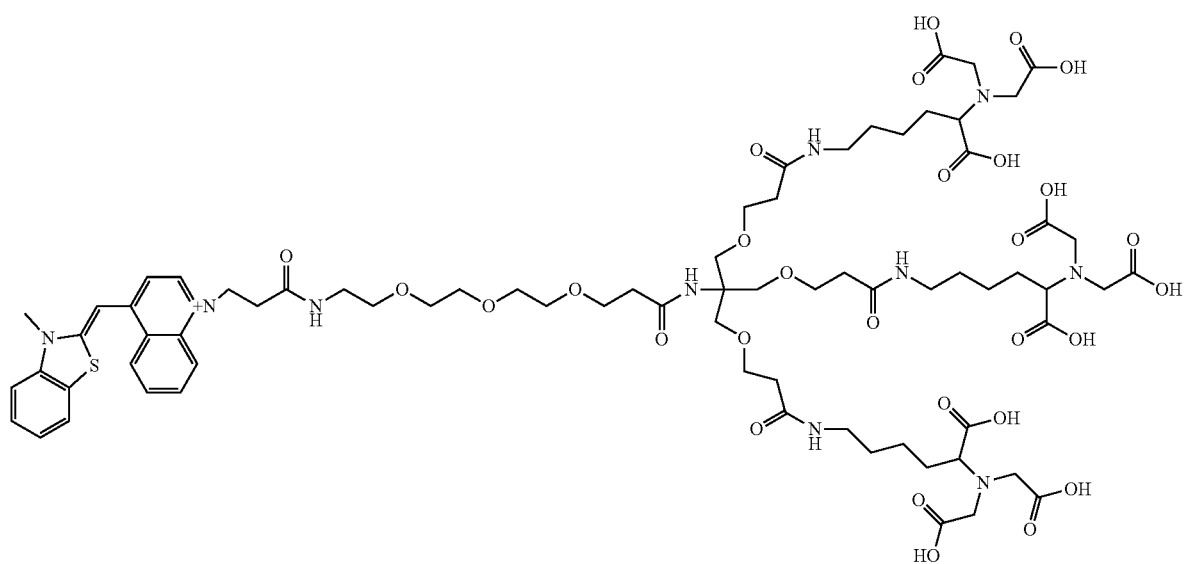
408

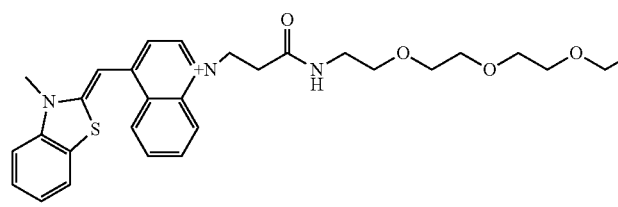
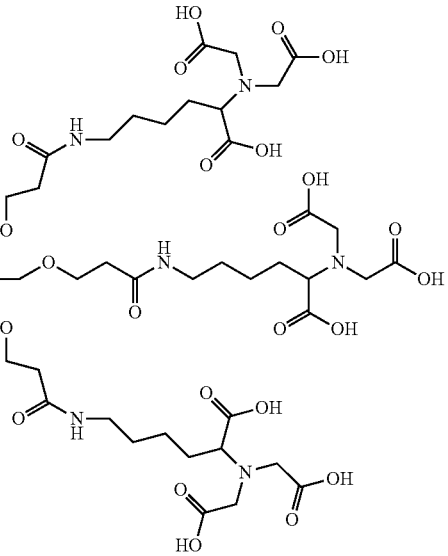

409

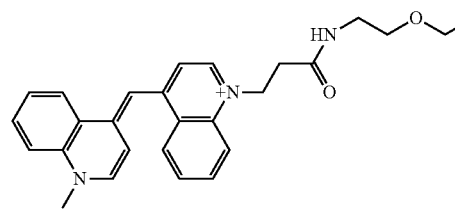
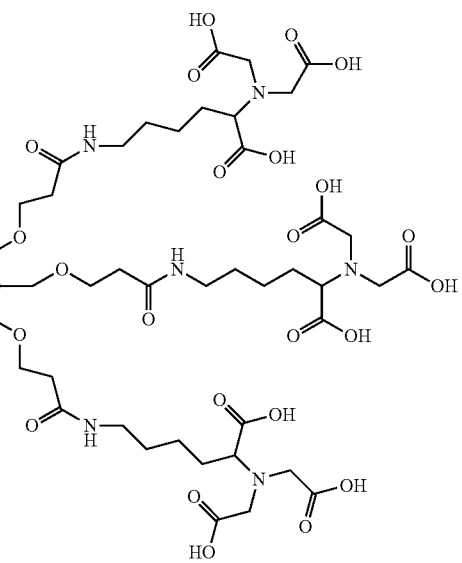

410

4. A fluorescent probe that can selectively label a His-tagged polypeptide, comprising the compound of claim 1 complexed to at least one metal ion.

5. The fluorescent probe of claim 4,
wherein the compound is complexed to three Ni(II) ions;
wherein said probe specifically binds to an oligohistidine sequence (His-tag) of a His-tagged polypeptide to generate a fluorescent signal;
wherein said fluorescent probe does not perturb living cells function;
wherein said fluorescent probe is capable of traversing a biological membrane;
or any combination thereof.

6. A method for imaging a His-tagged polypeptide of interest within a cell, said method comprises:
a. expressing said His-tagged polypeptide in a recombinant cell;
b. incubating said recombinant cell with a fluorescent probe according to claim 4; and
c. visualizing the fluorescence emission of said fluorescent probe.

7. A method for measuring the expression level of a His-tagged polypeptide of interest in a cell, said method comprises the steps of:
a. expressing a His-tagged polypeptide in a cell;
b. incubating said cell with a fluorescent probe according to claim 4; and
c. measuring the fluorescence of said cell;
wherein detection of a fluorescent signal is dependent on the formation of a His-tagged polypeptide:fluorescent probe complex.

8. The method of claim 7, wherein the cell is a living cell, wherein the fluorescent probe does not perturb living cells function, or combination thereof.

* * * * *

SEQUENCE LISTING

<160> NUMBER OF SEQ ID NOS: 26

<210> SEQ ID NO 1
<211> LENGTH: 13
<212> TYPE: DNA

```
<213> ORGANISM: Artificial Sequence
<220> FEATURE:
<223> OTHER INFORMATION: CY5-ODN-1

<400> SEQUENCE: 1
gcggcgaggc agc                                                        13

<210> SEQ ID NO 2
<211> LENGTH: 25
<212> TYPE: DNA
<213> ORGANISM: Artificial Sequence
<220> FEATURE:
<223> OTHER INFORMATION: TAMRA-ODN-1

<400> SEQUENCE: 2
gtcacgtcat agctgcctga tccta                                           25

<210> SEQ ID NO 3
<211> LENGTH: 19
<212> TYPE: DNA
<213> ORGANISM: Artificial Sequence
<220> FEATURE:
<223> OTHER INFORMATION: ODN-1 and ODN-1a

<400> SEQUENCE: 3
tcatagctgc ctgatccta                                                  19

<210> SEQ ID NO 4
<211> LENGTH: 25
<212> TYPE: DNA
<213> ORGANISM: Artificial Sequence
<220> FEATURE:
<223> OTHER INFORMATION: ODN-1b

<400> SEQUENCE: 4
ggtacaacta gacgatcgac agtag                                           25

<210> SEQ ID NO 5
<211> LENGTH: 25
<212> TYPE: DNA
<213> ORGANISM: Artificial Sequence
<220> FEATURE:
<223> OTHER INFORMATION: ODN-1c

<400> SEQUENCE: 5
cgcaacgaaa aaaaaaaaag cgcgc                                           25

<210> SEQ ID NO 6
<211> LENGTH: 25
<212> TYPE: DNA
<213> ORGANISM: Artificial Sequence
<220> FEATURE:
<223> OTHER INFORMATION: TAMRA-ODN-2

<400> SEQUENCE: 6
taggatcagg cagctatgac gtgac                                           25

<210> SEQ ID NO 7
<211> LENGTH: 25
<212> TYPE: DNA
<213> ORGANISM: Artificial Sequence
<220> FEATURE:
<223> OTHER INFORMATION: ODN-2 or ODN-2a

<400> SEQUENCE: 7
taggatcagg cagctatgac gtgac                                           25
```

<210> SEQ ID NO 8
<211> LENGTH: 24
<212> TYPE: DNA
<213> ORGANISM: Artificial Sequence
<220> FEATURE:
<223> OTHER INFORMATION: ODN-2b

<400> SEQUENCE: 8
tactgtcgat cgtctagttg tacc                                              24

<210> SEQ ID NO 9
<211> LENGTH: 25
<212> TYPE: DNA
<213> ORGANISM: Artificial Sequence
<220> FEATURE:
<223> OTHER INFORMATION: ODN-2c

<400> SEQUENCE: 9
gcgcgctttt tttttttcg ttgcg                                              25

<210> SEQ ID NO 10
<211> LENGTH: 25
<212> TYPE: DNA
<213> ORGANISM: Artificial Sequence
<220> FEATURE:
<223> OTHER INFORMATION: ODN-3

<400> SEQUENCE: 10
gtcacgtcat agctgcctga tccta                                             25

<210> SEQ ID NO 11
<211> LENGTH: 54
<212> TYPE: DNA
<213> ORGANISM: Artificial Sequence
<220> FEATURE:
<223> OTHER INFORMATION: OmpC_FpET21

<400> SEQUENCE: 11
tttgtttaac tttaagaagg agatatacat atgaaagtta agtactgtc cctc              54

<210> SEQ ID NO 12
<211> LENGTH: 52
<212> TYPE: DNA
<213> ORGANISM: Artificial Sequence
<220> FEATURE:
<223> OTHER INFORMATION: OmpC_RpET21

<400> SEQUENCE: 12
ttcctttcgg gctttgttag cagccggatc ttagaactgg taaaccagac cc               52

<210> SEQ ID NO 13
<211> LENGTH: 11
<212> TYPE: PRT
<213> ORGANISM: Artificial Sequence
<220> FEATURE:
<223> OTHER INFORMATION: OmpC-(6His)1

<400> SEQUENCE: 13

Ser Ala Gly His His His His His His Gly Thr
1               5                   10

<210> SEQ ID NO 14
<211> LENGTH: 48
<212> TYPE: DNA
<213> ORGANISM: Artificial Sequence

```
<220> FEATURE:
<223> OTHER INFORMATION: OmpC_His1

<400> SEQUENCE: 14
catcatcacc atggtacctc taaaggtaaa aacctgggtc gtggctac                    48

<210> SEQ ID NO 15
<211> LENGTH: 60
<212> TYPE: DNA
<213> ORGANISM: Artificial Sequence
<220> FEATURE:
<223> OTHER INFORMATION: OmpC_His1R

<400> SEQUENCE: 15
atggtgatga tgatgatgac ccgcggaggt accatggtga tgatggtgat gacccgcgga      60

<210> SEQ ID NO 16
<211> LENGTH: 22
<212> TYPE: PRT
<213> ORGANISM: Artificial Sequence
<220> FEATURE:
<223> OTHER INFORMATION: OmpC-(6His)2

<400> SEQUENCE: 16

Ser Ala Gly His His His His His His Gly Thr Ser Ala Gly His His
1               5                   10                  15

His His His His Gly Thr
            20

<210> SEQ ID NO 17
<211> LENGTH: 40
<212> TYPE: DNA
<213> ORGANISM: Artificial Sequence
<220> FEATURE:
<223> OTHER INFORMATION: OmpC_His2FInverse

<400> SEQUENCE: 17
caccatcacg gtacctctaa aggtaaaaac ctgggtcgtg                            40

<210> SEQ ID NO 18
<211> LENGTH: 42
<212> TYPE: DNA
<213> ORGANISM: Artificial Sequence
<220> FEATURE:
<223> OTHER INFORMATION: OmpC_His2RInverse

<400> SEQUENCE: 18
gtgatggtga cccgcggagg taccatggtg atgatggtga tg                        42

<210> SEQ ID NO 19
<211> LENGTH: 40
<212> TYPE: DNA
<213> ORGANISM: Artificial Sequence
<220> FEATURE:
<223> OTHER INFORMATION: OmpC_His3FInverse

<400> SEQUENCE: 19
catcatcatg gtacctctaa aggtaaaaac ctgggtcgtg                            40

<210> SEQ ID NO 20
<211> LENGTH: 42
<212> TYPE: DNA
<213> ORGANISM: Artificial Sequence
<220> FEATURE:
<223> OTHER INFORMATION: OmpC_His3RInverse
```

```
<400> SEQUENCE: 20
atgatgatga cccgcggagg taccgtgatg gtggtgatgg tg                          42

<210> SEQ ID NO 21
<211> LENGTH: 33
<212> TYPE: PRT
<213> ORGANISM: Artificial Sequence
<220> FEATURE:
<223> OTHER INFORMATION: OmpC-(6His)3

<400> SEQUENCE: 21

Ser Ala Gly His His His His His His Gly Thr Ser Ala Gly His His
1               5                   10                  15

His His His His Gly Thr Ser Ala Gly His His His His His Gly
            20                  25                  30

Thr

<210> SEQ ID NO 22
<211> LENGTH: 4
<212> TYPE: PRT
<213> ORGANISM: Artificial Sequence
<220> FEATURE:
<223> OTHER INFORMATION: Artificial Peptide Sequence

<400> SEQUENCE: 22

Ile Leu Ser Gly
1

<210> SEQ ID NO 23
<211> LENGTH: 4
<212> TYPE: PRT
<213> ORGANISM: Artificial Sequence
<220> FEATURE:
<223> OTHER INFORMATION: Artificial Peptide Sequence

<400> SEQUENCE: 23

Gly Glu Ser Glu
1

<210> SEQ ID NO 24
<211> LENGTH: 4
<212> TYPE: PRT
<213> ORGANISM: Artificial Sequence
<220> FEATURE:
<223> OTHER INFORMATION: Artificial Peptide Sequence

<400> SEQUENCE: 24

Ser Gly Ser Ser
1

<210> SEQ ID NO 25
<211> LENGTH: 4
<212> TYPE: PRT
<213> ORGANISM: Artificial Sequence
<220> FEATURE:
<223> OTHER INFORMATION: Artificial Peptide Sequence

<400> SEQUENCE: 25

Ser Lys Ser Lys
1

<210> SEQ ID NO 26
<211> LENGTH: 6
<212> TYPE: PRT
<213> ORGANISM: Artificial Sequence
```

```
<220> FEATURE:
<223> OTHER INFORMATION: Artificial Peptide Sequence

<400> SEQUENCE: 26

Ile Leu Lys Ser Ile Lys
1               5
```